US008962296B2

(12) United States Patent
Hayashi et al.

(10) Patent No.: US 8,962,296 B2
(45) Date of Patent: Feb. 24, 2015

(54) ISOPRENE SYNTHASE AND GENE ENCODING THE SAME, AND METHOD FOR PRODUCING ISOPRENE MONOMER

(71) Applicants: Bridgestone Corporation, Tokyo (JP); Ajinomoto Co., Inc., Tokyo (JP)

(72) Inventors: Yasuyuki Hayashi, Kodaira (JP); Minako Harada, Kodaira (JP); Saaya Takaoka, Kodaira (JP); Yasuo Fukushima, Kodaira (JP); Keiichi Yokoyama, Kawasaki (JP); Yosuke Nishio, Kawasaki (JP); Yoshinori Tajima, Kawasaki (JP); Yoko Mihara, Kawasaki (JP); Kunio Nakata, Kawasaki (JP)

(73) Assignees: Bridgestone Corporation, Tokyo (JP); Ajinomoto Co., Inc., Tokyo (JP)

( * ) Notice: Subject to any disclaimer, the term of this patent is extended or adjusted under 35 U.S.C. 154(b) by 40 days.

(21) Appl. No.: 13/832,260

(22) Filed: Mar. 15, 2013

(65) Prior Publication Data

US 2014/0113344 A1 Apr. 24, 2014

Related U.S. Application Data

(60) Provisional application No. 61/653,084, filed on May 30, 2012, provisional application No. 61/653,049, filed on May 30, 2012.

(51) Int. Cl.
| | |
|---|---|
| C12N 9/88 | (2006.01) |
| C12P 21/06 | (2006.01) |
| C12P 19/34 | (2006.01) |
| C12N 15/00 | (2006.01) |
| C12N 1/20 | (2006.01) |
| C12N 1/00 | (2006.01) |
| C12P 5/02 | (2006.01) |
| C07H 21/04 | (2006.01) |
| C07K 1/00 | (2006.01) |
| C12P 5/00 | (2006.01) |

(52) U.S. Cl.
CPC . *C12P 5/007* (2013.01); *C12N 9/88* (2013.01); *C12Y 402/03027* (2013.01); *C12P 5/00* (2013.01)
USPC ...... 435/232; 435/69.1; 435/91.1; 435/320.1; 435/252.3; 435/252.33; 435/254.11; 435/254.21; 435/167; 536/23.1; 536/23.2; 536/23.4; 530/350

(58) Field of Classification Search
CPC ...... C12N 9/1022; C12N 9/1205; C12N 9/88; C12N 9/90
USPC ............... 435/232, 69.1, 91.1, 320.1, 252.3, 435/252.32, 252.33, 254.11, 254.21, 167; 536/23.1, 23.2, 23.4; 530/350
See application file for complete search history.

(56) References Cited

U.S. PATENT DOCUMENTS 8,173,410 B2  5/2012  Bott et al.
8,288,148 B2 * 10/2012  Cervin et al. ............ 435/252.33
2009/0203102 A1  8/2009  Cervin et al.
2010/0003716 A1 *  1/2010  Cervin et al. ............... 435/40.5
2011/0045563 A1 *  2/2011  Melis ............................ 435/167
2013/0071908 A1  3/2013  Cervin et al.
2013/0078699 A1  3/2013  Cervin et al.
2013/0330709 A1 * 12/2013  Beatty et al. ...................... 435/4

FOREIGN PATENT DOCUMENTS

JP    2011-505841 A       3/2011
JP    2011-518564 A       6/2011
WO   WO 2010/031079   *   3/2010

OTHER PUBLICATIONS

Scholnick et al., From genes to protein structure and function: novel applications of computational approaches in the genomic era. Trends in Biotechnology, 18 (1):34-39, 2000.*
Burgess et al, Possible Dissociation of the Heparin-binding and Mitogenic Activities of Heparin-binding (Acidic Fibroblast) Growth Factor-I from Its Receptor-binding Activities by Site-directed Mutagenesis of a Single Lysine Residue. Journal of Cell Biology vol. 111: 2129-2138, 1990.*
Lazar et al Transforming Growth Factor α: Mutation of Aspartic Acid 47 and Leucine 48 Results in Different Biological Activities. Molecular and Cellular Biology. vol. 8: No. 3, 1247-1252, 1998.*
Zhao et al., Biosynthesis of isoprene in *Escherichia coli* via methylerythritol phosphate (MEP) pathway. Appl. Microbiol. Biotechnol. 90: 1915-1922, 2011, hereinafter, Zhao, in IDS.*
J. Kesselmeier, et al., "Biogenic Volatile Organic Compounds (VOC): An Overview on Emission, Physiology and Ecology", Journal of Atmospheric Chemistry, vol. 33, 1999, pp. 23-88.
Russell K. Monson, et al., "Relationships among Isoprene Emission Rate, Photosynthesis, and Isoprene Synthase Activity as Influenced by Temperature", Plant Physiol., vol. 98, 1992, pp. 1175-1180.
Jennifer Kuzma, et al., "Leaf Isoprene Emission Rate Is Dependent on Leaf Development and the level of Isoprene Synthase", Plant Physiol., vol. 101, 1993, pp. 435-440.
International Search Report issued Apr. 9, 2013 in PCT/JP2013/056866 with English Translation of Category of Cited Documents.
Yaru Zhao et al., "Biosynthesis of Isoprene in *Escherichia coli* via Methylerythritol Phosphate (MEP) Pathway", Appl. Microbiol. Biotechnol., vol. 90, No. 6, Jun. 2011, pp. 1915-1922.

* cited by examiner

*Primary Examiner* — Ganapathirama Raghu
(74) *Attorney, Agent, or Firm* — Oblon, Spivak, McClelland, Maier & Neustadt, L.L.P.

(57) ABSTRACT

The present invention provides means useful for establishing an excellent isoprene monomer production system. Specifically, the present invention provides a polynucleotide of the following (a), (b), or (c):
(a) a polynucleotide comprising (i) the nucleotide sequence represented by SEQ ID NO:1, or (ii) the nucleotide sequence consisting of the nucleotide residues at positions 133 to 1785 in the nucleotide sequence represented by SEQ ID NO:1;
(b) a polynucleotide that comprises a nucleotide sequence having 90% or more identity to the nucleotide sequence of (i) or (ii) above, and encodes a protein having an isoprene synthase activity; or
(c) a polynucleotide that hybridizes under a stringent condition with a polynucleotide consisting of a nucleotide sequence complementary to the nucleotide sequence of (i) or (ii) above, and encodes a protein having an isoprene synthase activity; and the like.

14 Claims, 2 Drawing Sheets pstS-attTn7-KKDyI-glmS rc pstS-attTn7-Ptac-KKDyI-glmS Tet(S) rc

US 8,962,296 B2

ISOPRENE SYNTHASE AND GENE ENCODING THE SAME, AND METHOD FOR PRODUCING ISOPRENE MONOMER

CROSS-REFERENCE TO RELATED APPLICATION

This application claims benefits of the priority of U.S. Patent Provisional Application No. 61/653,049 filed on May 30, 2012 and U.S. Patent Provisional Application No. 61/653,084 filed on May 30, 2012, the entire contents of which are incorporated herein by reference.

TECHNICAL FIELD

The present invention relates to an isoprene synthase and a gene encoding the same, and the like.

BACKGROUND ART

Natural rubber is a very important raw material in tire and rubber industries. While its demand will be expanded in future due to motorization mainly in emerging countries, it is not easy to increase agricultural farms in view of regulation for deforestation and competition with palm, and increase in yield of natural rubber is hardly expected. Thus, balance of demand and supply is predicted to become tight. Synthesized polyisoprene is available as a material in place of the natural rubber. Its raw material monomer (isoprene (2-methyl-1,3-butadiene)) is mainly obtained by extracting from a C5 fraction obtained by cracking of naphtha. However in recent years, with the use of light feed crackers, an amount of produced isoprene tends to decrease and its supply is concerned. Also in recent years, since variation of oil price greatly influences, it is requested to establish a system in which isoprene derived from non-oil sources is produced inexpensively in order to stably ensure the supply of an isoprene monomer.

Concerning such a request, a method in which the isoprene monomer is produced using a transformant obtained by introducing an isoprene synthase gene and a mutant thereof derived from isolated Kudzu or Poplar into a microorganism for fermental production has been disclosed (see, Patent literatures 1 and 2).

PRIOR ART REFERENCES

Patent Literatures

Patent literature 1: JP Publication No. 2011-505841
Patent literature 2: JP Publication No. 2011-518564

Non-Patent Literatures

Non-Patent Literature 1: Kesselmeier J. et al., Journal of Atmospheric Chemistry, vol. 33, pp. 23-88, 1999.
Non-Patent Literature 2: Monson R. K. et al., Plant Physiol., vol. 98, pp. 1175-1180, 1992.
Non-Patent Literature 3: Kuzma J. et al., Plant Physiol., vo. 101, pp. 435-440, 1993.

DISCLOSURE OF INVENTION

Problem to be Solved by the Invention

However, an enzymatic activity of the isoprene synthase described in Patent literatures 1 and 2 was low, and there was still room to improve it in terms of producing isoprene with high productivity when these isoprene synthase genes were used.

The present invention has been made in the light of the above circumstance, and it is an object of the present invention to provide means useful for establishing an excellent isoprene monomer production system.

Means for Solving Problem

As a result of an extensive study for solving the above problem, the present inventors have found that an isoprene synthase derived from *Mucuna* (*Mucuna pruriens*) is excellent in ability to produce the isoprene monomer, and have completed the present invention.

Accordingly, the present invention is as follows.

[1] A polynucleotide of the following (a), (b), or (c):
(a) a polynucleotide comprising (i) the nucleotide sequence represented by SEQ ID NO:1, or (ii) the nucleotide sequence consisting of the nucleotide residues at positions 133 to 1785 in the nucleotide sequence represented by SEQ ID NO:1;
(b) a polynucleotide that comprises a nucleotide sequence having 90% or more identity to the nucleotide sequence of (i) or (ii), and encodes a protein having an isoprene synthase activity; or
(c) a polynucleotide that hybridizes under a stringent condition with a polynucleotide consisting of the nucleotide sequence complementary to the nucleotide sequence of (i) or (ii), and encodes a protein having an isoprene synthase activity.

[2] The polynucleotide according to [1], wherein the polynucleotide is derived from *Mucuna*.

[3] A protein of the following (A), (B), or (C):
(A) a protein comprising (i') the full length amino acid sequence represented by SEQ ID NO:2, or (ii') the amino acid sequence consisting of the amino acid residues at positions 45 to 594 in the amino acid sequence represented by SEQ OD NO:2;
(B) a protein that comprises an amino acid sequence having 90% or more identity to the amino acid sequence of (i') or (ii'), and has an isoprene synthase activity; or
(C) a protein that comprises an amino acid sequence having a deletion, substitution, addition or insertion of one or several amino acids in the amino acid sequence of (i') or (ii'), and has an isoprene synthase activity.

[4] An expression vector comprising the polynucleotide according to [1].

[5] A transformant prepared by introducing the expression vector according to [1] into a host.

[6] The transformant according to [1], wherein the host has an ability to synthesize dimethylallyl diphosphate via a methylerythritol phosphate pathway.

[7] The transformant according to [1], wherein the host is *Escherichia coli*.

[8] The transformant according to [5], wherein the transformant has an ability to synthesize dimethylallyl diphosphate via both a mevalonate pathway and a methylerythritol phosphate pathway.

[9] The transformant according to [5], wherein the host is a microorganism belonging to genus *Corynebacterium*, genus *Pantoea*, genus *Enterobacter*, or genus *Saccharomyces*.

[10] A method of producing a protein, comprising forming the protein using the transformant according to [5], wherein the protein is encoded by a polynucleotide of the following (a), (b) or (c):

(a) a polynucleotide comprising (i) the nucleotide sequence represented by SEQ ID NO:1, or (ii) the nucleotide sequence consisting of the nucleotide residues at positions 133 to 1785 in the nucleotide sequence represented by SEQ ID NO:1;

(b) a polynucleotide that comprises a nucleotide sequence having 90% or more identity to the nucleotide sequence of (i) or (ii), and encodes a protein having an isoprene synthase activity; or (c) a polynucleotide that hybridizes under a stringent condition with a polynucleotide consisting of the nucleotide sequence complementary to the nucleotide sequence of (i) or (ii), and encodes a protein having an isoprene synthase activity.

[11] A method of producing an isoprene monomer, comprising forming the isoprene monomer from dimethylallyl diphosphate in the presence of the protein which is encoded by a polynucleotide of the following (a), (b) or (c):

(a) a polynucleotide comprising (i) the nucleotide sequence represented by SEQ ID NO:1, or (ii) the nucleotide sequence consisting of the nucleotide residues at positions 133 to 1785 in the nucleotide sequence represented by SEQ ID NO:1;

(b) a polynucleotide that comprises a nucleotide sequence having 90% or more identity to the nucleotide sequence of (i) or (ii), and encodes a protein having an isoprene synthase activity; or (c) a polynucleotide that hybridizes under a stringent condition with a polynucleotide consisting of the nucleotide sequence complementary to the nucleotide sequence of (i) or (ii), and encodes a protein having an isoprene synthase activity.

[12] The method according to [11], wherein the isoprene monomer is formed by culturing a transformant prepared by introducing an expression vector comprising the polynucleotide into a host.

[13] The method according to [12], wherein the dimethylallyl diphosphate is supplied from a carbon source in a medium by culturing the transformant.

[14] A method of producing an isoprene polymer, comprising (I) and (II):

(I) forming an isoprene monomer by the method according to [11]; and (II) polymerizing the isoprene monomer to form the isoprene polymer.

Effect of the Invention

According to the present invention, it is possible to establish an excellent isoprene monomer production system.

EMBODIMENTS FOR CARRYING OUT THE INVENTION

<Polynucleotide Encoding Isoprene Synthase>

Figure 1:
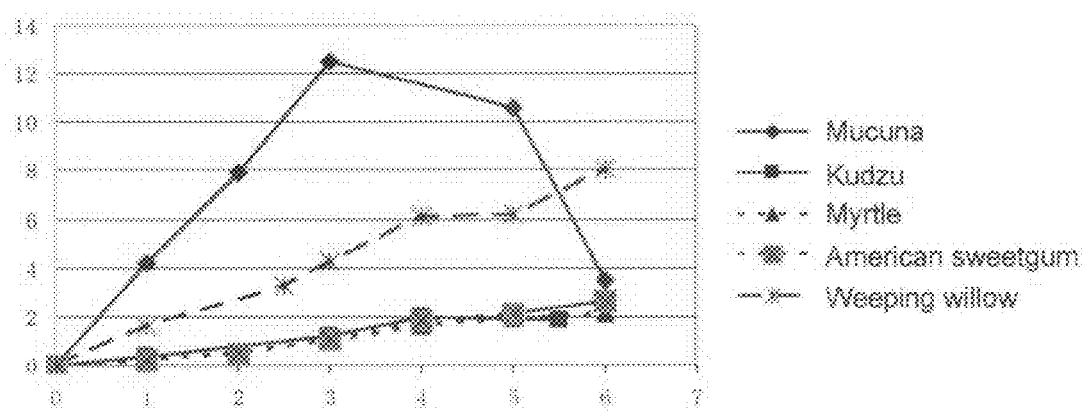
FIG. 1 is a graph showing an amount of isoprene produced per unit weight of dry leaves from various plants.

The present invention provides a polynucleotide encoding an isoprene synthase.

The isoprene synthase is an enzyme that converts dimethylallyl diphosphate into isoprene. The present inventors firstly evaluated an ability to produce isoprene in various plants under the same condition at high temperature. As a result, it was found that the ability of Mucuna (*Mucuna bracteata*) to produce isoprene was several times to several ten times higher than the ability of Poplar (*Populus nigra* var. *italic*) and Kudzu (*Pueraria lobata*) to produce isoprene. However, it is not clarified whether this high ability to produce isoprene is attributed to a high ability of the plant to produce dimethylallyl diphosphate, high production of the isoprene synthase by the plant, or a high specific enzymatic activity of the isoprene synthase that the plant has. In particular, pH dependency and the like of an isoprene synthase activity in *Mucuna*, was examined using the enzyme partially purified by ammonium sulfate fractionation by Monson and Kuzma et al. in Non-Patent Literatures 2 and 3, but it was not clear whether the specific activity in *Mucuna* was higher than that in Kudzu and Poplar or not. Thus, the present inventors partially purified the isoprene synthase from leaves of *Mucuna* and Kudzu by the ammonium sulfate fractionation, and examined the specific activity of the crude extract solution. As a result, it was found that the specific activity of the isoprene synthase derived from *Mucuna* was several times to several ten times higher than that derived from Kudzu. It was also demonstrated that the measured specific activity of the isoprene synthase from *Mucuna* was several times to several ten times higher than the specific activity of the isoprene synthase in the crude enzyme from Poplar reported in Patent Literatures 1 and 2. From the above, it was suggested that *Mucuna* potentially had highly functional isoprene synthase.

Subsequently, a nucleotide sequence of an isoprene synthase gene from *Mucuna* was analyzed. One example of analysis methods will be described below.

It is known that the isoprene synthase is expressed only in the leaves in the plant and its expression level is increased under strong light and high temperature. Thus, total RNA was firstly extracted from the leaves of *Mucuna* where transcription of isoprene synthase mRNA had been induced under light illumination at temperature of 40° C. It was confirmed that the extracted total RNA was not decomposed and not contaminated with genomic DNA. Then, the total RNA was converted into a double strand and fragmented, and only nucleotide sequences having a poly A sequence at a 3' end were analyzed using a high performance sequencer. Overlapped sequences were assembled to obtain a plurality of contig sequences. BLAST search was performed for these contig sequences, and a contig sequence having homology (identity of nucleotide sequences) to registered sequences of the known isoprene synthase genes from Kudzu and Poplar was detected, and a partial sequence of the isoprene synthase gene from *Mucuna* was obtained. Based on this partial sequence, 5' RACE (Rapid Amplification of cDNA Ends) was performed using standard methods to analyze a full length nucleotide sequence of the isoprene synthase gene from *Mucuna*, which is represented by SEQ ID NO:1.

cDNA of the isoprene synthase from *Mucuna* can be obtained, for example, by RT-PCR with the total RNA obtained above as a template using primers designed based on the analyzed nucleotide sequence information of the isoprene synthase gene from *Mucuna*.

In one embodiment, the polynucleotide of the present invention is a polynucleotide comprising (i) the nucleotide sequence represented by SEQ ID NO:1, or (ii) the nucleotide sequence consisting of the nucleotide residues at positions 133 to 1785 in the nucleotide sequence represented by SEQ ID NO:1. The nucleotide sequence represented by SEQ ID NO:1 can encode the amino acid sequence represented by SEQ ID NO:2, a nucleotide sequence consisting of the nucleotide residues at positions 1 to 132 can encode a putative chloroplast localization signal, and the nucleotide sequence consisting of the nucleotide residues at positions 133 to 1785 can encode an amino acid sequence of mature isoprene synthase.

In another embodiment, the polynucleotide of the present invention is a polynucleotide that comprises a nucleotide sequence having 90% or more identity to the nucleotide sequence of (i) or (ii) above, and encodes a protein having an isoprene synthase activity. The percent identity to the nucleotide sequence may be 91%, 92%, 93%, 94%, 95%, 96%, 97%, 98%, or 99% or more. The isoprene synthase activity refers to an activity to form isoprene from dimethylallyl diphosphate (DMAPP) (the same meaning shall apply hereinafter).

The percent identity of the nucleotide sequences, and the percent identity of the amino acid sequences as described later can be determined using algorithm BLAST (Pro. Natl. Acad. Sci. USA, 90, 5873 (1993)) by Karlin and Altschul, and FASTA (Methods Enzymol., 183, 63 (1990)) by Pearson. The programs referred to as BLASTP and BLASTN were developed based on this algorithm BLAST (see www.ncbi.nlm.nih.gov). Thus, the percent identity of the nucleotide sequences and the amino acid sequences may be calculated using these programs with default setting. Also, for example, a numerical value obtained by calculating similarity as a percentage at a setting of "unit size to compare=2" using the full length of a polypeptide portion encoded in ORF with the software GENETYX Ver. 7.0.9 from Genetyx Corporation employing Lipman-Pearson method may be used as the homology of the amino acid sequences. The lowest value among the values derived from these calculations may be employed as the percent identity of the nucleotide sequences and the amino acid sequences.

In still another embodiment, the polynucleotide of the present invention is a polynucleotide that hybridizes under a stringent condition with a polynucleotide consisting of the nucleotide sequence complementary to the nucleotide sequence of (i) or (ii) above, and encodes a protein having an isoprene synthase activity.

The "stringent condition" refers to a condition where a so-called specific hybrid is formed whereas a non-specific hybrid is not formed. It is difficult to clearly quantify such a condition. However, to cite a case, such a condition is a condition where substantially the same polynucleotides having the high identity, for example, the polynucleotides having the percent identity described above hybridize each other whereas polynucleotides having the lower identity than above do not hybridize each other. Specifically, such a condition may include hybridization in 6×SCC (sodium chloride/sodium citrate) at about 45° C. followed by one or two or more washings in 0.2×SCC and 0.1% SDS at 50 to 65° C.

The polynucleotide of the present invention may be DNA or RNA, and is preferably DNA. The polynucleotide of the present invention can be derived from *Mucuna*. The polynucleotide of the present invention may also be one encoding the protein of the present invention described later.

<Isoprene Synthase>

The present invention also provides a protein having an isoprene synthase activity. The isoprene synthase activity is as described above.

In one embodiment, the protein of the present invention is a protein comprising (i') the full length amino acid sequence represented by SEQ ID NO:2, or (ii') the amino acid sequence consisting of the amino acid residues at positions 45 to 594 in the amino acid sequence represented by SEQ ID NO:2. The amino acid sequence consisting of the amino acid residues at positions 1 to 44 in the amino acid sequence represented by SEQ ID:2 can encode a putative chloroplast localization signal, and the amino acid sequence consisting of the amino acid residues at positions 45 to 594 in the amino acid sequence represented by SEQ ID:2 can encode the mature isoprene synthase.

In another embodiment, the protein of the present invention is a protein that comprises an amino acid sequence having 90% or more identity to the amino acid sequence of (i') or (ii') above, and has an isoprene synthase activity. The percent identity to the amino acid sequence may be 91%, 92%, 93%, 94%, 95%, 96%, 97%, 98% or 99% or more.

In still another embodiment, the protein of the present invention is a protein that comprises an amino acid sequence having a mutation of one or several amino acids in the amino acid sequence of (i') or (ii') above, and has an isoprene synthase activity. Examples of the mutation of the amino acid residues may include deletion, substitution, addition and insertion of amino acid residues. The mutation of one or several amino acids may be introduced into one region or multiple different regions in the amino acid sequence. The term "one or several" indicates a range in which a three-dimensional structure and an activity of the protein are not impaired greatly. In the case of the protein, the number represented by "one or several" is, for example, 1 to 100, preferably 1 to 80, more preferably 1 to 50, 1 to 30, 1 to 20, 1 to 10, or 1 to 5. The protein of the present invention may have a tag for purification, such as a histidine tag.

The protein of the present invention preferably has an isoprene synthase activity that is 50% or more, 60% or more, 70% or more, 80% or more, 90% or more, or 95% or more of the isoprene synthase activity of the protein comprising the amino acid sequence of either one of (i') or (ii') above when measured under the same condition. In terms of stability, it is also preferable that the protein of the present invention has a remaining activity that is 30% or more, 40% or more, 50% or more, 60% or more or 65% or more of the original activity when the protein is stored in a certain buffer [e.g., a solution of 50 mM Tris-HCl (pH 8.0), and 0.15 mM $MgCl_2$] at 4° C. for 48 hours.

In the protein of the present invention, the mutation may be introduced into sites in a catalytic domain and sites other than the catalytic domain as long as an objective activity is retained. The positions of amino acid residues to be mutated which is capable of retaining the objective activity are understood by a person skilled in the art. Specifically, a person skilled in the art can recognize a correlation between structure and function, since a person skilled in the art can 1) compare the amino acid sequences of multiple proteins having the same type of activity (e.g., the amino acid sequence represented by SEQ ID NO:2 and amino acid sequences of other isoprene synthases), 2) clarify regions that are relatively conserved and regions that are not relatively conserved, and then 3) predict regions capable of playing a functionally important role and regions incapable of playing a functionally important role from the regions that are relatively conserved and the regions that are not relatively conserved, respectively. Therefore, a person skilled in the art can identify the positions of the amino acid residues to be mutated in the amino acid sequence of the isoprene synthase.

When the amino acid residue is mutated by substitution, the substitution of the amino acid residue may be conservative substitution. As used herein, the term "conservative substitution" refers to substitution of a certain amino acid residue with an amino acid residue having a similar side chain. Families of the amino acid residues having the similar side chain are well-known in the art. Examples of such families may include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a hydroxyl group (e.g., alcoholic, phenolic)-containing side chain (e.g., serine, threonine, tyrosine), and amino acids having a sulfur-containing side chain (e.g., cysteine, methionine). Preferably, the conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

<Expression Vector>

The present invention provides an expression vector. The expression vector of the present invention comprises the polynucleotide of the present invention or the polynucleotide encoding the protein of the present invention.

Examples of the expression vector of the present invention may include a cell system vector that expresses a protein in a host cell and a cell-free system vector that utilizes a protein translation system. The expression vector may also be a plasmid or an integrative vector. The expression vector may further be a DNA vector or an RNA vector.

A known vector suitable for the host cell is used as the cell system vector. Examples of the expression vector may include ColE-based plasmids typified by pBR322 derivatives, pACYC-based plasmids having a p15A origin, pSC-based plasmids, and mini F plasmids derived from an F factor of Bac and the like in *Escherichia coli*. In addition, expression vectors having a tryptophan promoter such as trc and tac, a lac promoter, a T7 promoter, a T5 promoter, a T3 promoter, an SP6 promoter, an arabinose induction promoter, a cold shock promoter, a tetracycline induction promoter, and the like may also be included.

Examples of the cell-free system vector may include expression vectors having the T7 promoter or the T3 promoter exemplified in the cell system vector; and vectors for synthesizing proteins in wheat cell-free system, such as pEU-based plasmids having the SP6 promoter or the T7 promoter.

In protein synthesis using the cell-free system vector, cDNA for an objective protein is firstly transcribed to synthesize mRNA using a transcription system. Such a transcription system may include those known conventionally and publicly in which the cDNA is transcribed by RNA polymerase. Examples of the RNA polymerase may include T7 RNA polymerase.

Subsequently, mRNA is translated to synthesize a protein using a cell-free protein synthesis system that is a translation system. In this system, factors such as ribosome, a translation initiation factor, a translation elongation factor, a dissociation factor, and aminoacyl tRNA synthetase that are required for the translation are included. Examples of such a protein translation system may include an *E. coli* extract, a rabbit reticulocyte extract, and a wheat germ extract.

Further, a reconstituted cell-free protein synthesis system composed of factors required for the above translation, which are independently purified, may also be included.

The protein synthesis using the cell system vector will be described later in <Transformants>.

A protein synthesized using the cell system vector or the cell-free system vector may be purified. Examples of the methods for purification may include methods using a salting-out method and various chromatographic methods. When the expression vector is designed to express a tag sequence such as a histidine tag at an N terminus or a C terminus of the objective protein, a method for purification using affinity chromatography using a substance such as nickel or cobalt having an affinity to this tag can be employed. In addition, a purity of the protein of the present invention can be increased by an appropriate purification method in combination with ion exchange chromatography, gel filtration chromatography, or the like.

<Transformants>

The present invention provides a transformant comprising the expression vector of the present invention. The transformant of the present invention is one obtained by introducing the expression vector of the present invention into a host. The host used for the present invention is preferably a bacterium or a fungus. The bacterium may be a gram-positive bacterium or a gram-negative bacterium.

Examples of the gram-positive bacterium may include bacteria belonging to genera *Bacillus, Listeria, Staphylococcus, Streptococcus, Enterococcus, Clostridium, Corynebacterium*, and *Streptomyces*. Bacteria belonging to genera *Bacillus* and *Corynebacterium* are preferable.

Examples of the bacteria belonging to genus *Bacillus* may include *Bacillus subtilis, Bacillus anthracis*, and *Bacillus cereus. Bacillus subtilis* is more preferable.

Examples of the bacteria belonging to genus *Corynebacterium* may include *Corynebacterium glutamicum, Corynebacterium efficiens*, and *Corynebacterium callunae. Corynebacterium glutamicum* is more preferable.

Examples of the gram-negative bacterium may include bacteria belonging to genera *Escherichia, Pantoea, Salmonella, Vivrio, Serratia*, and *Enterobacter*. The bacteria belonging to genera *Escherichia, Pantoea* and *Enterobacter* are preferable.

*Escherichia coli* is preferable as the bacteria belonging to genus *Escherichia*.

Examples of the bacteria belonging to genus *Pantoea* may include *Pantoea ananatis, Pantoea stewartii, Pantoea agglomerans*, and *Pantoea citrea. Pantoea ananatis* and *Pantoea citrea* are preferable. Strains exemplified in European Patent Application Publication 0952221 may be used as the bacteria belonging to genus *Pantoea*. Examples of representative strains of the bacteria belonging to genus *Pantoea* may include *Pantoea ananatis* AJ13355 strain (FERM BP-6614) and *Pantoea ananatis* AJ13356 strain (FERM BP-6615) disclosed in European Patent Application Publication 0952221.

Examples of the bacteria belonging to genus *Enterobacter* may include *Enterobacter agglomerans* and *Enterobacter aerogenes. Enterobacter aerogenes* is preferable. The bacterial strains exemplified in European Patent Application Publication 0952221 may be used as the bacteria belonging to genus *Enterobacter*. Examples of representative strains of the bacteria belonging to genus *Enterobacter* may include *Enterobacter agglomerans* ATCC12287 strain, *Enterobacter aerogenes* TACC13048 strain, *Enterobacter aerogenes* NBRC12010 strain (Biotechnol. Bioeng., 2007, Mar. 27; 98 (2): 340-348), and *Enterobacter aerogenes* AJ110637 (FERM BP-10955). The *Enterobacter aerogenes* AJ110637 strain was deposited to International Patent Organism Depositary (IPOD), National Institute of Advanced Industrial Science and Technology (AIST) (Chuo No. 6, Higashi 1-1-1, Tsukuba City, Ibaraki Pref., JP, Postal code 305-8566) as of Aug. 22, 2007, and was transferred to the international deposition based on Budapest Treaty on Mar. 13, 2008, and an accession number FERM BP-10955 was given thereto.

Examples of the fungus may include microorganisms belonging to genera *Saccharomyces, Schizosaccharomyces, Yarrowia, Trichoderma, Aspergillus, Fusarium*, and *Mucor*. The microorganisms belonging to genera *Saccharomyces, Schizosaccharomyces, Yarrowia*, or *Trichoderma* are preferable.

Examples of the microorganisms belonging to genus *Saccharomyces* may include *Saccharomyces carlsbergensis, Saccharomyces cerevisiae, Saccharomyces diastaticus, Saccharomyces douglasii, Saccharomyces kluyveri, Saccharomyces norbensis*, and *Saccharomyces oviformis*. *Saccharomyces cerevisiae* is preferable.

*Schizosaccharomyces pombe* is preferable as the microorganisms belonging to genus *Schizosaccharomyces*.

*Yarrowia lypolytica* is preferable as the microorganisms belonging to genus *Yarrowia*.

Examples of the microorganisms belonging to genus *Trichoderma* may include *Trichoderma harzianum, Trichoderma koningii, Trichoderma longibrachiatum, Trichoderma reesei*, and *Trichoderma viride*. *Trichoderma reesei* is preferable.

In addition, the host used for the present invention is not particularly limited as long as the host has an ability to synthesize dimethylallyl diphosphate (DMAPP) via a mevalonic acid (MVA) pathway and/or a methylerythritol phosphate (MEP) pathway that are involved in synthesis of dimethylallyl diphosphate that is a substrate of the isoprene synthase, and may be an insect cell, an animal cell, a plant cell, and the like.

In the transformant of the present invention, the pathway to synthesize dimethylallyl diphosphate (DMAPP) that is the substrate of the isoprene synthase may be enhanced. For such an enhancement, an expression vector that expresses an isopentenyl-diphosphate delta isomerase having an ability to convert isopentenyl diphosphate (IPP) into dimethylallyl diphosphate (DMAPP) may be introduced into the transformant of the present invention. An expression vector that expresses one or more enzymes involved in the mevalonate pathway and/or methylerythritol phosphate pathway associated with formation of IPP and/or DMAPP may also be introduced into the transformant of the present invention. The expression vector for such an enzyme may be a plasmid or an integrative vector. The expression vector for such an enzyme may also be a DNA vector or an RNA vector. The expression vector for such an enzyme may further express a plurality of enzymes (e.g., one, two, three or four or more) involved in the mevalonate pathway and/or the methylerythritol phosphate pathway, and may be, for example, an expression vector for polycistronic mRNA. Origin of one or more enzymes involved in the mevalonate pathway and/or the methylerythritol phosphate pathway may be homologous or heterologous to the host. When the origin of the enzyme involved in the mevalonate pathway and/or the methylerythritol phosphate pathway is homologous to the host, for example, the host may be a bacterium as described above (e.g., *Escherichia coli*) and the enzyme involved in the mevalonate pathway may be derived from a fungus (e.g., *Saccharomyces cerevisiae*). In addition, when the host inherently produces the enzyme involved in the methylerythritol phosphate pathway, an expression vector to be introduced into the host may express the enzyme involved in the mevalonate pathway.

Examples of isopentenyl-diphosphate delta isomerase (EC: 5.3.3.2) may include Idi1p (ACCESSION ID NP_015208), AT3G02780 (ACCESSION ID NP_186927), AT5G16440 (ACCESSION ID NP_197148) and Idi (ACCESSION ID NP_417365).

Examples of the enzymes involved in the mevalonate (MVA) pathway may include mevalonate kinase (EC: 2.7.1.36; example 1, Erg12p, ACCESSION ID NP_013935; example 2, AT5G27450, ACCESSION ID NP_001190411), phosphomevalonate kinase (EC: 2.7.4.2; example 1, Erg8p, ACCESSION ID NP_013947; example 2, AT1G31910, ACCESSION ID NP_001185124), diphosphomevalonate decarboxylase (EC: 4.1.1.33; example 1, Mvd1p, ACCESSION ID NP_014441; example 2, AT2G38700, ACCESSION ID NP_181404; example 3, AT3G54250, ACCESSION ID NP_566995), acetyl-CoA-C-acetyltransferase (EC: 2.3.1.9; example 1, Erg10p, ACCESSION ID NP_015297; example 2, AT5G47720, ACCESSION ID NP_001032028; example 3, AT5G48230, ACCESSION ID NP_568694), hydroxymethylglutaryl-CoA synthase (EC: 2.3.3.10; example 1, Erg13p, ACCESSION ID NP_013580; example 2, AT4G11820, ACCESSION ID NP_192919; example 3, MvaS, ACCESSION ID AAG02438), hydroxymethylglutaryl-CoA reductase (EC: 1.1.1.34; example 1, Hmg2p, ACCESSION ID NP_013555; example 2, Hmg1p, ACCESSION ID NP_013636; example 3, AT1G76490, ACCESSION ID NP_177775; example 4, AT2G17370, ACCESSION ID NP_179329, EC: 1.1.1.88, example, MvaA, ACCESSION ID P13702), and acetyl-CoA-C-acetyltransferase/hydroxymethylglutaryl-CoA reductase (EC: 2.3.1.9/1.1.1.34, example, MvaE, ACCESSION ID AAG02439).

Examples of the enzymes involved in the methylerythritol phosphate (MEP) pathway may include 1-deoxy-D-xylulose-5-phosphate synthase (EC: 2.2.1.7, example 1, Dxs, ACCESSION ID NP_414954; example 2, AT3G21500, ACCESSION ID NP_566686; example 3, AT4G15560, ACCESSION ID NP_193291; example 4, AT5G11380, ACCESSION ID NP_001078570), 1-deoxy-D-xylulose-5-phosphate reductoisomerase (EC: 1.1.1.267; example 1, Dxr, ACCESSION ID NP_414715; example 2, AT5G62790, ACCESSION ID NP_001190600), 4-diphosphocytidyl-2-C-methyl-D-erythritol synthase (EC: 2.7.7.60; example 1, IspD, ACCESSION ID NP_417227; example 2, AT2G02500, ACCESSION ID NP_565286), 4-diphosphocytidyl-2-C-methyl-D-erythritol kinase (EC: 2.7.1.148; example 1, IspE, ACCESSION ID NP_415726; example 2, AT2G26930, ACCESSION ID NP_180261), 2-C-methyl-D-erythritol-2,4-cyclodiphosphate synthase (EC: 4.6.1.12; example 1, IspF, ACCESSION ID NP_417226; example 2, AT1G63970, ACCESSION ID NP_564819), 1-hydroxy-2-methyl-2-(E)-butenyl-4-diphosphate synthase (EC: 1.17.7.1; example 1, IspG, ACCESSION ID NP_417010; example 2, AT5G60600, ACCESSION ID NP_001119467), and 4-hydroxy-3-methyl-2-butenyl diphosphate reductase (EC: 1.17.1.2; example 1, IspH, ACCESSION ID NP_414570; example 2, AT4G34350, ACCESSION ID NP_567965).

The introduction of the expression vector incorporating a gene into a host (transformation) can be carried out using known methods. Examples of such a method may include a competent cell method using a microbial cell treated with calcium and an electroporation method. The gene may be introduced by infecting the microbial cell with a phage vector rather than the plasmid vector.

Further, a gene encoding the enzyme involved in the mevalonate pathway or the methylerythritol phosphate pathway that synthesizes dimethylallyl diphosphate that is the substrate of the isoprene synthase may also be introduced into the transformant of the present invention.

Such an enzyme may include 1-deoxy-D-xylose-5-phosphate synthase that converts a pyruvate and D-glycelaldehyde-3-phosphate into 1-deoxy-D-xylose-5-phosphate, and isopentyl diphosphate isomerase that converts isopentenyl diphosphate into dimethylallyl diphosphate.

The protein of the present invention may be extracted or purified from the transformant of the present invention, and isoprene may be produced by culturing the transformant that expresses the protein of the present invention.

<Methods of Producing Isoprene Monomer and Isoprene Polymer>

The present invention provides a method of producing an isoprene monomer. The method of producing the isoprene monomer according to the present invention comprises forming the isoprene monomer from dimethylallyl diphosphate in the presence of the protein of the present invention.

The method of producing the isoprene monomer according to the present invention is not particularly limited as long as the method is performed in the presence of the protein of the present invention, and can be performed by utilizing an enzymatic reaction system with the protein itself (e.g., purified protein) of the present invention or culturing the transformant of the present invention that produces the protein of the present invention. Preferably, it is performed by culturing the transformant of the present invention. When the transformant of the present invention is used in the method of producing the isoprene monomer according to the present invention, dimethylallyl diphosphate that is a raw material of the isoprene monomer is efficiently supplied from a carbon source in a culture medium by the transformant of the present invention. The transformant of the present invention produces the isoprene monomer mainly as an outgas from the carbon source in the culture medium. Thus, the isoprene monomer is recovered by collecting gas produced from the transformant. Dimethylallyl diphosphate that is the substrate of the isoprene synthase is synthesized from the carbon source in the culture medium via the mevalonate pathway or the methylerythritol phosphate pathway in the host.

The culture medium for culturing the transformant of the present invention preferably contains a carbon source to be converted into isoprene. The carbon source may include carbohydrates such as monosaccharides, disaccharides, oligosaccharides and polysaccharides; invert sugars obtained by hydrolyzing sucrose; glycerol; compounds having one carbon atom (hereinafter referred to as a C1 compound) such as methanol, formaldehyde, formate, carbon monoxide and carbon dioxide; oils such as corn oil, palm oil and soybean oil; acetate; animal fats; animal oils; fatty acids such as saturated fatty acids and unsaturated fatty acids; lipids; phospholipids; glycerolipids; glycerine fatty acid esters such as monoglyceride, diglyceride and triglyceride; polypeptides such as microbial proteins and plant proteins; renewable carbon sources such as hydrolyzed biomass carbon sources; yeast extracts, or combinations thereof. For a nitrogen source, inorganic ammonium salts such as ammonium sulfate, ammonium chloride and ammonium phosphate, organic nitrogen such as hydrolyzed soybeans, ammonia gas, ammonia water, and the like can be used. It is desirable to contain required substances such as vitamin B1 and L-homoserine, or the yeast extract and the like in an appropriate amount as an organic trace nutrient source. In addition thereto, potassium phosphate, magnesium sulfate, iron ion, manganese ion, and the like are added in a small amount if necessary. The culture medium used in the present invention may be a natural medium or a synthesized medium as long as it contains the carbon source, the nitrogen source, inorganic ions, and optionally the other organic trace ingredients.

Examples of the monosaccharides may include triose such as ketotriose (dihydroxyacetone) and aldotriose (glyceraldehyde); tetrose such as ketotetrose (erythrulose) and aldotetrose (erythrose, threose); pentose such as ketopentose (ribulose, xylulose), aldopentose (ribose, arabinose, xylose, lyxose) and deoxysaccharide (deoxyribose); hexose such as ketohexose (psychose, fructose, sorbose, tagatose), aldohexose (allose, altrose, glucose, mannose, gulose, idose, galactose, tallose), and deoxysaccharide (fucose, fucrose, rhamnose); and heptose such as sedoheptulose. C6 sugars such as fructose, mannose, galactose and glucose; and C5 sugars such as xylose and arabinose are preferable.

Examples of the disaccharides may include sucrose, lactose, maltose, trehalose, turanose, and cellobiose. Sucrose and lactose are preferable.

Examples of the oligosaccharides may include trisaccharides such as raffinose, melezitose and maltotriose; tetrasaccharides such as acarbose and stachyose; and other oligosaccharides such as fructooligosaccharide (FOS), galactooligosaccharide (GOS) and mannan-oligosaccharide (MOS).

Examples of the polysaccharides may include glycogen, starch (amylose, amylopectin), cellulose, dextrin, and glucan ($\beta$1,3-glucan), and starch and cellulose are preferable.

Examples of the microbial protein may include polypeptides derived from a yeast or bacterium.

Examples of the plant protein may include polypeptides derived from soybean, corn, canola, Jatropha, palm, peanut, sunflower, coconut, mustard, cotton seed, Palm kernel oil, olive, safflower, sesame and linseed.

Examples of the lipid may include substances containing one or more saturated or unsaturated fatty acids of C4 or more.

The oil is preferably the lipid that contains one or more saturated or unsaturated fatty acids of C4 or more and is liquid at room temperature, and examples of the oil may include lipids derived from soybean, corn, canola, Jatropha, palm, peanut, sunflower, coconut, mustard, cotton seed, Palm kernel oil, olive, safflower, sesame, linseed, oily microbial cells, Chinese tallow tree, and a combination of two or more thereof.

Examples of the fatty acid may include compounds represented by a formula RCOOH ("R" represents a hydrocarbon group).

The unsaturated fatty acid is a compound having at least one double bond between two carbon atoms in "R", and examples of the unsaturated fatty acid may include oleic acid, vaccenic acid, linoleic acid, palmitelaidic acid and arachidonic acid.

The saturated fatty acid is a compound where the "R" is a saturated aliphatic group, and examples of the saturated fatty acid may include docosanoic acid, eicosanoic acid, octadecanoic acid, hexadecanoic acid, tetradecanoic acid, and dodecanoic acid.

Among them, those containing one or more C2 to C22 fatty acids are preferable as the fatty acid, and those containing C12 fatty acid, C14 fatty acid, C16 fatty acid, C18 fatty acid, C20 fatty acid and C22 fatty acid are more preferable.

The carbon source may include salts and derivatives of these fatty acids and salts of these derivatives. Examples of the salt may include lithium salts, potassium salts and sodium salts.

Examples of the carbon source may also include combinations of carbohydrate such as glucose with the lipid, the oil, the fats, the fatty acid and glycerine fatty acid ester.

Examples of the renewable carbon source may include hydrolyzed biomass carbon sources.

Examples of the biomass carbon source may include cellulose-based substrates such as waste materials of woods, papers and pulps, leafy plants, and fruit pulps; and partial plants such as stalks, grain particles, roots and tubers.

Examples of the plants to be used as the biomass carbon source may include corn, wheat, rye, sorghum, triticate, rice, millet, barley, cassava, legume such as pea, potato, sweet potato, banana, sugar cane and tapioca.

When the renewable carbon source such as biomass is added to the culture medium, the carbon source is preferably pretreated. Examples of the pretreatment may include an enzymatic pretreatment, a chemical pretreatment, and a combination of the enzymatic pretreatment and the chemical pretreatment.

It is preferred that the renewable carbon source is entirely or partially hydrolyzed before being added to the culture medium.

Examples of the carbon source may also include the yeast extract and a combination of the yeast extract with the other carbon source such as glucose. The combination of the yeast extract with the C1 compound such as carbon dioxide and methanol is preferable.

In the method of culturing the transformant in connection with the present invention, it is preferable to culture the cell in a standard medium containing saline and nutrients.

The culture medium is not particularly limited, and examples of the culture medium may include ready-made general media that is commercially available such as Luria Bertani (LB) broth, Sabouraud dextrose (SD) broth, and yeast medium (YM) broth. The medium suitable for the cultivation of the specific host can be selected appropriately for the use.

It is desirable to contain appropriate minerals, salts, supplemental elements, buffers, and ingredients known for those skilled in the art to be suitable for the cultivation and to facilitate the production of isoprene in addition to the appropriate carbon source in the cell medium.

It is preferable to add the sugar, a metal salt, an antimicrobial substance, and the like to the medium in order to keep the expression of the protein of the present invention in the transformant of the present invention.

A culture condition for the transformant of the present invention is not particularly limited as long as the protein of the present invention can be expressed, and a standard cell culture condition can be used.

A culture temperature is preferably 20 to 37° C., a gas composition is preferably about 6 to 84% of $CO_2$ concentration, and a pH value is preferably about 5 to about 9.

The transformant is preferably cultured under an aerobic, oxygen-free, or anaerobic condition depending on a nature of the host.

Examples of the method of culturing the transformant may include a method using a known fermentation method such as a batch cultivation method, a feeding cultivation method or a continuous cultivation method.

In the batch cultivation method, a medium composition is added at start of the fermentation, and the transformant is inoculated in the medium composition and cultured while pH and an oxygen concentration are controlled.

In the cultivation of the transformant by the batch cultivation method, the growth of the transformant starts from a mild induction phase, passes through a logarithmic growth phase and finally goes to a stationary phase in which a growth speed is reduced or stopped. Isoprene is produced by the transformant in the logarithmic growth phase and the stationary phase.

In the feeding cultivation method, in addition to the above batch method, the carbon source is gradually added according to the progress of a fermentation process. The feeding cultivation method is effective when an amount of the carbon source is to be restricted in the medium because metabolism of the transformant tends to be reduced due to catabolite suppression. The feed cultivation can be performed using a restricted amount or an excessive amount of the carbon source such as glucose.

In the continuous cultivation method, a certain amount of the medium is continuously supplied to a bioreactor at a constant rate while the same amount of the medium is removed. In the continuous cultivation method, the culture can be kept constantly at high concentration and the transformant in the culture medium is generally in the logarithmic growth phase.

The nutrition can be supplemented by entirely or partly exchanging the medium appropriately, and accumulation of metabolic byproducts that potentially have adverse effects on the growth of the transformant, and the accumulation of dead cells can be prevented.

A promoter possessed by the expression vector of the present invention may include constitutive promoters and inducible promoters. When the expression vector of the present invention has the inducible promoter such as a lac promoter, the expression of the protein of the present invention may be induced by adding IPTG (isopropyl-β-thiogalactopyranoside) into the culture medium.

Examples of the method of evaluating an amount of isoprene produced by culturing the transformant of the present invention may include a method in which a gas phase is collected by a headspace method and this gas phase is analyzed by gas chromatography.

In detail, the isoprene monomer in a headspace which is obtained by culturing the transformant in a sealed vial with shaking the culture medium is analyzed by standard gas chromatography. Then, an area calculated by a curve measured by gas chromatography is converted into the amount of the isoprene monomer produced with the transformant using a standard curve.

Examples of the method of collecting the isoprene monomer obtained by culturing the transformant of the present invention may include gas stripping, fractional distillation, or dissociation of the isoprene monomer adsorbed to a solid phase by heat or vacuum, or extraction with a solvent.

In the gas stripping, isoprene gas is continuously removed from the outgas. Such removal of the isoprene gas can be performed by various methods. Examples of the removal may include adsorption to the solid phase, separation into a liquid phase, and a method in which the isoprene gas is directly condensed.

The isoprene monomer can be collected by a single step or multiple steps. When the isoprene monomer is collected by the single step, the isoprene monomer is converted into the liquid phase simultaneously with separating the isoprene monomer from the outgas. The isoprene monomer can also be directly condensed from the outgas to make the liquid phase. When the isoprene monomer is collected by the multiple stages, the isoprene monomer is separated from off-gas and subsequently converted into the liquid phase. For example, the isoprene monomer is adsorbed to the solid phase, and extracted from the solid phase with the solvent.

The method of collecting the isoprene monomer may further comprise purifying the isoprene monomer. Examples of the purification may include separation from a liquid phase extract by distillation and various chromatographic methods.

The protein of the present invention is more excellent in ability to produce isoprene than conventional isoprene synthase. Thus, the isoprene monomer can be produced efficiently using the transformant that expresses the protein of the present invention.

The present invention also provides a method of producing an isoprene polymer. The method of producing the isoprene polymer according to the present invention comprises the following (I) and (II):

(I) forming an isoprene monomer by the method of the present invention; and
(II) polymerizing the isoprene monomer to form an isoprene polymer.

The step (I) can be performed in the same manner as in the method of producing the isoprene monomer according to the present invention described above. The polymerization of the isoprene monomer in the step (II) can be performed by any method known in the art.

EXAMPLES

Hereinafter, the present invention will be described in detail with reference to Examples, but the present invention is not limited to the following Examples.

Example 1

Evaluation of Ability to Produce Isoprene in Plants 1-1) Measurement of Amount of Isoprene Formed Per Unit Weight of Dry Leaves First, an amount of isoprene formed per 1 g of dry leaves in the plant was measured for evaluating an ability to produce isoprene in plants. *Mucuna* (*Mucuna bracteata*), Weeping willow (*Salix babylonica*), American sweetgum (*Liquidambar styraciflua*), Myrtle (*Myrtus communis*), and Kudzu (*Pueraria lobata*) were used as the plants.

In the measurement of an amount of formed isoprene, a gas replaceable desiccator (trade name: Vacuum Desiccator, manufactured by AS ONE Corporation) was housed in an incubator (trade name: Growth Chamber MLR-351H, manufactured by SANYO), and the incubator was set to a high temperature induction condition (an illuminance of 100 μmol E/$m^2$/s at 40° C.) while a fan for stirring the gas, which was provided in the gas replaceable desiccator, was driven to stir an atmosphere in space in the gas replaceable desiccator. After the temperature of the atmosphere in the gas replaceable desiccator reached 40° C., a plant body of *Mucuna* planted in a planter was housed therein and kept for 3 hours in a state where the gas replaceable desiccator was sealed. Then, a gas component released from *Mucuna* was aspirated from the space in the gas replaceable desiccator by an aspiration pump through a silicon tube, an adsorption tube and a gas collection tube. Thereby, water vapor (water content) contained in the gas component released from *Mucuna* was adsorbed and separated in the adsorption tube, the gas component from which the water vapor had been separated was led to the gas collection tube, and the gas component was collected in the gas collection tube. Subsequently, isoprene contained in the gas component collected in the gas collection tube was quantitatively analyzed using gas chromatograph (trade name: GC-FID6890, manufactured by Agilent).

For the weight of dry leaves, a leaf area of a fresh individual leaf, and a dry weight when the fresh individual leaf is dried by a dryer at 80° C. for 8 hours establish a very good positive correlation. Thus, a formula for converting from the leaf area to the dry weight was derived, and the dry weight was estimated from the entire leaf area from the plant body of *Mucuna* used for the measurement of an amount of formed isoprene.

The amount of formed isoprene per 1 g of the dry leaf was obtained by dividing the amount of formed isoprene from the entire plant body of *Mucuna* by the estimated weight of the entire plant body.

As a result, it was demonstrated that *Mucuna* was excellent in amount of formed isoprene per unit weight of the dry leaf (FIG. 1).

1-2) Measurement of Amount of Formed Isoprene Per Amount of Total Protein

Then, the amount of formed isoprene per amount of total protein extracted from leaves of various plants was measured. *Mucuna* (samples 1 and 2), Weeping willow, American sweetgum, Myrtle, and Kudzu were used as the plants.

For extraction of the protein, a buffer solution (50 mM Tris-HCl, 20 mM MgC1, 5% glycerol. 0.02% Triton-X100, pH 8.0) was made, and 10% Polyclar AT, 20 mM DTT, protease complete tablet (one tablet/50 mL), and 1 mM benzamidine HCl (final concentrations, each) were added just before the use, and was used as a protein extraction buffer. 50 mL of the protein extraction buffer was added to 5 g of the sample, then the mixture was ground well in a cold mortar on ice and filtrated though doubly overlapped Miracloth. A filtrate was centrifuged at 12,000 G for 20 minutes and 40,000 G for 40 minutes to obtain a supernatant, and the supernatant was used as a crude extract.

Subsequently, this crude extract was fractionated with ammonium sulfate. Proteins precipitated in a range of 40% to 55% of final concentrations of ammonium sulfate were centrifuged at 40,000 G for 40 minutes, and an obtained pellet was re-dissolved in the protein extraction buffer to obtain an ammonium sulfate fraction.

A total (ammonium sulfate fraction) protein mass was calculated by measuring the ammonium sulfate fraction using Bradford assay. A Bradford reagent was reacted with the standard protein, bovine serum albumin, and absorbance at a wavelength of 595 nm was measured using a spectrophotometer. A standard curve for the protein was made using the obtained absorbance values. The absorbance at a wavelength of 595 nm was also measured in the ammonium sulfate fraction diluted to 50 times, and the amount of the total (ammonium sulfate fraction) protein was estimated from the standard curve for the standard protein.

In the measurement of the amount of formed isoprene, 100 μL of the crude extract or 100 μL of a crude enzyme solution boiled at 100° C. was placed in a 4 mL glass vial, and then 2 μL of a 0.5 M $MgCl_2$ solution and 5 μL of a 0.2 M DMAPP solution were added thereto. The vial was tightly closed with a screw cap with a septum, and then the vial was gently vortexed and set in an incubator at 40° C. After 0.5, 1 and 2 hours, 0.5 to 2 mL of a gas layer in a headspace was sampled by a gas-tight syringe, and the amount of formed isoprene was measured using gas chromatograph (trade name: GC-FID6890, manufactured by Agilent). The amount of formed isoprene using the crude enzyme after 0.5, 1 and 2 hours was calculated by subtracting a measured value in the case of using the crude enzyme solution boiled at 100° C. from a measured value in the case of using the crude enzyme. An enzymatic activity per 1 mg of the total protein (specific activity) was calculated from the amount of the formed isoprene per one hour. The amount of formed isoprene was measured with keeping the amount of DMAPP that was the substrate of the isoprene synthase constant.

Figure 2:
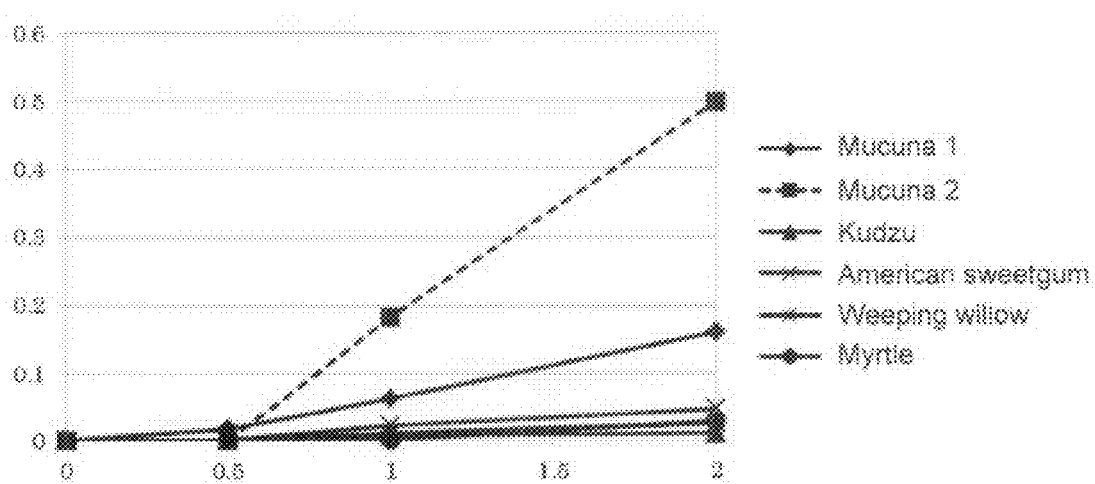
FIG. 2 is a graph showing an amount of isoprene produced per amount of total protein extracted from leaves of various plants.

As a result, it was demonstrated that *Mucuna* was excellent in amount of formed isoprene per amount of total protein (FIG. 2, Table 1). As described above, it was shown that *Mucuna* was excellent in ability to produce isoprene.

TABLE 1

Amount of formed isoprene per amount of total protein (index numbers relative to case of Kudzu)

| | 0 hour* | 0.5 hour* | 1 hour* | 2 hours* | Specific activity index (Value from Kudzu was set to 1) |
|---|---|---|---|---|---|
| Mucuna 1 | 0 | 16.947 | 61.895 | 160.632 | 16.87842808 |
| Mucuna 2 | 0 | 0 | 183.587 | 449.514 | 47.23274141 |
| American sweetgum | 0 | 0 | 22.063 | 46.132 | 4.847325838 |
| Weeping willow | 0 | 0 | 9.756 | 24.39 | 2.562782389 |
| Myrtle | 0 | 0 | 0 | 27.451 | 2.884417358 |
| Kudzu | 0 | 0 | 6.662 | 9.517 | 1 |

*Unit is μg isoprene/mg protein

Example 2

Cloning of Isoprene Synthase Gene Derived from *Mucuna*

2-1) Evaluation of Sampling Time

Isoprene gas released from leaves of *Mucuna* illuminated with light for 1, 2, 3 and 5 hours at temperature of 40° C. was sampled and the amount of produced isoprene was quantified by gas chromatography described later, and production of 4, 8, 12 and 10 μg of isoprene/g DW leaf was confirmed. Thus, it was confirmed that an optimal light illumination time was 3 hours.

2-2) Extraction of Total RNA Lysis Solution

A total RNA was extracted from leaves of *Mucuna* with total RNA lysis solution according to the following procedures.

(1) The leaves of *Mucuna* illuminated with light for 3 hours at temperature of 40° C. were sampled.
(2) 100 mg of leaf tissue was pulverized in a mortar with rapidly freezing the leaf tissue with liquid nitrogen, then the leaf tissue together with the liquid nitrogen was dispensed in an RNA-free 2 mL Eppendorf tube, and the liquid nitrogen was gasified.
(3) To this Eppendorf tube, 450 μL of a dissolution buffer RLT (containing 2-mercaptoethanol) attached to RNeasy Plant Kit (manufactured by Qiagen), and mixed vigorously with Vortex to obtain a leaf tissue lysate.
(4) This leaf tissue lysate was applied to QIAshredder spin column attached to RNeasy Plant Kit, and centrifuged at 15,000 rpm for 2 minutes.
(5) A supernatant alone of a column eluate was transferred to a new RNA-free 2 mL Eppendorf tube, then special grade ethanol in a half volume of the supernatant was added to the supernatant, and the obtained solution was mixed by pipetting to obtain about 650 μL of a solution.
(6) This solution was applied to RNeasy spin column attached to RNeasy Plant Kit, centrifuged at 10,000 rpm for 15 seconds, and a filtrate was discarded.
(7) 700 μL of RW1 buffer attached to RNeasy Plant Kit was added to this RNeasy spin column, centrifuged at 10,000 rpm for 15 seconds, and a filtrate was discarded.
(8) 500 μL of BPE buffer attached to RNeasy Plant Kit was added to this RNeasy spin column, centrifuged at 10,000 rpm for 15 seconds, and a filtrate was discarded.
(9) 500 μL of BPE buffer was again added to this RNeasy spin column, centrifuged at 10,000 rpm for 2 minutes, and a filtrate was discarded.
(10) This RNeasy spin column was set to a 2 mL collective tube attached to RNeasy Plant Kit, centrifuged at 15,000 rpm for one minute, and a filtrate was discarded.
(11) This RNeasy spin column was set to a 1.5 mL collective tube attached to RNeasy Plant Kit.
(12) RNA-free distilled water attached to RNeasy Plant Kit was directly added to a membrane of this RNeasy spin column using a Pipetman, centrifuged at 10,000 rpm for one minute, and total RNA was collected. This step was repeated twice to obtain about 100 μg of total RNA.

2-3) Analysis of Nucleotide Sequence of Isoprene Synthase Gene Derived from *Mucuna*

Quality of RNA in the extracted total RNA solution was checked using nano-chips for RNA provided by BioAnalyzer (Agilent Technologies, Inc.), and it was confirmed that the solution was not contaminated with genomic DNA and RNA was not decomposed in the solution.

This total RNA was converted into a double strand using reverse transcriptase, and then fragmented using a nebulizer. Nucleotide sequences of 198,179 fragments having a poly A sequence at a 3' end were analyzed using 454 titanium FLX high performance sequencer (manufactured by Roche Applied Science). Overlapped sequences in the obtained fragment sequences were aligned to obtain 13,485 contig sequences. BLAST search was performed for these contig sequences, and 6 contig sequences having the homology (identity of nucleotide sequences) to registered and known isoprene synthase gene sequences from Kudzu and Poplar were extracted. These sequences were further analyzed in detail, and 3 sequences in these 6 contig sequences were found to be derived from the same gene. Thus, a partial sequence of the isoprene synthase gene derived from *Mucuna* was obtained. 5' RACE was performed based on this partial sequence to obtain a full length nucleotide sequence of the isoprene synthase gene derived from *Mucuna*, which was represented by SEQ ID NO:1.

Example 3

Preparation of Expression Plasmid for Isoprene Synthase Derived from Various Plants 3-1) Chemical Synthesis of Isoprene Synthase Derived from *Pueraria montana* var. *lobata* (Kudzu)

The nucleotide sequence and the amino acid sequence of the isoprene synthase derived from *Pueraria montana* var. *lobata* were already known (ACCESSION: AAQ84170: *P. montana* var. *lobata* isoprene synthase (IspS)). The amino acid sequence of the IspS protein derived from *P. montana* and the nucleotide sequence of its gene are represented by SEQ ID NO:3 and SEQ ID NO:4, respectively. The IspS gene was optimized for codon usage frequency in *E. coli* in order to efficiently express the IspS gene in *E. coli*, and further designed to cut off the chloroplast localization signal. The designed gene was designated as IspSK. A nucleotide sequence of IspSK is represented by SEQ ID NO:5. The IspSK gene was chemically synthesized, then cloned into pUC57 (manufactured by GenScript), and the resulting plasmid was designated as pUC57-IspSK.

3-2) Chemical Synthesis of Isoprene Synthase Derived from *Populus alba×Populus tremula* (Poplar)

The nucleotide sequence and the amino acid sequence of the isoprene synthase derived from *P. alba×P. tremula* were already known (ACCESSION: CAC35696: *P. alba×P. tremula* (Poplar) isoprene synthase). The amino acid sequence of the IspS protein derived from *P. alba×P. tremula* and the nucleotide sequence of its gene are represented by SEQ ID NO:6 and SEQ ID NO:7, respectively. An IspS gene that was optimized for the codon usage frequency in *E. coli* in the same manner as above and in which the chloroplast localization signal was cut off was designed and designated as IspSP. A nucleotide sequence of IspSP is represented by SEQ ID NO:8. The IspSP gene was chemically synthesized, then cloned into pUC57 (manufactured by GenScript), and the resulting plasmid was designated as pUC57-IspSP.

3-3) Chemical Synthesis of Isoprene Synthase Derived from *Mucuna pruriens* (Mucuna)

Based on the nucleotide sequence derived from *M. pruriens*, an IspS gene that was optimized for the codon usage frequency in *E. coli* was designed in the same manner as above. One in which the chloroplast localization signal had been conferred was designated as IspSM (L), and one in which the chloroplast localization signal had been cut off was designated as IspSM. Nucleotide sequences for IspSM (L) and IspSM are represented by SEQ ID NO:9 and SEQ ID NO:10, respectively. The IspSM gene and the IspSM (L) gene were chemically synthesized, then cloned into pUC57 (manufactured by GenScript), and the resulting plasmids were designated as pUC57-IspSM and pUC57-IspSM (L).

3-4) Construction of Expression Plasmid, pSTV28-Ptac-Ttrp

An expression plasmid pSTV28-Ptac-Ttrp for expressing IspS derived from various plants in *E. coli* was constructed. First, a DNA fragment comprising a tac promoter (synonym: Ptac) region (deBoer, et al., (1983) Proc. Natl. Acad. Sci. U.S.A., 80, 21-25) and a terminator region of tryptophan operon (synonym: Ttrp) derived from *E. coli* (Wu et al., (1978) Proc. Natl. Acad. Sci. U.S.A., 75, 442-5446) and having a KpnI site at a 5' terminus and a BamHI site at a 3' end was synthesized chemically (the nucleotide sequence of Ptac-Ttrp is represented by SEQ ID NO:11). The resulting Ptac-Ttrp DNA fragment was digested with KpnI and BamHI, and ligated to pSTV28 (manufactured by Takara Bio Inc.) similarly digested with KpnI and BamHI by a ligation reaction with DNA ligase. The resulting plasmid was designated as pSTV28-Ptac-Ttrp (its nucleotide sequence is represented by SEQ ID NO:12). This plasmid can amplify the expression of the IspS gene by cloning the IspS gene downstream of Ptac.

3-5) Construction of Plasmid for Expressing IspS Gene Derived from Various Plants Plasmids for expressing the IspSK gene, the IspSP gene, the IspSM gene and the IspSM (L) gene in *E. coli* were constructed by the following procedure. PCR was performed with Prime Star polymerase (manufactured by Takara Bio Inc.) using synthesized oligonucleotides consisting of the nucleotide sequences represented by SEQ ID NOS:13 and 14 as primers with pUC57-IspSK as a template, synthesized oligonucleotides consisting of the nucleotide sequences represented by SEQ ID NOS:15 and 16 as primers with pUC57-IspSP as a template, synthesized oligonucleotides consisting of the nucleotide sequences represented by SEQ ID NOS:17 and 18 as primers with pUC57-IspSM as a template, or further synthesized oligonucleotides consisting of the nucleotide sequences represented by SEQ ID NOS:19 and 20 as primers with pUC57-IspSM (L) as a template. A reaction solution was prepared according to a composition attached to the kit, and a reaction at 98° C. for 10 seconds, 54° C. for 20 seconds and 68° C. for 120 seconds was performed in 40 cycles. As a result, a PCR product containing the IspSK gene, the IspSP gene, the IspSM gene or the IspSM (L) gene was obtained. Likewise, PCR was performed with Prime Star polymerase (manufactured by Takara Bio Inc.) using synthesized oligonucleotides consisting of the nucleotide sequences represented by SEQ ID NOS:21 and 22 as primers with pSTV28-Ptac-Ttrp as a template. A reaction solution was prepared according to a composition attached to the kit, and a reaction at 98° C. for 10 seconds, 54° C. for 20 seconds and 68° C. for 210 seconds was performed in 40 cycles. As a result, a PCR product containing pSTV28-Ptac-Ttrp was obtained. Subsequently, the purified IspSK gene, IspSP gene, IspSM gene, and IspSM (L) gene fragments were ligated to the PCR product for pSTV28-Ptac-Ttrp using In-Fusion HD Cloning Kit (manufactured by Clontech). The resulting plasmids for expressing the IspSK gene, the IspSP gene, IspSM gene and IspSM (L) gene were designated as pSTV28-Ptac-IspSK, pSTV28-Ptac-IspSP, pSTV28-Ptac-IspSM, and pSTV28-Ptac-IspSM (L), respectively.

TABLE 2

Primer sequences used for construction of plasmids for expressing IspS genes derived from various plants

| Subject for amplification | Sequence name | Sequence (5'-) |
|---|---|---|
| IspSK | Ptac-IspS(K)F | GATAACAATTTCACACAATAATTTTGTTTAACTTTAAGAAGGAGATATAATGTGTGCGACCTCTTCTCAATTTACTCAG (SEQ ID NO: 13) |
| IspSK | IspS(K)R-MCSR | ACGGCCAGTGAATTCTTAGACATACATCAGCTGGTTAATCGG (SEQ ID NO: 14) |
| IspSP | Ptac-IspS(P)F | GATAACAATTTCACACAATAATTTTGTTTAACTTTAAGAAGGAGATATAATGTGCTCTGTTTCTACCGAGAACGTTTCC (SEQ ID NO: 15) |
| IspSP | IspS(P)R-MCSR | ACGGCCAGTGAATTCTTAACGTTCGAACGGCAGAATCGGTTCG (SEQ ID NO: 16) |
| IspSM | Ptac-IspS(M)F | GATAACAATTTCACACAATAATTTTGTTTAACTTTAAGAAGGAGATATAATGTCCGCCGTTTCAAGCCA (SEQ ID NO: 17) |

TABLE 2-continued

Primer sequences used for construction of plasmids
for expressing IspS genes derived from various plants

| Subject for amplification | Sequence name | Sequence (5'-) |
|---|---|---|
| IspSM | IspS(M)R-MCSR | ACGGCCAGTGAATTCTTAGTTAATCGGGAACGGGT (SEQ ID NO: 18) |
| IspSM(L) | Ptac-IspS(M(L))F | GATAACAATTTCACACAATAATTTTGTTTAACTTTAAGAAGGAGATATAATGGCTACCAACCCGTCCTGTCTGTCAACC (SEQ ID NO: 19) |
| IspSM(L) | IspS(M(L))R-MCSR | ACGGCCAGTGAATTCTCAGTTAATCGGGAACGGGT (SEQ ID NO: 20) |
| pSTV28-Ptac-Ttrp | pSTV28-F | GTGTGAAATTGTTATCCGCTCACAATTCC (SEQ ID NO: 21) |
| pSTV28-Ptac-Ttrp | pSTV28-R | GAATTCACTGGCCGTCGTTTTACAACG (SEQ ID NO: 22) |

Example 4

Measurement of Enzymatic Activity of Isoprene Synthase Derived from Various Plants Using Crude Enzyme Extract Derived from E. coli 4-1) Construction of E. coli MG1655 Strain Having Ability To Produce Isoprene Competent cells of E. coli MG1655 strain (ATCC 700926) were prepared, and then pSTV28-Ptac-Ttrp, pSTV28-Ptac-IspSK, pSTV28-Ptac-IspSP, pSTV28-Ptac-IspSM, or further pSTV28-Ptac-IspSM (L) was introduced therein. A suspension of the cells was evenly applied onto an LB plate containing 60 mg/L of chloramphenicol, and cultured at 37° C. for 18 hours. Subsequently, transformants that were resistant to chloramphenicol were obtained from the resulting plate. A strain in which pSTV28-Ptac-Ttrp, pSTV28-Ptac-IspSK, pSTV28-Ptac-IspSP, pSTV28-Ptac-IspSM, or further pSTV28-Ptac-IspSM (L) was introduced into E. coli MG1655 strain were designated as MG1655/pSTV28-Ptac-Ttrp, MG1655/pSTV28-Ptac-IspSK, MG1655/pSTV28-Ptac-IspSP, MG1655/pSTV28-Ptac-IspSM, or further MG1655/pSTV28-Ptac-IspSM (L) strain, respectively.

4-2) Method of Preparing Crude Enzyme Extract

Microbial cells of MG1655/pSTV28-Ptac-Ttrp, MG1655/pSTV28-Ptac-IspSK, MG1655/pSTV28-Ptac-IspSP, MG1655/pSTV28-Ptac-IspSM, or MG1655/pSTV28-Ptac-IspSM (L) strain were evenly applied to the LB plate containing 60 mg/L of chloramphenicol, and cultured at 37° C. for 18 hours. The microbial cells corresponding to ⅙ of the resulting plate were inoculated to a Sakaguchi flask in which 20 mL of LB containing 60 mg/L of chloramphenicol had been added, and cultured at 37° C. for 6 hours. The microbial cells from the culture medium were centrifuged at 5000 rpm at 4° C. for 5 minutes, and washed twice with ice-cold isoprene synthase buffer (50 mM Tris-HCl, pH 8.0, 20 mM $MgCl_2$, 5% glycerol). The washed microbial cells were suspended in 1.8 mL of the same buffer. About 0.9 mL of beads for disruption (YBG01, diameter 0.1 mm) and 0.9 mL of the microbial cell suspension were placed in a 2 mL tube specific for a multibead shocker, and the microbial cells were disrupted using the multibead shocker manufactured by Yasui Kikai Corporation at 2500 rpm at 4° C. for 3 cycles of ON for 30 seconds/OFF for 30 seconds. After the disruption, the tube was centrifuged at 20,000 g at 4° C. for 20 minutes, and a supernatant was used as a crude enzyme extract.

4-3) Measurement of Isoprene Synthase Activity

The crude enzyme extract from MG1655/pSTV28-Ptac-Ttrp, MG1655/pSTV28-Ptac-IspSK, MG1655/pSTV28-Ptac-IspSP, MG1655/pSTV28-Ptac-IspSM, or MG1655/pSTV28-Ptac-IspSM (L) strain (containing 2 mg as amount of total protein) together with the isoprene buffer in a total volume of 0.5 mL was placed in a headspace vial (22 mL CLEAR CRIMP TOP VIAL (Cat #B0104236) manufactured by Perkin Elmer), then 0.025 mL of a 0.5 M $MgCl_2$ solution and 0.01 mL of a 0.2 M DMAPP (manufactured by Cayman, Catalog No. 63180) solution were added thereto, and the mixture was lightly vortexed. Then immediately, the vial was tightly sealed with a cap with a butyl rubber septum for the headspace vial (CRIMPS (Cat #B0104240) manufactured by Perkin Elmer), and kept at 37° C. for 2 hours.

After completion of the reaction, a concentration of isoprene in the headspace of the vial was measured by gas chromatography. An analysis condition for the gas chromatography will be described below.

Headspace sampler (manufactured by Perkin Elmer, Turbo Matrix 40)
Temperature for keeping vial warm: 40° C.
Time period for keeping vial warm: 30 minutes
Pressurization time: 3.0 minutes
Injection time: 0.02 minute
Needle temperature: 70° C.
Transfer temperature: 80° C.
Carrier gas pressure (high purity helium): 124 kPa
Gas chromatography (manufactured by Shimadzu Corporation, GC-2010 Plus AF)
Column (Rxi (registered trademark)-1 ms: length 30 m, internal diameter 0.53 mm, liquid phase film thickness 1.5 μm, Cat #13370)
Column temperature: 37° C.
Pressure: 24.8 kPa
Column flow: 5 mL/minute
Influx method: Split 1:0 (actually measured 1:18)
Transfer flow: 90 mL
GC injection volume: 1.8 mL (transfer flow×injection time)
Injection volume of sample into column: 0.1 mL
Inlet temperature: 250° C.
Detector: FID (hydrogen 40 mL/minute, air 400 mL/minute, makeup gas helium 30 mL/minute)
Detector temperature: 250° C.
Preparation of Isoprene Standard Sample A reagent isoprene (specific gravity 0.681) was diluted to 10, 100, 1000, 10000 and 100000 times with cold methanol to prepare standard solutions for addition. Subsequently, 1 μL of each standard solution for addition was added to a headspace vial in which 1 mL of water had been added, and used as a standard sample.

The amount of formed isoprene after the reaction of each microbial strain for 2 hours is described in Table 3.

TABLE 3

Amount of formed isoprene after reaction for 2 hours

| Name of microbial strain | Amount of formed isoprene (mg/L) |
|---|---|
| MG1655/pSTV28-Ptac-Ttrp | 0.10 ± 0.01 |
| MG1655/pSTV28-Ptac-IspSK | 0.45 ± 0.02 |
| MG1655/pSTV28-Ptac-IspSM | 28.93 ± 6.04 |
| MG1655/pSTV28-Ptac-IspSM(L) | 5.06 ± 0.13 |
| MG1655/pSTV28-Ptac-IspSP | 0.10 ± 0.01 |

From the result in Table 3, the amount of formed isoprene was larger in order of MG1655/pSTV28-Ptac-IspSM, MG1655/pSTV28-Ptac-IspSM (L) and MG1655/pSTV28-Ptac-IspSK strains, and was almost equal in MG1655/pSTV28-Ptac-IspSP and MG1655/pSTV28-Ptac-Ttrp strains. From the above result, the crude enzyme extract from the strain introduced with the isoprene synthase derived from *Mucuna* exhibited the highest activity to form isoprene.

Example 5

Effects of Introduction of Isoprene Synthase Derived from Various Plants on *E. coli* MG1655 Strain From the result of the crude enzymatic activity in Example 4, the highest activity was confirmed in the isoprene synthase derived from *Mucuna* that deleted the chloroplast localization signal. Thus, an ability to produce isoprene from glucose was compared in all isoprene synthase-introduced strains in which the chloroplast localization signal had been deleted. Microbial cells of MG1655/pSTV28-Ptac-Ttrp, MG1655/pSTV28-Ptac-IspSK, MG1655/pSTV28-Ptac-IspSP, or MG1655/pSTV28-Ptac-IspSM strain were evenly applied onto the LB plate containing 60 mg/L of chloramphenicol, and cultured at 37° C. for 18 hours. One loopful of the microbial cells from the resulting plate was inoculated to 1 mL of M9 glucose medium in a headspace vial. The vial was tightly sealed with the cap with the butyl rubber septum for the headspace vial (CRIMPS (Cat #B0104240) manufactured by Perkin Elmer), and the microbial cells were cultured at 30° C. for 24 hours using a reciprocal shaking cultivation apparatus (120 rpm). A composition of the M9 glucose medium is as described in Table 4.

TABLE 4

Composition of M9 glucose medium

| Glucose | 1.0 g/L |
|---|---|
| Na$_2$HPO$_4$ | 6.0 g/L |
| KH$_2$PO$_4$ | 3.0 g/L |
| NaCl | 0.5 g/L |
| NH$_4$Cl | 1.0 g/L |
| 1M MgSO$_4$ (autoclaved) | 1.0 mL |
| 1M CaCl$_2$ (autoclaved) | 0.1 mL |

Further, chloramphenicol was added at a final concentration of 60 mg/L. The volume was adjusted to 1 L and the medium was then sterilized by filtration.

After completion of the cultivation, the concentration of isoprene in the headspace in the vial was measured by the gas chromatography. An OD value was also measured at 600 nm using a spectrophotometer (HITACHI U-2900). The concentration of isoprene and the OD value in each microbial strain at the time of completing the cultivation are described in Table 5.

TABLE 5

OD value, and amount (μg/L) of isoprene produced by MG1655/pSTV28-Ptac-Ttrp, MG1655/pSTV28-Ptac-IspSK, MG1655/pSTV28-Ptac-IspSP and MG1655/pSTV28-Ptac-IspSM strains at the time of completing cultivation

| Name of microbial strain | OD value | Amount (μg/L) of formed isoprene |
|---|---|---|
| MG1655/pSTV28-Ptac-Ttrp | 1.68 ± 0.04 | ND |
| MG1655/pSTV28-Ptac-IspSK | 1.60 ± 0.09 | 43 ± 6 |
| MG1655/pSTV28-Ptac-IspSM | 1.45 ± 0.03 | 56 ± 7 |
| MG1655/pSTV28-Ptac-IspSP | 1.59 ± 0.07 | 26 ± 3 |

From the results in Table 5, it was found that the amount of produced isoprene was larger in order of MG1655/pSTV28-Ptac-IspSM, MG1655/pSTV28-Ptac-IspSK, MG1655/pSTV28-Ptac-IspSP and MG1655/pSTV28-Ptac-Ttrp strains. From the above results, the strain introduced with the isoprene synthase derived from *Mucuna* exhibited the highest activity to produce isoprene in the wild strains.

Example 6

Effects of Introduction of Isoprene Synthase Derived from Various Plants on *E. coli* MG1655 Strain in Which MEP (Methylerythritol) Pathway is Enhanced 6-1) Construction of Plasmid for Expressing dxs Gene (pMW219-dxs)

It was already reported that the amount of formed isoprene was enhanced (Appl. Microbiol. Biotechnol., (2011) 90, 1915-1922), when the expression of a dxs (1-deoxy-D-xylulose-5-phosphate synthase) gene that constitutes the MEP pathway was enhanced in *E. coli* strain in which the isoprene synthase was introduced. Thus, it was confirmed whether an ability to produce isoprene was also different due to an origin of the isoprene synthase in the strain in which the expression of the dxs gene was enhanced. The entire genomic nucleotide sequence of *E. coli* K-12 strain was already shown (GenBank Accession No. U00096) (Science, (1997) 277, 1453-1474). pMW219 (manufactured by Nippon Gene Co., Ltd.) was used for amplifying the gene. This plasmid can increase an expression level of an objective gene when isopropyl-β-thiogalactopyranoside (IPTG) is added by introducing the objective gene into a multicloning site. Synthesized oligonucleotides were synthesized from the nucleotide sequences represented by SEQ ID NOS:23 and 24 based on the nucleotide sequence of the dxs gene in the genomic nucleotide sequence of *E. coli*. Subsequently, PCR was performed with Prime Star polymerase (manufactured by Takara Bio Inc.) using the synthesized oligonucleotides consisting of the nucleotide sequences represented by SEQ ID NOS:23 and 24 as the primers with MR1655 strain genomic DNA as the template. A reaction solution was prepared according to the composition attached to the kit, and a reaction at 98° C. for 10 seconds, 54° C. for 20 seconds and 68° C. for 120 seconds was performed in 40 cycles. As a result, a PCR product containing the dxs gene was obtained. Likewise, PCR was performed with Prime Star polymerase (manufactured by Takara Bio Inc.) using the synthesized oligonucleotides consisting of the nucleotide sequences represented by SEQ ID NOS:25 and 26 as the primers with pMW219 as the template. A reaction solution was prepared according to the composition attached to the kit, and a reaction at 98° C. for 10 seconds, 54° C. for 20 seconds and 68° C. for 240 seconds was performed in 40 cycles. As a result, a PCR product containing pMW219 was obtained. Subsequently, the purified dxs gene fragment was ligated to the PCR product of pMW219 using In-Fusion HD Cloning Kit (manufactured by Clontech). The resulting plasmid for expressing the dxs gene was designated as pMW219-dxs.

TABLE 6

Primer sequences used for construction of plasmid for expressing dxs gene

| Sequence name | Sequence (5'-) |
|---|---|
| dxs-F | CAGGAAACAGCTATGAGTTTTGATATTGCCAAATACCCGAC (SEQ ID NO: 23) |
| dxs-R | GCTGCCACTCCTGCTATACTCGTCATAC (SEQ ID NO: 24) |
| pMW219-F | CATAGCTGTTTCCTGTGTGAAATTGTTATC (SEQ ID NO: 25) |
| pMW219-R | AGCAGGAGTGGCAGCGAATTCGAGCTCGGTACCCGGGGAT (SEQ ID NO: 26) |

6-2) Introduction of pMW219-Dxs into *E. coli* MG1655 Strain Having Ability to Produce Isoprene Competent cells of MG1655/pSTV28-Ptac-Ttrp, MG1655/pSTV28-Ptac-IspSK, MG1655/pSTV28-Ptac-IspSM, or further MG1655/pSTV28-Ptac-IspSP strain were prepared, and pMW219-dxs was introduced therein by an electroporation method. The cells were evenly applied onto the LB medium containing 60 mg/L of chloramphenicol and 50 mg/L of kanamycin hydrochloride, and the cells were cultured at 37° C. for 18 hours. Transformants that were resistant to chloramphenicol and kanamycin were obtained from the resulting LB plates. Strains in which pMW219-dxs had been introduced into MG1655/pSTV28-Ptac-Ttrp, MG1655/pSTV28-Ptac-IspSK, MG1655/pSTV28-Ptac-IspSM, or further MG1655/pSTV28-Ptac-IspSP strain were designated as MG1655/pSTV28-Ptac-Ttrp/pMW219-dxs, MG1655/pSTV28-Ptac-IspSK/pMW219-dxs, MG1655/pSTV28-Ptac-IspSM/pMW219-dxs, or further MG1655/pSTV28-Ptac-IspSP/pMW219-dxs strain, respectively.

6-3) Effects of Introduction of Isoprene Synthase Derived From Various Plants on *E. coli* MG1655 Strain in which Expression of DXS is Enhanced MG1655/pSTV28-Ptac-Ttrp/pMW219-dxs, MG1655/pSTV28-Ptac-IspSK/pMW219-dxs, MG1655/pSTV28-Ptac-IspSM/pMW219-dxs, or further MG1655/pSTV28-Ptac-IspSP/pMW219-dxs strain were evenly applied onto the LB medium containing 60 mg/L of chloramphenicol and 50 mg/L of kanamycin hydrochloride, and were cultured at 37° C. for 18 hours. Subsequently, the cultivation in the headspace vial was evaluated as described in Example 5. The amount (μg/L) of produced isoprene and the OD value upon completion of the cultivation are described in Table 7.

TABLE 7

Amount (μg/L) of produced isoprene and OD value when the cultivation was completed in various strains having enhanced isoprene synthase which are prepared from *E. coli* MG1655 strain having enhanced DXS as host.

| Name of microbial strain | OD value | Amount (μg/L) of produced isoprene |
|---|---|---|
| MG1655/pSTV28-Ptac-Ttrp/pMW219-dxs | 1.46 ± 0.04 | ND |
| MG1655/pSTV28-Ptac-IspSK/pMW219-dxs | 1.13 ± 0.02 | 101 ± 28 |
| MG1655/pSTV28-Ptac-IspSM/pMW219-dxs | 1.76 ± 0.06 | 126 ± 23 |
| MG1655/pSTV28-Ptac-IspSP/pMW219-dxs | 2.21 ± 0.12 | 42 ± 17 |

From the results in Table 7, the amount of produced isoprene was larger in order of MG1655/pSTV28-Ptac-IspSM/pMW219-dxs, MG1655/pSTV28-Ptac-IspSK/pMW219-dxs, MG1655/pSTV28-Ptac-IspSP/pMW219-dxs and MG1655/pSTV28-Ptac-Ttrp/pMW219-dxs strains. From the above results, the strain introduced with the isoprene synthase derived from *Mucuna* also exhibited the highest ability to produce isoprene in the MEP pathway-enhanced strains.

Example 7

Effects of Introduction of Isoprene Synthase Derived from Various Plants on *E. coli* MG1655 Strain in Which MVA (Mevalonic Acid) Pathway is Introduced 7-1) Cloning Gene Downstream of Mevalonate Pathway which is Derived from Yeast A downstream region of the mevalonate pathway was obtained from *Saccharomyces cerevisiae* (WO2009076676, *Saccharomyces* Genome database www.yeastgenome.org/# Nucleic Acids Res., January 2012; 40: D700-D705). An ERG12 gene encoding mevalonate kinase, an ERG8 gene encoding phosphomevalonate kinase, an ERG19 gene encoding diphosphomevalonate decarboxylase, and an IDI1 gene encoding isopentenyl diphosphate delta isomerase were amplified by PCR with genomic DNA of *S. cerevisiae* as the template using the primer shown below (Table 8). Prime Star Max Premix sold by Takara Bio Inc. was used for a PCR enzyme, and the reaction was performed at 98° C. for 2 minutes and for 30 cycles of 98° C. for 10 seconds, 55° C. for 5 seconds and 72° C. for 5 seconds/kb. Cloning and construction of an expression vector were performed by introducing the PCR fragment into the pSTV28-Ptac-Ttrp vector (SEQ ID NO:12) treated with the restriction enzyme SmaI by an in-fusion cloning method. *E. coli* DH5α was transformed with the expression vector, clones having assumed sequence length from each gene were selected, a plasmid was extracted according to standard methods, and its sequence was confirmed. The nucleotide sequences of these amplified genes and the amino acid sequences of the enzymes encoded by these genes are available on *Saccharomyces* Genome database www.yeastgenome.org/#.

TABLE 8

Primer sequences used for cloning of genes downstream of mevalonate pathway

| Amplified gene | Sequence name | Sequence (5'-) |
| --- | --- | --- |
| ERG12 | MVK-IFS_5742-33-1 | ACACAAGGAGACTCCCATGTCATTACCGTTCTTAA CTTCT (SEQ ID NO: 27) |
| ERG12 | MVK-IFA_5742-33-2 | GGAACTGGCGGCTCCCGGGTTATTATGAAGTCCAT GGTAAATTCGT (SEQ ID NO: 28) |
| ERG8 | PMK-IFS_5742-33-3 | ACACAAGGAGACTCCCATGTCAGAGTTGAGAGCCT TCA (SEQ ID NO: 29) |
| ERG8 | PMK-IFA_5742-33-4 | GGAACTGGCGGCTCCCGGGTTATTATTTATCAAGA TAAGTTTCCGG (SEQ ID NO: 30) |
| ERG19 | MVD-IFS_5742-33-5 | ACACAAGGAGACTCCCATGACCGTTTACACAGCAT CC (SEQ ID NO: 31) |
| ERG19 | MVD-IFA_5742-33-6 | GGAACTGGCGGCTCCCGGGTTATTATTCCTTTGGT AGACCAGTCTT (SEQ ID NO: 32) |
| IDI1 | yIDI-IFS_5742-33-7 | ACACAAGGAGACTCCCATGCCCCATGGTGCAGTAT C (SEQ ID NO: 33) |
| IDI1 | yIDI-IFA_5742-33-8 | GGAACTGGCGGCTCCCGGGTTATTATAGCATTCTA TGAATTTGCCTGTC (SEQ ID NO: 34) |

7-2) Construction of Artificial Operon Downstream of Mevalonate Pathway

A sequence in which the gene encoding the mevalonate kinase and the gene encoding the phosphomevalonate kinase were arranged in straight was constructed by the in-fusion cloning method. The ERG12 gene encoding the mevalonate kinase and the ERG8 gene encoding the phosphomevalonate kinase were amplified by PCR with genomic DNA from *Saccharomyces cerevisiae* as the template using the primers shown in Table 9. KOD plus sold by Toyobo was used for the PCR enzyme, and the reaction was performed at 94° C. for 2 minutes and for 30 cycles of 94° C. for 15 seconds, 45° C. for 30 seconds and 68° C. for 1 minute/kb. The cloning and the construction of an expression vector were performed by inserting the PCR fragment into pUC118 vector treated with the restriction enzyme SmaI by the in-fusion cloning method. *E. coli* JM109 was transformed with the expression vector, clones having assumed sequence length of each gene were selected, a plasmid was extracted according to standard methods, and its sequence was confirmed. The produced plasmid was designated as pUC-mvk-pmk. The nucleotide sequence of pUC-mvk-pmk is represented by SEQ ID NO:35.

TABLE 9

Primer sequences used for ligating mevalonate kinase and phosphomevalonate kinase

| Amplified gene | Sequence name | Sequence (5'-) |
|---|---|---|
| ERG12 | KKS1-6038-2-1 | TCGAGCTCGGTACCCATGTCATTACCGTTCTTAACTTCT (SEQ ID NO: 36) |
| ERG12 | KKA1-6038-2-2 | TTAAGGGTGCAGGCCTATCGCAAATTAGCTTATGAAGTCC ATGGTAAATTCGT (SEQ ID NO: 37) |
| ERG8 | KKS2-6083-2-3 | GGCCTGCACCCTTAAGGAGGAAAAAAACATGTCAGAGTTG AGAGCCTTCA (SEQ ID NO: 38) |
| ERG8 | KKA2-6083-2-4 | CTCTAGAGGATCCCCTTATTTATCAAGATAAGTTTCCGG (SEQ ID NO: 39) |

A sequence in which a gene encoding diphosphomevalonate decarboxylase and a gene encoding isopentenyl diphosphate delta isomerase were arranged in straight was constructed by the in-fusion cloning method. The ERG19 gene encoding the diphosphomevalonate decarboxylase and the IDI1 gene encoding the isopentenyl diphosphate delta isomerase were amplified by PCR with genomic DNA of Saccharomyces cerevisiae as the template using the primers shown in Table 10. KOD plus sold by Toyobo was used for the PCR enzyme, and the reaction was performed at 94° C. for 2 minutes and for 30 cycles of 94° C. for 15 seconds, 45° C. for 30 seconds and 68° C. for 1 minute/kb, and then at 68° C. for 10 minutes. The cloning and the construction of an expression vector were performed by inserting the PCR fragment into pTWV228 vector treated with the restriction enzyme SmaI by the in-fusion cloning method. E. coli DH5α was transformed with the expression vector, clones having assumed sequence length of each gene were selected, a plasmid was extracted according to standard methods, and its sequence was confirmed. The produced plasmid was designated as pTWV-dmd-yidi. The nucleotide sequence of pTWV-dmd-yidi is represented by SEQ ID NO:40.

A sequence in which a gene encoding mevalonate kinase, a gene encoding phosphomevalonate kinase, a gene encoding diphosphomevalonate decarboxylase and a gene encoding isopentenyl diphosphate delta isomerase were arranged in straight was constructed by the in-fusion cloning method. An expression vector in which these four enzyme genes were arranged in straight was constructed by amplifying the gene encoding the mevalonate kinase and the gene encoding the diphosphomevalonate kinase by PCR with pUC-mvk-pmk as the template using the primers shown in Table 11 and amplifying the gene encoding the diphosphomevalonate decarboxylase and the gene encoding the isopentenyl diphosphate delta isomerase by PCR with pTWV-dmd-yidi as the template using the primers shown in Table 11, followed by cloning the amplified products into pTrcHis2B vector by the in-fusion cloning method. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. The PCR fragment was inserted into pTrcHis2B vector treated with the restriction enzymes NcoI and PstI to construct the expression vector. E. coli JM109 was transformed with the expression vector, clones having an objective sequence length were selected, a plasmid was extracted according to standard methods, and its sequence was confirmed. The constructed expression vector was designated as pTrc-KKDyI (β). The nucleotide sequence of pTrc-KKDyI (β) is represented by SEQ ID NO:45.

TABLE 10

Primer sequences used for ligating diphosphomevalonate decarboxylase and isopentenyl diphosphate delta isomerase.

| Amplified gene | Sequence name | Sequence (5'-) |
|---|---|---|
| ERG19 | DyIS1-6083-2-5 | TCGAGCTCGGTACCCATGACCGTTTACACAGCATCC (SEQ ID NO: 41) |
| ERG19 | DyIA1-6083-2-6 | TTTTTTTACCTCCTAAGGGCGATGCAGCGAATTGATC TTATTCCTTTGGTAGACCAGTCTT (SEQ ID NO: 42) |
| IDI1 | DyIS2-6083-2-7 | TAGGAGGTAAAAAAAAATGACTGCCGACAACAATAGT ATGCCCCATGGTGCAGTATC (SEQ ID NO: 43) |
| IDI1 | DyIA2-6083-2-8 | CTCTAGAGGATCCCCTTATAGCATTCTATGAATTTGC CTGTC (SEQ ID NO: 44) |

TABLE 11

Primer sequences used for amplifying genes for constructing pTrc-KKDyI (β)

| Template plasmid | Sequence name | Sequence (5'-) |
|---|---|---|
| pUC-mvk-pmk | KKDS2_6038-3-2 | GAGGAATAAACCATGTCATTACCGTTCTTAACTTCT (SEQ ID NO: 46) |
| pUC-mvk-pmk | KKMyIA_6038-2-9 | AAGGGCGAATTCTGCATGCAGCTACCTTAAGTTATT TATCAAGATAAGTTTCCGG (SEQ ID NO: 47) |
| pTWV-dmd-yidi | KMS_6038-6-1 | GCAGAATTCGCCCTTAAGGAGGAAAAAAAAATGACC GTTTACACAGCATCC (SEQ ID NO: 48) |
| pTWV-dmd-yidi | KDyIA_6038-3-3 | CCATATGGTACCAGCTGCAGTTATAGCATTCTATGA ATTTGCCTGTC (SEQ ID NO: 49) |

7-3) Fixation of Downstream Region of Mevalonate Pathway on Chromosome

The sequence in which the gene encoding the mevalonate kinase, the gene encoding the diphosphomevalonate kinase, the gene encoding the diphosphomevalonate decarboxylase and the gene encoding the isopentenyl diphosphate delta isomerase were arranged in straight was expressed on a chromosome. A glucose isomerase promoter was used for the expression of the gene, and a transcription termination region of aspA gene in E. coli was used for the termination of the transcription (WO2010031062). A translocation site of Tn7 was used as a chromosomal site to be fixed (Mol Gen Genet., 1981; 183 (2): 380-7). A cat gene was used as a drug marker after the fixation of the chromosome. A T7 downstream region in the chromosome region to be fixed was amplified by PCR with genomic DNA of E. coli as the template using the primers shown in Table 12. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. A cat gene region containing a λ phage attachment site was amplified by PCR with pMW118-attL-Cm-attR plasmid as the template using the primers shown in Table 12 (WO2010-027022). Prime Star HS DNA polymerase sold by Takara Bio Inc. was used for the PCR enzyme, and the reaction was carried out at 95° C. for 3 minutes followed by in 2 cycles of 95° C. for 1 minute, 34° C. for 30 seconds and 72° C. for 40 seconds, 2 cycles of 95° C. for 30 seconds, 50° C. for 30 seconds and 72° C. for 40 seconds, and then at 72° C. for 5 minutes. A sequence downstream of the mevalonate pathway to which a promoter and a transcription termination region had been added (hereinafter abbreviated as KKDyI) was amplified with pTrc-KKDyI (β) as the template using the primers shown in Table 12. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. A vector was constructed using these PCR products and pMW219 treated with the restriction enzyme SmaI by the in-fusion cloning method. E. coli JM109 was transformed with the expression vector, clones having an objective sequence length were selected, a plasmid was extracted according to standard methods, and its sequence was confirmed. The resulting plasmid was designated as pMW219-KKDyI-TaspA. The nucleotide sequence of pMW219-KKDyI-TaspA is represented by SEQ ID NO:50.

Subsequently, a Tn7 upstream region in the chromosome region to be fixed was amplified by PCR with the genomic DNA of E. coli as the template using the primers shown in Table 13. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. A vector was constructed using the PCR product and pMW219-KKDyI-TaspA treated with the restriction enzyme SalI by the in-fusion cloning method. E. coli JM109 was transformed with the expression vector, clones having an objective sequence length were selected, a plasmid was extracted according to standard methods, and its sequence was confirmed. The resulting plasmid was designated as pMW-Tn7-Pgi-KKDyI-TaspA-Tn7. The sequence of the constructed plasmid is represented by SEQ ID NO:51.

Figure 3:
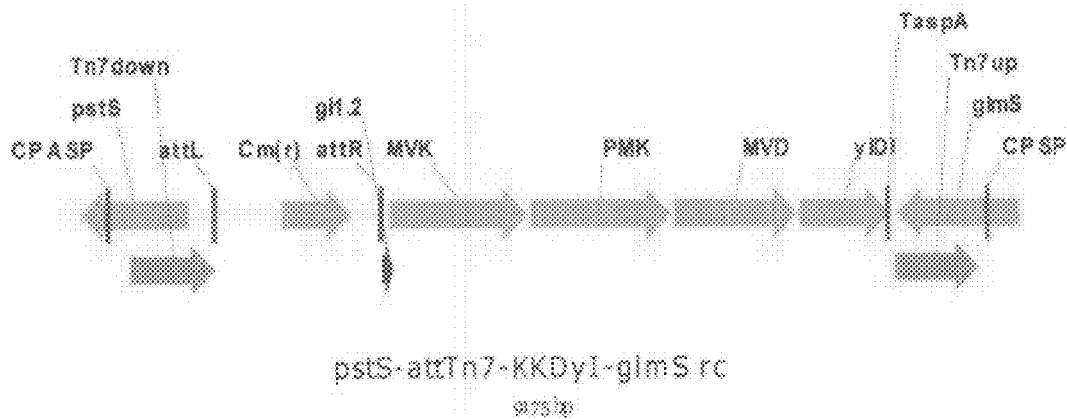
FIG. 3 is a view showing an outline of a downstream and its proximal region of a mevalonate pathway on a fixed chromosome.

Subsequently, a chromosome having a region including the chloramphenicol resistance gene, the glucose isomerase promoter, the operon downstream of the mevalonate pathway, and the aspA gene transcription termination region was fixed using λ-Red method. A fragment for chromosome fixation was prepared by extracting the plasmid pMW-Tn7-Pgi-KKDyI-TaspA-Tn7 and then treating it with the restriction enzymes PvuI and SalI followed by purifying it. E. coli MG1655 containing a plasmid pKD46 having a temperature-sensitive replication capacity (hereinafter referred to as MG1655/pKD46) was used for the electroporation. The plasmid pKD46 [Proc. Natl. Acad. Sci. USA, 2000, vol. 97, No. 12, p6640-6645] contains a DNA fragment of total 2154 nucleotides (GenBank/EMBL Accession No. J02459, 31088th to 33241st) of λ phage containing λ Red system genes (λ, β, exo genes) controlled by an arabinose-inducible ParaB Promoter. After the electroporation, a colony that had acquired the resistance to chloramphenicol was obtained, subsequently genomic DNA was extracted, and it was confirmed by PCR using the primers shown in Table 14 that the objective region was fixed on the chromosome. Further, the sequence of the objective region was confirmed by confirming the sequence of the PCR fragment. The nucleotide sequence of the mevalonate pathway downstream and its proximal region fixed on the chromosome is represented by SEQ ID NO:52, and its construction outline is shown in FIG. 3. The resulting mutant was designated as MG1655 cat-Pgi-KKDyI.

The drug marker in MG1655 cat-Pgi-KKDyI was removed by the following procedure. Competent cells of MG1655 cat-Pgi-KKDyI was made, and then pMW-int-xis was introduced therein. pMW-int-xis is a plasmid containing a gene encoding integrase (Int) of the λ phage and a gene encoding excisionase (Xis) of the λ phage and having the temperature-sensitive replication capacity (WO2007/037460, JP 2005-058827).

The chloramphenicol-resistant gene located in a region sandwiched with attL and attR that are the attachment site of the λ phage is dropped off from the chromosome by introducing pMW-int-xis. As a result, it is known that the host loses the resistance to chloramphenicol. And, a chloramphenicol-sensitive strain was obtained from the resulting colony, and subsequently cultured on the LB medium at 42° C. for 6 hours. The cultured microbial cells were applied onto the LB plate medium to allow colonies to appear. A colony that had lost the resistance to ampicillin was selected from these colonies to remove the drug resistance. The mutant obtained as above was designated as MG1655 Pgi-KKDyI.

7-4) Substitution of Promoter Downstream of Mevalonate Pathway on Chromosome

The promoter of the operon downstream of the mevalonate pathway on the chromosome was substituted by the λ-red method. A genomic fragment having attL-Tet-attR-Ptac was used as the template for PCR. This is one in which the tac promoter, and attL and attR that are the attachment sites for a tetracycline resistant drug marker and the λ phage are aligned. This sequence is represented by SEQ ID NO:63. A PCR fragment was prepared using the promoter shown in Table 15. LA-Taq polymerase sold by Takara Bio Inc. was used for the PCR enzyme, and the reaction was carried out at 92° C. for 1 minute, then for 40 cycles of 92° C. for 10 seconds, 50° C. for 20 seconds and 72° C. for 1 minute/kb, and further at 72° C. for 7 minutes. The PCR product was purified. MG1655 Pgi-KKDyI containing the plasmid pKD46 (hereinafter referred to as MG1655 Pgi-KKDyI/pKD46) having the temperature-sensitive replication capacity was used for the electroporation. The plasmid pKD46 [Proc. Natl. Acad. Sci. USA, 2000, vol. 97, No. 12, p6640-6645] contains a DNA fragment of total 2154 nucleotides (GenBank/EMBL Accession No. J02459, 31088th to 33241st) of λ phage containing λ Red system genes (λ, β, exo genes) controlled by an arabinose-inducible ParaB Promoter. The plasmid pKD46 is required for incorporating the PCR product into MG1655 Pgi-KKDyI.

Competent cells for the electroporation were prepared as follows. MG1655 Pgi-KKDyI/pKD46 cultured in the LB medium containing 100 mg/L of ampicillin at 30° C. over-

TABLE 12

Primers for making PCR fragments used for construction of pMW219-KKDyI-TaspA

| Template DNA | Amplified region | Sequence name | Sequence (5'-) |
|---|---|---|---|
| E. coli genome | Tn7 downstream | Tn7dS_6038-7-1 | TCGAGCTCGGTACCCTGTTTTTCCACTCTTCGTT CACTTT (SEQ ID NO: 53) |
| E. coli genome | Tn7 downstream | Tn7dA_6038-7-2 | AGGCTTCATTTTAATCAAACATCCTGCCAACTC (SEQ ID NO: 54) |
| pMW-attL-Cm-attR | attL-cat-attR | Tn7dattLcmS 6038-7-4 | ATTAAAATGAAGCCTGCTTTTTTAT (SEQ ID NO: 55) |
| pMW-attL-Cm-attR | attL-cat-attR | PgiattRcmA_ 6038-7-5 | GGCATCGTCAAGGGCCGCTCAAGTTAGTATAA (SEQ ID NO: 56) |
| pTrc-KKDyI(β) | KKDyI | gi1.2-MVK-S_6038-7-6 | GCCCTTGACGATGCCACATCCTGAGCAAATAATT CAACCACTAATTGTGAGCGGATAACACAAGGAGG AAACAGCTATGTCATTACCGTTCTTAACTTC (SEQ ID NO: 57) |
| pTrc-KKDyI(β) | KKDyI | pMW-TaspA-yIDIA_6038-7-7 | CTCTAGAGGATCCCCCGGCCCCAAGAAAAAAGGCA CGTCATCTGACGTGCCTTTTTTATTTGTAGACGC GTTGTTATAGCATTCTATGAATTTGCCT (SEQ ID NO: 58) |

TABLE 13

Primers for making PCR fragments used for construction of pMW-Tn7-Pgi-KKDyI-TaspA-Tn7

| Template DNA | Amplified region | Sequence name | Sequence (5'-) |
|---|---|---|---|
| E. coli genome | Tn7 upstream | Tn7upSv02_6038-24-1 | ATCCTCTAGAGTCGAAAGAAAAATGCCCCG CTTACG (SEQ ID NO: 59) |
| E. coli genome | Tn7 upstream | Tn7upAv02_6038-24-2 | ATGCCTGCAGGTCGACTGTCACAGTCTGGC GAAACCG (SEQ ID NO: 60) |

TABLE 14

PCR primers for confirming chromosome fixation of mevalonate pathway downstream

| Sequence name | Sequence (5'-) |
|---|---|
| Tn7v02-F_6038-22-5 | ACGAACTGCTGTCGAAGGTT (SEQ ID NO: 61) |
| Tn7v02-R_6038-22-6 | GGTGTACGCCAGGTTGTTCT (SEQ ID NO: 62) | night were diluted to 100 times with 5 mL of LB medium containing ampicillin and L-arabinose (1 mM). The resulting cells in diluted suspension were grown until OD600 reached about 0.6 with ventilating at 30° C., and subsequently washed three times with ice-cold 10% glycerol solution to use for the electroporation. The electroporation was performed using 50 μL of the competent cells and about 100 ng of the PCR product. The cells after the electroporation in 1 mL of SOC medium [Molecular Cloning: Laboratory Manuals, 2nd Edition, Sambrook, J. et al., Cold Spring Harbor Laboratory Press (1989)] were cultured at 37° C. for one hour, and subjected to a plate culture on LB agar medium at 37° C. to select a chloramphenicol-resistant transformant. Subsequently, in order to remove the pKD46 plasmid, the transformant was subcultured on the LB agar medium containing tetracycline at 37° C. The ampicillin resistance was examined in the obtained colonies, and an ampicillin-resistant strain having no pKD46 was obtained. A mutant containing the tac promoter substitution that could be distinguished by the tetracycline-resistant gene was obtained. The obtained mutant was designated as MG1655 tet-Ptac-KKDyI.

Figure 4:
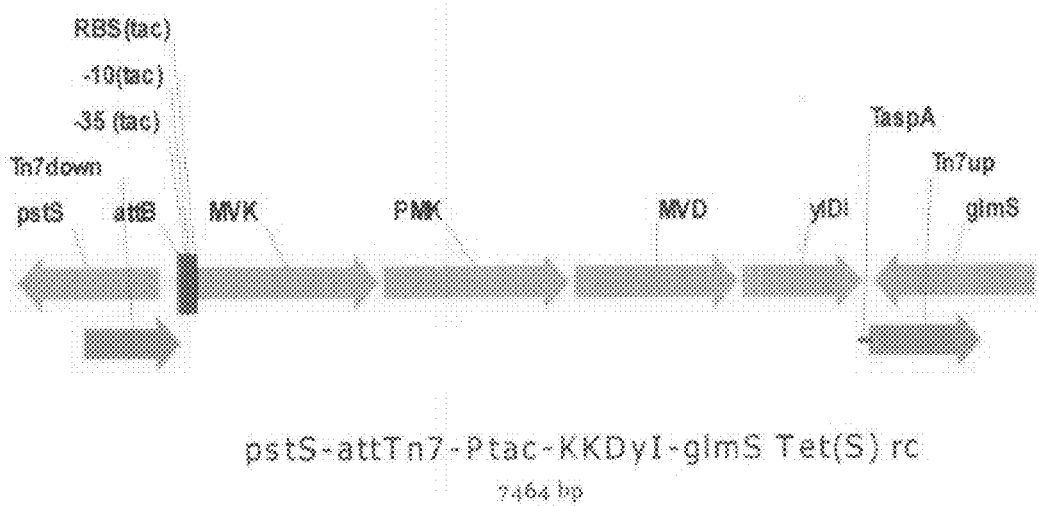
FIG. 4 is a view showing the downstream and its proximal region of a mevalonate pathway controlled by a tac promoter on a chromosome.

The antibiotic marker was removed by the following procedure. Competent cells of MG1655 tet-Ptac-KKDyI were made, and then pMW-int-xis was introduced therein. pMW-int-xis is a plasmid containing the genes encoding integrase (Int) and excisionase (Xis) of the λ phage and having the temperature-sensitive replication capacity (WO2007/037460, JP Publication No. 2005-058827). The tetracycline-resistant gene located in a region sandwiched with attL and attR that are the attachment site of the λ phage is dropped off from the chromosome by introducing pMW-int-xis. As a result, it is known that the host loses the resistance to tetracycline. Thus, a tetracycline-sensitive strain was obtained from the resulting colonies. Cells of this strain were cultured on the LB medium at 42° C. for 6 hours, and the cultured cells were applied onto the LB plate medium to allow colonies to appear. A clone that had lost the resistance to ampicillin was selected to remove the drug resistance. The resulting mutant was designated as MG1655 Ptac-KKDyI. The nucleotide sequence of the mevalonate pathway downstream and its proximal region controlled by the tac promoter on the chromosome is represented by SEQ ID NO:64, and its outline is shown in FIG. 4.

7-5) Introduction of Isoprene Synthase Derived from Various Plants into MG1655 Ptac-KKDyI Strain Competent cells of MG1655 Ptac-KKDyI strain were prepared, and then pSTV28-Ptac-Ttrp, pSTV28-Ptac-IspSK, pSTV28-Ptac-IspSM, or further pSTV28-Ptac-IspSP was introduced therein. The cells were evenly applied onto the LB plate containing 60 mg/L of chloramphenicol, and the cells were cultured at 37° C. for 18 hours. Transformants that exhibited the chloramphenicol resistance were obtained from the resulting plate. A strain in which pSTV28-Ptac-Ttrp, pSTV28-Ptac-IspSK, pSTV28-Ptac-IspSM, or pSTV28-Ptac-IspSP had been introduced into MG1655 Ptac-KKDyI strain was designated as MG1655 Ptac-KKDyI/pSTV28-Ptac-Ttrp, MG1655 Ptac-KKDyI/pSTV28-Ptac-IspSK, MG1655 Ptac-KKDyI/pSTV28-Ptac-IspSM, or MG1655 Ptac-KKDyI/pSTV28-Ptac-IspSP, respectively.

7-6) Effects of Introduction of Isoprene Synthase Derived From Various Plants on MG1655 Strain in which MVA Pathway is Enhanced Microbial cells of MG1655 Ptac-KKDyI/pSTV28-Ptac-Ttrp, MG1655 Ptac-KKDyI/pSTV28-Ptac-IspSK, MG1655 Ptac-KKDyI/pSTV28-Ptac-IspSM, or further MG1655 Ptac-KKDyI/pSTV28-Ptac-IspSP were evenly applied onto the LB plate containing 60 mg/L of chloramphenicol, and the cells were cultured at 37° C. for 18 hours. One loopful of the microbial cells from the resulting LB plate was inoculated to 1 mL of M9 glucose (containing mevalonic acid) medium in a headspace vial (22 mL CLEAR CRIMP TOP VIAL (Cat #B0104236) manufactured by Perkin Elmer), and subsequently the cultivation was evaluated according to the method described in Example 2. A composition of the M9 glucose (containing mevalonic acid) medium is described in Table 16. The amount of produced isoprene and the OD value upon completion of the cultivation are described in Table 17.

TABLE 16

| Composition of M9 glucose (containing mevalonic acid) medium | |
|---|---|
| Glucose | 2.0 g/L |
| $Na_2HPO_4$ | 6.0 g/L |
| $KH_2PO_4$ | 3.0 g/L |
| NaCl | 0.5 g/L |
| $NH_4Cl$ | 1.0 g/L |
| Mevalonic acid (manufactured by ADEKA) | 1.0 g/L |
| 1M $MgSO_4$ (autoclaved) | 1.0 mL |
| 1M $CaCl_2$ (autoclaved) | 0.1 mL |

TABLE 15

| Primers for making PCR fragments for promoter substitution | |
|---|---|
| Sequence name | Sequence (5'-) |
| APtacKKDyIv03_6038-36-5 | gataaagtcttcagtctgatttaaataagcgttgatattcagtc aattactgaagcctgcttttttatac (SEQ ID NO: 65) |
| SPtacKKDyIv02_6038-36-3 | tcaccaaaaataataacctttcccggtgcagaagttaagaacgg taatgaCATggcagtctccttgtgtga (SEQ ID NO: 66) |

Chloramphenicol was added at a final concentration of 60 mg/L.

A total volume was adjusted to 1 L, and the medium was sterilized by filtration.

TABLE 17

Amount (mg/L) of produced isoprene and OD value when cultivation of MG1655 Ptac-KKDyI/pSTV28-Ptac-Ttrp, MG1655 Ptac-KKDyI/pSTV28-Ptac-IspSK, MG1655 Ptac-KKDyI/pSTV28-Ptac-IspSM, or further MG1655 Ptac-KKDyI/pSTV28-Ptac-IspSP was completed

| Name of microbial strain | OD value | Amount (mg/L) of produced isoprene |
|---|---|---|
| MG1655 Ptac-KKDyI/pSTV28-Ptac-Ttrp | 2.08 ± 0.07 | 0.07 ± 0.01 |
| MG1655 Ptac-KKDyI/pSTV28-Ptac-IspSK | 2.48 ± 0.13 | 30.96 ± 3.04 |
| MG1655 Ptac-KKDyI/pSTV28-Ptac-IspSM | 2.48 ± 0.09 | 57.13 ± 15.00 |
| MG1655 Ptac-KKDyI/pSTV28-Ptac-IspSP | 1.95 ± 0.09 | 0.52 ± 0.01 |

From the results in Table 17, the amount of produced isoprene was larger in order of MG1655 Ptac-KKDyI/pSTV28-Ptac-IspSM, MG1655 Ptac-KKDyI/pSTV28-Ptac-IspSK, MG1655 Ptac-KKDyI/pSTV28-Ptac-IspSP, and MG1655 Ptac-KKDyI/pSTV28-Ptac-Ttrp strains. From the above results, the strain introduced with the isoprene synthase derived from *Mucuna* also exhibited the highest ability to produce isoprene in the strains introduced with the MVA pathway.

Example 8

Measurement of Enzymatic Activity of Isoprene Synthase Derived from Various Plants Using Crude Enzyme Extract Derived from *Corynebacterium glutamicum*

1) Construction of Plasmid for Expressing IspS Gene Derived From Various Plants

*C. glutamicum* 2256 strain (ATCC13869) was used as a coryneform bacterium (Okumura et al., 1962, Santamaria et al., 1984, Tsuchida et al., 1986). Plasmids for expressing the IspSK gene, the IspSP gene and the IspSM gene in *C. glutamicum* were constructed by the following procedure. PCR was performed with Prime Star polymerase (manufactured by Takara Bio Inc.) using the synthesized oligonucleotides represented by SEQ ID NOS:67 and 68 as the primers with pUC57-IspSK as the template, the synthesized oligonucleotides represented by SEQ ID NOS:69 and 70 as the primers with pUC57-IspSP as the template, or synthesized oligonucleotides represented by SEQ ID NOS:71 and 72 as the primers with pUC57-IspSM as the template. A reaction solution was prepared according to the composition attached to the kit, and the reaction was carried out for 30 cycles of 98° C. for 10 seconds, 55° C. for 5 seconds and 72° C. for 120 seconds. As a result, the PCR product containing the IspSK gene, the IspSP gene, or the IspSM gene was obtained. Subsequently, for the purpose of obtaining a promoter sequence of the elongation factor Tu (hereinafter $P_{0480}$), PCR was performed using chromosomal DNA of *C. glutamicum* 2256 strain as the template. For the purpose of combining the IspSK gene with $P_{0480}$, the synthesized nucleotides represented by SEQ ID NOS:73 and 74 were used as the primers for PCR. Also for the purpose of combining the IspSP gene with $P_{0480}$, the synthesized nucleotides represented by SEQ ID NOS:73 and 75 were used as the primers for PCR. Also for the purpose of combining the IspSM gene with $P_{0480}$, the synthesized nucleotides represented by SEQ ID NOS:73 and 76 were used as the primers for PCR. Prime Star polymerase (manufactured by Takara Bio Inc.) was used for PCR. A reaction solution was prepared according to the composition attached to the kit, and the reaction was carried out for 30 cycles of 98° C. for 10 seconds, 55° C. for 5 seconds and 72° C. for 30 seconds. As a result, the PCR products containing $P_{0480}$ were obtained. Information for the sequence of $P_{0480}$ is represented by SEQ ID NO:77. A shuttle vector pVK9 for *C. glutamicum* and *E. coli* was digested with the restriction enzyme XbaI (manufactured by Takara Bio Inc.) (Miwa et al., 1985). Information for the sequence of pVK9 is represented by SEQ ID NO:78. The purified fragment of the IspSK gene, IspSP gene or IspSM gene, the PCR product of $P_{0480}$ and purified pVK9 treated with XbaI were ligated using In-fusion HD Cloning Kit (manufactured by Clontech). The resulting plasmids for expressing the IspSK gene, the IspSP gene and IspSM gene were designated as pVK9-$P_{0480}$-IspSK, pVK9-$P_{0480}$-IspSP and pVK9-$P_{0480}$-IspSM, respectively, and their sequence information were represented by SEQ ID NOS:79, 80 and 81, respectively.

2) Construction of *C. glutamicum* 2256 Strain Having Ability To Produce Isoprene Microbial cells of *C. glutamicum* 2256 strain were inoculated to a test tube containing 4 mL of CM-Dex medium, and cultured to a logarithmic growth phase at 30° C. at 120 rpm. These microbial cells were collected, washed two to three times with ice-cold 10% glycerol, concentrated to about 100 to 200 times, and used as competent cells. The competent cells and each plasmid of pVK9, pVK9-$P_{0480}$-IspSK, pVK9-$P_{0480}$-IspSP or pVK9-$P_{0430}$-IspSM were mixed well, and pulse was applied thereto. The pulse application was performed under the condition of 1.8 kV, 25 µF and 200Ω using GenePulserXCell manufactured by BIORAD. After the pulse application, the cells were recovered by culturing in a CM-Dex medium for about 1 to 2 hours, subsequently applied onto a CM-Dex plate medium containing 50 µg/mL of Km, and cultured at 30° C. for 18 to 24 hours. Transformants exhibiting the resistance to kanamycin were obtained from the plate after the cultivation. The composition of the DM-Dex medium is shown in Table 18. A strain in which pVK9, pVK9-$P_{0480}$-IspSK, pVK9-$P_{0480}$-IspSP or pVK9-$P_{0480}$-IspSM had been introduced into *C. glutamicum* 2256 strain was designated as 2256/pVK9, 2256/pVK9-$P_{0480}$-IspSK, 2256/pVK9-$P_{0480}$-IspSP or 2256/pVK9-$P_{0480}$-IspSM, respectively.

TABLE 18

Composition of DM-Dex medium

| | |
|---|---|
| Glucose | 5 g/L |
| Polypeptone | 10 g/L |
| Yeast extract | 10 g/L |
| $KH_2PO_4$ | 1 g/L |
| $MgSO_4 \cdot 7H_2O$ | 0.4 g/L |
| $FeSO_4 \cdot H_2O$ | 0.01 g/L |
| $MnSO_4 \cdot H_2O$ | 0.01 g/L |
| Urea | 3 g/L |
| Hydrolyzed soybeans | 1.2 g/L (as total nitrogen concentration) |
| pH 7.5 (NaOH) | |

The medium was sterilized at 120° C. for 20 minutes. If necessary, kanamycin was added at a final concentration of 50 mg/L.

In the case of the plate, 20 g/L of agar was added.

3) Method of Preparing Crude Enzyme Extract

Microbial cells of 2256/pVK9, 2256/pVK9-$P_{0480}$-IspSK, 2256/pVK9-$P_{0480}$-IspSP or 2256/pVK9-$P_{0480}$-IspSM were evenly applied onto the CM-Dex plate medium containing 50 mg/L of kanamycin, and cultured at 30° C. for 18 hours. The microbial cells corresponding to ⅙ of the cultured plate were inoculated to a Sakaguchi flask in which 20 mL of the CM-Dex medium containing 50 mg/L of kanamycin, and cultured at 30° C. for 6 hours. The microbial cells were separated from the culture medium by centrifugation at 5,000 rpm for 5 minutes, and washed twice with the isoprene synthase buffer (50 mM Tris-HCl (pH 8.0), 20 mM $MgCl_2$, 5% glycerol). The microbial cells after the washing were resuspended in 1.8 mL of the same buffer. Subsequently, about 0.9 mL of beads for disruption (YBG01, diameter 0.1 mm) and 0.9 mL of the microbial cell suspension were placed in a 2 mL tube specific for the multibead shocker. The microbial cells were disrupted using the multibead shocker (MB701 (S) model) manufactured by Yasui Kikai Corporation at 2500 rpm for 6 cycles of ON for 60 seconds/OFF for 60 seconds. After the disruption, the tube was centrifuged at 20,000 g for 20 minutes, and the obtained supernatant was used as a crude enzyme extract.

4) Measurement of Isoprene Synthase Activity

A protein concentration of the crude enzyme extracts from 2256/pVK9, 2256/pVK9-$P_{0480}$-IspSK, 2256/pVK9-$P_{0480}$-IspSP and 2256/pVK9-$P_{0480}$-IspSM strains was measured by a bicinchonic acid method (BCA method). BCA protein assay reagent kit (Thermo Scientific Japan, Cat #23227) was used as reagents for the measurement. 2 mg of the crude enzyme extract as the amount of total protein and the isoprene buffer were combined and prepared to make total 0.5 mL. This was placed in a headspace vial, subsequently 0.025 mL of a 0.5 M $MgCl_2$ solution and 0.01 mL of a 0.2 M DMAPP (manufactured by Cayman, Cat No. 63180) solution were added thereto, and the mixture was lightly vortexed. Then immediately, the vial was tightly sealed, and the reaction was carried out at 37° C. for 2 hours. After the reaction, the concentration of isoprene in the headspace in the vial was measured by gas chromatography. 22 mL CLEAR CRIMP TOP VIAL (Cat #B0104236) manufactured by Perkin Elmer was used as the headspace vial and a cap with a butyl rubber septum for the headspace vial (Cat #B0104240) manufactured by Perkin Elmer was used as a cap for tight sealing.

The amounts of isoprene formed after the reaction for 2 hours in various microbial strains are described in Table 19.

TABLE 19

Amounts of isoprene formed after the reaction for 2 hours in 2256/pVK9, 2256/pVK9-$P_{0480}$-IspSK, 2256/pVK9-$P_{0480}$-IspSP and 2256/pVK9-$P_{0480}$-IspSM strains

| Name of microbial strain | Amount (mg/L) of formed isoprene |
|---|---|
| C. glutamicum 2256/pVK9 | 0.05 ± 0.02 |
| C. glutamicum 2256/pVK9-$P_{0480}$-ispSP | 0.05 ± 0.02 |
| C. glutamicum 2256/pVK9-$P_{0480}$-ispSK | 0.68 ± 0.14 |
| C. glutamicum 2256/pVK9-$P_{0480}$-ispSM | 3.48 ± 0.55 |

From the results in Table 19, the amount of formed isoprene was larger in 2256/pVK9-$P_{0480}$-IspSM strain than in 2256/pVK9-$P_{0480}$-IspSK strain. The amount of formed isoprene in 2256/pVK9-$P_{0480}$-IspSP strain was as low as in 2256/pVK9 strain. From the above results, the crude enzyme extract derived from the strain introduced with the isoprene synthase derived from *Mucuna* exhibited the highest activity to form isoprene.

Example 9

Effects of Introduction of Isoprene Synthase Derived from Various Plants on *Corynebacterium glutamicum* 2256 Strain 1) Effects of Introduction of Isoprene Synthase Derived From Various Plants on *C. glutamicum* 2256 Strain Microbial cells of 2256/pVK9, 2256/pVK9-$P_{0480}$-IspSK, 2256/pVK9-$P_{0480}$-IspSP or 2256/pVK9-$P_{0480}$-IspSM strain were evenly applied onto the CM-Dex plate containing 50 mg/L of kanamycin, and cultured at 30° C. for 18 to 24 hours. One loopful of the microbial cells from the resulting plate were inoculated to 1 mL of MM-glucose medium in a headspace vial. Next, the headspace vial was tightly sealed, and then the cells were cultured in a reciprocal shaking apparatus at 30° C. at 120 rpm for 24 hours. 22 mL CLEAR CRIMP TOP VIAL (Cat #B0104236) manufactured by Perkin Elmer was used as the headspace vial and the cap with the butyl rubber septum for the headspace vial (Cat #B0104240) manufactured by Perkin Elmer was used as the cap for tight sealing.

The composition of the MM-glucose medium is as described in Table 20.

TABLE 20

| Composition of MM-glucose medium | |
|---|---|
| Glucose | 10 g/L |
| $(NH_4)_2SO_4$ | 2.5 g/L |
| Urea | 2 g/L |
| MOPS | 40 g/L |
| $KH_2PO_4$ | 0.5 g/L |
| $MgSO_4 \cdot 7H_2O$ | 0.25 g/L |
| $CaCl_2$ | 10 mg/L |
| $FeSO_4$ | 10 mg/L |
| $MnSO_4$ | 10 mg/L |
| $CuSO_4$ | 0.02 mg/L |
| Biotin | 50 µg/L |
| Vitamin B1 | 100 µg/L |
| Protocatechuic acid | 15 mg/L | pH 7.0 (KOH)

If necessary, kanamycin was added at a final concentration of 50 mg/L.

A total volume was adjusted to 1 mL and the medium was sterilized by filtration.

After the completion of the culture, the concentration of isoprene in the headspace in the vial was measured by gas chromatography. The OD value was measured at 660 nm using the spectrophotometer (HITACHI U-2900).

The concentrations of isoprene formed from various microbial strains upon completion of the culture are described in Table 21.

TABLE 21

Amounts of isoprene produced in 2256/pVK9, 2256/pVK9-$P_{0480}$-IspSK, 2256/pVK9-$P_{0480}$-IspSP and 2256/pVK9-$P_{0480}$-IspSM strains upon completion of the culture

| Name of microbial strain | OD value | Amount (µg/L) of formed isoprene |
|---|---|---|
| C. glutamicum 2256/pVK9 | 2.22 ± 0.06 | ND |
| C. glutamicum 2256/pVK9-$P_{0480}$-ispSP | 2.48 ± 0.02 | ND |
| C. glutamicum 2256/pVK9-$P_{0480}$-ispSK | 2.38 ± 0.09 | 21.9 ± 0.2 |

TABLE 21-continued

Amounts of isoprene produced in 2256/pVK9, 2256/pVK9-$P_{O480}$-IspSK, 2256/pVK9-$P_{O480}$-IspSP and 2256/pVK9-$P_{O480}$-IspSM strains upon completion of the culture

| Name of microbial strain | OD value | Amount (µg/L) of formed isoprene |
|---|---|---|
| C. glutamicum 2256/pVK9-$P_{O480}$-ispSM | 2.33 ± 0.13 | 24.2 ± 0.1 |

From the results in Table 21, the amount of produced isoprene was larger in order of 2256/pVK9-$P_{O480}$-IspSM and 2256/pVK9-$P_{O480}$-IspSK. No isoprene was detected in 2256/pVK9 and 2256/pVK9-$P_{O480}$-IspSP. From the above results, the strain introduced with the isoprene synthase derived from *Mucuna* exhibited the highest ability to produce isoprene in wild strains of *C. glutamicum* 2256.

Example 10

Measurement of Enzymatic Activity of Isoprene Synthase Derived from Various Plants Using Crude Enzyme Extract Derived from *P. ananatis*

1) Construction of *P. ananatis* AJ13355 Strain Having Ability to Produce Isoprene Competent cells of *P. ananatis* AJ13355 were prepared, subsequently pSTV28-Ptac-Ttrp, pSTV28-Ptac-IspSK, pSTV28-Ptac-IspSP, or further pSTV28-Ptac-IspSM was introduced therein by the electroporation method, and the cells were evenly applied onto the LB plate containing 60 mg/L chloramphenicol and cultured at 30° C. for 18 hours. Subsequently, transformants exhibiting the resistance to chloramphenicol were obtained from the resulting plates. A strain in which pSTV28-Ptac-Ttrp, pSTV28-Ptac-IspSK, pSTV28-Ptac-IspSP, or pSTV28-Ptac-IspSM had been introduced into *P. ananatis* AJ13355 strain was designated as AJ13355/pSTV28-Ptac-Ttrp, AJ13355/pSTV28-Ptac-IspSK, AJ13355/pSTV28-Ptac-IspSP, or AJ13355/pSTV28-Ptac-IspSM strain, respectively.

2) Method of Preparing Crude Enzyme Extract

The activity of the crude enzyme was measured according to the method described in Example 4. Microbial cells of AJ13355/pSTV28-Ptac-Ttrp, AJ13355/pSTV28-Ptac-IspSK, AJ13355/pSTV28-Ptac-IspSP, or AJ13355/pSTV28-Ptac-IspSM strain were evenly applied onto the LB plate containing 60 mg/L of chloramphenicol and cultured at 30° C. for 18 hours. The microbial cells corresponding to ⅙ of the resulting plate were inoculated to a Sakaguchi flask in which 20 mL of LB containing 60 mg/L of chloramphenicol had been added, and cultured at 34° C. for 6 hours. The microbial cells from the culture medium were centrifuged at 6000 rpm at 4° C. for 5 minutes, and washed twice with ice-cold isoprene synthase buffer (50 mM Tris-HCl, pH 8.0, 20 mM $MgCl_2$, 5% glycerol). The washed microbial cells were suspended in 1.8 mL of the same buffer. About 0.9 mL of beads for disruption (YBG01, diameter 0.1 mm) and 0.9 mL of the microbial cell suspension were placed in a 2 mL tube specific for the multibead shocker, and the microbial cells were disrupted using the multibead shocker manufactured by Yasui Kikai Corporation at 2500 rpm at 4° C. for 3 cycles of ON for 30 seconds/OFF for 30 seconds. After the disruption, the tube was centrifuged at 20,000 g at 4° C. for 20 minutes, and a supernatant was used as a crude enzyme extract.

3) Measurement of Isoprene Synthase Activity

A total volume of 0.5 mL of the crude enzyme extract from AJ13355/pSTV28-Ptac-Ttrp, AJ13355/pSTV28-Ptac-IspSK, AJ13355/pSTV28-Ptac-IspSP, or AJ13355/pSTV28-Ptac-IspSM strain (quantified to be 2 mg as the amount of total protein by Bradford method) and the isoprene buffer was placed in a headspace vial (22 mL CLEAR CRIMP TOP VIAL (Cat #B0104236) manufactured by Perkin Elmer), then 0.025 mL of the 0.5 M $MgCl_2$ solution and 0.01 mL of the 0.2 M DMAPP (manufactured by Cayman, Catalog No. 63180) solution were added thereto, and the mixture was lightly vortexed. Then immediately, the vial was tightly sealed with the cap with the butyl rubber septum for the headspace vial (CRIMPS (Cat #B0104240) manufactured by Perkin Elmer), and kept at 37° C. for 2 hours.

After the completion of the reaction, the concentration of isoprene in the headspace of the vial was measured by gas chromatography.

TABLE 22

Results of measuring isoprene synthase activity in *P. ananatis* AJ13355 strains

| Microbial strain | Amount (mg/L) of formed isoprene |
|---|---|
| AJ13355/pSTV28-Ptac-Ttrp | 0.13 ± 0.02 |
| AJ13355/pSTV28-Ptac-IspSK | 0.58 ± 0.10 |
| AJ13355/pSTV28-Ptac-IspSM | 13.42 ± 1.67 |
| AJ13355/pSTV28-Ptac-IspSP | 0.23 ± 0.04 |

From the results in Table 22, the amount of formed isoprene was larger in order of AJ13355/pSTV28-Ptac-IspSM, AJ13355/pSTV28-Ptac-IspSK, AJ13355/pSTV28-Ptac-IspSP, and AJ13355/pSTV28-Ptac-Ttrp. From the above results, the crude enzyme extract from the strain introduced with the isoprene synthase derived from *Mucuna* exhibited the highest activity to form isoprene.

Example 11

Effects of Introduction of Isoprene Synthase Derived from Various Plants on *P. ananatis* AJ13355 Strain The ability to produce isoprene from glucose was compared in various *P. ananatis* AJ13355 strains in which the chloroplast localization signal had been deleted and the isoprene synthase had been introduced. Microbial cells of AJ13355/pSTV28-Ptac-Ttrp, AJ13355/pSTV28-Ptac-IspSK, AJ13355/pSTV28-Ptac-IspSP, or AJ13355/pSTV28-Ptac-IspSM strain were evenly applied onto the LB plate containing 60 mg/L of chloramphenicol and cultured at 30° C. for 18 hours. One loopful of the microbial cells from the resulting plate was inoculated to a 1 mL of M9 glucose medium in a headspace vial. Next, the vial was tightly sealed with the cap with the butyl rubber septum for the headspace vial (CRIMPS (Cat #B0104240) manufactured by Perkin Elmer), and cultured in the reciprocal shaking cultivation apparatus (120 rpm) at 30° C. for 24 hours. After completion of the cultivation, the concentration of isoprene in the headspace in the vial was measured by gas chromatography. The OD value was measured at 600 nm using the spectrophotometer (HITACHI U-2900). The concentration of isoprene and the OD value in various microbial strains upon completion of the cultivation are described in Table 23.

TABLE 23

Amount (µg/L) of produced isoprene and OD value when the cultivation was completed in AJ13355/pSTV28-Ptac-Ttrp, AJ13355/pSTV28-Ptac-IspSK, AJ13355/pSTV28-Ptac-IspSP, and AJ13355/pSTV28-Ptac-IspSM strains

| Name of microbial strain | OD value | Amount (µg/L) of produced isoprene |
|---|---|---|
| AJ13355/pSTV28-Ptac-Ttrp | 2.36 ± 0.11 | N.D. |
| AJ13355/pSTV28-Ptac-IspSK | 2.18 ± 0.09 | 50.0 ± 13.0 |
| AJ13355/pSTV28-Ptac-IspSM | 2.44 ± 0.11 | 63.0 ± 6.0 |
| AJ13355/pSTV28-Ptac-IspSP | 2.25 ± 0.18 | 12.0 ± 1.0 |

N.D. not detected

From the results in Table 23, the amount of produced isoprene was larger in order of AJ13355/pSTV28-Ptac-IspSM, AJ13355/pSTV28-Ptac-IspSK, AJ13355/pSTV28-Ptac-IspSP and AJ13355/pSTV28-Ptac-Ttrp strains. From the above results, the strain introduced with the isoprene synthase derived from *Mucuna* also exhibited the highest ability to produce isoprene in *P. ananatis* AJ13355 strains.

Example 12

Measurement of Enzymatic Activity of Isoprene Synthase Derived from Various Plants Using Crude Enzyme Extract Derived from *E. aerogenes* AJ110637

1) Construction of *E. aerogenes* AJ110637 Strain Having Ability to Produce Isoprene Competent cells of *E. aerogenes* AJ110637 were prepared, subsequently pSTV28-Ptac-Ttrp, pSTV28-Ptac-IspSK, pSTV28-Ptac-IspSP, or further pSTV28-Ptac-IspSM was introduced therein by the electroporation method, and the cells were evenly applied onto the LB plate containing 60 mg/L chloramphenicol and cultured at 37° C. for 18 hours. Subsequently, transformants exhibiting the resistance to chloramphenicol were obtained from the resulting plates. A strain in which pSTV28-Ptac-Ttrp, pSTV28-Ptac-IspSK, pSTV28-Ptac-IspSP, or pSTV28-Ptac-IspSM had been introduced into *E. aerogenes* AJ110637 strain was designated as AJ110637/pSTV28-Ptac-Ttrp, AJ110637/pSTV28-Ptac-IspSK, AJ110637/pSTV28-Ptac-IspSP, or AJ110637/pSTV28-Ptac-IspSM strain, respectively.

2) Method of Preparing Crude Enzyme Extract

The activity of the crude enzyme was measured according to the method described in Example 4. Microbial cells of AJ110637/pSTV28-Ptac-Ttrp, AJ110637/pSTV28-Ptac-IspSK, AJ110637/pSTV28-Ptac-IspSP, or AJ110637/pSTV28-Ptac-IspSM strain were evenly applied onto the LB plate containing 60 mg/L of chloramphenicol and cultured at 37° C. for 18 hours. The microbial cells corresponding to ⅙ of the resulting plate were inoculated to a Sakaguchi flask in which 20 mL of LB containing 60 mg/L of chloramphenicol had been added, and cultured at 37° C. for 4 hours. The microbial cells from the culture medium were centrifuged at 8,000 rpm at 4° C. for 10 minutes, and washed twice with ice-cold isoprene synthase buffer (50 mM Tris-HCl, pH 8.0, 20 mM $MgCl_2$, 5% glycerol). The washed microbial cells were suspended in 1.8 mL of the same buffer. About 0.9 mL of beads for disruption (YBG01, diameter 0.1 mm) and 0.9 mL of the microbial cell suspension were placed in a 2 mL tube specific for the multibead shocker, and the microbial cells were disrupted using the multibead shocker (MB701 (S) model) manufactured by Yasui Kikai Corporation at 2500 rpm at 4° C. for 3 cycles of ON for 30 seconds/OFF for 30 seconds. After the disruption, the tube was centrifuged at 20,000 g at 4° C. for 20 minutes, and a supernatant was used as a crude enzyme extract.

3) Measurement of Isoprene Synthase Activity

A total volume of 0.5 mL of the crude enzyme extract from AJ110637/pSTV28-Ptac-Ttrp, AJ110637/pSTV28-Ptac-IspSK, AJ110637/pSTV28-Ptac-IspSP, or AJ110637/pSTV28-Ptac-IspSM strain (quantified to be 2 mg as the amount of total protein by Bradford method) and the isoprene buffer was placed in a headspace vial (22 mL CLEAR CRIMP TOP VIAL (Cat #B0104236) manufactured by Perkin Elmer), then 0.025 mL of the 0.5 M $MgCl_2$ solution and 0.01 mL of the 0.2 M DMAPP (manufactured by Cayman, Catalog No. 63180) solution were added thereto, and the mixture was lightly vortexed. Then immediately, the vial was tightly sealed with the cap with the butyl rubber septum for the headspace vial (CRIMPS (Cat #B0104240) manufactured by Perkin Elmer), and kept at 37° C. for 2 hours.

After the completion of the reaction, the concentration of isoprene in the headspace of the vial was measured by gas chromatography.

The amount of formed isoprene in each microbial strain after reaction for 2 hours is described in Table 24.

TABLE 24

Results of measuring isoprene synthase activity in *E. aerogenes* AJ110637 strains

| Name of microbial strain | Amount (mg/L) of formed isoprene |
|---|---|
| AJ110637/pSTV28-Ptac-Ttrp | 0.13 ± 0.02 |
| AJ110637/pSTV28-Ptac-IspSK | 0.30 ± 0.04 |
| AJ110637/pSTV28-Ptac-IspSM | 1.46 ± 0.18 |
| AJ110637/pSTV28-Ptac-IspSP | 0.17 ± 0.03 |

From the results in Table 24, the amount of formed isoprene was larger in order of AJ110637/pSTV28-Ptac-IspSM, AJ110637/pSTV28-Ptac-IspSK, AJ110637/pSTV28-Ptac-IspSP and AJ110637/pSTV28-Ptac-Ttrp strains. From the above results, the crude enzyme extract from the strain introduced with the isoprene synthase derived from *Mucuna* exhibited the highest activity to form isoprene.

Example 13

Effects of Introduction of Isoprene Synthase Derived from Various Plants on *E. aerogenes* AJ110637 Strain The ability to produce isoprene from glucose was compared in various *E. aerogenes* AJ110637 strains in which the chloroplast localization signal had been deleted and the isoprene synthase had been introduced. Microbial cells of AJ110637/pSTV28-Ptac-Ttrp, AJ110637/pSTV28-Ptac-IspSK, AJ110637/pSTV28-Ptac-IspSP, or AJ110637/pSTV28-Ptac-IspSM strain were evenly applied onto the LB plate containing 60 mg/L of chloramphenicol and cultured at 30° C. for 18 hours. One loopful of the microbial cells from the resulting plate was inoculated to a 1 mL of M9 glucose medium in a headspace vial. Next, the vial was tightly sealed with the cap with the butyl rubber septum for the headspace vial (CRIMPS (Cat #B0104240) manufactured by Perkin Elmer), and cultured in the reciprocal shaking cultivation apparatus (120 rpm) at 30° C. for 24 hours. After completion of the cultivation, the concentration of isoprene in the headspace in the vial was measured by gas chromatography. The OD value was measured at 600 nm using the spectrophotometer (HITACHI U-2900). The concentration of isoprene and the OD value in various microbial strains upon completion of the cultivation are described in Table 25.

TABLE 25

Amount (μg/L) of produced isoprene and OD value when cultivation was completed in AJ110637/pSTV28-Ptac-Ttrp, AJ110637/pSTV28-Ptac-IspSK, AJ110637/pSTV28-Ptac-IspSP, and AJ110637/pSTV28-Ptac-IspSM strains

| Name of microbial strain | OD value | Amount (μg/L) of produced isoprene |
|---|---|---|
| AJ110637/pSTV28-Ptac-Ttrp | 3.12 ± 0.21 | N.D. |
| AJ110637/pSTV28-Ptac-IspSK | 3.08 ± 0.14 | 130.2 ± 14.3 |
| AJ110637/pSTV28-Ptac-IspSM | 3.20 ± 0.18 | 316.1 ± 26.2 |
| AJ110637/pSTV28-Ptac-IspSP | 3.09 ± 0.12 | 12.5 ± 0.8 |

N.D. not detected

From the results in Table 25, the amount of produced isoprene was larger in order of AJ110637/pSTV28-Ptac-IspSM, AJ110637/pSTV28-Ptac-IspSK, AJ110637/pSTV28-Ptac-IspSP and AJ110637/pSTV28-Ptac-Ttrp. From the above results, the strain introduced with the isoprene synthase derived from *Mucuna* also exhibited the highest ability to produce isoprene in *E. aerogenes* AJ110637 strains.

Example 14

Measurement of Enzymatic Activity of Isoprene Synthase Derived from Various Plants Using Crude Enzyme Extract Derived from *Saccharomyces cerevisiae*

1) Construction of Plasmid for Expressing IspS Gene Derived From Various Plants

Plasmids for expressing the IspSK gene, the IspSP gene and the IspSM gene in *S. cerevisiae* were constructed by the following procedure. PCR was performed with Prime Star polymerase (manufactured by Takara Bio Inc.) using the synthesized oligonucleotides represented by SEQ ID NOS:82 and 83 as the primers with pUC57-IspSK as the template, the synthesized oligonucleotides represented by SEQ ID NOS: 84 and 85 as the primers with pUC57-IspSP as the template, or the synthesized oligonucleotides represented by SEQ ID NOS:86 and 87 as the primers with pUC57-IspSM as the template. A reaction solution was prepared according to the composition attached to the kit, and the reaction was carried out for 30 cycles of 98° C. for 10 seconds, 55° C. for seconds and 72° C. for 120 seconds. As a result, PCR products containing the IspSK gene, the IspSP gene and the IspSM gene were obtained. Meanwhile, the shuttle vector pYES2 for *S. cerevisiae* and *E. coli* (Invitrogen, Cat No. V825-20) was digested with the restriction enzyme KpnI (manufactured by Takara Bio Inc.). Subsequently, the purified PCR fragment containing the IspSK gene was ligated to purified pYES2 treated with KpnI using In-fusion HD Cloning Kit (manufactured by Clontech). The resulting plasmid for expressing the IspSK gene was designated as pYES2-IspSK. Likewise, the purified PCR fragment containing the IspSP gene was ligated to purified pYES2 treated with KpnI using In-fusion HD Cloning Kit (manufactured by Clontech). The resulting plasmid for expressing the IspSP gene was designated as pYES2-IspSP. Likewise, the purified PCR fragment containing the IspSM gene was ligated to purified pYES2 treated with KpnI using In-fusion HD Cloning Kit (manufactured by Clontech). The resulting plasmid for expressing the IspSM gene was designated as pYES2-IspSM.

2) Construction of *S. cerevisiae* S288C Strain Having Ability to Produce Isoprene Competent cells of *S. cerevisiae* S288C were prepared using Frozen-EZ Yeast Transformation Kit II (ZYMO RESEARCH Cat. No. T2001). pYES2, pYES2-IspSK, pYES2-IspSP, or pYES2-IspSM was introduced into the competent cells of *S. cerevisiae* S288C strain according to the protocol of the same kit. The cells were evenly applied onto an SD-Ura plate, and cultured at 30° C. for 2 days. Subsequently, transformants that had lost Ura requirement were obtained from the resulting plates. The composition of the SD-Ura medium is as described in Table 26. A strain in which pYES2, pYES2-IspSK, pYES2-IspSP, or pYES2-IspSM had been introduced into *S. cerevisiae* S288C strain was designated as S288C/pYES2, S288C/pYES2-IspSK, S288C/pYES2-IspSP, or S288C/pYES2-IspSM strain, respectively.

TABLE 26

| SD-Ura medium | |
|---|---|
| Yeast Nitrogen Base w/o AA (Difco, Cat No. 291940) | 6.7 g/L |
| -Ura DO supplement (Clontech, Cat No. 630416) | 0.77 g/L |
| Glucose | 20 g/L (sterilized separately) |
| Agar | 20 g/L (only when required) | pH 5.6 to 6.0 (KOH)
Sterilized at 120° C. for 15 minutes

3) Method of Preparing Crude Enzyme Extract

Microbial cells of S288C/pYES2, S288C/pYES2-IspSK, S288C/pYES2-IspSP, or S288C/pYES2-IspSM strain were evenly applied to the SD-Ura plate and cultured at 30° C. for 24 hours. The microbial cells corresponding to ¼ of the resulting plate were inoculated to a Sakaguchi flask in which 50 mL of SD-Ura galactose (SD-Ura medium in which glucose was replaced with galactose), and cultured at 30° C. for 16 hours. The composition of the SD-Ura galactose medium is shown in Table 27. The microbial cells were separated from the culture medium by centrifugation at 3,000 rpm for 5 minutes, and washed twice with the isoprene synthase buffer (50 mM Tris-HCl, pH 8.0, 20 mM $MgCl_2$, 5% glycerol). The washed microbial cells were suspended in 1.8 mL of the same buffer. About 0.9 mL of beads for disruption (YBG05, diameter 0.5 mm) and 0.9 mL of the microbial cell suspension were placed in a 2 mL tube specific for the multibead shocker, and the microbial cells were disrupted using the multibead shocker (MB701 (S) model) manufactured by Yasui Kikai Corporation at 2500 rpm for 12 cycles of ON for 60 seconds/OFF for 60 seconds. After the disruption, the tube was centrifuged at 20,000 g for 20 minutes, and a supernatant was used as a crude enzyme extract.

TABLE 27

| SD-Ura Galactose medium | |
|---|---|
| Yeast Nitrogen Base w/o AA (Difco, Cat No. 291940) | 6.7 g/L |
| -Ura DO supplement (Clontech, Cat No. 630416) | 0.77 g/L |
| Galactose | 20 g/L (sterilized separately) |
| Agar | 20 g/L (only when required) | pH 5.6 to 6.0 (KOH)
Sterilized at 120° C. for 15 minutes

4) Measurement of Isoprene Synthase Activity

A protein concentration of the crude enzyme extracts from S288C/pYES2, S288C/pYES2-IspSK, S288C/pYES2-IspSP and S288C/pYES2-IspSM strains was measured by the bicinchonic acid method (BCA method). BCA protein assay reagent kit (Thermo Scientific Japan, Cat #23227) was used as reagents for the measurement. 0.4 mg of the crude enzyme extract as the amount of total protein and the isoprene buffer were combined and prepared to make total 0.25 mL. This was placed in a headspace vial, subsequently 0.0125 mL of the 0.5 M $MgCl_2$ solution and 0.005 mL of the 0.2 M DMAPP (manufactured by Cayman, Cat No. 63180) solution were added thereto, and the mixture was lightly vortexed. Then immediately, the vial was tightly sealed with the cap with the butyl rubber septum for the headspace vial (Cat #B0104240) manufactured by Perkin Elmer, and the reaction was carried out at 37° C. for 2 hours. After the reaction, the concentration of isoprene in the headspace in the vial was measured by gas chromatography. 22 mL CLEAR CRIMP TOP VIAL (Cat #B0104236) manufactured by Perkin Elmer was used as the headspace vial and the cap with the butyl rubber septum for the headspace vial (Cat #B0104240) manufactured by Perkin Elmer was used as the cap for tight sealing.

The amounts of isoprene formed in various microbial strains after the reaction for 2 hours are described in Table 28.

TABLE 28

Amounts of isoprene formed in S288C/pYES2, S288C/pYES2-IspSK, S288C/pYES2-IspSP and S288C/pYES2-IsoSM strains after reaction for 2 hours

| Name of microbial strain | Amount (µg/L) of formed isoprene |
|---|---|
| S. cerevisiae S288C/pYES2 | 70.33 ± 5.64 |
| S. cerevisiae S288C/pYES2-IspSP | 66.74 ± 0.09 |
| S. cerevisiae S288C/pYES2-IspSK | 86.02 ± 3.05 |
| S. cerevisiae S288C/pYES2-IspSM | 119.72 ± 6.57 |

From the results in Table 28, the amount of formed isoprene was larger in S288C/pYES2-IspSM strain than in S288C/pYES2-IspSK strain, and lower in S288C/pYES2-IspSP strain and S288C/pYES2 strain. From the above results, the crude enzyme extract from the strain introduced with the isoprene synthase derived from Mucuna exhibited the highest activity to form isoprene.

Example 15

Effects of Introduction of Isoprene Synthase Derived from Various Plants on *Saccharomyces cerevisiae* S288C Strain 1) Effects of Introduction of Isoprene Synthase Derived From Various Plants on *S. cerevisiae* S288C Strain Microbial cells of S288C/pYES2, S288C/pYES2-IspSK, S288C/pYES2-IspSP or S288C/pYES2-IspSM were evenly applied onto a YDP plate, and cultured at 30° C. for 18 to 24 hours. One loopful of the microbial cells from the resulting plate were inoculated to 1 mL of SD-Ura2 medium (containing each 1 g/L of glucose and galactose) in a headspace vial (22 mL CLEAR CRIMP TOP VIAL (Cat #B0104236) manufactured by Perkin Elmer), the vial was tightly sealed with a cap with butyl rubber septum for the head space vial (CRIMPS (Cat #B0104240) manufactured by Perkin Elmer), and the microbial cells were cultured at 30° C. at 120 rpm for 24 hours using the reciprocal shaking cultivation apparatus. The compositions of the YPD medium and SD-Ura2 medium are described in Tables 29 and 30, respectively.

TABLE 29

Composition of YPD medium

| Yeast extract | 10 g/L |
| Peptone | 10 g/L |
| Glucose | 20 g/L (sterilized separately) |
| Agar | 20 g/L (only when required) | pH 5.6 to 6.0 (KOH)
Sterilized at 120° C. for 15 minutes

TABLE 30

SD-Ura2 medium

| Yeast nitrogen base w/o AA (Difco,0 Cat No. 291940 | 6.7 g/L |
| -Ura D0 supplement (Clontech, Cat No. 630416) | 0.77 g/L |
| Glucose | 1 g/L (sterilized separately) |
| Galactose | 1 g/L (sterilized separately) |
| Agar | 20 g/L (only when required) | pH 5.6 to 6.0 (KOH)
Sterilized at 120° C. for 15 minutes

After completion of the cultivation, the concentration of isoprene in the headspace in the vial was measured by gas chromatography.

The OD value was measured at 600 nm using the spectrophotometer (HITACHI U-2900). The concentration in each microbial strain upon completion of the cultivation is described in Table 31.

TABLE 31

Amounts (µg/L) of produced isoprene when cultivation was completed in S288C/pYES2, S288C/pYES2-IspSK, S288C/pYES2-IspSP and S288C/pYES2-IspSM strains

| Strains | OD600 | Isoprene (µg/L) |
|---|---|---|
| S. cerevisiae S288C/pYES2_2 | 2.76 ± 0.48 | ND |
| S. cerevisiae S288C/pYES2-ispSK-72 | 2.59 ± 0.09 | 13.05 ± 0.09 |
| S. cerevisiae S288C/pYES2-ispSP-101 | 2.48 ± 0.20 | ND |
| S. cerevisiae S288C/pYES2-ispSM-201 | 2.76 ± 0.18 | 16.15 ± 0.09 |

From the results in Table 31, the amount of produced isoprene was larger in S288C/pYES2-IspSM than S288C/pYES2-IspSK. No isoprene was detected in S288C/pYES2 and S288C/pYES2-IspSP. From the above results, the strain introduced with the isoprene synthase derived from Mucuna exhibited the highest ability to produce isoprene in the wild strains.

Example 16

Comparison of Stability of Isoprene Synthase

1) Construction of Plasmid for Expression

A plasmid for abundantly expressing the isoprene synthase derived from Mucuna was constructed by the following procedure. A vector was made by PCR using the synthesized oligonucleotides represented by SEQ ID NO:88 and 89 with pCold-TF (manufactured by TaKaRa, #3365, its sequence information is obtained from GenBank/EMBL/DDBJ accession ID AB213654) as the template. An insert was made by PCR using the synthesized oligonucleotides represented by SEQ ID NOS:90 and 91 with pUC57-IspSM as the template. PrimeStar HS (manufactured by Takara Bio Inc.) was used as the polymerase for PCR. The reaction solution was prepared according to the composition attached to the kit. The reaction was carried out by repeating a cycle of 95° C. for 10 seconds, 55° C. for 5 seconds and 72° C. for 6 minutes 30 times. The resulting these DNA fragments were ligated using In-Fusion HD Cloning Kit (manufactured by Clontech). The constructed plasmid was designated as pCold-TF-IspSM. The nucleotide sequence of pCold-TF-IspSM is represented by SEQ ID NO:92.

A plasmid for abundantly expressing the isoprene synthase derived from Poplar was constructed by the following procedure. A vector was made by PCR using the synthesized oligonucleotides represented by SEQ ID NO:88 and 89 with pCold-TF as the template. An insert was made by PCR using the synthesized oligonucleotides represented by SEQ ID NOS:93 and 94 with pUC57-ispSP as the template. PrimeStar HS (manufactured by Takara Bio Inc.) was used as the polymerase for PCR. The reaction solution was prepared according to the composition attached to the kit. The reaction was carried out by repeating a cycle of 95° C. for 10 seconds, 55° C. for 5 seconds and 72° C. for 6 minutes 30 times. The resulting these DNA fragments were ligated using In-Fusion HD Cloning Kit (manufactured by Clontech). The constructed plasmid was designated as pCold-TF-IspSP. The nucleotide sequence of pCold-TF-IspSP is represented by SEQ ID NO:95.

A plasmid for abundantly expressing the isoprene synthase derived from Kudzu was constructed by the following procedure. A vector was made by PCR using the synthesized oligonucleotides represented by SEQ ID NO:88 and 89 with pCold-TF as the template. An insert was made by PCR using the synthesized oligonucleotides represented by SEQ ID NOS:96 and 97 with pUC57-ispSK as the template. PrimeStar HS (manufactured by Takara Bio Inc.) was used as the polymerase for PCR. The reaction solution was prepared according to the composition attached to the kit. The reaction was carried out by repeating a cycle of 95° C. for 10 seconds, 55° C. for 5 seconds and 72° C. for 6 minutes 30 times. The resulting these DNA fragments were ligated using In-Fusion HD Cloning Kit (manufactured by Clontech). The constructed plasmid was designated as pCold-TF-IspSK. The nucleotide sequence of pCold-TF-IspSK is represented by SEQ ID NO:98.

In the construction of these expression vectors, the isoprene synthase was designed to be expressed as a protein fused with a trigger factor (TF) at its N terminus. The fusion protein of the isoprene synthase and TF was designated as TF-IspS. The fusion proteins derived from *Mucuna*, Poplar and Kudzu were designated as TF-IspSM, TF-IspSP and TF-IspSK, respectively.

Competent cells of *E. coli* BL21 (DE3) (one shot BL21 (DE3) manufactured by Life Technologies) were transformed with pCold-TF-IspSM, pCold-TF-IspSP or pCold-TF-IspSK by a heat shock method. After heat shock at 42° C. for 30 seconds, the cells were recovered by culturing in SOC medium at 37° C. at 120 rpm for one hour. Subsequently, all of the cells were seeded on the LB plate containing 100 mg/L of ampicillin and cultured statically at 37° C. for 14 hours.

2) Cultivation for Preparation of Isoprene Synthase in Large Amount

A formed colony was picked up, inoculated to 5 mL of the LB medium containing 100 mg/L of ampicillin, and cultured at 37° C. at 200 rpm until OD600 value reached 1.0. After confirming that the OD value reached 1.0, the total cells were inoculated to a 500 mL Sakaguchi flask in which 100 mL of LB medium containing 100 mg/L of ampicillin, and cultured at 37° C. at 200 rpm until OD600 value reached 1.0. Subsequently, 1 M isopropyl-β-thiogalactopyranoside (IPTG) was added at a final concentration of 1 mM, and the cells were cultured at 15° C. at 100 rpm overnight. After completion of the cultivation, the microbial cells were collected by centrifugation at 8,000×g for 10 minutes, and stored at −20° C. until the purification was performed.

3) Purification of Isoprene Synthase

The isoprene synthase was purified using a His-tag column. The microbial cells obtained from 100 mL of the broth after completion of the cultivation were suspended in 240 mL of a disruption buffer composed of 50 mM phosphate buffer (pH 8.0) and 500 mM NaCl, and disrupted using a sonication machine (Sonifier 250 manufactured by Baransan) under a condition of duty cycle 50% and output control 6 on ice for 8 minutes. After the sonication, a disruption supernatant was obtained by centrifugation at 14,000×g for 20 minutes. The following purification steps were all carried out at 4° C. His-select nickel affinity gel (manufactured by Sigma) corresponding to 2 mL of a bed volume was applied to a polyprep column (manufactured by BioRad) and filled by a gravity method. Subsequently, 10 mL of the disruption buffer was applied to the column, and equilibrated by the gravity method. A total volume of the disruption supernatant after the sonication was applied to this column and TF-IspS was adsorbed to the column.

It was confirmed that the total volume of the applied disruption supernatant passed through the column, and then the column was washed with 10 mL of the disruption buffer. The column was further additionally washed with 10 mL of buffer for measuring the activity, composed of 50 mM Tris-HCl (pH 8.0) and 15 mM $MgCl_2$. Subsequently, 4 mL of a washing solution composed of 50 mM Tris-HCl (pH 8.0), 15 mM $MgCl_2$ and 10 mM imidazole was applied to the column, and a passed solution was discarded. Finally, 4 mL of an eluant composed of 50 mM Tris-HCl (pH 8.0), 15 mM $MgCl_2$ and 200 mM imidazole was applied to the column to elute TF-IspS. TF-IspS after the elution was concentrated by a gel filtration column (Amicon Ultra MWCO100k manufactured by Millipore).

Subsequently, the fused portion of the TF-IspS fusion protein was cleaved. Factor Xa (manufactured by Novagen) was used for the cleavage. A reaction buffer was composed of 50 mM Tris-HCl (pH 8.0), 100 mM NaCl and 5 mM $CaCl_2$, 26 U of Factor Xa was added, and the reaction was carried out at 4° C. for 14 hours. TF was removed from the reaction solution by utilizing the fact that TF alone is adsorbed to the His-select nickel affinity gel by passing the reaction solution after the reaction through the His-select nickel affinity gel. Subsequently, IspS was concentrated by a gel filtration column (Amicon Ultra MWCO50k manufactured by Millipore). The resulting concentrated solution was developed on NuPAGE 4 to 12% (manufactured by Life Technologies) to test a purity. As a result of staining the developed gel with CBB, no band derived from impurities other than IspS was observed. Thus, the purity was estimated to be about 99%.

The IspSM solution and the IspSK solution thus obtained were stored in the buffer for measuring the activity, to which glycerol was added at a final concentration of 5%, in a freezer at −80° C. until being subjected to the measurement of the activity. The IspSP solution was stored in the same buffer to which PEG600 was added at a final concentration of 5% in the freezer at −80° C. until being subjected to the measurement of the activity.

4) Measurement of Isoprene Synthase Activity

IspSM, IspSK and IspSP were thawed on ice, and glycerol and PEG600 were removed by buffer exchange. Protein concentrations were unified by colorimetric quantification on SDS-PAGE. 50 μL of an isoprene reaction solution was composed of 50 mM Tris-HCl, pH 8.0, 15 mM $MgCl_2$, 4 mM DMAPP and 1 µg of IspS. This 50 µL of the isoprene reaction solution was placed in a 0.2 mL PCR tube (manufactured by Nippon Genetics Co., Ltd.), and a hole was made in its cap. Subsequently, this tube was placed in a 22 mL vial (manufactured by Perkin Elmer) in which 450 µL of purified water had been added, and then immediately the vial was tightly sealed with the cap with the butyl rubber septum for the headspace vial (manufactured by Perkin Elmer). The reaction for forming isoprene was carried out at 40° C. for 238 hours. Formed isoprene was quantified according to the method described in 4-2) and 4-3). The results are shown in Table 32. As is shown in the results, it was demonstrated that the isoprene synthase derived from Mucuna had about 10 times higher ability to produce isoprene than the isoprene synthase derived from Kudzu.

TABLE 32

Comparison of accumulated isoprene amounts by IspS (238 hours, reaction at 40° C.)

| Type of IspS | isp (µmol/L/mg IspS) | SEM (n = 2) | Conc.* | Purity** |
|---|---|---|---|---|
| IspSM | 254.7 | 4.2 | 20 mg/L | >99% |
| IspSK | 25.7 | 4.0 | 20 mg/L | >99% |

*Concentration of IspS
**Purity of IspS

5) Comparison of Stability of Isoprene Synthase

Each IspS purified by the above method was stored in a solution of 50 mM Tris-HCl (pH 8.0) and 15 mM $MgCl_2$ at 4° C. for 48 hours. The amount of isoprene produced by the enzymatic reaction of each isoprene synthase before and after the storage was analyzed by gas chromatography according to the aforementioned method. The residual activities were compared by dividing the amount of isoprene produced after the storage by the amount of isoprene produced before the storage. As a result, it was demonstrated that the isoprene synthase derived from Mucuna had the more excellent stability than the isoprene synthase derived from Kudzu and the isoprene synthase derived from Poplar.

TABLE 33

Comparison of residual activity of each IspS (after stored at 4° C. for 48 hours)

| Type of IspS | Residual activity |
|---|---|
| IspSM | 66% |
| IspSK | 9% |
| IspSP | 23% |

The invention claimed is:

1. An isolated complementary DNA (cDNA) of the following (a) or (b):
   (a) a DNA comprising (i) the nucleotide sequence of SEQ ID NO:1, or (ii) the nucleotide sequence consisting of the nucleotide residues at positions 133 to 1785 in the nucleotide sequence of SEQ ID NO:1; or
   (b) a DNA that comprises a nucleotide sequence having 95% or more identity to the nucleotide sequence of (i) or (ii), and encodes a protein having an isoprene synthase activity.

2. The cDNA according to claim 1, wherein the polynucleotide is obtained from Mucuna.

3. An isolated protein of the following (A), (B), or (C):
   (A) a protein comprising a methionine residue at the N-terminus and (1) the amino acid sequence consisting of the amino acid residues at positions 45 to 594 in the amino acid sequence of SEQ ID NO:2, wherein the methionine residue is linked to the amino acid sequence (1);
   (B) a protein that comprises a methionine residue at the N-terminus and (2) an amino acid sequence having 95% or more identity to the amino acid sequence of (1), and has an isoprene synthase activity, wherein the methionine residue is linked to the amino acid sequence (2); or
   (C) a protein that comprises a methionine residue at the N-terminus and (3) an amino acid sequence having a deletion, substitution, addition or insertion of one to twenty amino acids in the amino acid sequence of (1), and has an isoprene synthase activity, wherein the methionine residue is linked to the amino acid sequence (3).

4. An expression vector comprising a polynucleotide of the following (a), (b), or (c):
   (a) a polynucleotide comprising (i) the nucleotide sequence of SEQ ID NO:1, or (ii) the nucleotide sequence consisting of the nucleotide residues at positions 133 to 1785 in the nucleotide sequence of SEQ ID NO:1;
   (b) a polynucleotide that comprises a nucleotide sequence having 95% or more identity to the nucleotide sequence of (i) or (ii), and encodes a protein having an isoprene synthase activity; or
   (c) a polynucleotide that hybridizes under a stringent condition with a polynucleotide consisting of the nucleotide sequence complementary to the nucleotide sequence of (i) or (ii), and encodes a protein having an isoprene synthase activity, wherein the stringent condition is hybridization in 6×SCC at about 45° C. followed by one or two or more washings in 0.2×SCC and 0.1% SDS at 65° C., or
   a polynucleotide encoding a protein of the following (A), (B), or (C):
   (A) a protein comprising (i') the full length amino acid sequence of SEQ ID NO:2, or (ii') the amino acid sequence consisting of the amino acid residues at positions 45 to 594 in the amino acid sequence of SEQ ID NO:2;
   (B) a protein that comprises an amino acid sequence having 95% or more identity to the amino acid sequence of (i') or (ii'), and has an isoprene synthase activity; or
   (C) a protein that comprises an amino acid sequence having a deletion, substitution, addition or insertion of one to twenty amino acids in the amino acid sequence of (i') or (ii'), and has an isoprene synthase activity.

5. An isolated transformant prepared by introducing the expression vector according to claim 4 into a host.

6. The transformant according to claim 5, wherein the host has an ability to synthesize dimethylallyl diphosphate via a methylerythritol phosphate pathway.

7. The transformant according to claim 6, wherein the host is *Escherichia coli*.

8. The transformant according to claim 5, wherein the transformant has an ability to synthesize dimethylallyl diphosphate via both a mevalonate pathway and a methylerythritol phosphate pathway.

9. The transformant according to claim 5, wherein the host is a microorganism belonging to the genus *Corynebacterium, Pantoea, Enterobacter*, or *Saccharomyces*.

10. A method of producing a protein, comprising forming the protein using the transformant according to claim 5, wherein the protein is encoded by a polynucleotide of the following (a), (b) or (c):
   (a) a polynucleotide comprising (i) the nucleotide sequence of SEQ ID NO:1, or (ii) the nucleotide sequence consisting of the nucleotide residues at positions 133 to 1785 in the nucleotide sequence of SEQ ID NO:1;
   (b) a polynucleotide that comprises a nucleotide sequence having 95% or more identity to the nucleotide sequence of (i) or (ii), and encodes a protein having an isoprene synthase activity; or
   (c) a polynucleotide that hybridizes under a stringent condition with a polynucleotide consisting of the nucleotide sequence complementary to the nucleotide sequence of (i) or (ii), and encodes a protein having an isoprene synthase activity, wherein the stringent condition is hybridization in 6×SCC at about 45° C. followed by one or two or more washings in 0.2×SCC and 0.1% SDS at 65° C., or
   a polynucleotide encoding a protein of the following (A), (B), or (C):
   (A) a protein comprising (i') the full length amino acid sequence of SEQ ID NO:2, or (ii') the amino acid sequence consisting of the amino acid residues at positions 45 to 594 in the amino acid sequence of SEQ ID NO:2;
   (B) a protein that comprises an amino acid sequence having 95% or more identity to the amino acid sequence of (i') or (ii'), and has an isoprene synthase activity; or
   (C) a protein that comprises an amino acid sequence having a deletion, substitution, addition or insertion of one to twenty amino acids in the amino acid sequence of (i') or (ii'), and has an isoprene synthase activity.

11. A method of producing an isoprene monomer, comprising forming the isoprene monomer from dimethylallyl diphosphate in the presence of the protein which is encoded by a polynucleotide of the following (a), (b) or (c):
   (a) a polynucleotide comprising (i) the nucleotide sequence of SEQ ID NO:1, or (ii) the nucleotide sequence consisting of the nucleotide residues at positions 133 to 1785 in the nucleotide sequence of SEQ ID NO:1;
   (b) a polynucleotide that comprises a nucleotide sequence having 95% or more identity to the nucleotide sequence of (i) or (ii), and encodes a protein having an isoprene synthase activity; or
   (c) a polynucleotide that hybridizes under a stringent condition with a polynucleotide consisting of the nucleotide sequence complementary to the nucleotide sequence of (i) or (ii), and encodes a protein having an isoprene synthase activity, wherein the stringent condition is hybridization in 6×SCC at about 45° C. followed by one or two or more washings in 0.2×SCC and 0.1% SDS at 65° C., or
   a polynucleotide encoding a protein of the following (A), (B), or (C):
   (A) a protein comprising (i') the full length amino acid sequence of SEQ ID NO:2, or (ii') the amino acid sequence consisting of the amino acid residues at positions 45 to 594 in the amino acid sequence of SEQ ID NO:2;
   (B) a protein that comprises an amino acid sequence having 95% or more identity to the amino acid sequence of (i') or (ii'), and has an isoprene synthase activity; or
   (C) a protein that comprises an amino acid sequence having a deletion, substitution, addition or insertion of one to twenty amino acids in the amino acid sequence of (i') or (ii'), and has an isoprene synthase activity.

12. The method according to claim 11, wherein the isoprene monomer is formed by culturing a transformant prepared by introducing an expression vector comprising the polynucleotide into a host.

13. The method according to claim 12, wherein the dimethylallyl diphosphate is supplied from a carbon source in a medium by culturing the transformant.

14. A method of producing an isoprene polymer, comprising (I) and (II):
   (I) forming an isoprene monomer by the method according to claim 11; and
   (II) polymerizing the isoprene monomer to form the isoprene polymer.

\* \* \* \* \*

SEQUENCE LISTING

```
<160> NUMBER OF SEQ ID NOS: 98

<210> SEQ ID NO 1
<211> LENGTH: 1785
<212> TYPE: DNA
<213> ORGANISM: Mucuna pruriens
<220> FEATURE:
<221> NAME/KEY: CDS
<222> LOCATION: (1)..(1785)

<400> SEQUENCE: 1 atg gca acc aac cct tca tgc tta tct act cca ttt ttg tcc tcc aca        48
Met Ala Thr Asn Pro Ser Cys Leu Ser Thr Pro Phe Leu Ser Ser Thr
1               5                   10                  15 cca gca cta agt act aga ttt cca tta agt gag aac ttc aca caa aaa        96
Pro Ala Leu Ser Thr Arg Phe Pro Leu Ser Glu Asn Phe Thr Gln Lys
            20                  25                  30 aca tct ctt gtc aat ccc aaa cct tgg cca ctt att tct gca gtc agc       144
Thr Ser Leu Val Asn Pro Lys Pro Trp Pro Leu Ile Ser Ala Val Ser
        35                  40                  45 tct caa ttt agc caa ata gca gaa gat aat agt cgt cgt tca gct aat       192
Ser Gln Phe Ser Gln Ile Ala Glu Asp Asn Ser Arg Arg Ser Ala Asn
    50                  55                  60 tac cac cca aac ctc tgg gat ttt gaa ttt ctg cag tct ctc gaa aat       240
Tyr His Pro Asn Leu Trp Asp Phe Glu Phe Leu Gln Ser Leu Glu Asn
65                  70                  75                  80 gac tct aag atg gaa aag ctg gaa gag aaa gca aca aag ttg gag gag       288
Asp Ser Lys Met Glu Lys Leu Glu Glu Lys Ala Thr Lys Leu Glu Glu
                85                  90                  95 gaa gtg cga aac atg atg aac gaa gca aag aca gaa gca cta agc tta       336
Glu Val Arg Asn Met Met Asn Glu Ala Lys Thr Glu Ala Leu Ser Leu
            100                 105                 110 ttg gaa ttg ata gac gac gtc cag cgt ctg gga ttg acc tac aag ttt       384
Leu Glu Leu Ile Asp Asp Val Gln Arg Leu Gly Leu Thr Tyr Lys Phe
        115                 120                 125
```

```
gag aag gac ata atc aaa gcc ctt gag aag att gtt cca ttg gat gag      432
Glu Lys Asp Ile Ile Lys Ala Leu Glu Lys Ile Val Pro Leu Asp Glu
    130                 135                 140 agt ggg ctg cat gtt act tct ctc agc ttc cgt ata ctt aga caa cat      480
Ser Gly Leu His Val Thr Ser Leu Ser Phe Arg Ile Leu Arg Gln His
145                 150                 155                 160 ggc ttt gag gtt tcc caa gat gtg ttt aag aga ttt aag gac aag gag      528
Gly Phe Glu Val Ser Gln Asp Val Phe Lys Arg Phe Lys Asp Lys Glu
                165                 170                 175 gga ggt ttt tgt gct gaa ctt aaa gac gat gtt caa ggg ttg cta agt      576
Gly Gly Phe Cys Ala Glu Leu Lys Asp Asp Val Gln Gly Leu Leu Ser
            180                 185                 190 cta tat gaa gca tcc tat ctt ggt ttt gag gga gaa agt ctc tta gac      624
Leu Tyr Glu Ala Ser Tyr Leu Gly Phe Glu Gly Glu Ser Leu Leu Asp
        195                 200                 205 gag gca agg gca ttt tca ata aca cat ctc aag aac aac cta aac aaa      672
Glu Ala Arg Ala Phe Ser Ile Thr His Leu Lys Asn Asn Leu Asn Lys
    210                 215                 220 gga ata aac acc aaa gta gcc caa caa gtt agc cat gca ctg gaa ctt      720
Gly Ile Asn Thr Lys Val Ala Gln Gln Val Ser His Ala Leu Glu Leu
225                 230                 235                 240 cct tat cat cga aga ctg cat aga ctg gaa gca cga tgg ctc ctt gac      768
Pro Tyr His Arg Arg Leu His Arg Leu Glu Ala Arg Trp Leu Leu Asp
                245                 250                 255 aaa tat gaa cca aag gaa ccc cac cat cat tta cta cac gag ctt gca      816
Lys Tyr Glu Pro Lys Glu Pro His His His Leu Leu His Glu Leu Ala
            260                 265                 270 aag ttg gat ttc aat ttg gtc caa tca ttg tac cag aaa gag ttg cga      864
Lys Leu Asp Phe Asn Leu Val Gln Ser Leu Tyr Gln Lys Glu Leu Arg
        275                 280                 285 gaa ttg tca ctg tgg tgg agg gag att ggg ctc aca agc aag ttg gac      912
Glu Leu Ser Leu Trp Trp Arg Glu Ile Gly Leu Thr Ser Lys Leu Asp
    290                 295                 300 ttt gtt cga gac aga tta atg gaa gtg tac ttt tgg gcg ctg gga atg      960
Phe Val Arg Asp Arg Leu Met Glu Val Tyr Phe Trp Ala Leu Gly Met
305                 310                 315                 320 gca cct gat cct caa ttt agt gaa tgt cgt aaa gtc gtc act aaa atg     1008
Ala Pro Asp Pro Gln Phe Ser Glu Cys Arg Lys Val Val Thr Lys Met
                325                 330                 335 ttt ggg cta gtt act atc atc gat gat gta tat gac gtt tac ggt act     1056
Phe Gly Leu Val Thr Ile Ile Asp Asp Val Tyr Asp Val Tyr Gly Thr
            340                 345                 350 ttg gac gag cta caa ctc ttc acc gat gct gtt gag aga tgg gac gtg     1104
Leu Asp Glu Leu Gln Leu Phe Thr Asp Ala Val Glu Arg Trp Asp Val
        355                 360                 365 aat gcg ata aat aca ctt cca gac tat atg aaa ttg tgc tat tta gcc     1152
Asn Ala Ile Asn Thr Leu Pro Asp Tyr Met Lys Leu Cys Tyr Leu Ala
    370                 375                 380 ctt tat aac acc gtc aat gac aca gct tat agc atc ctt aaa gaa aag     1200
Leu Tyr Asn Thr Val Asn Asp Thr Ala Tyr Ser Ile Leu Lys Glu Lys
385                 390                 395                 400 gga cat aac aac att tct tat ttg aca aaa tct tgg tgt gag ttg tgc     1248
Gly His Asn Asn Ile Ser Tyr Leu Thr Lys Ser Trp Cys Glu Leu Cys
                405                 410                 415 aaa gca ttc ctc caa gaa gca aaa tgg tca aac aac aaa atc att cca     1296
Lys Ala Phe Leu Gln Glu Ala Lys Trp Ser Asn Asn Lys Ile Ile Pro
            420                 425                 430 gca ttc aac aag tac cta gac aat gca tcg gtg tcc tcc tct ggt gtg     1344
Ala Phe Asn Lys Tyr Leu Asp Asn Ala Ser Val Ser Ser Ser Gly Val
```

```
                    435                 440                 445
gct ttg ctt gct cct tcc tac ttc tta gtg tgc caa gaa caa gac att    1392
Ala Leu Leu Ala Pro Ser Tyr Phe Leu Val Cys Gln Glu Gln Asp Ile
450                 455                 460 tca gac caa gct ctt cat tcc tta act aat ttc cat ggc ctt gtg cgt    1440
Ser Asp Gln Ala Leu His Ser Leu Thr Asn Phe His Gly Leu Val Arg
465                 470                 475                 480 tca tca tgc acc att ttt agg ctt tgc aat gat ctg gct acc tca tcg    1488
Ser Ser Cys Thr Ile Phe Arg Leu Cys Asn Asp Leu Ala Thr Ser Ser
                485                 490                 495 gct gag cta gag aga ggt gaa aca aca aat tca atc aca tcg tac atg    1536
Ala Glu Leu Glu Arg Gly Glu Thr Thr Asn Ser Ile Thr Ser Tyr Met
            500                 505                 510 cat gag aat gag act tct gag gag caa gca tgt aag gag ttg aga aat    1584
His Glu Asn Glu Thr Ser Glu Glu Gln Ala Cys Lys Glu Leu Arg Asn
        515                 520                 525 ttg atc gat gca gag tgg aag aag atg aat gaa gag cga gtt tca aat    1632
Leu Ile Asp Ala Glu Trp Lys Lys Met Asn Glu Glu Arg Val Ser Asn
    530                 535                 540 tct aca ctc cca aaa gca ttt agg gaa ata gct att aac atg gct cgg    1680
Ser Thr Leu Pro Lys Ala Phe Arg Glu Ile Ala Ile Asn Met Ala Arg
545                 550                 555                 560 att tcc cat tgc aca tac caa tat gga gac gga ctt gga agg ccc gac    1728
Ile Ser His Cys Thr Tyr Gln Tyr Gly Asp Gly Leu Gly Arg Pro Asp
                565                 570                 575 tac acc aca gag aac agg ata aag ttg cta cta ata gac cct ttt cca    1776
Tyr Thr Thr Glu Asn Arg Ile Lys Leu Leu Leu Ile Asp Pro Phe Pro
            580                 585                 590 att aat tag                                                        1785
Ile Asn

<210> SEQ ID NO 2
<211> LENGTH: 594
<212> TYPE: PRT
<213> ORGANISM: Mucuna pruriens

<400> SEQUENCE: 2

Met Ala Thr Asn Pro Ser Cys Leu Ser Thr Pro Phe Leu Ser Ser Thr
1               5                   10                  15

Pro Ala Leu Ser Thr Arg Phe Pro Leu Ser Glu Asn Phe Thr Gln Lys
            20                  25                  30

Thr Ser Leu Val Asn Pro Lys Pro Trp Pro Leu Ile Ser Ala Val Ser
        35                  40                  45

Ser Gln Phe Ser Gln Ile Ala Glu Asp Asn Ser Arg Arg Ser Ala Asn
    50                  55                  60

Tyr His Pro Asn Leu Trp Asp Phe Glu Phe Leu Gln Ser Leu Glu Asn
65                  70                  75                  80

Asp Ser Lys Met Glu Lys Leu Glu Glu Lys Ala Thr Lys Leu Glu Glu
                85                  90                  95

Glu Val Arg Asn Met Met Asn Glu Ala Lys Thr Glu Ala Leu Ser Leu
            100                 105                 110

Leu Glu Leu Ile Asp Asp Val Gln Arg Leu Gly Leu Thr Tyr Lys Phe
        115                 120                 125

Glu Lys Asp Ile Ile Lys Ala Leu Glu Lys Ile Val Pro Leu Asp Glu
    130                 135                 140

Ser Gly Leu His Val Thr Ser Leu Ser Phe Arg Ile Leu Arg Gln His
145                 150                 155                 160
```

-continued

```
Gly Phe Glu Val Ser Gln Asp Val Phe Lys Arg Phe Lys Asp Lys Glu
            165                 170                 175
Gly Gly Phe Cys Ala Glu Leu Lys Asp Asp Val Gln Gly Leu Leu Ser
        180                 185                 190
Leu Tyr Glu Ala Ser Tyr Leu Gly Phe Glu Gly Glu Ser Leu Leu Asp
    195                 200                 205
Glu Ala Arg Ala Phe Ser Ile Thr His Leu Lys Asn Asn Leu Asn Lys
210                 215                 220
Gly Ile Asn Thr Lys Val Ala Gln Gln Val Ser His Ala Leu Glu Leu
225                 230                 235                 240
Pro Tyr His Arg Arg Leu His Arg Leu Glu Ala Arg Trp Leu Leu Asp
                245                 250                 255
Lys Tyr Glu Pro Lys Glu Pro His His Leu Leu His Glu Leu Ala
            260                 265                 270
Lys Leu Asp Phe Asn Leu Val Gln Ser Leu Tyr Gln Lys Glu Leu Arg
        275                 280                 285
Glu Leu Ser Leu Trp Trp Arg Glu Ile Gly Leu Thr Ser Lys Leu Asp
    290                 295                 300
Phe Val Arg Asp Arg Leu Met Glu Val Tyr Phe Trp Ala Leu Gly Met
305                 310                 315                 320
Ala Pro Asp Pro Gln Phe Ser Glu Cys Arg Lys Val Val Thr Lys Met
                325                 330                 335
Phe Gly Leu Val Thr Ile Ile Asp Asp Val Tyr Asp Val Tyr Gly Thr
            340                 345                 350
Leu Asp Glu Leu Gln Leu Phe Thr Asp Ala Val Glu Arg Trp Asp Val
        355                 360                 365
Asn Ala Ile Asn Thr Leu Pro Asp Tyr Met Lys Leu Cys Tyr Leu Ala
    370                 375                 380
Leu Tyr Asn Thr Val Asn Asp Thr Ala Tyr Ser Ile Leu Lys Glu Lys
385                 390                 395                 400
Gly His Asn Asn Ile Ser Tyr Leu Thr Lys Ser Trp Cys Glu Leu Cys
                405                 410                 415
Lys Ala Phe Leu Gln Glu Ala Lys Trp Ser Asn Asn Lys Ile Ile Pro
            420                 425                 430
Ala Phe Asn Lys Tyr Leu Asp Asn Ala Ser Val Ser Ser Ser Gly Val
        435                 440                 445
Ala Leu Leu Ala Pro Ser Tyr Phe Leu Val Cys Gln Glu Gln Asp Ile
    450                 455                 460
Ser Asp Gln Ala Leu His Ser Leu Thr Asn Phe His Gly Leu Val Arg
465                 470                 475                 480
Ser Ser Cys Thr Ile Phe Arg Leu Cys Asn Asp Leu Ala Thr Ser Ser
                485                 490                 495
Ala Glu Leu Glu Arg Gly Glu Thr Thr Asn Ser Ile Thr Ser Tyr Met
            500                 505                 510
His Glu Asn Glu Thr Ser Glu Glu Gln Ala Cys Lys Glu Leu Arg Asn
        515                 520                 525
Leu Ile Asp Ala Glu Trp Lys Lys Met Asn Glu Glu Arg Val Ser Asn
    530                 535                 540
Ser Thr Leu Pro Lys Ala Phe Arg Glu Ile Ala Ile Asn Met Ala Arg
545                 550                 555                 560
Ile Ser His Cys Thr Tyr Gln Tyr Gly Asp Gly Leu Gly Arg Pro Asp
                565                 570                 575
Tyr Thr Thr Glu Asn Arg Ile Lys Leu Leu Leu Ile Asp Pro Phe Pro
```

580             585             590

Ile Asn

<210> SEQ ID NO 3
<211> LENGTH: 608
<212> TYPE: PRT
<213> ORGANISM: Pueraria montana

<400> SEQUENCE: 3

Met Ala Thr Asn Leu Leu Cys Leu Ser Asn Lys Leu Ser Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                  45

Ser Ser Gln Phe Thr Gln Ile Thr Glu His Asn Ser Arg Arg Ser Ala
    50                  55                  60

Asn Tyr Gln Pro Asn Leu Trp Asn Phe Glu Phe Leu Gln Ser Leu Glu
65                  70                  75                  80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
    130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175

Arg Phe Lys Asp Lys Glu Gly Gly Phe Ser Gly Glu Leu Lys Gly Asp
            180                 185                 190

Val Gln Gly Leu Leu Ser Leu Tyr Glu Ala Ser Tyr Leu Gly Phe Glu
        195                 200                 205

Gly Glu Asn Leu Leu Glu Glu Ala Arg Thr Phe Ser Ile Thr His Leu
    210                 215                 220

Lys Asn Asn Leu Lys Glu Gly Ile Asn Thr Lys Val Ala Glu Gln Val
225                 230                 235                 240

Ser His Ala Leu Glu Leu Pro Tyr His Gln Arg Leu His Arg Leu Glu
                245                 250                 255

Ala Arg Trp Phe Leu Asp Lys Tyr Glu Pro Lys Glu Pro His His Gln
            260                 265                 270

Leu Leu Leu Glu Leu Ala Lys Leu Asp Phe Asn Met Val Gln Thr Leu
        275                 280                 285

His Gln Lys Glu Leu Gln Asp Leu Ser Arg Trp Trp Thr Glu Met Gly
    290                 295                 300

Leu Ala Ser Lys Leu Asp Phe Val Arg Asp Arg Leu Met Glu Val Tyr
305                 310                 315                 320

Phe Trp Ala Leu Gly Met Ala Pro Asp Pro Gln Phe Gly Glu Cys Arg
                325                 330                 335

Lys Ala Val Thr Lys Met Phe Gly Leu Val Thr Ile Ile Asp Asp Val
            340                 345                 350

Tyr Asp Val Tyr Gly Thr Leu Asp Glu Leu Gln Leu Phe Thr Asp Ala

```
                    355                 360                 365
Val Glu Arg Trp Asp Val Asn Ala Ile Asn Thr Leu Pro Asp Tyr Met
    370                 375                 380

Lys Leu Cys Phe Leu Ala Leu Tyr Asn Thr Val Asn Asp Thr Ser Tyr
385                 390                 395                 400

Ser Ile Leu Lys Glu Lys Gly His Asn Asn Leu Ser Tyr Leu Thr Lys
                405                 410                 415

Ser Trp Arg Glu Leu Cys Lys Ala Phe Leu Gln Glu Ala Lys Trp Ser
                420                 425                 430

Asn Asn Lys Ile Ile Pro Ala Phe Ser Lys Tyr Leu Glu Asn Ala Ser
                435                 440                 445

Val Ser Ser Gly Val Ala Leu Leu Ala Pro Ser Tyr Phe Ser Val
    450                 455                 460

Cys Gln Gln Gln Glu Asp Ile Ser Asp His Ala Leu Arg Ser Leu Thr
465                 470                 475                 480

Asp Phe His Gly Leu Val Arg Ser Ser Cys Val Ile Phe Arg Leu Cys
                485                 490                 495

Asn Asp Leu Ala Thr Ser Ala Ala Glu Leu Glu Arg Gly Glu Thr Thr
                500                 505                 510

Asn Ser Ile Ile Ser Tyr Met His Glu Asn Asp Gly Thr Ser Glu Glu
                515                 520                 525

Gln Ala Arg Glu Glu Leu Arg Lys Leu Ile Asp Ala Glu Trp Lys Lys
    530                 535                 540

Met Asn Arg Glu Arg Val Ser Asp Ser Thr Leu Leu Pro Lys Ala Phe
545                 550                 555                 560

Met Glu Ile Ala Val Asn Met Ala Arg Val Ser His Cys Thr Tyr Gln
                565                 570                 575

Tyr Gly Asp Gly Leu Gly Arg Pro Asp Tyr Ala Thr Glu Asn Arg Ile
                580                 585                 590

Lys Leu Leu Leu Ile Asp Pro Phe Pro Ile Asn Gln Leu Met Tyr Val
                595                 600                 605

<210> SEQ ID NO 4
<211> LENGTH: 1827
<212> TYPE: DNA
<213> ORGANISM: Pueraria montana

<400> SEQUENCE: 4
atggcaacca accttttatg cttgtctaat aaattatcgt cccccacacc aacaccaagt     60
actagatttc cacaaagtaa gaacttcatc acacaaaaaa catctcttgc caatcccaaa    120
ccttggcgag ttatttgtgc tacgagctct caatttaccc aaataacaga cataatagt     180 cggcgttcag ctaattacca gccaaacctc tggaattttg aatttctgca gtctctggaa    240
aatgacctta aggtggaaaa actagaagag aaggcaacaa gctagagga ggaggtacga     300 tgcatgatca acagagtaga cacacaacca ttaagcttac tagaattgat cgacgatgtc    360
cagcgtctag gattgaccta caagtttgag aaggacataa tcaaagccct tgagaatatt    420
gttttgctgg atgagaataa gaaaaataaa agtgacctcc atgctactgc tctcagcttc    480
cgtttactta dacaacatgg ctttgaggtt tcccaagatg tgtttgagag atttaaggac    540
aaggagggag gtttcagtgg tgaacttaaa ggtgatgtgc aagggttgct gagtctatat    600
gaagcatcct atcttggctt tgagggagaa aatctcttgg aggaggcaag gacattttca    660
ataacacatc tcaagaacaa cctaaaagaa ggaataaaca ccaaagtggc agaacaagtt    720
```

```
agtcatgcac tggaacttcc ctatcatcaa agattgcata gactagaagc acgatggttc    780
cttgacaaat atgaaccaaa ggaaccccac catcagttac tactcgagct tgcaaagcta    840
gatttcaata tggtgcaaac attgcaccag aaagaactgc aagacctgtc aaggtggtgg    900
acggagatgg ggctagcaag caagctagac tttgtccgag acagattaat ggaagtgtat    960
ttttgggcgt tgggaatggc acctgatcct caattcggtg aatgtcgtaa agctgtcact   1020
aaaatgtttg gattggtcac catcatcgat gatgtatatg acgtttatgg tactttggat   1080
gagctacaac tcttcactga tgctgttgag agatgggacg tgaatgccat aaacacactt   1140
ccagactaca tgaagttgtg cttcctagca ctttataaca ccgtcaatga cacgtcttat   1200
agcatcctta agaaaaagg acacaacaac ctttcctatt tgacaaaatc ttggcgtgag   1260
ttatgcaaag cattccttca agaagcaaaa tggtcgaaca acaaaatcat tccagcattt   1320
agcaagtacc tggaaaatgc atcggtgtcc tcctccggtg tggctttgct tgctccttcc   1380
tacttctcag tgtgccaaca acaagaagat atctcagacc atgctcttcg ttctttaact   1440
gatttccatg gccttgtgcg ctcctcatgc gtcattttca gactctgcaa tgatttggct   1500
acctcagcgg ctgagctaga gaggggtgag acgacaaatt caataatatc ttatatgcat   1560
gagaatgacg gcacttctga agagcaagca cgtgaggagt tgagaaaatt gatcgatgca   1620
gagtggaaga agatgaaccg agagcgagtt tcagattcta cactactccc aaaagctttt   1680
atggaaatag ctgttaacat ggctcgagtt tcgcattgca cataccaata tggagacgga   1740
cttggaaggc cagactacgc cacagagaat agaatcaagt tgctacttat agacccctttt   1800 ccaatcaatc aactaatgta cgtgtaa                                       1827

<210> SEQ ID NO 5
<211> LENGTH: 1695
<212> TYPE: DNA
<213> ORGANISM: Artificial Sequence
<220> FEATURE:
<223> OTHER INFORMATION: Polynucleotide having modified codons, which
      encodes isoprene synthase derived from Pueraria montana (IspSK
      gene)

<400> SEQUENCE: 5
atgtgtgcga cctcttctca atttactcag attaccgagc ataattcccg tcgttccgca     60
aactatcagc caaacctgtg gaatttcgaa ttcctgcaat ccctggagaa cgacctgaaa    120
gtggaaaagc tggaggagaa agcgaccaaa ctggaggaag aagttcgctg catgatcaac    180
cgtgtagaca cccagccgct gtccctgctg gagctgatcg acgatgtgca cgcgcctgggt   240 ctgacctaca aatttgaaaa agacatcatt aaagccctgg aaaacatcgt actgctggac    300
gaaaacaaaa agaacaaatc tgacctgcac gcaaccgctc tgtctttccg tctgctgcgt    360
cagcacggtt tcgaggtttc tcaggatgtt tttgagcgtt tcaaggataa agaaggtggt    420
ttcagcggtg aactgaaagg tgacgtccaa ggcctgctga gcctgtatga agcgtcttac    480
ctgggtttcg agggtgagaa cctgctggag gaggcgcgta ccttttccat cacccacctg    540
aagaacaacc tgaaagaagg cattaatacc aaggttgcag aacaagtgag ccacgccctg    600
gaactgccat atcaccagcg tctgcaccgt tggaggcac gttggttcct ggataaaatac   660 gaaccgaaag aaccgcatca ccagctgctg ctggagctgg cgaagctgga tttttaacatg   720 gtacagaccc tgcaccagaa agagctgcaa gatctgtccc gctggtggac cgagatgggc    780
ctggctagca aactggattt tgtacgcgac cgcctgatgg aagtttattt ctgggcactg    840
ggtatggcgc cagacccgca gtttggtgaa tgtcgcaaag ctgttactaa aatgtttggt    900
```

```
ctggtgacga tcatcgatga cgtgtatgac gtttatggca ctctggacga actgcaactg    960
ttcaccgatg ctgtagagcg ctgggacgtt aacgctatta cacccctgcc ggactatatg   1020
aaactgtgtt tcctggcact gtacaacacc gttaacgaca cgtcctattc tattctgaaa   1080
gagaaaggtc ataacaacct gtcctatctg acgaaaagct ggcgtgaact gtgcaaagcc   1140
tttctgcaag aggcgaaatg gtccaacaac aaaattatcc cggctttctc caagtacctg   1200
gaaaacgcca gcgtttcctc ctccggtgta gcgctgctgg cgccgtctta cttttccgta   1260
tgccagcagc aggaagacat ctccgaccac gcgctgcgtt ccctgaccga cttccatggt   1320
ctggtgcgtt ctagctgcgt tatcttccgc ctgtgcaacg atctggccac ctctgcggcg   1380
gagctggaac gtggcgagac taccaattct atcattagct acatgcacga aaacgatggt   1440
accagcgagg aacaggcccg cgaagaactg cgtaaactga tcgacgccga atggaaaaag   1500
atgaatcgtg aacgcgttag cgactccacc ctgctgccta aagcgttcat ggaaatcgca   1560
gttaacatgg cacgtgtttc ccactgcacc taccagtatg cgatggtct gggtcgccca   1620 gactacgcga ctgaaaaccg catcaaactg ctgctgattg acccttttccc gattaaccag   1680 ctgatgtatg tctaa                                                    1695
```

<210> SEQ ID NO 6
<211> LENGTH: 595
<212> TYPE: PRT
<213> ORGANISM: Populus alba x Populus tremula

<400> SEQUENCE: 6

```
Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Phe Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Arg Val Phe Ala Ile Ser His Leu Lys Glu Leu Ser Glu
    210                 215                 220
```

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
            245                 250                 255

Glu Ala Tyr Arg Lys Glu Asp Ala Asn Gln Val Leu Leu Glu Leu
        260                 265                 270

Ala Ile Leu Asp Tyr Asn Met Ile Gln Ser Val Tyr Gln Arg Asp Leu
    275                 280                 285

Arg Glu Thr Ser Arg Trp Trp Arg Arg Val Gly Leu Ala Thr Lys Leu
    290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
                340                 345                 350

Thr Leu Asp Glu Leu Glu Leu Phe Thr Asp Ala Val Glu Arg Trp Asp
            355                 360                 365

Val Asn Ala Ile Asn Asp Leu Pro Asp Tyr Met Lys Leu Cys Phe Leu
370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
                420                 425                 430

Pro Thr Phe Asp Asp Tyr Phe Gly Asn Ala Trp Lys Ser Ser Ser Gly
            435                 440                 445

Pro Leu Gln Leu Ile Phe Ala Tyr Phe Ala Val Val Gln Asn Ile Lys
        450                 455                 460

Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
                500                 505                 510

Thr Lys Gly Ile Ser Glu Glu Leu Ala Thr Glu Ser Val Met Asn Leu
            515                 520                 525

Ile Asp Glu Thr Cys Lys Lys Met Asn Lys Glu Lys Leu Gly Gly Ser
530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595

<210> SEQ ID NO 7
<211> LENGTH: 1788
<212> TYPE: DNA
<213> ORGANISM: Populus alba x Populus tremula

<400> SEQUENCE: 7

```
atggcaactg aattattgtg cttgcaccgt ccaatctcac tgacacacaa actgttcaga    60
aatcccttac ctaaagtcat ccaggccact cccttaactt tgaaactcag atgttctgta   120
agcacagaaa acgtcagctt cacagaaaca gaaacagaag ccagacggtc tgccaattat   180
gaaccaaata gctgggatta tgattttttg ctgtcttcag acactgacga atcgattgaa   240
gtatacaaag acaaggccaa aaagctggag gctgaggtga aagagagat taacaatgaa   300
aaggcagagt ttttgactct gcttgaactg atagataatg tccaaaggtt aggattgggt   360
taccggttcg agagtgacat aaggagagcc ctcgacagat ttgtttcttc aggaggattt   420
gatggtgtta caaaaactag ccttcatgct actgctctta gcttcaggct tctcagacag   480
catggctttg aggtctctca agaagcgttc agtggattca aggatcaaaa tggcaatttc   540
ttggaaaacc ttaaggagga caccaaggca atactaagcc tatatgaagc ttcatttctt   600
gcattagaag gagaaaatat cttggatgag gccagggtgt tgcaatatc acatctaaaa   660
gagctcagcg aagaaaagat tggaaaagag ctggccgaac aggtgaatca tgcattggag   720
cttccattgc atcgcaggac gcaaagacta gaagctgttt ggagtattga agcataccgt   780
aaaaaggaag atgcaaatca agtactgcta gaacttgcta tattggacta caacatgatt   840
caatcagtat accaaagaga tcttcgcgag acatcaaggt ggtggaggcg agtgggtctt   900
gcaacaaagt tgcattttgc taaagacagg ttaattgaaa gcttttactg ggcagttgga   960
gttgcgttcg aacctcaata cagtgattgc cgtaattcag tagcaaaaat gttttcattt  1020
gtaacaatca ttgatgatat ctatgatgtt tatggtactc tggatgagct ggagctattt  1080
acagatgctg ttgagagatg ggatgttaac gccatcaatg atcttccgga ttatatgaag  1140
ctctgcttcc tagctctcta caacactatc aatgagatag cttatgacaa tctgaaggac  1200
aagggggaaa acattcttcc atacctaaca aaagcgtggg cagatttatg caatgcattc  1260
ctacaagaag caaaatggct gtacaataag tccacaccaa catttgatga ctatttcgga  1320
aatgcatgga atcatcctc agggcctctt caactaattt ttgcctactt tgccgtggtt  1380
caaaacatca gaaagagga aattgaaaac ttacaaaagt atcatgatat catcagtagg  1440
ccttcccaca tctttcgtct ttgcaacgac ctggcttcag catcggctga atagcgaga   1500
ggtgaaactg cgaattccgt atcctgctac atgcgtacaa aaggcatttc tgaggaactt  1560
gctactgaat ccgtaatgaa tttgatcgac gaaacctgta aaaagatgaa caaagaaaag  1620
cttggtggct ctttgtttgc aaaaccttt gtcgaaacag ctattaaccct tgcacggcaa  1680
tcccattgca cttatcataa cggagatgcg catacttcac cagacgagct aactaggaaa  1740
cgtgtcctgt cagtaatcac agagcctatt ctacccttg agagataa                1788
```

<210> SEQ ID NO 8
<211> LENGTH: 1680
<212> TYPE: DNA
<213> ORGANISM: Artificial Sequence
<220> FEATURE:
<223> OTHER INFORMATION: Polynucleotide having modified codons, which
      encodes isoprene synthase derived from Populus alba x Populus
      tremula (IspSP gene)

<400> SEQUENCE: 8

```
atgtgctctg tttctaccga gaacgtttcc ttcactgaga cggaaaccga ggcacgtcgt    60
agcgcgaact acgagccgaa tagctgggac tacgatttcc tgctgtcttc cgatactgac   120
gaatctattg aggtgtacaa agacaaagca agaaactgg aggctgaagt gcgccgcgaa   180
```

```
attaacaacg agaaagctga attcctgact ctgctggagc tgatcgataa cgtacagcgc    240
ctgggtctgg gttaccgctt cgaatctgat atccgtcgcg cactggatcg tttcgtaagc    300
agcggcggtt tcgatggcgt gaccaaaacg agcctgcacg ctaccgcgct gtccttccgt    360
ctgctgcgtc agcacggctt cgaagtttct caggaagcat tctccggttt caaagatcaa    420
aacggtaact tcctggaaaa cctgaaagaa gacactaagg cgatcctgag cctgtatgag    480
gcaagctttc tggccctgga gggtgagaac atcctggatg aggcgcgcgt attcgccatc    540
tcccatctga aagagctgtc tgaagagaaa atcggtaagg aactggcaga gcaggttaat    600
cacgcactgg aactgccgct gcatcgtcgt acccagcgtc tggaggcggt ttggtccatc    660
gaagcgtacc gcaaaaagga ggatgctaac caggttctgc tggaactggc catcctggac    720
tacaacatga tccagtccgt ttaccagcgt gatctgcgtg aaacctcccg ttggtggcgc    780
cgtgtgggcc tggcgaccaa actgcacttc gctaaggacc gcctgattga gtcttttttac   840 tgggcagtcg gcgttgcgtt cgaacctcag tattctgact gccgtaacag cgttgcgaaa    900
atgttcagct tcgttactat tatcgacgac atctacgacg tttacggtac tctggacgag    960
ctggaactgt ttaccgacgc tgtcgaacgt tgggatgtta acgccatcaa cgatctgcct   1020
gactacatga aactgtgctt cctggcactg tataacacga tcaacgaaat tgcatacgac   1080
aacctgaaag acaaaggtga aaacatcctg ccgtacctga ctaaagcgtg gcggatctg    1140 tgtaacgctt ttctgcaaga agcgaaatgg ctgtataaca aatccactcc gacctttgac   1200
gattatttcg gcaatgcctg gaaatccagc tctggcccgc tgcaactgat cttcgcttat   1260
tttgcggttg tccaaaacat caaaaaggag gaaattgaaa acctgcaaaa ataccacgat   1320
atcattagcc gtccttctca tatctttcgc ctgtgcaacg acctggcaag cgcgtccgca   1380
gagatcgcac gtggcgaaac cgctaactct gtttcctgct acatgcgcac caagggcatt   1440
tccgaagagc tggcaaccga gagcgtaatg aatctgatcg acgaaacctg taagaaaatg   1500
aacaaagaaa aactgggtgg ctccctgttc gctaaaccgt tcgtagagac tgctattaac   1560
ctggcacgtc agagccactg cacctaccac aatggtgacg cacatactag cccggatgaa   1620
ctgactcgta acgtgtgtact gtctgttatc accgaaccga ttctgccgtt cgaacgttaa   1680
```

<210> SEQ ID NO 9  
<211> LENGTH: 1785  
<212> TYPE: DNA  
<213> ORGANISM: Artificial Sequence  
<220> FEATURE:  
<223> OTHER INFORMATION: Polynucleotide which encodes isoprene synthase derived from Mucuna pururiens and which is fused with chloroplast-localization signal (IspSM(L) gene)

<400> SEQUENCE: 9

```
atggctacca acccgtcctg tctgtcaacc ccgttcctgt cttcaacccc ggctctgtcc     60
acccgcttcc cgctgtccga aaacttcacc cagaaaacga gcctggttaa cccgaaaccg    120
tggccgctga tttctgcggt cagctctcag tttagtcaaa tcgcggaaga taattctcgt    180
cgcagtgcca actatcatcc gaatctgtgg gatttttgaat tcctgcagtc gctggaaaac    240
gacagcaaaa tggaaaaact ggaagaaaaa gcgaccaaac tggaagaaga agtgcgtaac    300
atgatgaatg aagcgaaaac ggaagccctg tctctgctgg aactgattga tgacgttcaa    360 cgcctggtc tgacctacaa attcgaaaaa gatatcatca aagccctgga aaaaattgtc    420
ccgctggacg aatcaggtct gcacgtgacc tccctgtcat ttcgtatcct gcgccagcat    480
ggcttcgaag tttcgcaaga tgtctttaaa cgtttcaaag acaaagaagg cggtttctgc   540
```

```
gcagaactga aagatgacgt gcagggtctg ctgtctctgt atgaagctag ttacctgggt      600
tttgaaggcg aatccctgct ggatgaagcg cgcgccttct caattaccca cctgaaaaac      660
aatctgaaca aaggcatcaa tacgaaagtg gcacagcaag ttagtcatgc tctggaactg      720
ccgtatcacc gtcgcctgca tcgtctggaa gcccgctggc tgctggataa atacgaaccg      780
aaagaaccgc atcaccatct gctgcacgaa ctggcaaaac tggactttaa tctggttcag      840
tcgctgtatc aaaaagaact gcgtgaactg agcctgtggt ggcgcgaaat tggtctgacc      900
tctaaactgg attttgtgcg tgaccgcctg atggaagttt acttctgggc actgggcatg      960
gctccggatc gcagtttag cgaatgccgt aaagtggtta ccaaaatgtt cggtctggtg      1020
acgattatcg atgacgtcta tgatgtgtac ggcaccctgg acgaactgca actgttcacg      1080
gatgcagtcg aacgctggga cgtgaacgct atcaataccc tgccggatta tatgaaactg      1140
tgttatctgg cactgtacaa caccgttaat gacacggctt acagcatcct gaaagaaaaa      1200
ggtcataaca acatctccta cctgaccaaa tcatggtgcg aactgtgtaa agcgtttctg      1260
caggaagcca atggtctaa caataaaatt atcccggcgt tcaacaaata tctggataat      1320
gccagtgtta gttcctcagg cgtcgcactg ctggctccgt cctactttct ggtctgtcag      1380
gaacaagata tttcggacca ggcactgcac agcctgacca actttcatgg tctggttcgt      1440
tcgagctgca ccatcttccg cctgtgtaat gatctggcga cgtctagtgc cgaactggaa      1500
cgtggcgaaa ccacgaactc cattacctca tatatgcacg aaaatgaaac gagtgaagaa      1560
caggcgtgca aagaactgcg taacctgatc gatgccgaat ggaagaaaat gaacgaagaa      1620
cgcgtgtcga atagcaccct gccgaaagcc tttcgtgaaa ttgcaatcaa tatggctcgc      1680
atttcccatt gtacgtatca gtacggcgat ggtctgggcc gcccggacta cacgaccgaa      1740
aaccgcatta aactgctgct gattgacccg ttcccgatta actga                      1785
```

<210> SEQ ID NO 10
<211> LENGTH: 1656
<212> TYPE: DNA
<213> ORGANISM: Artificial Sequence
<220> FEATURE:
<223> OTHER INFORMATION: Polynucleotide without chloroplast-localization signal, which encodes isoprene synthase derived from Mucuna pururiens (IspSM gene)

<400> SEQUENCE: 10

```
atgtccgccg tttcaagcca gttctctcaa atcgccgaag acaatagccg tcgctcagca      60
aattatcatc cgaatctgtg ggactttgaa tttctgcagt ctctggaaaa cgatagtaaa      120
atggaaaaac tggaagaaaa agccaccaaa ctggaagaag aagtgcgtaa catgatgaat      180
gaagcgaaaa cggaagccct gagcctgctg gaactgattg atgacgtcca acgcctgggt      240
ctgacctaca aattcgaaaa agatatcatc aaagcactgg aaaaaattgt cccgctggac      300
gaatcaggtc tgcacgtgac gtctctgagt tttcgtatcc tgcgccagca tggcttcgaa      360
gtttcgcaag atgtctttaa acgtttcaaa gacaaagaag gcggtttctg cgcggaactg      420
aaagatgacg tgcagggtct gctgtccctg tatgaagcct catacctggg ttttgaaggc      480
gaatccctgc tggatgaagc gcgcgccttc tcaattaccc acctgaaaaa caatctgaac      540
aaaggcatca atacgaaagt ggcacagcaa gttagccatg ctctggaact gccgtatcac      600
cgtcgcctgc atcgtctgga agcacgctgg ctgctggata aatacgaacc gaaagaaccg      660
catcaccatc tgctgcacga actggcgaaa ctggacttta tctggttca gtcgctgtat      720
```

| | |
|---|---|
| caaaaagaac tgcgtgaact gagcctgtgg tggcgcgaaa ttggtctgac ctctaaactg | 780 |
| gattttgtgc gtgaccgcct gatggaagtt tacttctggg cactgggcat ggctccggat | 840 |
| ccgcagttta gcgaatgccg taaagtggtt accaaaatgt tcggtctggt cacgattatc | 900 |
| gatgacgtct atgatgtgta cggcaccctg gacgaactgc aactgttcac ggatgcggtc | 960 |
| gaacgctggg acgtgaacgc catcaatacc ctgccggatt atatgaaact gtgttatctg | 1020 |
| gcgctgtaca acaccgttaa tgacacggcc tatagcatcc tgaaagaaaa aggtcataac | 1080 |
| aacatctcgt acctgaccaa agctggtgc gaactgtgta agcgtttct gcaggaagcc | 1140 |
| aaatggtcta acaacaaaat catcccggca ttcaacaaat acctggataa tgctagtgtt | 1200 |
| agctctagtg gcgtcgcact gctggctccg tcctactttc tggtgtgtca ggaacaagat | 1260 |
| atttctgacc aggcgctgca cagtctgacc aactttcatg gtctggttcg ttcctcatgc | 1320 |
| accatcttcc gcctgtgtaa tgatctggcg acgtcgagcg ccgaactgga acgtggcgaa | 1380 |
| accacgaact cgattaccag ctatatgcac gaaaatgaaa cgagtgaaga acaggcatgc | 1440 |
| aaagaactgc gtaacctgat cgatgctgaa tggaagaaaa tgaacgaaga acgcgtgtcc | 1500 |
| aattcaaccc tgccgaaagc ctttcgtgaa attgcaatca atatggctcg catttcccat | 1560 |
| tgtacgtatc agtacggcga tggtctgggc cgcccggact acacgaccga aaaccgtatt | 1620 |
| aaactgctgc tgattgaccc gttcccgatt aactaa | 1656 |

<210> SEQ ID NO 11
<211> LENGTH: 399
<212> TYPE: DNA
<213> ORGANISM: Artificial Sequence
<220> FEATURE:
<223> OTHER INFORMATION: Ptac-Ttrp

<400> SEQUENCE: 11

| | |
|---|---|
| ggtaccagat ctccctgttg acaattaatc atcggctcta atgtgtgg aatcgtgagc | 60 |
| ggataacaat ttcacacaag gagactcccg ggagccgcca gttccgctgg cgcatttta | 120 |
| actttcttta tgaagccgg aaaaatccta aattcattta atatttatct ttttaccgtt | 180 |
| tcgcttaccc cggtcgaacg tcaacttacg tcattttcc gcccaacagt aatataatca | 240 |
| aacaaattaa tcccgcaaca taacaccagt aaaatcaata attttctcta agtcacttat | 300 |
| tcctcaggta attgttaata tatccagaat gttcctcaaa atatattttc cctctatctt | 360 |
| ctcgttgcgc ttaatttgac taattctcat tagggatcc | 399 |

<210> SEQ ID NO 12
<211> LENGTH: 3383
<212> TYPE: DNA
<213> ORGANISM: Artificial Sequence
<220> FEATURE:
<223> OTHER INFORMATION: Expression plasmid pSTV28-Ptac-Ttrp

<400> SEQUENCE: 12

| | |
|---|---|
| cgtatggcaa tgaaagacgg tgagctggtg atatgggata gtgttcaccc ttgttacacc | 60 |
| gttttccatg agcaaactga acgttttca tcgctctgga gtgaatacca cgacgatttc | 120 |
| cggcagtttc tacacatata ttcgcaagat gtggcgtgtt acggtgaaaa cctggcctat | 180 |
| ttccctaaag ggtttattga gaatatgttt ttcgtctcag ccaatccctg ggtgagtttc | 240 |
| accagttttg atttaaacgt ggccaatatg gacaacttct tcgccccgt tttcaccatg | 300 |
| ggcaaatatt atacgcaagg cgacaaggtg ctgatgccgc tggcgattca ggttcatcat | 360 |
| gccgtttgtg atggcttcca tgtcggcaga atgcttaatg aattacaaca gtactgcgat | 420 |

```
gagtggcagg gcggggcgta attttttaa ggcagttatt ggtgcccta aacgcctggt    480 gctacgcctg aataagtgat aataagcgga tgaatggcag aaattcgaaa gcaaattcga    540
cccggtcgtc ggttcagggc agggtcgtta aatagccgct tatgtctatt gctggtttac    600
cggtttattg actaccggaa gcagtgtgac cgtgtgcttc tcaaatgcct gaggccagtt    660
tgctcaggct ctccccgtgg aggtaataat tgacgatatg atcatttatt ctgcctccca    720
gagcctgata aaacggtta gcgcttcgtt aatacagatg taggtgttcc acagggtagc    780
cagcagcatc ctgcgatgca gatccggaac ataatggtgc agggcgcttg tttcggcgtg    840
ggtatggtgg caggccccgt ggccggggga ctgttgggcg ctgccggcac ctgtcctacg    900
agttgcatga taaagaagac agtcataagt gcggcgacga tagtcatgcc ccgcgcccac    960
cggaaggagc taccggacag cggtgcggac tgttgtaact cagaataaga aatgaggccg   1020
ctcatggcgt tccaatacgc aaaccgcctc tccccgcgcg ttggccgatt cattaatgca   1080
gctggcacga caggtttccc gactggaaag cgggcagtga gcgcaacgca attaatgtga   1140
gttagctcac tcattaggca ccccaggctt tacactttat gcttccggct cgtatgttgt   1200
gtggaattgt gagcggataa caatttcaca caggaaacag ctatgaccat gattacgaat   1260
tcgagctcgg taccagatct ccctgttgac aattaatcat cggctctata tgtgtggaa   1320 tcgtgagcgg ataacaattt cacacaagga ctcccggg agccgccagt tccgctggcg   1380
gcattttaac tttctttaat gaagccggaa aaatcctaaa ttcatttaat atttatcttt   1440
ttaccgtttc gcttaccccg gtcgaacgtc aacttacgtc attttccgc ccaacagtaa   1500 tataatcaaa caaattaatc cgcaacata acaccagtaa aatcaataat tttctctaag   1560
tcacttattc ctcaggtaat tgttaatata tccagaatgt tcctcaaaat atattttccc   1620
tctatcttct cgttgcgctt aatttgacta attctcatta gggatcctct agagtcgacc   1680
tgcaggcatg caagcttggc actggccgtc gttttacaac gtcgtgactg ggaaaaccct   1740
ggcgttaccc aacttaatcg ccttgcagca catccccctt tcgccagctg gcgtaatagc   1800
gaagaggccc gcaccgatcg cccttcccaa cagttgcgca gcctgaatgg cgaatgagct   1860
tatcgatgat aagctgtcaa acatgagaat tacaacttat atcgtatggg gctgacttca   1920
ggtgctacat ttgaagagat aaattgcact gaaatctaga aatatttat ctgattaata   1980 agatgatctt cttgagatcg ttttggtctg cgcgtaatct cttgctctga aaacgaaaaa   2040
accgccttgc agggcggttt ttcgaaggtt ctctgagcta ccaactcttt gaaccgaggt   2100
aactggcttg gaggagcgca gtcaccaaaa cttgtccttt cagtttagcc ttaaccggcg   2160
catgacttca agactaactc ctctaaatca attaccagtg gctgctgcca gtggtgcttt   2220
tgcatgtctt tccggttggg actcaagacg atagttaccg gataaggcgc agcggtcgga   2280
ctgaacgggg ggttcgtgca tacagtccag cttggagcga actgcctacc cggaactgag   2340
tgtcaggcgt ggaatgagac aaacgcggcc ataacagcgg aatgacaccg gtaaaccgaa   2400
aggcaggaac aggagagcgc acgagggagc cgccagggga aacgcctggt atctttatag   2460
tcctgtcggg tttcgccacc actgatttga gcgtcagatt tcgtgatgct tgtcaggggg   2520
gcggagccta tggaaaaacg gctttgccgc ggccctctca cttccctgtt aagtatcttc   2580
ctggcatctt ccaggaaatc tccgccccgt tcgtaagcca tttccgctcg ccgcagtcga   2640
acgaccgagc gtagcgagtc agtgagcgag gaagcggaat atatcctgta tcacatattc   2700
tgctgacgca ccggtgcagc ctttttctc ctgccacatg aagcacttca ctgacaccct   2760
```

```
catcagtgcc aacatagtaa gccagtatac actccgctag cgctgatgtc cggcggtgct      2820
tttgccgtta cgcaccaccc cgtcagtagc tgaacaggag ggacagctga tagaaacaga      2880
agccactgga gcacctcaaa aacaccatca tacactaaat cagtaagttg gcagcatcac      2940
ccgacgcact ttgcgccgaa taaatacctg tgacggaaga tcacttcgca gaataaataa      3000
atcctggtgt ccctgttgat accgggaagc cctgggccaa cttttggcga aaatgagacg      3060
ttgatcggca cgtaagaggt tccaactttc accataatga aataagatca ctaccgggcg      3120 tatttttga gttatcgaga ttttcaggag ctaaggaagc taaaatggag aaaaaaatca      3180
ctggatatac caccgttgat atatcccaat ggcatcgtaa agaacatttt gaggcatttc      3240
agtcagttgc tcaatgtacc tataaccaga ccgttcagct ggatattacg gcctttttaa      3300
agaccgtaaa gaaaataag cacaagtttt atccggcctt tattcacatt cttgcccgcc      3360
tgatgaatgc tcatccggaa ttt                                             3383
```

<210> SEQ ID NO 13
<211> LENGTH: 79
<212> TYPE: DNA
<213> ORGANISM: Artificial Sequence
<220> FEATURE:
<223> OTHER INFORMATION: Primer for amplifying IspSK gene
      (Ptac-IspS(K)F)

<400> SEQUENCE: 13

```
gataacaatt tcacacaata attttgttta actttaagaa ggagatataa tgtgtgcgac      60
ctcttctcaa tttactcag                                                   79
```

<210> SEQ ID NO 14
<211> LENGTH: 42
<212> TYPE: DNA
<213> ORGANISM: Artificial Sequence
<220> FEATURE:
<223> OTHER INFORMATION: Primer for amplifying IspSK gene
      (IspS(K)R-MCSR)

<400> SEQUENCE: 14

```
acggccagtg aattcttaga catacatcag ctggttaatc gg                         42
```

<210> SEQ ID NO 15
<211> LENGTH: 79
<212> TYPE: DNA
<213> ORGANISM: Artificial Sequence
<220> FEATURE:
<223> OTHER INFORMATION: Primer for amplifying IspSP gene
      (Ptac-IspS(P)F)

<400> SEQUENCE: 15

```
gataacaatt tcacacaata attttgttta actttaagaa ggagatataa tgtgctctgt      60
ttctaccgag aacgtttcc                                                   79
```

<210> SEQ ID NO 16
<211> LENGTH: 43
<212> TYPE: DNA
<213> ORGANISM: Artificial Sequence
<220> FEATURE:
<223> OTHER INFORMATION: Primer for amplifying IspSP gene
      (IspS(P)R-MCSR)

<400> SEQUENCE: 16

```
acggccagtg aattcttaac gttcgaacgg cagaatcggt tcg                        43
```

```
<210> SEQ ID NO 17
<211> LENGTH: 69
<212> TYPE: DNA
<213> ORGANISM: Artificial Sequence
<220> FEATURE:
<223> OTHER INFORMATION: Primer for amplifying IspSM gene
      (Ptac-IspS(K)F)

<400> SEQUENCE: 17
gataacaatt tcacacaata attttgttta actttaagaa ggagatataa tgtccgccgt      60
ttcaagcca                                                             69

<210> SEQ ID NO 18
<211> LENGTH: 35
<212> TYPE: DNA
<213> ORGANISM: Artificial Sequence
<220> FEATURE:
<223> OTHER INFORMATION: Primer for amplifying IspSM gene

<400> SEQUENCE: 18
acggccagtg aattcttagt taatcgggaa cgggt                                35

<210> SEQ ID NO 19
<211> LENGTH: 79
<212> TYPE: DNA
<213> ORGANISM: Artificial Sequence
<220> FEATURE:
<223> OTHER INFORMATION: Primer for amplifying IspSM(L) gene

<400> SEQUENCE: 19
gataacaatt tcacacaata attttgttta actttaagaa ggagatataa tggctaccaa      60
cccgtcctgt ctgtcaacc                                                  79

<210> SEQ ID NO 20
<211> LENGTH: 35
<212> TYPE: DNA
<213> ORGANISM: Artificial Sequence
<220> FEATURE:
<223> OTHER INFORMATION: Primer for amplifying IspSM(L) gene

<400> SEQUENCE: 20
acggccagtg aattctcagt taatcgggaa cgggt                                35

<210> SEQ ID NO 21
<211> LENGTH: 29
<212> TYPE: DNA
<213> ORGANISM: Artificial Sequence
<220> FEATURE:
<223> OTHER INFORMATION: Primer for amplifying IpSTV28-Ptac-Ttrp
      construct (pSTV28-F)

<400> SEQUENCE: 21
gtgtgaaatt gttatccgct cacaattcc                                       29

<210> SEQ ID NO 22
<211> LENGTH: 27
<212> TYPE: DNA
<213> ORGANISM: Artificial Sequence
<220> FEATURE:
<223> OTHER INFORMATION: Primer for amplifying pSTV28-Ptac-Ttrp
      construct (pSTV28-R)

<400> SEQUENCE: 22
gaattcactg gccgtcgttt tacaacg                                         27
```

<210> SEQ ID NO 23
<211> LENGTH: 41
<212> TYPE: DNA
<213> ORGANISM: Artificial Sequence
<220> FEATURE:
<223> OTHER INFORMATION: Primer for amplifying dxs gene (dxs-F)

<400> SEQUENCE: 23
caggaaacag ctatgagttt tgatattgcc aaatacccga c                41

<210> SEQ ID NO 24
<211> LENGTH: 28
<212> TYPE: DNA
<213> ORGANISM: Artificial Sequence
<220> FEATURE:
<223> OTHER INFORMATION: Primer for amplifying dxs gene (dxs-R)

<400> SEQUENCE: 24
gctgccactc ctgctatact cgtcatac                               28

<210> SEQ ID NO 25
<211> LENGTH: 30
<212> TYPE: DNA
<213> ORGANISM: Artificial Sequence
<220> FEATURE:
<223> OTHER INFORMATION: Primer for amplifying dxs gene (pMW219-F)

<400> SEQUENCE: 25
catagctgtt tcctgtgtga aattgttatc                             30

<210> SEQ ID NO 26
<211> LENGTH: 40
<212> TYPE: DNA
<213> ORGANISM: Artificial Sequence
<220> FEATURE:
<223> OTHER INFORMATION: Primer for amplifying dxs gene (pMW219-R)

<400> SEQUENCE: 26
agcaggagtg gcagcgaatt cgagctcggt acccggggat                  40

<210> SEQ ID NO 27
<211> LENGTH: 40
<212> TYPE: DNA
<213> ORGANISM: Artificial Sequence
<220> FEATURE:
<223> OTHER INFORMATION: Primer for amplifying ERG12 gene
      (MVK-IFS_5742-33-1)

<400> SEQUENCE: 27
acacaaggag actcccatgt cattaccgtt cttaacttct                  40

<210> SEQ ID NO 28
<211> LENGTH: 46
<212> TYPE: DNA
<213> ORGANISM: Artificial Sequence
<220> FEATURE:
<223> OTHER INFORMATION: Primer for amplifying ERG12 gene
      (MVK-IFA_5742-33-2)

<400> SEQUENCE: 28
ggaactggcg gctcccgggt tattatgaag tccatggtaa attcgt           46

<210> SEQ ID NO 29
<211> LENGTH: 38
<212> TYPE: DNA
<213> ORGANISM: Artificial Sequence
<220> FEATURE:

<223> OTHER INFORMATION: Primer for amplifying ERG8 gene
      (PMK-IFS_5742-33-3)

<400> SEQUENCE: 29
acacaaggag actcccatgt cagagttgag agccttca                              38

<210> SEQ ID NO 30
<211> LENGTH: 46
<212> TYPE: DNA
<213> ORGANISM: Artificial Sequence
<220> FEATURE:
<223> OTHER INFORMATION: Primer for amplifying ERG8 gene
      (PMK-IFA_5742-33-4)

<400> SEQUENCE: 30
ggaactggcg gctcccgggt tattatttat caagataagt ttccgg                     46

<210> SEQ ID NO 31
<211> LENGTH: 37
<212> TYPE: DNA
<213> ORGANISM: Artificial Sequence
<220> FEATURE:
<223> OTHER INFORMATION: Primer for amplifying ERG19 gene
      (MVD-IFS_5742-33-5)

<400> SEQUENCE: 31
acacaaggag actcccatga ccgtttacac agcatcc                               37

<210> SEQ ID NO 32
<211> LENGTH: 46
<212> TYPE: DNA
<213> ORGANISM: Artificial Sequence
<220> FEATURE:
<223> OTHER INFORMATION: Primer for amplifying ERG19 gene
      (MVD-IFA_5742-33-6)

<400> SEQUENCE: 32
ggaactggcg gctcccgggt tattattcct ttggtagacc agtctt                     46

<210> SEQ ID NO 33
<211> LENGTH: 36
<212> TYPE: DNA
<213> ORGANISM: Artificial Sequence
<220> FEATURE:
<223> OTHER INFORMATION: Primer for amplifying IDI1 gene
      (yIDI-IFS_5742-33-7)

<400> SEQUENCE: 33
acacaaggag actcccatgc cccatggtgc agtatc                                36

<210> SEQ ID NO 34
<211> LENGTH: 49
<212> TYPE: DNA
<213> ORGANISM: Artificial Sequence
<220> FEATURE:
<223> OTHER INFORMATION: Primer for amplifying IDI1 gene
      (yIDI-IFA_5742-33-8)

<400> SEQUENCE: 34
ggaactggcg gctcccgggt tattatagca ttctatgaat ttgcctgtc                  49

<210> SEQ ID NO 35
<211> LENGTH: 5892
<212> TYPE: DNA
<213> ORGANISM: Artificial Sequence
<220> FEATURE:
<223> OTHER INFORMATION: Nucleotide sequence of prepared plasmid pUC-mvk-pmk

<400> SEQUENCE: 35

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gaattcgagc     240
tcggtaccca tgtcattacc gttcttaact tctgcaccgg gaaaggttat tattttggt      300
gaacactctg ctgtgtacaa caagcctgcc gtcgctgcta gtgtgtctgc gttgagaacc     360
tacctgctaa taagcgagtc atctgcacca gatactattg aattggactt cccggacatt     420
agctttaatc ataagtggtc catcaatgat ttcaatgcca tcaccgagga tcaagtaaac     480
tcccaaaaat tggccaaggc tcaacaagcc accgatggct gtctcagga actcgttagt      540
cttttggatc cgttgttagc tcaactatcc gaatccttcc actaccatgc agcgttttgt     600
ttcctgtata tgtttgtttg cctatgcccc catgccaaga atattaagtt ttctttaaag     660
tctactttac ccatcggtgc tgggttgggc tcaagcgcct ctatttctgt atcactggcc     720
ttagctatgg cctacttggg ggggttaata ggatctaatg acttggaaaa gctgtcagaa     780
aacgataagc atatagtgaa tcaatgggcc ttcataggtg aaaagtgtat tcacggtacc     840
ccttcaggaa tagataacgc tgtggccact tatggtaatg ccctgctatt tgaaaaagac     900
tcacataatg gaacaataaa cacaaacaat tttaagttct tagatgattt cccagccatt     960
ccaatgatcc taacctatac tagaattcca aggtctacaa agatcttgt tgctcgcgtt    1020
cgtgtgttgg tcaccgagaa atttcctgaa gttatgaagc caattctaga tgccatgggt    1080
gaatgtgccc tacaaggctt agagatcatg actaagttaa gtaaatgtaa aggcaccgat    1140
gacgaggctg tagaaactaa taatgaactg tatgaacaac tattggaatt gataagaata    1200
aatcatggac tgcttgtctc aatcggtgtt tctcatcctg gattagaact tattaaaaat    1260
ctgagcgatg atttgagaat tggctccaca aaacttaccg gtgctggtgg cggcggttgc    1320
tctttgactt tgttacgaag agacattact caagagcaaa ttgacagctt caaaaagaaa    1380
ttgcaagatg atttttagtta cgagacattt gaaacagact gggtgggac tggctgctgt    1440
ttgttaagcg caaaaaattt gaataaagat cttaaaatca atccctagt attccaatta    1500
tttgaaaata aaactaccac aaagcaacaa attgacgatc tattattgcc aggaaacacg    1560
aatttaccat ggacttcata agctaattg cgataggcct gcaccttaa ggaggaaaaa     1620
aacatgtcag agttgagagc cttcagtgcc ccagggaaag cgttactagc tggtggatat    1680
ttagttttag atacaaaata tgaagcatttt gtagtcggat tatcggcaag aatgcatgct    1740
gtagcccatc cttacggttc attgcaaggg tctgataagt ttgaagtgcg tgtgaaaagt    1800
aaacaattta aagatgggga gtggctgtac catataagtc ctaaaagtgg cttcattcct    1860
gtttcgatag gcggatctaa gaacccttttc attgaaaaag ttatcgctaa cgtatttagc    1920
tactttaaac ctaacatgga cgactactgc aatagaaact tgttcgttat tgatatttc     1980
tctgatgatg cctaccattc tcaggaggat agcgttaccg aacatcgtgg caacagaaga    2040
ttgagttttc attcgcacag aattgaagaa gttcccaaaa cagggctggg ctcctcggca    2100
ggtttagtca cagtttaac tacagctttg gcctcctttt ttgtatcgga cctggaaaat    2160
aatgtagaca aatatagaga agttattcat aatttagcac aagttgctca ttgtcaagct    2220
cagggtaaaa ttggaagcgg gtttgatgta gcggcggcag catatggatc tatcagatat    2280
```

```
agaagattcc cacccgcatt aatctctaat ttgccagata ttggaagtgc tacttacggc    2340
agtaaactgg cgcatttggt tgatgaagaa gactggaata ttacgattaa aagtaaccat    2400
ttaccttcgg gattaacttt atggatgggc gatattaaga atggttcaga aacagtaaaa    2460
ctggtccaga aggtaaaaaa ttggtatgat tcgcatatgc cagaaagctt gaaaatatat    2520
acagaactcg atcatgcaaa ttctagattt atggatggac tatctaaact agatcgctta    2580
cacgagactc atgacgatta cagcgatcag atatttgagt ctcttgagag gaatgactgt    2640
acctgtcaaa agtatcctga atcacagaa gttagagatg cagttgccac aattagacgt    2700
tcctttagaa aaataactaa agaatctggt gccgatatcg aacctcccgt acaaactagc    2760
ttattggatg attgccagac cttaaaagga gttcttactt gcttaatacc tggtgctggt    2820
ggttatgacg ccattgcagt gattactaag caagatgttg atcttagggc tcaaaccgct    2880
aatgacaaaa gattttctaa ggttcaatgg ctggatgtaa ctcaggctga ctggggtgtt    2940
aggaaagaaa aagatccgga aacttatctt gataaataag gggatcctct agagtcgacc    3000
tgcaggcatg caagcttggc actggccgtc gttttacaac gtcgtgactg ggaaaaccct    3060
ggcgttaccc aacttaatcg ccttgcagca catcccccett cgccagctg gcgtaatagc    3120 gaagaggccc gcaccgatcg cccttcccaa cagttgcgca gcctgaatgg cgaatggcgc    3180
ctgatgcggt attttctcct tacgcatctg tgcggtattt cacaccgcat acgtcaaagc    3240
aaccatagta cgcgccctgt agcggcgcat taagcgcggc gggtgtggtg gttacgcgca    3300
gcgtgaccgc tacacttgcc agcgccctag cgcccgctcc tttcgctttc ttcccttcct    3360
ttctcgccac gttcgccggc tttccccgtc aagctctaaa tcggggggctc cctttagggt    3420 tccgatttag tgctttacgg cacctcgacc ccaaaaaact tgatttgggt gatggttcac    3480
gtagtgggcc atcgccctga tagacggttt ttcgcccttt gacgttggag tccacgttct    3540
ttaatagtgg actcttgttc caaactggaa caacactcaa ccctatctcg gctattctt    3600 ttgatttata agggattttg ccgatttcgg cctattggtt aaaaaatgag ctgatttaac    3660
aaaaatttaa cgcgaatttt aacaaaatat taacgtttac aattttatgg tgcactctca    3720
gtacaatctg ctctgatgcc gcatagttaa gccagccccg acacccgcca cacccgctg    3780 acgcgccctg acgggcttgt ctgctcccgg catccgctta cagacaagct gtgaccgtct    3840
ccgggagctg catgtgtcag aggttttcac cgtcatcacc gaaacgcgcg agacgaaagg    3900
gcctcgtgat acgcctattt ttataggtta atgtcatgat aataatggtt tcttagacgt    3960
caggtggcac ttttcgggga atgtgcgcg gaacccctat ttgtttattt ttctaaatac    4020
attcaaatat gtatccgctc atgagacaat aaccctgata aatgcttcaa taatattgaa    4080
aaaggaagag tatgagtatt caacatttcc gtgtcgccct tattcccttt tttgcggcat    4140
tttgccttcc tgttttttgct cacccagaaa cgctggtgaa agtaaaagat gctgaagatc    4200
agttgggtgc acgagtgggt tacatcgaac tggatctcaa cagcggtaag atccttgaga    4260
gttttcgccc cgaagaacgt tttccaatga tgagcacttt taaagttctg ctatgtggcg    4320
cggtattatc ccgtattgac gccgggcaag agcaactcgg tcgccgcata cactattctc    4380
agaatgactt ggttgagtac tcaccagtca cagaaaagca tcttacgat ggcatgacag    4440 taagagaatt atgcagtgct gccataacca tgagtgataa cactgcggcc aacttacttc    4500
tgacaacgat cggaggaccg aaggagctaa ccgcttttt gcacaacatg gggatcatg    4560 taactcgcct tgatcgttgg gaaccggagc tgaatgaagc cataccaaac gacgagcgtg    4620
```

```
acaccacgat gcctgtagca atggcaacaa cgttgcgcaa actattaact ggcgaactac    4680
ttactctagc ttcccggcaa caattaatag actggatgga ggcggataaa gttgcaggac    4740
cacttctgcg ctcggccctt ccggctggct ggtttattgc tgataaatct ggagccggtg    4800
agcgtgggtc tcgcggtatc attgcagcac tggggccaga tggtaagccc tcccgtatcg    4860
tagttatcta cacgacgggg agtcaggcaa ctatggatga acgaaataga cagatcgctg    4920
agataggtgc ctcactgatt aagcattggt aactgtcaga ccaagtttac tcatatatac    4980
tttagattga tttaaaactt cattttttaat ttaaaaggat ctaggtgaag atcctttttg    5040
ataatctcat gaccaaaatc ccttaacgtg agttttcgtt ccactgagcg tcagaccccg    5100
tagaaaagat caaaggatct tcttgagatc ctttttttct gcgcgtaatc tgctgcttgc    5160
aaacaaaaaa accaccgcta ccagcggtgg tttgtttgcc ggatcaagag ctaccaactc    5220
tttttccgaa ggtaactggc ttcagcagag cgcagatacc aaatactgtc cttctagtgt    5280
agccgtagtt aggccaccac ttcaagaact ctgtagcacc gcctacatac ctcgctctgc    5340
taatcctgtt accagtggct gctgccagtg gcgataagtc gtgtcttacc gggttggact    5400
caagacgata gttaccggat aaggcgcagc ggtcgggctg aacggggggt tcgtgcacac    5460
agcccagctt ggagcgaacg acctacaccg aactgagata cctacagcgt gagctatgag    5520
aaagcgccac gcttcccgaa gggagaaagg cggacaggta tccggtaagc ggcagggtcg    5580
gaacaggaga gcgcacgagg gagcttccag ggggaaacgc ctggtatctt tatagtcctg    5640
tcgggtttcg ccacctctga cttgagcgtc gatttttgtg atgctcgtca ggggggcgga    5700
gcctatggaa aaacgccagc aacgcggcct ttttacggtt cctggccttt tgctggcctt    5760
ttgctcacat gttctttcct gcgttatccc ctgattctgt ggataaccgt attaccgcct    5820
ttgagtgagc tgataccgct cgccgcagcc gaacgaccga gcgcagcgag tcagtgagcg    5880
aggaagcgga ag                                                        5892

<210> SEQ ID NO 36
<211> LENGTH: 39
<212> TYPE: DNA
<213> ORGANISM: Artificial Sequence
<220> FEATURE:
<223> OTHER INFORMATION: Primer for amplifying ERG12 gene
      (KKS1-6038-2-1)

<400> SEQUENCE: 36
tcgagctcgg tacccatgtc attaccgttc ttaacttct                             39

<210> SEQ ID NO 37
<211> LENGTH: 53
<212> TYPE: DNA
<213> ORGANISM: Artificial Sequence
<220> FEATURE:
<223> OTHER INFORMATION: Primer for amplifying ERG12 gene
      (KKA1-6038-2-2)

<400> SEQUENCE: 37
ttaagggtgc aggcctatcg caaattagct tatgaagtcc atggtaaatt cgt             53

<210> SEQ ID NO 38
<211> LENGTH: 50
<212> TYPE: DNA
<213> ORGANISM: Artificial Sequence
<220> FEATURE:
<223> OTHER INFORMATION: Primer for amplifying ERG8 gene (KKS2-6083-2-3)

<400> SEQUENCE: 38
```

```
ggcctgcacc cttaaggagg aaaaaaacat gtcagagttg agagccttca        50
```

<210> SEQ ID NO 39
<211> LENGTH: 39
<212> TYPE: DNA
<213> ORGANISM: Artificial Sequence
<220> FEATURE:
<223> OTHER INFORMATION: Primer for amplifying ERG8 gene (KKA2-6083-2-4)

<400> SEQUENCE: 39

```
ctctagagga tccccttatt tatcaagata agtttccgg                    39
```

<210> SEQ ID NO 40
<211> LENGTH: 6135
<212> TYPE: DNA
<213> ORGANISM: Artificial Sequence
<220> FEATURE:
<223> OTHER INFORMATION: Nucleotide sequence of prepared plasmid pTWV-dmd-yidi

<400> SEQUENCE: 40

```
gacgaaaggg cctcgtgata cgcctatttt tataggttaa tgtcatgata ataatggttt    60
cttagacgtc aggtggcact tttcggggaa atgtgcgcgg aacccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attcccttt   240
ttgcggcatt ttgccttcct gttttgctc acccagaaac gctggtgaaa gtaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc attttttaatt taaaaggatc taggtgaaga  1140
tcctttttga atctcatg accaaaatcc cttaacgtga gttttcgttc cactgagcgt  1200
cagacccgt agaaaagatc aaaggatctt cttgagatcc tttttttctg cgcgtaatct  1260
gctgcttgca acaaaaaaaa ccaccgctac cagcggtggt ttgtttgccg gatcaagagc  1320
taccaactct ttttccgaag gtaactggct tcagcagagc gcagatacca atactgtcc  1380
ttctagtgta gccgtagtta ggccaccact tcaagaactc tgtagcaccg cctacatacc  1440
tcgctctgct aatcctgtta ccagtggctg ctgccagtgg cgataagtcg tgtcttaccg  1500
ggttggactc aagacgatag ttaccggata aggcgcagcg tcgggctga acggggggt  1560
cgtgcacaca gcccagcttg gagcgaacga cctacaccga actgagatac ctacagcgtg  1620
```

```
agctatgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg attttgtga tgctcgtcag     1800
gggggcggag cctatggaaa aacgccagca acgcggcctt tttacggttc ctggccttt    1860
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcctga tgcggtattt tctccttacg catctgtgcg    2040
gtatttcaca ccgcatatgg tgcactctca gtacaatctg ctctgatgcc gcatagttaa    2100
gccagtatac actccgctat cgctacgtga ctgggtcatg gctgcgcccc gacacccgcc    2160
aacacccgct gacgcgccct gacgggcttg tctgctcccg gcatccgctt acagacaagc    2220
tgtgaccgtc tccgggagct gcatgtgtca gaggttttca ccgtcatcac cgaaacgcgc    2280
gaggcagctg cggtaaagct catcagcgtg gtcgtgaagc gattcacaga tgtctgcctg    2340
ttcatccgcg tccagctcgt tgagtttctc cagaagcgtt aatgtctggc ttctgataaa    2400
gcggccatg ttaagggcgg ttttttcctg tttggtcact gatgcctccg tgtaaggggg    2460
atttctgttc atgggggtaa tgataccgat gaaacgagag aggatgctca cgatacgggt    2520
tactgatgat gaacatgccc ggttactgga acgttgtgag ggtaaacaac tggcggtatg    2580
gatgcggcgg gaccagagaa aaatcactca gggtcaatgc cagcgcttcg ttaatacaga    2640
tgtaggtgtt ccacagggta gccagcagca tcctgcgatg cagatccgga acataatggt    2700
gcagggcgct gacttccgcg tttccagact ttacgaaaca cggaaaccga agaccattca    2760
tgttgttgct caggtcgcag acgttttgca gcagcagtcg cttcacgttc gctcgcgtat    2820
cggtgattca ttctgctaac cagtaaggca accccgccag cctagccggg tcctcaacga    2880
caggagcacg atcatgcgca cccgtggcca ggacccaacg ctgcccgaga tgcgccgcgt    2940
gcggctgctg gagatggcgg acgcgatgga tatgttctgc caagtaatgt gagttagctc    3000
actcattagg caccccaggc tttacacttt atgcttccgg ctcgtatgtt gtgtggaatt    3060
gtgagcggat aacaatttca cacaggaaac agctatgacc atgattacga attcgagctc    3120
ggtacccatg accgtttaca cagcatccgt taccgcaccc gtcaacatcg caacccttaa    3180
gtattggggg aaaagggaca cgaagttgaa tctgcccacc aattcgtcca tatcagtgac    3240
tttatcgcaa gatgacctca gaacgttgac ctctgcggct actgcacctg agtttgaacg    3300
cgacactttg tggttaaatg gagaaccaca cagcatcgac aatgaaagaa ctcaaaattg    3360
tctgcgcgac ctacgccaat taagaaagga aatggaatcg aaggacgcct cattgcccac    3420
attatctcaa tggaaactcc acattgtctc cgaaaataac tttcctacag cagctggttt    3480
agcttcctcc gctgctggct ttgctgcatt ggtctctgca attgctaagt tataccaatt    3540
accacagtca acttcagaaa tatctagaat agcaagaaag gggtctggtt cagcttgtag    3600
atcgttgttt ggcggatacg tggcctggga atgggaaaa gctgaagatg gtcatgattc     3660
catggcagta caaatcgcag acagctctga ctggcctcag atgaaagctt gtgtcctagt    3720
tgtcagcgat attaaaaagg atgtgagttc cactcagggt atgcaattga ccgtggcaac    3780
ctccgaacta tttaaagaaa gaattgaaca tgtcgtacca aagagatttg aagtcatgcg    3840
taaagccatt gttgaaaaag atttcgccac ctttgcaaag gaaacaatga tggattccaa    3900
ctcttttccat gccacatgtt tggactcttt ccctccaata ttctacatga atgacacttc    3960
```

```
caagcgtatc atcagttggt gccacaccat taatcagttt tacggagaaa caatcgttgc    4020
atacacgttt gatgcaggtc caaatgctgt gttgtactac ttagctgaaa atgagtcgaa    4080
actctttgca tttatctata aattgtttgg ctctgttcct ggatgggaca agaaatttac    4140
tactgagcag cttgaggctt tcaaccatca atttgaatca tctaacttta ctgcacgtga    4200
attggatctt gagttgcaaa aggatgttgc cagagtgatt ttaactcaag tcggttcagg    4260
cccacaagaa acaaacgaat ctttgattga cgcaaagact ggtctaccaa aggaataaga    4320
tcaattcgct gcatcgccct taggaggtaa aaaaaaatga ctgccgacaa caatagtatg    4380
ccccatggtg cagtatctag ttacgccaaa ttagtgcaaa accaaacacc tgaagacatt    4440
ttggaagagt ttcctgaaat tattccatta caacaaagac ctaatacccg atctagtgag    4500
acgtcaaatg acgaaagcgg agaaacatgt ttttctggtc atgatgagga gcaaattaag    4560
ttaatgaatg aaaattgtat tgttttggat tgggacgata atgctattgg tgccggtacc    4620
aagaaagttt gtcatttaat ggaaaatatt gaaaagggtt tactacatcg tgcattctcc    4680
gtctttattt tcaatgaaca aggtgaatta cttttacaac aaagagccac tgaaaaaata    4740
actttccctg atctttggac taacacatgc tgctctcatc cactatgtat tgatgacgaa    4800
ttaggtttga agggtaagct agacgataag attaagggcg ctattactgc ggcggtgaga    4860
aaactagatc atgaattagg tattccagaa gatgaaacta agacaagggg taagtttcac    4920
tttttaaaca gaatccatta catggcacca agcaatgaac catggggtga acatgaaatt    4980
gattacatcc tattttataa gatcaacgct aaagaaaact tgactgtcaa cccaaacgtc    5040
aatgaagtta gagacttcaa atgggtttca ccaaatgatt tgaaaactat gtttgctgac    5100
ccaagttaca agtttacgcc ttggtttaag attatttgcg agaattactt attcaactgg    5160
tgggagcaat tagatgacct ttctgaagtg aaaatgaca ggcaaattca tagaatgcta    5220 taagggatc ctctagagtc gacctgcagg catgcaagct tggcactggc cgtcgtttta    5280
caacgtcgtg actgggaaaa ccctggcgtt acccaactta atcgccttgc agcacatccc    5340
cctttcgcca gctggcgtaa tagcgaagag gcccgcaccg atcgcccttc ccaacagttg    5400
cgcagcctga atggcgaatg gcgcctgatg cggtattttc tccttacgca tctgtgcggt    5460
atttcacacc gcatacgtca aagcaaccat agtacgcgcc ctgtagcggc gcattaagcg    5520
cggcgggtgt ggtggttacg cgcagcgtga ccgctacact tgccagcgcc ctagcgcccg    5580
ctcctttcgc tttcttccct cctttctcg ccacgttcgc cggctttccc cgtcaagctc    5640
taaatcgggg gctcccttta gggttccgat ttagtgcttt acggcacctc gaccccaaaa    5700
aacttgattt gggtgatggt tcacgtagtg ggccatcgcc ctgatagacg ttttttcgcc    5760
ctttgacgtt ggagtccacg ttctttaata gtggactctt gttccaaact ggaacaacac    5820
tcaaccctat ctcgggctat tcttttgatt tataagggat tttgccgatt tcggcctatt    5880
ggttaaaaaa tgagctgatt taacaaaaat ttaacgcgaa ttttaacaaa atattaacgt    5940
ttacaatttt atggtgcact ctcagtacaa tctgctctga tgccgcatag ttaagccagc    6000
cccgacaccc gccaacaccc gctgacgcgc cctgacgggc ttgtctgctc ccggcatccg    6060
cttacagaca gctgtgaccg tctccgggag ctgcatgtg tcagaggttt tcaccgtcat    6120
caccgaaacg cgcga                                                     6135
```

<210> SEQ ID NO 41
<211> LENGTH: 36
<212> TYPE: DNA
<213> ORGANISM: Artificial Sequence

```
<220> FEATURE:
<223> OTHER INFORMATION: Primer for amplifying ERG19 gene
      (DyIS1-6083-2-5)

<400> SEQUENCE: 41
tcgagctcgg tacccatgac cgtttacaca gcatcc                                   36

<210> SEQ ID NO 42
<211> LENGTH: 61
<212> TYPE: DNA
<213> ORGANISM: Artificial Sequence
<220> FEATURE:
<223> OTHER INFORMATION: Primer for amplifying ERG19 gene
      (DyIA1-6083-2-6)

<400> SEQUENCE: 42
tttttttacc tcctaagggc gatgcagcga attgatctta ttcctttggt agaccagtct         60
t                                                                         61

<210> SEQ ID NO 43
<211> LENGTH: 57
<212> TYPE: DNA
<213> ORGANISM: Artificial Sequence
<220> FEATURE:
<223> OTHER INFORMATION: Primer for amplifying IDI1 gene
      (DyIS2-6083-2-7)

<400> SEQUENCE: 43
taggaggtaa aaaaaaatga ctgccgacaa caatagtatg ccccatggtg cagtatc            57

<210> SEQ ID NO 44
<211> LENGTH: 42
<212> TYPE: DNA
<213> ORGANISM: Artificial Sequence
<220> FEATURE:
<223> OTHER INFORMATION: Primer for amplifying IDI1 gene
      (DyIA2-6083-2-8)

<400> SEQUENCE: 44
ctctagagga tccccttata gcattctatg aatttgcctg tc                            42

<210> SEQ ID NO 45
<211> LENGTH: 9257
<212> TYPE: DNA
<213> ORGANISM: Artificial Sequence
<220> FEATURE:
<223> OTHER INFORMATION: Nucleotide sequence of prepared plasmid
      pTrc-KKDyI(beta))

<400> SEQUENCE: 45
gtttgacagc ttatcatcga ctgcacggtg caccaatgct tctggcgtca ggcagccatc         60
ggaagctgtg gtatggctgt gcaggtcgta atcactgca taattcgtgt cgctcaaggc        120
gcactcccgt tctggataat gttttttgcg ccgacatcat aacggttctg gcaaatattc       180
tgaaatgagc tgttgacaat taatcatccg gctcgtataa tgtgtggaat tgtgagcgga       240
taacaatttc acacaggaaa cagcgccgct gagaaaaagc gaagcggcac tgctctttaa       300
caatttatca gacaatctgt gtgggcactc gaccggaatt atcgattaac tttattatta      360
aaaattaaag aggtatatat taatgtatcg attaaataag gaggaataaa ccatgtcatt       420
accgttctta acttctgcac cgggaaaggt tattattttt ggtgaacact gctgtgta         480 caacaagcct gccgtcgctg ctagtgtgtc tgcgttgaga acctacctgc taataagcga       540
gtcatctgca ccagatacta ttgaattgga cttcccggac attagcttta atcataagtg       600
```

-continued

```
gtccatcaat gatttcaatg ccatcaccga ggatcaagta aactcccaaa aattggccaa    660
ggctcaacaa gccaccgatg gcttgtctca ggaactcgtt agtcttttgg atccgttgtt    720
agctcaacta tccgaatcct tccactacca tgcagcgttt tgtttcctgt atatgtttgt    780
ttgcctatgc ccccatgcca agaatattaa gttttctttta aagtctactt tacccatcgg   840
tgctgggttg ggctcaagcg cctctatttc tgtatcactg gccttagcta tggcctactt    900
gggggggtta ataggatcta atgacttgga aaagctgtca gaaaacgata agcatatagt    960
gaatcaatgg gccttcatag gtgaaaagtg tattcacggt accccttcag gaatagataa   1020
cgctgtggcc acttatggta atgccctgct atttgaaaaa gactcacata atggaacaat   1080
aaacacaaac aatttttaagt tcttagatga tttcccagcc attccaatga tcctaaccta  1140
tactagaatt ccaaggtcta caaaagatct tgttgctcgc gttcgtgtgt tggtcaccga   1200
gaaatttcct gaagttatga agccaattct agatgccatg ggtgaatgtg ccctacaagg   1260
cttagagatc atgactaagt taagtaaatg taaaggcacc gatgacgagg ctgtagaaac   1320
taataatgaa ctgtatgaac aactattgga attgataaga ataaatcatg gactgcttgt   1380
ctcaatcggt gtttctcatc ctggattaga acttattaaa aatctgagcg atgatttgag   1440
aattggctcc acaaaactta ccggtgctgg tggcggcggt tgctctttga ctttgttacg   1500
aagagacatt actcaagagc aaattgacag cttcaaaaag aaattgcaag atgattttag   1560
ttacgagaca tttgaaacag acttgggtgg gactggctgc tgtttgttaa gcgcaaaaaa   1620
tttgaataaa gatcttaaaa tcaaatccct agtattccaa ttatttgaaa ataaaactac   1680
cacaaagcaa caaattgacg atctattatt gccaggaaac acgaatttac catggacttc   1740
ataagctaat ttgcgatagg cctgcaccct taaggaggaa aaaacatgt cagagttgag    1800
agccttcagt gccccaggga aagcgttact agctggtgga tatttagttt tagatacaaa   1860
atatgaagca tttgtagtcg gattatcggc aagaatgcat gctgtagccc atccttacgg   1920
ttcattgcaa gggtctgata agtttgaagt gcgtgtgaaa agtaaacaat ttaaagatgg   1980
ggagtggctg taccatataa gtcctaaaag tggcttcatt cctgtttcga taggcggatc   2040
taagaaccct ttcattgaaa aagttatcgc taacgtattt agctacttta aacctaacat   2100
ggacgactac tgcaatagaa acttgttcgt tattgatatt ttctctgatg atgcctacca   2160
ttctcaggag gatagcgtta ccgaacatcg tggcaacaga agattgagtt ttcattcgca   2220
cagaattgaa gaagttccca aaacagggct gggctcctcg gcaggtttag tcacagtttt   2280
aactacagct ttggcctcct ttttttgtatc ggacctggaa ataatgtag acaaatatag   2340
agaagttatt cataatttag cacaagttgc tcattgtcaa gctcagggta aaattggaag   2400
cgggtttgat gtagcggcgg cagcatatgg atctatcaga tatagaagat tcccacccgc   2460
attaatctct aatttgccag atattggaag tgctacttac ggcagtaaac tggcgcattt   2520
ggttgatgaa gaagactgga atattacgat aaaagtaac catttacctt cgggattaac   2580
tttatggatg ggcgatatta agaatggttc agaaacagta aaactggtcc agaaggtaaa   2640
aaattggtat gattcgcata tgccagaaag cttgaaaata tatacagaac tcgatcatgc   2700
aaattctaga tttatggatg gactatctaa actagatcgc ttcacgagaa ctcatgacga   2760
ttacagcgat cagatatttg agtctcttga gaggaatgac tgtacctgtc aaaagtatcc   2820
tgaaatcaca gaagttagag atgcagttgc cacaattaga cgttcctttta gaaaaataac   2880
taaagaatct ggtgccgata tcgaacctcc cgtacaaact agcttattgg atgattgcca   2940
```

```
gaccttaaaa ggagttctta cttgcttaat acctggtgct ggtggttatg acgccattgc   3000
agtgattact aagcaagatg ttgatcttag ggctcaaacc gctaatgaca aagattttc    3060 taaggttcaa tggctggatg taactcaggc tgactggggt gttaggaaag aaaaagatcc   3120
ggaaacttat cttgataaat aacttaaggt agctgcatgc agaattcgcc cttaaggagg   3180
aaaaaaaaat gaccgtttac acagcatccg ttaccgcacc cgtcaacatc gcaacccta    3240 agtattgggg gaaagggac acgaagttga atctgcccac caattcgtcc atatcagtga    3300
ctttatcgca agatgacctc agaacgttga cctctgcggc tactgcacct gagtttgaac   3360
gcgacacttt gtggttaaat ggagaaccac acagcatcga caatgaaaga actcaaaatt   3420
gtctgcgcga cctacgccaa ttaagaaagg aaatggaatc gaaggacgcc tcattgccca   3480
cattatctca atggaaactc cacattgtct ccgaaaataa ctttcctaca gcagctggtt   3540
tagcttcctc cgctgctggc tttgctgcat tggtctctgc aattgctaag ttataccaat   3600
taccacagtc aacttcagaa atatctagaa tagcaagaaa ggggtctggt tcagcttgta   3660
gatcgttgtt tggcggatac gtggcctggg aaatgggaaa agctgaagat ggtcatgatt   3720
ccatggcagt acaaatcgca gacagctctg actggcctca gatgaaagct tgtgtcctag   3780
ttgtcagcga tattaaaaag gatgtgagtt ccactcaggg tatgcaattg accgtggcaa   3840
cctccgaact atttaaagaa agaattgaac atgtcgtacc aaagagattt gaagtcatgc   3900
gtaaagccat tgttgaaaaa gatttcgcca cctttgcaaa ggaaacaatg atggattcca   3960
actctttcca tgccacatgt ttggactctt tccctccaat attctacatg aatgacactt   4020
ccaagcgtat catcagttgg tgccacacca ttaatcagtt ttacggagaa caatcgttg    4080 catacacgtt tgatgcaggt ccaaatgctg tgttgtacta cttagctgaa atgagtcga    4140 aactctttgc atttatctat aaattgtttg gctctgttcc tggatgggac aagaaattta   4200
ctactgagca gcttgaggct ttcaaccatc aatttgaatc atctaacttt actgcacgtg   4260
aattggatct tgagttgcaa aaggatgttg ccagagtgat tttaactcaa gtcggttcag   4320
gcccacaaga aacaaacgaa tctttgattg acgcaaagac tggtctacca aaggaataag   4380
atcaattcgc tgcatcgccc ttaggaggta aaaaaaaatg actgccgaca acaatagtat   4440
gccccatggt gcagtatcta gttacgccaa attagtgcaa aaccaaacac ctgaagacat   4500
tttggaagag tttcctgaaa ttattccatt acaacaaaga cctaatacccc gatcagtga   4560 gacgtcaaat gacgaaagcg gagaaacatg ttttttctggt catgatgagg agcaaattaa   4620
gttaatgaat gaaaattgta ttgttttgga ttgggacgat aatgctattg gtgccggtac   4680
caagaaagtt tgtcatttaa tggaaaatat tgaaagggt ttactacatc gtgcattctc    4740
cgtctttatt ttcaatgaac aaggtgaatt acttttacaa caaagagcca ctgaaaaaat   4800
aactttccct gatctttgga ctaacacatg ctgctctcat ccactatgta ttgatgacga   4860
attaggtttg aagggtaagc tagacgataa gattaagggc gctattactg cggcggtgag   4920
aaaactagat catgaattag gtattccaga agatgaaact aagacaaggg gtaagttttca  4980 ctttttaaac agaatccatt acatggcacc aagcaatgaa ccatggggtg aacatgaaat   5040
tgattacatc ctattttata agatcaacgc taaagaaaac ttgactgtca acccaaacgt   5100
caatgaagtt agagacttca atgggtttc accaaatgat ttgaaaacta tgtttgctga    5160
cccaagttac aagtttacgc cttggtttaa gattatttgc gagaattact tattcaactg   5220
gtgggagcaa ttagatgacc tttctgaagt ggaaaatgac aggcaaattc atagaatgct   5280
ataactgcag ctggtaccat atgggaattc gaagctttct agaacaaaaa ctcatctcag   5340
```

-continued

```
aagaggatct gaatagcgcc gtcgaccatc atcatcatca tcattgagtt taaacggtct   5400
ccagcttggc tgttttggcg gatgagagaa gattttcagc ctgatacaga ttaaatcaga   5460
acgcagaagc ggtctgataa aacagaattt gcctggcggc agtagcgcgg tggtcccacc   5520
tgaccccatg ccgaactcag aagtgaaacg ccgtagcgcc gatggtagtg tggggtctcc   5580
ccatgcgaga gtagggaact gccaggcatc aaataaaacg aaaggctcag tcgaaagact   5640
gggcctttcg ttttatctgt tgtttgtcgg tgaacgctct cctgagtagg acaaatccgc   5700
cgggagcgga tttgaacgtt gcgaagcaac ggcccggagg gtggcgggca ggacgcccgc   5760
cataaactgc caggcatcaa attaagcaga aggccatcct gacggatggc cttttttgcgt   5820 ttctacaaac tcttttttgtt tattttttcta aatacattca aatatgtatc cgctcatgag   5880
acaataaccc tgataaatgc ttcaataata ttgaaaaagg aagagtatga gtattcaaca   5940
tttccgtgtc gcccttattc ccttttttgc ggcattttgc cttcctgttt ttgctcaccc   6000
agaaacgctg gtgaaagtaa aagatgctga agatcagttg ggtgcacgag tgggttacat   6060
cgaactggat ctcaacagcg gtaagatcct tgagagtttt cgccccgaag aacgttttcc   6120
aatgatgagc acttttaaag ttctgctatg tggcgcggta ttatcccgtg ttgacgccgg   6180
gcaagagcaa ctcggtcgcc gcatacacta ttctcagaat gacttggttg agtactcacc   6240
agtcacagaa aagcatctta cggatggcat gacagtaaga gaattatgca gtgctgccat   6300
aaccatgagt gataacactg cggccaactt acttctgaca acgatcggag gaccgaagga   6360
gctaaccgct tttttgcaca acatggggga tcatgtaact cgccttgatc gttgggaacc   6420
ggagctgaat gaagccatac caaacgacga gcgtgacacc acgatgcctg tagcaatggc   6480
aacaacgttg cgcaaactat taactggcga actacttact ctagcttccc ggcaacaatt   6540
aatagactgg atggaggcgg ataaagttgc aggaccactt ctgcgctcgg cccttccggc   6600
tggctggttt attgctgata aatctggagc cggtgagcgt gggtctcgcg gtatcattgc   6660
agcactgggg ccagatggta agccctcccg tatcgtagtt atctacacga cggggagtca   6720
ggcaactatg gatgaacgaa atagacagat cgctgagata ggtgcctcac tgattaagca   6780
ttggtaactg tcagaccaag tttactcata tatactttag attgatttaa aacttcattt   6840
ttaatttaaa aggatctagg tgaagatcct ttttgataat ctcatgacca aaatccctta   6900
acgtgagttt tcgttccact gagcgtcaga ccccgtagaa aagatcaaag gatcttcttg   6960
agatcctttt tttctgcgcg taatctgctg cttgcaaaca aaaaaaccac cgctaccagc   7020 ggtggttttgt tgccggatc aagagctacc aactctttttt ccgaaggtaa ctggcttcag   7080
cagagcgcag ataccaaata ctgtccttct agtgtagccg tagttaggcc accacttcaa   7140
gaactctgta gcaccgccta catacctcgc tctgctaatc ctgttaccag tggctgctgc   7200
cagtggcgat aagtcgtgtc ttaccgggtt ggactcaaga cgatagttac cggataaggc   7260
gcagcggtcg ggctgaacgg ggggttcgtg cacacagccc agcttggagc gaacgaccta   7320
caccgaactg agatacctac agcgtgagct atgagaaagc gccacgcttc ccgaagggag   7380
aaaggcggac aggtatccgg taagcggcag ggtcggaaca ggagagcgca cgagggagct   7440
tccaggggga aacgcctggt atctttatag tcctgtcggg tttcgccacc tctgacttga   7500
gcgtcgattt ttgtgatgct cgtcaggggg gcggagccta tggaaaaacg ccagcaacgc   7560 ggcctttttta cggttcctgg ccttttgctg gccttttgct cacatgttct ttcctgcgtt   7620 atccccctgat tctgtggata accgtattac cgcctttgag tgagctgata ccgctcgccg   7680
```

```
cagccgaacg accgagcgca gcgagtcagt gagcgaggaa gcggaagagc gcctgatgcg    7740
gtattttctc cttacgcatc tgtgcggtat ttcacaccgc atatggtgca ctctcagtac    7800
aatctgctct gatgccgcat agttaagcca gtatacactc cgctatcgct acgtgactgg    7860
gtcatggctg cgccccgaca cccgccaaca cccgctgacg cgccctgacg ggcttgtctg    7920
ctcccggcat ccgcttacag acaagctgtg accgtctccg ggagctgcat gtgtcagagg    7980
ttttcaccgt catcaccgaa acgcgcgagg cagcagatca attcgcgcgc gaaggcgaag    8040
cggcatgcat ttacgttgac accatcgaat ggtgcaaaac ctttcgcggt atggcatgat    8100
agcgcccgga agagagtcaa ttcagggtgg tgaatgtgaa accagtaacg ttatacgatg    8160
tcgcagagta tgccggtgtc tcttatcaga ccgtttcccg cgtggtgaac caggccagcc    8220
acgtttctgc gaaaacgcgg gaaaagtgg aagcggcgat ggcggagctg aattacattc    8280
ccaaccgcgt ggcacaacaa ctggcgggca aacagtcgtt gctgattggc gttgccacct    8340
ccagtctggc cctgcacgcg ccgtcgcaaa ttgtcgcggc gattaaatct cgcgccgatc    8400
aactgggtgc cagcgtggtg gtgtcgatgg tagaacgaag cggcgtcgaa gcctgtaaag    8460
cggcggtgca caatcttctc gcgcaacgcg tcagtgggct gatcattaac tatccgctgg    8520
atgaccagga tgccattgct gtggaagctg cctgcactaa tgttccggcg ttatttcttg    8580
atgtctctga ccagacaccc atcaacagta ttattttctc ccatgaagac ggtacgcgac    8640
tgggcgtgga gcatctggtc gcattgggtc accagcaaat cgcgctgtta gcgggcccat    8700
taagttctgt ctcggcgcgt ctgcgtctgg ctggctggca taaatatctc actcgcaatc    8760
aaattcagcc gatagcggaa cgggaaggcg actggagtgc catgtccggt tttcaacaaa    8820
ccatgcaaat gctgaatgag ggcatcgttc ccactgcgat gctggttgcc aacgatcaga    8880
tggcgctggg cgcaatgcgc gccattaccg agtccgggct gcgcgttggt gcggatatct    8940
cggtagtggg atacgacgat accgaagaca gctcatgtta tcccgccg tcaaccacca     9000 tcaaacagga ttttcgcctg ctggggcaaa ccagcgtgga ccgcttgctg caactctctc    9060
agggccaggc ggtgaagggc aatcagctgt tgcccgtctc actggtgaaa agaaaaacca    9120
ccctggcgcc caatacgcaa accgcctctc ccgcgcgtt ggccgattca ttaatgcagc    9180
tggcacgaca ggtttcccga ctggaaagcg ggcagtgagc gcaacgcaat taatgtgagt    9240
tagcgcgaat tgatctg                                                 9257

<210> SEQ ID NO 46
<211> LENGTH: 36
<212> TYPE: DNA
<213> ORGANISM: Artificial Sequence
<220> FEATURE:
<223> OTHER INFORMATION: Primer (KKDS2_6038-3-2)

<400> SEQUENCE: 46
gaggaataaa ccatgtcatt accgttctta acttct                              36

<210> SEQ ID NO 47
<211> LENGTH: 55
<212> TYPE: DNA
<213> ORGANISM: Artificial Sequence
<220> FEATURE:
<223> OTHER INFORMATION: Primer (KKMyIA_6038-2-9)

<400> SEQUENCE: 47
aagggcgaat tctgcatgca gctaccttaa gttatttatc aagataagtt tccgg          55
```

<210> SEQ ID NO 48
<211> LENGTH: 51
<212> TYPE: DNA
<213> ORGANISM: Artificial Sequence
<220> FEATURE:
<223> OTHER INFORMATION: Primer (KMS_6038-6-1)

<400> SEQUENCE: 48
gcagaattcg cccttaagga ggaaaaaaaa atgaccgttt acacagcatc c         51

<210> SEQ ID NO 49
<211> LENGTH: 47
<212> TYPE: DNA
<213> ORGANISM: Artificial Sequence
<220> FEATURE:
<223> OTHER INFORMATION: Primer (KDyIA_6038-3-3)

<400> SEQUENCE: 49
ccatatggta ccagctgcag ttatagcatt ctatgaattt gcctgtc             47

<210> SEQ ID NO 50
<211> LENGTH: 11386
<212> TYPE: DNA
<213> ORGANISM: Artificial Sequence
<220> FEATURE:
<223> OTHER INFORMATION: Nucleotide sequence of prepared plasmid
      pMW219-KKDyI-TaspA

<400> SEQUENCE: 50
gacagtaaga cgggtaagcc tgttgatgat accgctgcct tactgggtgc attagccagt      60
ctgaatgacc tgtcacggga taatccgaag tggtcagact ggaaaatcag agggcaggaa     120
ctgcagaaca gcaaaaagtc agatagcacc acatagcaga cccgccataa aacgccctga     180
gaagcccgtg acgggctttt cttgtattat gggtagtttc cttgcatgaa tccataaaag     240
gcgcctgtag tgccatttac ccccattcac tgccagagcc gtgagcgcag cgaactgaat     300
gtcacgaaaa agacagcgac tcaggtgcct gatggtcgga gacaaaagga atattcagcg     360
atttgcccga gcttgcgagg gtgctactta agcctttagg gttttaaggt ctgttttgta     420
gaggagcaaa cagcgtttgc gacatccttt tgtaatactg cggaactgac taaagtagtg     480
agttatacac agggctggga tctattcttt ttatcttttt ttattctttc tttattctat     540
aaattataac cacttgaata taaacaaaaa aaacacacaa aggtctagcg gaatttacag     600
agggtctagc agaatttaca gtttttccag caaaggtcta gcagaattta cagatacccca    660 caactcaaag gaaaaggact agtaattatc attgactagc ccatctcaat tggtatagtg     720
attaaaatca cctagaccaa ttgagatgta tgtctgaatt agttgttttc aaagcaaatg     780
aactagcgat tagtcgctat gacttaacgg agcatgaaac caagctaatt ttatgctgtg     840
tggcactact caaccccacg attgaaaacc ctacaaggaa agaacggacg gtatcgttca     900
cttataacca atacgctcag atgatgaaca tcagtaggga aatgcttat ggtgtattag      960 ctaaagcaac cagagagctg atgacgagaa ctgtggaaat caggaatcct ttggttaaag    1020
gctttgagat tttccagtgg acaaactatg ccaagttctc aagcgaaaaa ttagaattag    1080
tttttagtga agagatattg ccttatcttt tccagttaaa aaaattcata aaatataatc    1140
tggaacatgt taagtctttt gaaaacaaat actctatgag gatttatgag tggttattaa    1200
aagaactaac acaaaagaaa actcacaagg caaatataga gattagcctt gatgaattta    1260
agttcatgtt aatgcttgaa aataactacc atgagtttaa aaggcttaac caatgggttt    1320
tgaaaccaat aagtaaagat ttaaacactt acagcaatat gaaattggtg gttgataagc    1380

```
gaggccgccc gactgatacg ttgattttcc aagttgaact agatagacaa atggatctcg    1440
taaccgaact tgagaacaac cagataaaaa tgaatggtga caaaatacca acaaccatta    1500
catcagattc ctacctacat aacggactaa gaaaaacact acacgatgct ttaactgcaa    1560
aaattcagct caccagtttt gaggcaaaat ttttgagtga catgcaaagt aagcatgatc    1620
tcaatggttc gttctcatgg ctcacgcaaa acaacgaac cacactagag aacatactgg     1680
ctaaatacgg aaggatctga ggttcttatg gctcttgtat ctatcagtga agcatcaaga    1740
ctaacaaaca aaagtagaac aactgttcac cgttacatat caagggaaa actgtccata     1800 tgcacagatg aaaacggtgt aaaaagata gatacatcag agcttttacg agttttggt      1860 gcattcaaag ctgttcacca tgaacagatc gacaatgtaa cagatgaaca gcatgtaaca    1920
cctaatagaa caggtgaaac cagtaaaaca aagcaactag aacatgaaat tgaacacctg    1980
agacaacttg ttacagctca acagtcacac atagacagcc tgaaacaggc gatgctgctt    2040
atcgaatcaa agctgccgac aacacggag ccagtgacgc ctcccgtggg gaaaaaatca     2100
tggcaattct ggaagaaata gcgccattcg ccattcaggc tgcgcaactg ttgggaaggg    2160
cgatcggtgc gggcctcttc gctattacgc cagctggcga aaggggatg tgctgcaagg     2220 cgattaagtt gggtaacgcc agggttttcc cagtcacgac gttgtaaaac gacggccagt    2280
gaattcgagc tcggtaccct gttttttccac tcttcgttca ctttcgccag gtagctggtg    2340
aagacgaagg aagtcccgga gccatctgcg cggcgtacta cagcaatgtt ttgtgaaggc    2400
agtttcagac ccggattcag tttggcgatg gcttcatcat cccacttctt gattttgccc    2460
aggtagatgt cgccgagggt tttaccatcc agcaccagtt cgccagactt cagccctgga    2520
atgttaaccg ccagcaccac gccgccaatc acggtcggga actggaacag accttcctga    2580
gccagttttt cgtcagacag cggcgcgtca gaggcaccaa aatcaacggt attagcgata    2640
atctgtttta cgccaccgga agaaccgata ccctggtagt taactttatt accggtttct    2700
ttctggtaag tgtcagccca tttggcatac accggcgcag ggaaggttgc acctgcacct    2760
gtcaggcttg cttctgcaaa cacagagaaa gcactcatcg ataaggtcgc ggcgacaaca    2820
gttgcgacgg tggtacgcat aactttcata atgtctcctg ggaggattca taaagcattg    2880
tttgttggct acgagaagca aaataggaca aacaggtgac agttatatgt aaggaatatg    2940
acagttttat gacagagaga taaagtcttc agtctgattt aaataagcgt tgatattcag    3000
tcaattacaa acattaataa cgaagagatg acagaaaaat tttcattctg tgacagagaa    3060
aaagtagccg aagatgacgg tttgtcacat ggagttggca ggatgtttga ttaaaatgaa    3120
gcctgctttt ttatactaag ttggcattat aaaaaagcat tgcttatcaa tttgttgcaa    3180
cgaacaggtc actatcagtc aaaataaaat cattatttga tttcgaattc tcatgtttga    3240
cagcttatca tcgataagct ttaatgcggt agtttatcac agttaaattg ctaacgcagt    3300
caggcaccgt gtatgaaatc taacaatgcg ctcatcgtca tcctcggcac cgtcaccctg    3360
gatgctgtag gcataggctt ggttatgccg gtactgccgg gcctcttgcg ggatatcgtc    3420
cattccgaca gcatcgccag tcactatggc gtgctgctag cgctatatgc gttgatgcaa    3480
tttctatgcg cacccgttct cggagcactg tccgaccgct ttggccgccg cccagtcctg    3540
ctcgcttcgc tacttggagc cactatcgac tacgcgatca tggcgaccac accgtcctg    3600 tggatctccg ataagtagga cagcctgata agtcgcacga aaacaggta ttgacaacat     3660 gaagtaacat gcagtaagat acaaatcgct aggtaacact agcagcgtca accgggcgct    3720
```

```
ctagctagag ccaagctagc ttggccggat ccgagatttt caggagctaa ggaagctaaa    3780
atggagaaaa aaatcactgg atataccacc gttgatatat cccaatggca tcgtaaagaa    3840
catttgagg catttcagtc agttgctcaa tgtacctata accagaccgt tcagctggat     3900
attacggcct ttttaaagac cgtaaagaaa aataagcaca agttttatcc ggcctttatt    3960
cacattcttg cccgcctgat gaatgctcat ccggaattcc gtatggcaat gaaagacggt    4020
gagctggtga tatgggatag tgttcaccct tgttacaccg ttttccatga gcaaactgaa    4080
acgttttcat cgctctggag tgaataccac gacgatttcc ggcagtttct acacatatat    4140
tcgcaagatg tggcgtgtta cggtgaaaac ctggcctatt tccctaaagg gtttattgag    4200
aatatgtttt tcgtctcagc caatccctgg gtgagtttca ccagttttga tttaaacgtg    4260
gccaatatgg acaacttctt cgcccccgtt ttcaccatgg gcaaatatta tacgcaaggc    4320
gacaaggtgc tgatgccgct ggcgattcag gttcatcatg ccgtctgtga tggcttccat    4380
gtcggcagaa tgcttaatga attacaacag tactgcgatg agtggcaggg cggggcgtaa    4440
ttttttttaag gcagttattg gtgcccttaa acgcctggtg ctacgcctga ataagtgata    4500
ataagcggat gaatggcaga aattcgtcga agcttaacac agaaaaaagc ccgcacctga    4560
cagtgcgggc tttttttttc gaccactgca gtctgttaca ggtcactaat accatctaag    4620
tagttgattc atagtgactg catatgttgt gttttacagt attatgtagt ctgtttttta    4680
tgcaaaatct aatttaatat attgatattt atatcatttt acgttctcg ttcagctttt     4740
ttatactaac ttgagcggcc cttgacgatg ccacatcctg agcaaataat tcaaccacta    4800
attgtgagcg ataacacaa ggaggaaaca gctatgtcat taccgttctt aacttctgca     4860
ccgggaaagg ttattatttt tggtgaacac tctgctgtgt acaacaagcc tgccgtcgct    4920
gctagtgtgt ctgcgttgag aacctacctg ctaataagcg agtcatctgc accagatact    4980
attgaattgg acttcccgga cattagcttt aatcataagt ggtccatcaa tgatttcaat    5040
gccatcaccg aggatcaagt aaactcccaa aaattggcca aggctcaaca agccaccgat    5100
ggcttgtctc aggaactcgt tagtcttttg gatccgttgt tagctcaact atccgaatcc    5160
ttccactacc atgcagcgtt ttgtttcctg tatatgtttg tttgcctatg ccccatgcc     5220
aagaatatta gttttccctt aaagtctact ttacccatcg gtgctgggtt gggctcaagc    5280
gcctctatt ctgtatcact ggccttagct atggcctact tggggggggtt aataggatct     5340
aatgacttgg aaaagctgtc agaaaacgat aagcatatag tgaatcaatg ggccttcata    5400
ggtgaaaagt gtattcacgg tacccccttca ggaatagata cgctgtggc cacttatggt    5460
aatgccctgc tatttgaaaa agactcacat aatggaacaa taaacacaaa caattttaag   5520
ttcttagatg atttcccagc cattccaatg atcctaacct atactagaat tccaaggtct    5580
acaaaagatc ttgttgctcg cgttcgtgtg ttggtcaccg agaaatttcc tgaagttatg    5640
aagccaattc tagatgccat gggtgaatgt gccctacaag gcttagagat catgactaag    5700
ttaagtaaat gtaaaggcac cgatgacgag gctgtagaaa ctaataatga actgtatgaa    5760
caactattgg aattgataag aataaatcat ggactgcttg tctcaatcgg tgtttctcat    5820
cctggattag aacttattaa aaatctgagc gatgatttga gaattggctc cacaaaactt    5880
accggtgctg gtggcggcgg ttgctctttg actttgttac gaagagacat tactcaagag    5940
caaattgaca gcttcaaaaa gaaattgcaa gatgatttta gttacgagac atttgaaaca    6000
gacttgggtg gactggctg ctgttgtta agcgcaaaaa atttgaataa agatcttaaa       6060
atcaaatccc tagtattcca attatttgaa aataaaacta ccacaaagca acaaattgac    6120
```

```
gatctattat tgccaggaaa cacgaattta ccatggactt cataagctaa tttgcgatag    6180
gcctgcaccc ttaaggagga aaaaaacatg tcagagttga gagccttcag tgccccaggg    6240
aaagcgttac tagctggtgg atatttagtt ttagatacaa aatatgaagc atttgtagtc    6300
ggattatcgg caagaatgca tgctgtagcc catccttacg gttcattgca agggtctgat    6360
aagtttgaag tgcgtgtgaa aagtaaacaa tttaaagatg gggagtggct gtaccatata    6420
agtcctaaaa gtggcttcat tcctgtttcg ataggcggat ctaagaaccc tttcattgaa    6480
aaagttatcg ctaacgtatt tagctacttt aaacctaaca tggacgacta ctgcaataga    6540
aacttgttcg ttattgatat tttctctgat gatgcctacc attctcagga ggatagcgtt    6600
accgaacatc gtggcaacag aagattgagt tttcattcgc acagaattga agaagttccc    6660
aaaacagggc tgggctcctc ggcaggttta gtcacagttt taactacagc tttgcctcc    6720 ttttttgtat cggacctgga aaataatgta gacaaatata gagaagttat tcataattta    6780
gcacaagttg ctcattgtca agctcagggt aaaattggaa gcgggtttga tgtagcggcg    6840
gcagcatatg gatctatcag atatagaaga ttcccacccg cattaatctc taatttgcca    6900
gatattggaa gtgctactta cggcagtaaa ctggcgcatt tggttgatga agaagactgg    6960
aatattacga ttaaaagtaa ccatttacct tcgggattaa ctttatggat gggcgatatt    7020
aagaatggtt cagaaacagt aaaactggtc cagaaggtaa aaaattggta tgattcgcat    7080
atgccagaaa gcttgaaaat atatacagaa ctcgatcatg caaattctag atttatggat    7140
ggactatcta aactgatcg cttacacgag actcatgacg attacagcga tcagatattt    7200
gagtctcttg agaggaatga ctgtacctgt caaaagtatc ctgaaatcac agaagttaga    7260
gatgcagttg ccacaattag acgttccttt agaaaaataa ctaaagaatc tggtgccgat    7320
atcgaacctc ccgtacaaac tagcttattg gatgattgcc agaccttaaa aggagttctt    7380
acttgcttaa tacctggtgc tggtggttat gacgccattg cagtgattac taagcaagat    7440
gttgatctta gggctcaaac cgctaatgac aaaagatttt ctaaggttca atggctggat    7500
gtaactcagg ctgactgggg tgttaggaaa gaaaaagatc cggaaactta tcttgataaa    7560
taacttaagg tagctgcatg cagaattcgc ccttaaggag gaaaaaaaaa tgaccgttta    7620
cacagcatcc gttaccgcac ccgtcaacat cgcaacccct taagtatggg ggaaaaggga    7680
cacgaagttg aatctgccca ccaattcgtc catatcagtg actttatcgc aagatgacct    7740
cagaacgttg acctctgcgg ctactgcacc tgagtttgaa cgcgacactt tgtggttaaa    7800
tggagaacca cacagcatcg acaatgaaag aactcaaaat tgtctgcgcg acctacgcca    7860
attaagaaag gaaatggaat cgaaggacgc ctcattgccc acattatctc aatggaaact    7920
ccacattgtc tccgaaaata actttcctac agcagctggt ttagcttcct ccgctgctgg    7980
ctttgctgca ttggtctctg caattgctaa gttataccaa ttaccacagt caacttcaga    8040
aatatctaga atagcaagaa aggggtctgg ttcagcttgt agatcgttgt ttggcggata    8100
cgtggcctgg gaaatgggaa aagctgaaga tggtcatgat tccatggcag tacaaatcgc    8160
agacagctct gactggcctc agatgaaagc ttgtgtccta gttgtcagcg atattaaaaa    8220
ggatgtgagt tccactcagg gtatgcaatt gaccgtggca acctccgaac tatttaaaga    8280
aagaattgaa catgtcgtac caaagagatt tgaagtcatg cgtaaagcca ttgttgaaaa    8340
agatttcgcc acctttgcaa aggaaacaat gatggattcc aactctttcc atgccacatg    8400
tttggactct ttccctccaa tattctacat gaatgacact tccaagcgta tcatcagttg    8460
```

```
gtgccacacc attaatcagt tttacggaga aacaatcgtt gcatacacgt ttgatgcagg    8520
tccaaatgct gtgttgtact acttagctga aaatgagtcg aaactctttg catttatcta    8580
taaattgttt ggctctgttc ctggatggga caagaaattt actactgagc agcttgaggc    8640
tttcaaccat caatttgaat catctaactt tactgcacgt gaattggatc ttgagttgca    8700
aaaggatgtt gccagagtga ttttaactca agtcggttca ggcccacaag aaacaaacga    8760
atctttgatt gacgcaaaga ctggtctacc aaaggaataa gatcaattcg ctgcatcgcc    8820
cttaggaggt aaaaaaaaat gactgccgac aacaatagta tgccccatgg tgcagtatct    8880
agttacgcca aattagtgca aaaccaaaca cctgaagaca ttttggaaga gtttcctgaa    8940
attattccat tacaacaaag acctaatacc cgatctagtg agacgtcaaa tgacgaaagc    9000
ggagaaacat gttttttctgg tcatgatgag gagcaaatta agttaatgaa tgaaaattgt    9060
attgttttgg attgggacga taatgctatt ggtgccggta ccaagaaagt ttgtcatttta    9120 atggaaaata ttgaaaaggg tttactacat cgtgcattct ccgtctttat tttcaatgaa    9180
caaggtgaat tacttttaca acaaagagcc actgaaaaaa taactttccc tgatctttgg    9240
actaacacat gctgctctca tccactatgt attgatgacg aattaggttt gaagggtaag    9300
ctagacgata agattaaggg cgctattact gcggcggtga aaaactaga tcatgaatta    9360 ggtattccag aagatgaaac taagacaagg ggtaagtttc acttttttaaa cagaatccat    9420 tacatggcac caagcaatga accatgggt gaacatgaaa ttgattacat cctattttat    9480
aagatcaacg ctaagaaaa cttgactgtc aacccaaacg tcaatgaagt tagagacttc    9540
aaatgggttt caccaaatga tttgaaaact atgtttgctg acccaagtta caagtttacg    9600
ccttggttta agattatttg cgagaattac ttattcaact ggtgggagca attagatgac    9660
ctttctgaag tggaaaatga caggcaaatt catagaatgc tataacaacg cgtctacaaa    9720 taaaaaggc acgtcagatg acgtgccttt tttcttgggg ccggggatcc tctagagtcg    9780
acctgcaggc atgcaagctt ggcgtaatca tggtcatagc tgtttcctgt gtgaaattgt    9840
tatccgctca caattccaca acacatacga gccggaagca taaagtgtaa agcctggggt    9900
gcctaatgag tgagctaact cacattaatt gcgttgcgct cactgcccgc tttccagtcg    9960
ggaaacctgt cgtgccagct gcattaatga atcggccaac gcgcggggag aggcggtttg   10020
cgtattgggc gctttctcat agctcacgct gtaggtatct cagttcggtg taggtcgttc   10080
gctccaagct gggctgtgtg ccgaaccca gagtcccgct cagaagaact cgtcaagaag   10140
gcgatagaag gcgatgcgct gcgaatcggg agcggcgata ccgtaaagca cgaggaagcg   10200
gtcagcccat tcgccgccaa gctcttcagc aatatcacgg gtagccaacg ctatgtcctg   10260
atagcggtcc gccacaccca gccggccaca gtcgatgaat ccagaaaagc ggccattttc   10320
caccatgata ttcggcaagc aggcatcgcc atgggtcacg acgagatcct cgccgtcggg   10380
catgcgcgcc ttgagcctgg cgaacagttc ggctggcgcg agccctgat gctcttcgtc   10440 cagatcatcc tgatcgacaa gaccggcttc catccgagta cgtgctcgct cgatgcgatg   10500
tttcgcttgg tggtcgaatg ggcaggtagc cggatcaagc gtatgcagcc gccgcattgc   10560
atcagccatg atggatactt tctcggcagg agcaaggtga gatgacagga gatcctgccc   10620
cggcacttcg cccaatagca gccagtccct tcccgcttca gtgccaacgt cgagcacagc   10680
tgcgcaagga acgcccgtcg tggccagcca cgatagccgc gctgcctcgt cctgcagttc   10740
attcagggca ccggacaggt cggtcttgac aaaaagaacc gggcgcccct gcgctgacag   10800
ccggaacacg gcggcatcag agcagccgat tgtctgttgt gcccagtcat agccgaatag   10860
```

```
cctctccacc caagcggccg gagaacctgc gtgcaatcca tcttgttcaa tcatgcgaaa    10920
cgatcctcat cctgtctctt gatcactacc gcattaaagc atatcgatga taagctgtca    10980
aacatgagcg ttcttcgggg cgaaaactct caaggatctt accgctgttg agatccagtt    11040
cgatgtaacc cactcgtgca cccaactgat cttcagcatc ttttactttc accagcgttt    11100
ctgggtgagc aaaaacagga aggcaaaatg ccgcaaaaaa gggaataagg gcgacacgga    11160
aatgttgaat actcatactc ttccttttc aatattattg aagcatttat cagggttatt    11220
gtctcatgag cggatacata tttgaatgta tttagaaaaa taaacaaata ggggttccgc    11280
gcacatttcc ccgaaaagtg ccacctgacg tctaagaaac cattattatc atgacattaa    11340
cctataaaaa taggcgtatc acgaggccct ttcgtcttca agaatt                   11386
```

<210> SEQ ID NO 51
<211> LENGTH: 12232
<212> TYPE: DNA
<213> ORGANISM: Artificial Sequence
<220> FEATURE:
<223> OTHER INFORMATION: Nucleotide sequence of prepared plasmid
    pMW-Tn7-Pgi-KKDyI-TaspA-Tn7

<400> SEQUENCE: 51

```
gacagtaaga cgggtaagcc tgttgatgat accgctgcct tactgggtgc attagccagt      60
ctgaatgacc tgtcacggga taatccgaag tggtcagact ggaaaatcag agggcaggaa     120
ctgcagaaca gcaaaaagtc agatagcacc acatagcaga cccgccataa aacgccctga     180
gaagcccgtg acgggctttt cttgtattat gggtagtttc cttgcatgaa tccataaaag     240
gcgcctgtag tgccatttac ccccattcac tgccagagcc gtgagcgcag cgaactgaat     300
gtcacgaaaa agacagcgac tcaggtgcct gatggtcgga gacaaaagga atattcagcg     360
atttgcccga gcttgcgagg gtgctactta agcctttagg gttttaaggt ctgttttgta     420
gaggagcaaa cagcgtttgc gacatccttt tgtaatactg cggaactgac taaagtagtg     480
agttatacac agggctggga tctattcttt ttatcttttt ttattctttc tttattctat     540
aaattataac cacttgaata taaacaaaaa aaacacacaa aggtctagcg gaatttacag     600
agggtctagc agaatttaca agttttccag caaaggtcta gcagaattta cagatacccca    660 caactcaaag gaaaaggact agtaattatc attgactagc ccatctcaat ggtatagtg     720 attaaaatca cctagaccaa ttgagatgta tgtctgaatt agttgttttc aaagcaaatg     780
aactagcgat tagtcgctat gacttaacgg agcatgaaac caagctaatt ttatgctgtg     840
tggcactact caaccccacg attgaaaacc ctacaaggaa agaacggacg gtatcgttca     900
cttataacca atacgctcag atgatgaaca tcagtaggga aatgcttat ggtgtattag     960 ctaaagcaac cagagagctg atgacgagaa ctgtggaaat caggaatcct ttggttaaag    1020
gctttgagat tttccagtgg acaaactatg ccaagttctc aagcgaaaaa ttagaattag    1080
tttttagtga agagatattg ccttatcttt tccagttaaa aaaattcata aaatataatc    1140
tggaacatgt taagtctttt gaaaacaaat actctatgag gatttatgag tggttattaa    1200
aagaactaac acaaagaaaa actcacaagg caaatataga gattagcctt gatgaattta    1260
agttcatgtt aatgcttgaa ataactacc atgagtttaa aaggcttaac caatgggttt    1320
tgaaaccaat aagtaaagat ttaaacactt acagcaatat gaaattggtg gttgataagc    1380
gaggccgccc gactgatacg ttgatttttcc aagttgaact agatagacaa atggatctcg    1440
taaccgaact tgagaacaac cagataaaaa tgaatggtga caaaatacca acaaccatta    1500
```

-continued

```
catcagattc ctacctacat aacggactaa gaaaaacact acacgatgct ttaactgcaa    1560
aaattcagct caccagtttt gaggcaaaat ttttgagtga catgcaaagt aagcatgatc    1620
tcaatggttc gttctcatgg ctcacgcaaa acaacgaac cacactagag aacatactgg     1680
ctaaatacgg aaggatctga ggttcttatg gctcttgtat ctatcagtga agcatcaaga    1740
ctaacaaaca aaagtagaac aactgttcac cgttacatat caagggaaa actgtccata     1800 tgcacagatg aaaacggtgt aaaaagata gatacatcag agcttttacg agttttttggt    1860 gcattcaaag ctgttcacca tgaacagatc gacaatgtaa cagatgaaca gcatgtaaca    1920
cctaatagaa caggtgaaac cagtaaaaca aagcaactag aacatgaaat tgaacacctg    1980
agacaacttg ttacagctca acagtcacac atagacagcc tgaaacaggc gatgctgctt    2040
atcgaatcaa agctgccgac aacacggag ccagtgacgc ctcccgtggg gaaaaaatca    2100
tggcaattct ggaagaaata gcgccattcg ccattcaggc tgcgcaactg ttgggaaggg    2160
cgatcggtgc gggcctcttc gctattacgc cagctggcga aaggggatg tgctgcaagg    2220 cgattaagtt gggtaacgcc agggttttcc cagtcacgac gttgtaaaac gacggccagt    2280
gaattcgagc tcggtaccct gttttttccac tcttcgttca ctttcgccag gtagctggtg    2340
aagacgaagg aagtcccgga gccatctgcg cggcgtacta cagcaatgtt ttgtgaaggc    2400
agtttcagac ccggattcag tttggcgatg gcttcatcat cccacttctt gattttgccc    2460
aggtagatgt cgccgagggt tttaccatcc agcaccagtt cgccagactt cagccctgga    2520
atgttaaccg ccagcaccac gccgccaatc acggtcggga actggaacag accttcctga    2580
gccagttttt cgtcagacag cggcgcgtca gaggcaccaa aatcaacggt attagcgata    2640
atctgtttta cgccaccgga agaaccgata ccctggtagt taactttatt accggttttct    2700 ttctggtaag tgtcagccca tttggcatac accggcgcag ggaaggttgc acctgcacct    2760
gtcaggcttg cttctgcaaa cacagagaaa gcactcatcg ataaggtcgc ggcgacaaca    2820
gttgcgacgg tggtacgcat aactttcata atgtctcctg ggaggattca taaagcattg    2880
tttgttggct acgagaagca aaataggaca aacaggtgac agttatatgt aaggaatatg    2940
acagttttat gacagagaga taaagtcttc agtctgattt aaataagcgt tgatattcag    3000
tcaattacaa acattaataa cgaagagatg acagaaaaat tttcattctg tgacagagaa    3060
aaagtagccg aagatgacgg tttgtcacat ggagttggca ggatgtttga ttaaaatgaa    3120
gcctgctttt ttatactaag ttggcattat aaaaaagcat tgcttatcaa tttgttgcaa    3180
cgaacaggtc actatcagtc aaaataaaat cattatttga tttcgaattc tcatgtttga    3240
cagcttatca tcgataagct ttaatgcggt agtttatcac agttaaattg ctaacgcagt    3300
caggcaccgt gtatgaaatc taacaatgcg ctcatcgtca tcctcggcac cgtcaccctg    3360
gatgctgtag gcataggctt ggttatgccg gtactgccgg gcctcttgcg ggatatcgtc    3420
cattccgaca gcatcgccag tcactatggc gtgctgctag cgctatatgc gttgatgcaa    3480
tttctatgcg cacccgttct cggagcactg tccgaccgct ttggccgccg cccagtcctg    3540
ctcgcttcgc tacttggagc cactatcgac tacgcgatca tggcgaccac acccgtcctg    3600
tggatctccg gataagtaga cagcctgata agtcgcacga aaacaggta ttgacaacat    3660 gaagtaacat gcagtaagat acaaatcgct aggtaacact agcagcgtca accgggcgct    3720
ctagctagag ccaagctagc ttggccggat ccgagatttt caggagctaa ggaagctaaa    3780
atggagaaaa aaatcactgg atataccacc gttgatatat cccaatggca tcgtaaagaa    3840
```

```
cattttgagg catttcagtc agttgctcaa tgtacctata accagaccgt tcagctggat    3900
attacggcct ttttaaagac cgtaaagaaa aataagcaca agttttatcc ggcctttatt    3960
cacattcttg cccgcctgat gaatgctcat ccggaattcc gtatggcaat gaaagacggt    4020
gagctggtga tatgggatag tgttcaccct tgttacaccg ttttccatga gcaaactgaa    4080
acgttttcat cgctctggag tgaataccac gacgatttcc ggcagtttct acacatatat    4140
tcgcaagatg tggcgtgtta cggtgaaaac ctggcctatt tccctaaagg gtttattgag    4200
aatatgtttt tcgtctcagc caatccctgg gtgagtttca ccagttttga tttaaacgtg    4260
gccaatatgg acaacttctt cgcccccgtt ttcaccatgg gcaaatatta tacgcaaggc    4320
gacaaggtgc tgatgccgct ggcgattcag gttcatcatg ccgtctgtga tggcttccat    4380
gtcggcagaa tgcttaatga attacaacag tactgcgatg agtggcaggg cggggcgtaa    4440
ttttttttaag gcagttattg gtgcccttaa acgcctggtg ctacgcctga ataagtgata    4500
ataagcggat gaatggcaga aattcgtcga agcttaacac agaaaaaagc ccgcacctga    4560
cagtgcgggc ttttttttc gaccactgca gtctgttaca ggtcactaat accatctaag    4620
tagttgattc atagtgactg catatgttgt gttttacagt attatgtagt ctgttttta    4680
tgcaaaatct aatttaatat attgatattt atatcatttt acgtttctcg ttcagctttt    4740
ttatactaac ttgagcggcc cttgacgatg ccacatcctg agcaaataat tcaaccacta    4800
attgtgagcg gataacacaa ggaggaaaca gctatgtcat taccgttctt aacttctgca    4860
ccgggaaagg ttattatttt tggtgaacac tctgctgtgt acaacaagcc tgccgtcgct    4920
gctagtgtgt ctgcgttgag aacctacctg ctaataagcg agtcatctgc accagatact    4980
attgaattgg acttcccgga cattagcttt aatcataagt ggtccatcaa tgatttcaat    5040
gccatcaccg aggatcaagt aaactcccaa aaattggcca aggctcaaca agccaccgat    5100
ggcttgtctc aggaactcgt tagtcttttg gatccgttgt tagctcaact atccgaatcc    5160
ttccactacc atgcagcgtt ttgtttcctg tatatgtttg tttgcctatg ccccccatgcc    5220
aagaatatta agttttcctt aaagtctact ttacccatcg gtgctgggtt gggctcaagc    5280
gcctctatttt ctgtatcact ggccttagct atggcctact tggggggggtt aataggatct    5340
aatgacttgg aaaagctgtc agaaaacgat aagcatatag tgaatcaatg ggccttcata    5400
ggtgaaaagt gtattcacgg tacccccttca ggaatagata cgctgtggc cacttatggt    5460
aatgccctgc tatttgaaaa agactcacat aatggaacaa taaacacaaa caattttaag    5520
ttcttagatg atttcccagc cattccaatg atcctaacct atactagaat tccaaggtct    5580
acaaaagatc ttgttgctcg cgttcgtgtg ttggtcaccg agaaatttcc tgaagttatg    5640
aagccaattc tagatgccat gggtgaatgt gccctacaag gcttagagat catgactaag    5700
ttaagtaaat gtaaaggcac cgatgacgag gctgtagaaa ctaataatga actgtatgaa    5760
caactattgg aattgataag aataaatcat ggactgcttg tctcaatcgg tgtttctcat    5820
cctggattag aacttattaa aaatctgagc gatgatttga gaattggctc cacaaaactt    5880
accggtgctg gtggcggcgg ttgctctttg actttgttac aagagacat tactcaagag    5940
caaattgaca gcttcaaaaa gaaattgcaa gatgattta gttacgagac atttgaaaca    6000
gacttgggtg ggactggctg ctgtttgtta agcgcaaaaa atttgaataa agatcttaaa    6060
atcaaatccc tagtattcca attatttgaa aataaaacta ccacaaagca acaaattgac    6120
gatctattat tgccaggaaa cacgaattta ccatggactt cataagctaa tttgcgatag    6180
gcctgcaccc ttaaggagga aaaaaacatg tcagagttga gagccttcag tgccccaggg    6240
```

```
aaagcgttac tagctggtgg atatttagtt ttagatacaa aatatgaagc atttgtagtc    6300
ggattatcgg caagaatgca tgctgtagcc catccttacg gttcattgca agggtctgat    6360
aagtttgaag tgcgtgtgaa aagtaaacaa tttaaagatg gggagtggct gtaccatata    6420
agtcctaaaa gtggcttcat tcctgtttcg ataggcggat ctaagaaccc tttcattgaa    6480
aaagttatcg ctaacgtatt tagctacttt aaacctaaca tggacgacta ctgcaataga    6540
aacttgttcg ttattgatat tttctctgat gatgcctacc attctcagga ggatagcgtt    6600
accgaacatc gtggcaacag aagattgagt tttcattcgc acagaattga agaagttccc    6660
aaaacagggc tgggctcctc ggcaggttta gtcacagttt taactacagc tttggcctcc    6720 tttttgtat cggacctgga aaataatgta gacaaatata gagaagttat tcataattta    6780
gcacaagttg ctcattgtca agctcagggt aaaattggaa gcgggtttga tgtagcggcg    6840
gcagcatatg gatctatcag atatagaaga ttcccacccg cattaatctc taatttgcca    6900
gatattggaa gtgctactta cggcagtaaa ctggcgcatt tggttgatga agaagactgg    6960
aatattacga ttaaaagtaa ccatttacct tcgggattaa ctttatggat gggcgatatt    7020
aagaatggtt cagaaacagt aaaactggtc cagaaggtaa aaaattggta tgattcgcat    7080
atgccagaaa gcttgaaaat atatacagaa ctcgatcatg caaattctag atttatggat    7140
ggactatcta aactagatcg cttacacgag actcatgacg attacagcga tcagatattt    7200
gagtctcttg agaggaatga ctgtacctgt caaaagtatc ctgaaatcac agaagttaga    7260
gatgcagttg ccacaattag acgttccttt agaaaaataa ctaaagaatc tggtgccgat    7320
atcgaacctc ccgtacaaac tagcttattg gatgattgcc agaccttaaa aggagttctt    7380
acttgcttaa tacctggtgc tggtggttat gacgccattg cagtgattac taagcaagat    7440
gttgatctta gggctcaaac cgctaatgac aaaagatttt ctaaggttca atggctggat    7500
gtaactcagg ctgactgggg tgttaggaaa gaaaaagatc cggaaactta tcttgataaa    7560
taacttaagg tagctgcatg cagaattcgc ccttaaggag gaaaaaaaaa tgaccgttta    7620
cacagcatcc gttaccgcac ccgtcaacat cgcaaccctt aagtattggg ggaaaaggga    7680
cacgaagttg aatctgccca ccaattcgtc catatcagtg actttatcgc aagatgacct    7740
cagaacgttg acctctgcgg ctactgcacc tgagtttgaa cgcgacactt tgtggttaaa    7800
tggagaacca cacagcatcg acaatgaaag aactcaaaat tgtctgcgcg acctacgcca    7860
attaagaaag gaaatggaat cgaaggacgc ctcattgccc acattatctc aatggaaact    7920
ccacattgtc tccgaaaata actttcctac agcagctggt ttagcttcct ccgctgctgg    7980
ctttgctgca ttggtctctg caattgctaa gttataccaa ttaccacagt caacttcaga    8040
aatatctaga atagcaagaa aggggtctgg ttcagcttgt agatcgttgt ttggcggata    8100
cgtggcctgg gaaatgggaa aagctgaaga tggtcatgat tccatggcag tacaaatcgc    8160
agacagctct gactggcctc agatgaaagc ttgtgtccta gttgtcagcg atattaaaaa    8220
ggatgtgagt tccactcagg gtatgcaatt gaccgtggca acctccgaac tatttaaaga    8280
aagaattgaa catgtcgtac caaagagatt tgaagtcatg cgtaaagcca ttgttgaaaa    8340
agatttcgcc acctttgcaa aggaaacaat gatggattcc aactctttcc atgccacatg    8400
tttggactct ttccctccaa tattctacat gaatgacact tccaagcgta tcatcagttg    8460
gtgccacacc attaatcagt tttacggaga acaatcgtt gcatacacgt ttgatgcagg    8520
tccaaatgct gtgttgtact acttagctga aaatgagtcg aaactctttg catttatcta    8580
```

```
taaattgttt ggctctgttc ctggatggga caagaaattt actactgagc agcttgaggc    8640
tttcaaccat caatttgaat catctaactt tactgcacgt gaattggatc ttgagttgca    8700
aaaggatgtt gccagagtga ttttaactca agtcggttca ggcccacaag aaacaaacga    8760
atctttgatt gacgcaaaga ctggtctacc aaaggaataa gatcaattcg ctgcatcgcc    8820
cttaggaggt aaaaaaaaat gactgccgac aacaatagta tgcccatgg tgcagtatct    8880 agttacgcca aattagtgca aaaccaaaca cctgaagaca ttttggaaga gtttcctgaa    8940
attattccat tacaacaaag acctaatacc cgatctagtg agacgtcaaa tgacgaaagc    9000
ggagaaacat gtttttctgg tcatgatgag gagcaaatta agttaatgaa tgaaaattgt    9060
attgttttgg attgggacga taatgctatt ggtgccggta ccaagaaagt ttgtcattta    9120
atggaaaata ttgaaaaggg tttactacat cgtgcattct ccgtctttat tttcaatgaa    9180
caaggtgaat tacttttaca acaaagagcc actgaaaaaa taactttccc tgatctttgg    9240
actaacacat gctgctctca tccactatgt attgatgacg aattaggttt gaagggtaag    9300
ctagacgata agattaaggg cgctattact gcggcggtga aaaactaga tcatgaatta    9360 ggtattccag aagatgaaac taagacaagg ggtaagtttc actttttaaa cagaatccat    9420
tacatggcac aagcaatga accatggggt gaacatgaaa ttgattacat cctattttat    9480
aagatcaacg ctaaagaaaa cttgactgtc aacccaaacg tcaatgaagt tagagacttc    9540
aaatgggttt caccaaatga tttgaaaact atgtttgctg acccaagtta caagtttacg    9600
ccttggttta agattatttg cgagaattac ttattcaact ggtgggagca attagatgac    9660 cttttctgaag tggaaaatga caggcaaatt catagaatgc tataacaacg cgtctacaaa    9720 taaaaaggc acgtcagatg acgtgccttt tttcttgggg ccggggatcc tctagagtcg    9780
aaagaaaaat gccccgctta cgcagggcat ccatttatta ctcaaccgta accgattttg    9840
ccaggttacg cggctggtca acgtcggtgc ctttgatcag cgcgacatgg taagccagca    9900
gctgcagcgg aacggtgtag aagatcggtg caatcacctc ttccacatgc ggcatctcga    9960
tgatgtgcat gttatcgcta cttacaaaac ccgcatcctg atcggcgaag acatacaact   10020
gaccgccacg cgcgcgaact tcttcaatgt tggatttcag ttttttccagc aattcgttgt   10080 tcggtgcaac aacaataacc ggcatatcgg catcaattag cgccagcgga ccgtgtttca   10140
gttcgccagc agcgtaggct tcagcgtgaa tgtaagagat ctctttcaac ttcaatgcgc   10200
cttccagcgc gattgggtac tgatcgccac ggcccaggaa cagcgcgtga tgtttgtcag   10260
agaaatcttc tgccagcgct tcaatgcgtt tgtcctgaga cagcatctgc tcaatacggc   10320
tcggcagcgc ctgcagacca tgcacgatgt catgttcaat ggaggcatcc agacctttca   10380
ggcgagacag cttcgccacc agcatcaaca gcacagttaa ctgagtggtg aatgcttag   10440 tggatgccac gccgatttct gtacccgcgt tggtcattag cgccagatcg gattcgcgca   10500
ccagagaaga acccggaacg ttacagattg ccagtgaacc aaggtaaccc agctcttcg   10560 acagacgcag gccagccagg gtatccgcgg tttcgccaga ctgtgacagg ggatcctcta   10620
gagtcgacct gcaggcatgc aagcttggcg taatcatggt catagctgtt tcctgtgtga   10680
aattgttatc cgctcacaat tccacacaac atacgagccg gaagcataaa gtgtaaagcc   10740
tggggtgcct aatgagtgag ctaactcaca ttaattgcgt tgcgctcact gcccgctttc   10800
cagtcgggaa acctgtcgtg ccagctgcat taatgaatcg gccaacgcgc ggggagaggc   10860
ggtttgcgta ttgggcgctt tctcatagct cacgctgtag gtatctcagt tcggtgtagg   10920
tcgttcgctc caagctgggc tgtgtgccga accccagagt cccgctcaga agaactcgtc   10980
```

```
aagaaggcga tagaaggcga tgcgctgcga atcgggagcg gcgataccgt aaagcacgag    11040
gaagcggtca gcccattcgc cgccaagctc ttcagcaata tcacgggtag ccaacgctat    11100
gtcctgatag cggtccgcca cacccagccg gccacagtcg atgaatccag aaaagcggcc    11160
attttccacc atgatattcg gcaagcaggc atcgccatgg gtcacgacga atcctcgcc    11220 gtcgggcatg cgcgccttga gcctggcgaa cagttcggct ggcgcgagcc cctgatgctc    11280
ttcgtccaga tcatcctgat cgacaagacc ggcttccatc cgagtacgtg ctcgctcgat    11340
gcgatgtttc gcttggtggt cgaatgggca ggtagccgga tcaagcgtat gcagccgccg    11400
cattgcatca gccatgatgg atactttctc ggcaggagca aggtgagatg acaggagatc    11460
ctgccccggc acttcgccca atagcagcca gtcccttccc gcttcagtgc caacgtcgag    11520
cacagctgcg caaggaacgc ccgtcgtggc cagccacgat agccgcgctg cctcgtcctg    11580
cagttcattc agggcaccgg acaggtcggt cttgacaaaa agaaccgggc gccctgcgc    11640 tgacagccgg aacacggcgg catcagagca gccgattgtc tgttgtgccc agtcatagcc    11700
gaatagcctc tccacccaag cggccggaga acctgcgtgc aatccatctt gttcaatcat    11760
gcgaaacgat cctcatcctg tctcttgatc actaccgcat taaagcatat cgatgataag    11820
ctgtcaaaca tgagcgttct tcggggcgaa aactctcaag gatcttaccg ctgttgagat    11880
ccagttcgat gtaacccact cgtgcaccca actgatcttc agcatctttt actttcacca    11940
gcgtttctgg gtgagcaaaa acaggaaggc aaaatgccgc aaaaaaggga ataagggcga    12000 cacgaaatg ttgaatactc atactcttcc tttttcaata ttattgaagc atttatcagg    12060
gttattgtct catgagcgga tacatatttg aatgtattta gaaaaataaa caaatagggg    12120
ttccgcgcac atttccccga aaagtgccac ctgacgtcta agaaaccatt attatcatga    12180
cattaaccta taaaaatagg cgtatcacga ggccctttcg tcttcaagaa tt            12232

<210> SEQ ID NO 52
<211> LENGTH: 9175
<212> TYPE: DNA
<213> ORGANISM: Artificial Sequence
<220> FEATURE:
<223> OTHER INFORMATION: Nucleotide sequence containing genomic sequence
      encoding downstream enzymes in the mevalonate pathway

<400> SEQUENCE: 52
ttagtacagc ggcttaccgc tactgtcttt aatattggtc ttccacgcag cgcgaacctg      60
ttcaactaca ctatccggca ggctggcgta atccaggtcg ttcgcctgtt tagccccggt     120
tttgtacgcc cagtcgaaga atttcagcac ttctgtgcct tgttctggtt tcttctgatc     180
tttgtggatc agaatgaacg tggtagaggt aataggccat gcatcttcgc ctttctggtt     240
ggtcagatcc tgagcgaagg ttttgctcca gtctgcacct tttgctgcat tagcgaagtt     300
ttcttcggtc ggactaaccg gtttaccatc agcggagatc agtttggtgt acgccaggtt     360
gttctgcttc gcgtaagcat attcaacata accaattgca cccggcagac gctgaacgaa     420
cgcggcgata ccgtcgttac ctttaccgcc cagaccgatc ggccatttta cggtagagcc     480
agtaccaacg ttgtttttcc actcttcgtt cactttcgcc aggtagctgg tgaagacgaa     540
ggaagtcccg gagccatctg cgcggcgtac tacagcaatg ttttgtgaag gcagtttcag     600
acccggattc agtttggcga tggcttcatc atcccacttc ttgattttgc ccaggtagat     660
gtcgccgagg gttttaccat ccagcaccag ttcgccagac ttcagccctg gaatgttaac     720
cgccagcacc acgccgccaa tcacggtcgg gaactggaac agaccttcct gagccagttt     780
```

```
ttcgtcagac agcggcgcgt cagaggcacc aaaatcaacg gtattagcga taatctgttt    840
tacgccaccg gaagaaccga taccctggta gttaacttta ttaccggttt ctttctggta    900
agtgtcagcc catttggcat acaccggcgc agggaaggtt gcacctgcac ctgtcaggct    960
tgcttctgca aacacagaga aagcactcat cgataaggtc gcggcgacaa cagttgcgac   1020
ggtggtacgc ataactttca taatgtctcc tgggaggatt cataaagcat tgtttgttgg   1080
ctacgagaag caaaatagga caaacaggtg acagttatat gtaaggaata tgacagtttt   1140
atgacagaga gataaagtct tcagtctgat ttaaataagc gttgatattc agtcaattac   1200
aaacattaat aacgaagaga tgacagaaaa attttcattc tgtgacagag aaaaagtagc   1260
cgaagatgac ggtttgtcac atggagttgg caggatgttt gattaaaatg aagcctgctt   1320
ttttatacta agttggcatt ataaaaaagc attgcttatc aatttgttgc aacgaacagg   1380
tcactatcag tcaaaataaa atcattattt gatttcgaat tctcatgttt gacagcttat   1440
catcgataag cttaatgcg gtagtttatc acagttaaat tgctaacgca gtcaggcacc    1500
gtgtatgaaa tctaacaatg cgctcatcgt catcctcggc accgtcaccc tggatgctgt   1560
aggcataggc ttggttatgc cggtactgcc gggcctcttg cgggatatcg tccattccga   1620
cagcatcgcc agtcactatg gcgtgctgct agcgctatat gcgttgatgc aatttctatg   1680
cgcacccgtt ctcggagcac tgtccgaccg ctttggccgc cgcccagtcc tgctcgcttc   1740
gctacttgga gccactatcg actacgcgat catggcgacc acaccgtcc tgtggatctc    1800 cggataagta gacagcctga taagtcgcac gaaaaacagg tattgacaac atgaagtaac   1860
atgcagtaag atacaaatcg ctaggtaaca ctagcagcgt caaccgggcg ctctagctag   1920
agccaagcta gcttggccgg atccgagatt ttcaggagct aaggaagcta aaatggagaa   1980
aaaaatcact ggatatacca ccgttgatat atcccaatgg catcgtaaag aacatttga    2040 ggcatttcag tcagttgctc aatgtaccta taaccagacc gttcagctgg atattacggc   2100 cttttttaaag accgtaaaga aaaataagca caagttttat ccggccttta ttcacattct   2160
tgcccgcctg atgaatgctc atccggaatt ccgtatggca atgaaagacg gtgagctggt   2220
gatatgggat agtgttcacc cttgttacac cgttttccat gagcaaactg aaacgttttc   2280
atcgctctgg agtgaatacc acgacgattt ccggcagttt ctacacatat attcgcaaga   2340
tgtggcgtgt tacggtgaaa acctggccta tttccctaaa gggtttattg agaatatgtt   2400
tttcgtctca gccaatccct gggtgagttt caccagtttt gatttaaacg tggccaatat   2460
ggacaacttc ttcgccccg ttttcaccat gggcaaatat tatacgcaag cgacaaggt    2520 gctgatgccg ctggcgattc aggttcatca tgccgtctgt gatggcttcc atgtcggcag   2580
aatgcttaat gaattacaac agtactgcga tgagtggcag ggcggggcgt aattttttta   2640
aggcagttat tggtgccctt aaacgcctgg tgctacgcct gaataagtga taataagcgg   2700
atgaatggca gaaattcgtc gaagcttaac acagaaaaaa gcccgcacct gacagtgcgg   2760 gcttttttt tcgaccactg cagtctgtta caggtcacta ataccatcta agtagttgat   2820
tcatagtgac tgcatatgtt gtgttttaca gtattatgta gtctgttttt tatgcaaaat   2880
ctaatttaat atattgatat ttatatcatt ttacgtttct cgttcagctt ttttatacta   2940
acttgagcgg cccttgacga tgccacatcc tgagcaaata attcaaccac taattgtgag   3000
cggataacac aaggaggaaa cagctatgtc attaccgttc ttaacttctg caccgggaaa   3060
ggttattatt tttggtgaac actctgctgt gtacaacaag cctgccgtcg ctgctagtgt   3120
```

```
gtctgcgttg agaacctacc tgctaataag cgagtcatct gcaccagata ctattgaatt    3180
ggacttcccg gacattagct ttaatcataa gtggtccatc aatgatttca atgccatcac    3240
cgaggatcaa gtaaactccc aaaaattggc caaggctcaa caagccaccg atggcttgtc    3300
tcaggaactc gttagtcttt tggatccgtt gttagctcaa ctatccgaat ccttccacta    3360
ccatgcagcg ttttgtttcc tgtatatgtt tgtttgccta tgcccccatg ccaagaatat    3420
taagttttcc ttaaagtcta ctttacccat cggtgctggg ttgggctcaa gcgcctctat    3480
ttctgtatca ctggccttag ctatggccta cttgggggggg ttaataggat ctaatgactt    3540
ggaaaagctg tcagaaaacg ataagcatat agtgaatcaa tgggccttca taggtgaaaa    3600
gtgtattcac ggtacccctt caggaataga taacgctgtg gccacttatg gtaatgccct    3660
gctatttgaa aaagactcac ataatggaac aataaacaca acaattttta agttcttaga    3720
tgatttccca gccattccaa tgatcctaac ctatactaga attccaaggt ctacaaaaga    3780
tcttgttgct cgcgttcgtg tgttggtcac cgagaaattt cctgaagtta tgaagccaat    3840
tctagatgcc atgggtgaat gtgccctaca aggcttagag atcatgacta agttaagtaa    3900
atgtaaaggc accgatgacg aggctgtaga aactaataat gaactgtatg aacaactatt    3960
ggaattgata agaataaatc atggactgct tgtctcaatc ggtgtttctc atcctggatt    4020
agaacttatt aaaaatctga gcgatgattt gagaattggc tccacaaaac ttaccggtgc    4080
tggtggcggc ggttgctctt tgactttgtt acgaagagac attactcaag agcaaattga    4140
cagcttcaaa aagaaattgc aagatgattt tagttacgag acatttgaaa cagacttggg    4200
tgggactggc tgctgtttgt taagcgcaaa aaatttgaat aaagatctta aaatcaaatc    4260
cctagtattc caattatttg aaaataaaac taccacaaag caacaaattg acgatctatt    4320
attgccagga aacacgaatt taccatggac ttcataagct aatttgcgat aggcctgcac    4380
ccttaaggag gaaaaaaaca tgtcagagtt gagagccttc agtgccccag ggaaagcgtt    4440
actagctggt ggatatttag ttttagatac aaaaatatgaa gcatttgtag tcggattatc    4500
ggcaagaatg catgctgtag cccatcctta cggttcattg caagggtctg ataagtttga    4560
agtgcgtgtg aaaagtaaac aatttaaaga tggggagtgg ctgtaccata taagtcctaa    4620
aagtggcttc attcctgttt cgataggcgg atctaagaac ccttttcattg aaaaagttat    4680 cgctaacgta tttagctact ttaaacctaa catggacgac tactgcaata gaaacttgtt    4740
cgttattgat atttttctctg atgatgccta ccattctcag gaggatagcg ttaccgaaca    4800
tcgtggcaac agaagattga gttttcattc gcacagaatt gaagaagttc ccaaaacagg    4860
gctgggctcc tcggcaggtt tagtcacagt tttaactaca gctttggcct cctttttttgt    4920 atcggacctg gaaaataatg tagacaaata tagagaagtt attcataatt tagcacaagt    4980
tgctcattgt caagctcagg gtaaaattgg aagcgggttt gatgtagcgg cggcagcata    5040
tggatctatc agatatagaa gattcccacc cgcattaatc tctaatttgc cagatattgg    5100
aagtgctact tacggcagta aactggcgca tttggttgat gaagaagact ggaatattac    5160
gattaaaagt aaccatttac cttcgggatt aactttatgg atgggcgata ttaagaatgg    5220
ttcagaaaca gtaaaactgg tccagaaggt aaaaaattgg tatgattcgc atatgccaga    5280
aagcttgaaa atatatacag aactcgatca tgcaaattct agatttatgg atggactatc    5340
taaactagat cgcttacacg agactcatga cgattacagc gatcagatat ttgagtctct    5400
tgagaggaat gactgtacct gtcaaaagta tcctgaaatc acagaagtta gagatgcagt    5460
tgccacaatt agacgttcct ttagaaaaat aactaaagaa tctggtgccg atatcgaacc    5520
```

```
tcccgtacaa actagcttat tggatgattg ccagacctta aaaggagttc ttacttgctt    5580
aatacctggt gctggtggtt atgacgccat tgcagtgatt actaagcaag atgttgatct    5640
tagggctcaa accgctaatg acaaaagatt ttctaaggtt caatggctgg atgtaactca    5700
ggctgactgg ggtgttagga agaaaaaaga tcccggaaact tatcttgata aataacttaa   5760
ggtagctgca tgcagaattc gcccttaagg aggaaaaaaa aatgaccgtt tacacagcat    5820
ccgttaccgc acccgtcaac atcgcaaccc ttaagtattg ggggaaaagg gacacgaagt    5880
tgaatctgcc caccaattcg tccatatcag tgactttatc gcaagatgac ctcagaacgt    5940
tgacctctgc ggctactgca cctgagtttg aacgcgacac tttgtggtta aatggagaac    6000
cacacagcat cgacaatgaa agaactcaaa attgtctgcg cgacctacgc caattaagaa    6060
aggaaatgga atcgaaggac gcctcattgc ccacattatc tcaatggaaa ctccacattg    6120
tctccgaaaa taactttcct acagcagctg gtttagcttc ctccgctgct ggctttgctg    6180
cattggtctc tgcaattgct aagttatacc aattaccaca gtcaacttca gaaatatcta    6240
gaatagcaag aaaggggtct ggttcagctt gtagatcgtt gtttggcgga tacgtggcct    6300
gggaaatggg aaaagctgaa gatggtcatg attccatggc agtacaaatc gcagacagct    6360
ctgactggcc tcagatgaaa gcttgtgtcc tagttgtcag cgatattaaa aaggatgtga    6420
gttccactca gggtatgcaa ttgaccgtgg caacctccga actatttaaa gaaagaattg    6480
aacatgtcgt accaaagaga tttgaagtca tgcgtaaagc cattgttgaa aaagatttcg    6540
ccacctttgc aaaggaaaca atgatggatt ccaactcttt ccatgccaca tgtttggact    6600 cttccctcc aatattctac atgaatgaca cttccaagcg tatcatcagt tggtgccaca    6660
ccattaatca gttttacgga gaaacaatcg ttgcatacac gtttgatgca ggtccaaatg    6720
ctgtgttgta ctacttagct gaaaatgagt cgaaactctt tgcatttatc tataaattgt    6780
ttggctctgt tcctggatgg gacaagaaat ttactactga gcagcttgag gctttcaacc    6840
atcaatttga atcatctaac tttactgcac gtgaattgga tcttgagttg caaaaggatg    6900
ttgccagagt gattttaact caagtcggtt caggcccaca agaaacaaac gaatctttga    6960
ttgacgcaaa gactggtcta ccaaaggaat aagatcaatt cgctgcatcg cccttaggag    7020
gtaaaaaaaa atgactgccg acaacaatag tatgccccat ggtgcagtat ctagttacgc    7080
caaattagtg caaaaccaaa cacctgaaga cattttggaa gagtttcctg aaattattcc    7140
attacaacaa agacctaata cccgatctag tgagacgtca aatgacgaaa gcggagaaac    7200 atgttttctct ggtcatgatg aggagcaaat taagttaatg aatgaaaatt gtattgtttt    7260
ggattgggac gataatgcta ttggtgccgg taccaagaaa gtttgtcatt aatggaaaa    7320 tattgaaaag ggtttactac atcgtgcatt ctccgtcttt attttcaatg aacaaggtga    7380 attacttta caacaaagag ccactgaaaa aataactttc cctgatcttt ggactaacac    7440
atgctgctct catccactat gtattgatga cgaattaggt ttgaagggta agctagcga    7500 taagattaag ggcgctatta ctgcggcggt gagaaaacta gatcatgaat taggtattcc    7560
agaagatgaa actaagacaa ggggtaagtt tcacttttta aacagaatcc attacatggc    7620
accaagcaat gaaccatggg gtgaacatga aattgattac atcctatttt ataagatcaa    7680
cgctaaagaa aacttgactg tcaacccaaa cgtcaatgaa gttagagact caaatgggt    7740 ttcaccaaat gatttgaaaa ctatgttttgc tgacccaagt tacaagtttta cgccttggtt    7800 taagattatt tgcgagaatt acttattcaa ctggtgggag caattagatg acctttctga    7860
```

```
agtggaaaat gacaggcaaa ttcatagaat gctataacaa cgcgtctaca aataaaaaag    7920
gcacgtcaga tgacgtgcct ttttcttgg ggccgaaaaa tgccccgctt acgcagggca     7980
tccatttatt actcaaccgt aaccgattt gccaggttac gcggctggtc aacgtcggtg     8040
cctttgatca gcgcgacatg gtaagccagc agctgcagcg gaacggtgta gaagatcggt    8100
gcaatcacct cttccacatg cggcatctcg atgatgtgca tgttatcgct acttacaaaa    8160
cccgcatcct gatcggcgaa gacatacaac tgaccgccac gcgcgcgaac ttcttcaatg    8220
ttggatttca gttttccag caattcgttg ttcggtgcaa caacaataac cggcatatcg      8280
gcatcaatta gcgccagcgg accgtgtttc agttcgccag cagcgtaggc ttcagcgtga    8340
atgtaagaga tctctttcaa cttcaatgcg ccttccagcg cgattgggta ctgatcgcca    8400
cggcccagga acagcgcgtg atgtttgtca gagaaatctt ctgccagcgc ttcaatgcgt    8460
ttgtcctgag acagcatctg ctcaatacgg ctcggcagcg cctgcagacc atgcacgatg    8520
tcatgttcaa tggaggcatc cagacctttc aggcgagaca gcttcgccac cagcatcaac    8580
agcacagtta actgagtggt gaatgcttta gtggatgcca cgccgatttc tgtacccgcg    8640
ttggtcatta gcgccagatc ggattcgcgc accagagaag aacccggaac gttacagatt    8700
gccagtgaac caaggtaacc cagctctttc gacagacgcg ggccagccag ggtatccgcg    8760
gtttcgccag actgtgacaa ggtgatcatc aggctgttac gacgcacggc agatttgcga    8820
tagcggaatt cagaggcgat ttcgacgtcg cacggaatac ctgctagcga ttcaaaccag    8880
tagcgggaaa ccataccgga gttataagaa gtaccacagg cgaggatctg aatatgctca    8940
accttcgaca gcagttcgtc ggcgttcggt cccagctcgc ttaaatcaac ctgaccgtgg    9000
ctgatgcgtc cggtaagggt gttttgatc gcgttcggct gttcgtagat ctctttctgc      9060
atgtagtgac ggtaaatgcc tttatcgccc gcgtcatatt gcagattgga ttcgatatcc    9120
tgacgtttta cttccgcgcc agttttatcg aagatgttta ccgaacggcg agtga         9175
```

<210> SEQ ID NO 53
<211> LENGTH: 40
<212> TYPE: DNA
<213> ORGANISM: Artificial Sequence
<220> FEATURE:
<223> OTHER INFORMATION: Primer (Tn7dS_6038-7-1)

<400> SEQUENCE: 53
tcgagctcgg taccctgttt ttccactctt cgttcacttt                           40

<210> SEQ ID NO 54
<211> LENGTH: 33
<212> TYPE: DNA
<213> ORGANISM: Artificial Sequence
<220> FEATURE:
<223> OTHER INFORMATION: Primer (Tn7dA_6038-7-2)

<400> SEQUENCE: 54
aggcttcatt ttaatcaaac atcctgccaa ctc                                  33

<210> SEQ ID NO 55
<211> LENGTH: 25
<212> TYPE: DNA
<213> ORGANISM: Artificial Sequence
<220> FEATURE:
<223> OTHER INFORMATION: Primer (Tn7dattLcmS_6038-7-4)

<400> SEQUENCE: 55
attaaaatga agcctgcttt tttat                                           25

<210> SEQ ID NO 56
<211> LENGTH: 32
<212> TYPE: DNA
<213> ORGANISM: Artificial Sequence
<220> FEATURE:
<223> OTHER INFORMATION: Primer (PgiattRcmA_6038-7-5)

<400> SEQUENCE: 56
ggcatcgtca agggccgctc aagttagtat aa				32

<210> SEQ ID NO 57
<211> LENGTH: 99
<212> TYPE: DNA
<213> ORGANISM: Artificial Sequence
<220> FEATURE:
<223> OTHER INFORMATION: Primer (gi1.2-MVK-S_6038-7-6)

<400> SEQUENCE: 57
gcccttgacg atgccacatc ctgagcaaat aattcaacca ctaattgtga gcggataaca				60 caaggaggaa acagctatgt cattaccgtt cttaacttc				99

<210> SEQ ID NO 58
<211> LENGTH: 96
<212> TYPE: DNA
<213> ORGANISM: Artificial Sequence
<220> FEATURE:
<223> OTHER INFORMATION: Primer (pMW-TaspA-yIDIA_6038-7-7)

<400> SEQUENCE: 58
ctctagagga tccccggccc aagaaaaaa ggcacgtcat ctgacgtgcc ttttttattt				60 gtagacgcgt tgttatagca ttctatgaat ttgcct				96

<210> SEQ ID NO 59
<211> LENGTH: 36
<212> TYPE: DNA
<213> ORGANISM: Artificial Sequence
<220> FEATURE:
<223> OTHER INFORMATION: Primer (Tn7upSv02_6038-24-1)

<400> SEQUENCE: 59
atcctctaga gtcgaaagaa aaatgccccg cttacg				36

<210> SEQ ID NO 60
<211> LENGTH: 37
<212> TYPE: DNA
<213> ORGANISM: Artificial Sequence
<220> FEATURE:
<223> OTHER INFORMATION: Primer (Tn7upAv02_6038-24-2)

<400> SEQUENCE: 60
atgcctgcag gtcgactgtc acagtctggc gaaaccg				37

<210> SEQ ID NO 61
<211> LENGTH: 20
<212> TYPE: DNA
<213> ORGANISM: Artificial Sequence
<220> FEATURE:
<223> OTHER INFORMATION: Primer (Tn7v02-F_6038-22-5)

<400> SEQUENCE: 61
acgaactgct gtcgaaggtt				20

<210> SEQ ID NO 62

```
<211> LENGTH: 20
<212> TYPE: DNA
<213> ORGANISM: Artificial Sequence
<220> FEATURE:
<223> OTHER INFORMATION: Primer (Tn7v02-R_6038-22-6)

<400> SEQUENCE: 62
ggtgtacgcc aggttgttct                                                    20

<210> SEQ ID NO 63
<211> LENGTH: 2414
<212> TYPE: DNA
<213> ORGANISM: Artificial Sequence
<220> FEATURE:
<223> OTHER INFORMATION: Nucleotide sequence of genomic fragment
      containing attL-Tet-attR-Ptac

<400> SEQUENCE: 63
tgaagcctgc ttttttatac taagttggca ttataaaaaa gcattgctta tcaatttgtt      60
gcaacgaaca ggtcactatc agtcaaaata aaatcattat ttgatttcga attccccgga     120
tccgtcgacc tgcagggaaa aaggttatgc tgcttttaag acccactttc acatttaagt     180 tgttttttcta atccgcatat gatcaattca aggccgaata agaaggctgg ctctgcacct    240
tggtgatcaa ataattcgat agcttgtcgt aataatggcg gcatactatc agtagtaggt    300
gtttcccttt cttctttagc gacttgatgc tcttgatctt ccaatacgca acctaaagta    360
aaatgcccca cagcgctgag tgcatataat gcattctcta gtgaaaaacc ttgttggcat    420
aaaaaggcta attgattttc gagagtttca tactgttttt ctgtaggccg tgtacctaaa    480
tgtacttttg ctccatcgcg atgacttagt aaagcacatc taaaactttt agcgttatta    540
cgtaaaaaat cttgccagct ttcccccttct aaagggcaaa agtgagtatg gtgcctatct    600
aacatctcaa tggctaaggc gtcgagcaaa gcccgcttat tttttacatg ccaatacaat    660
gtaggctgct ctacacctag cttctgggcg agtttacggg ttgttaaacc ttcgattccg    720
acctcattaa gcagctctaa tgcgctgtta atcactttac ttttatctaa tctagacatc    780
attaattcct aattttttgtt gacactctat cattgataga gttatttac cactccctat    840 cagtgataga gaaaagtgaa atgaatagtt cgacaaagat cgcattggta attacgttac    900
tcgatgccat ggggattggc cttatcatgc cagtcttgcc aacgttatta cgtgaattta    960
ttgcttcgga agatatcgct aaccactttg gcgtattgct gcactttat gcgttaatgc    1020 aggttatctt tgctccttgg cttggaaaaa tgtctgaccg atttggtcgg cgcccagtgc    1080
tgttgttgtc attaataggc gcatcgctgg attacttatt gctggctttt tcaagtgcgc    1140
tttggatgct gtatttaggc cgtttgcttt cagggatcac aggagctact ggggctgtcg    1200
cggcatcggt cattgccgat accacctcag cttctcaacg cgtgaagtgg ttcggttggt    1260
taggggcaag ttttgggctt ggtttaatag cggggcctat tattggtggt tttgcaggag    1320
agatttcacc gcatagtccc ttttttatcg ctgcgttgct aaatattgtc actttccttg    1380
tggttatgtt ttggttccgt gaaaccaaaa atacacgtga ataacagat accgaagtag    1440 gggttgagac gcaatcgaat tcggtataca tcactttatt taaaacgatg cccattttgt    1500
tgattattta tttttcagcg caattgatag gccaaattcc cgcaacggtg tgggtgctat    1560
ttaccgaaaa tcgttttgga tggaatagca tgatggttgg cttttcatta gcgggtcttg    1620 gtctttttaca ctcagtattc caagccttttg tggcaggaag aatagccact aaatggggcg    1680
aaaaaacggc agtactgctc gaatttattg cagatagtag tgcatttgcc ttttttagcgt    1740
```

-continued

```
ttatatctga aggttggtta gatttccctg ttttaatttt attggctggt ggtgggatcg    1800
ctttacctgc attacaggga gtgatgtcta tccaaacaaa gagtcatgag caaggtgctt    1860
tacagggatt attggtgagc cttaccaatg caaccggtgt tattggccca ttactgttta    1920
ctgttattta taatcattca ctaccaattt gggatggctg gatttggatt attggtttag    1980
cgttttactg tattattatc ctgctatcga tgaccttcat gttaacccct caagctcagg    2040
ggagtaaaca ggagacaagt gcttagttat ttcgtcacca aatgatgtta ttccgcgaaa    2100
tataatgacc ctcttgataa cccaagaggg cattttttac gataaagaag atttagcttc    2160
tgcagtctgt tacaggtcac taataccatc taagtagttg attcatagtg actgcatatg    2220
ttgtgtttta cagtattatg tagtctgttt tttatgcaaa atctaattta atatattgat    2280
atttatatca ttttacgttt ctcgttcagc tttttatac taacttgagc gagatctccc     2340
tgttgacaat taatcatcgg ctctataatg tgtggaatcg tgagcggata acaatttcac    2400
acaaggagac tgcc                                                      2414
```

<210> SEQ ID NO 64
<211> LENGTH: 7464
<212> TYPE: DNA
<213> ORGANISM: Artificial Sequence
<220> FEATURE:
<223> OTHER INFORMATION: Nucleotide sequence containing genomic sequence encoding downstream enzymes in the mevalonate pathway under control of tac promoter

<400> SEQUENCE: 64

```
ttagtacagc ggcttaccgc tactgtcttt aatattggtc ttccacgcag cgcgaacctg      60
ttcaactaca ctatccggca ggctggcgta atccaggtcg ttcgcctgtt tagccccggt     120
tttgtacgcc cagtcgaaga atttcagcac ttctgtgcct tgttctggtt tcttctgatc     180
tttgtggatc agaatgaacg tggtagaggt aataggccat gcatcttcgc ctttctggtt     240
ggtcagatcc tgagcgaagg ttttgctcca gtctgcacct tttgctgcat tagcgaagtt     300
ttcttcggtc ggactaaccg gtttaccatc agcggagatc agtttggtgt acgccaggtt     360
gttctgcttc gcgtaagcat attcaacata accaattgca cccggcagac gctgaacgaa     420
cgcggcgata ccgtcgttac ctttaccgcc cagaccgatc ggccatttta cggtagagcc     480
agtaccaacg ttgttttttcc actcttcgtt cactttcgcc aggtagctgg tgaagacgaa    540
ggaagtcccg gagccatctg cgcggcgtac tacagcaatg ttttgtgaag gcagtttcag    600
acccggattc agtttggcga tggcttcatc atcccacttc ttgattttgc ccaggtagat    660
gtcgccgagg gttttaccat ccagcaccag ttcgccagac ttcagccctg gaatgttaac    720
cgccagcacc acgccgccaa tcacggtcgg gaactggaac agaccttcct gagccagttt    780
ttcgtcagac agcggcgcgt cagaggcacc aaaatcaacg gtattagcga taatctgttt    840
tacgccaccg gaagaaccga taccctggta gttaacttta ttaccggttt ctttctggta    900
agtgtcagcc catttggcat acaccggcgc agggaaggtt gcacctgcac ctgtcaggct    960
tgcttctgca aacacagaga aagcactcat cgataaggtc gcggcgacaa cagttgcgac   1020
ggtggtacgc ataactttca taatgtctcc tgggaggatt cataaagcat gtttgttgg    1080
ctacgagaag caaaatagga caaacaggtg acagttatat gtaaggaata tgacagtttt   1140
atgacagaga gataaagtct tcagtctgat ttaaataagc gttgatattc agtcaattac   1200
tgaagcctgc ttttttatac taacttgagc gagatctccc tgttgacaat taatcatcgg   1260
ctctataatg tgtggaatcg tgagcggata acaatttcac acaaggagac tgccatgtca   1320
```

```
ttaccgttct taacttctgc accgggaaag gttattattt ttggtgaaca ctctgctgtg   1380
tacaacaagc ctgccgtcgc tgctagtgtg tctgcgttga aacctacct gctaataagc    1440 gagtcatctg caccagatac tattgaattg acttcccgg acattagctt taatcataag    1500
tggtccatca atgatttcaa tgccatcacc gaggatcaag taaactccca aaaattggcc   1560
aaggctcaac aagccaccga tggcttgtct caggaactcg ttagtctttt ggatccgttg   1620
ttagctcaac tatccgaatc cttccactac catgcagcgt tttgtttcct gtatatgttt   1680
gtttgcctat gcccccatgc caagaatatt aagttttcct taaagtctac tttacccatc   1740
ggtgctgggt tgggctcaag cgcctctatt tctgtatcac tggccttagc tatggcctac   1800 ttggggggt aataggatc taatgacttg aaaagctgt cagaaaacga taagcatata     1860
gtgaatcaat gggccttcat aggtgaaaag tgtattcacg gtacccctc aggaatagat    1920 aacgctgtgg ccacttatgg taatgccctg ctatttgaaa aagactcaca taatggaaca   1980
ataaacacaa acaattttaa gttcttagat gatttcccag ccattccaat gatcctaacc   2040
tatactagaa ttccaaggtc tacaaaagat cttgttgctc gcgttcgtgt gttggtcacc   2100
gagaaatttc ctgaagttat gaagccaatt ctagatgcca tgggtgaatg tgccctacaa   2160
ggcttagaga tcatgactaa gttaagtaaa tgtaaaggca ccgatgacga ggctgtagaa   2220
actaataatg aactgtatga acaactattg gaattgataa gaataaatca tggactgctt   2280
gtctcaatcg gtgtttctca tcctggatta gaacttatta aaaatctgag cgatgatttg   2340
agaattggct ccacaaaact taccggtgct ggtggcggcg gttgctcttt gactttgtta   2400
cgaagagaca ttactcaaga gcaaattgac agcttcaaaa agaaattgca agatgatttt   2460
agttacgaga catttgaaac agacttgggt gggactggct gctgtttgtt aagcgcaaaa   2520
aatttgaata aagatcttaa aatcaaatcc ctagtattcc aattatttga aaataaaact   2580
accacaaagc aacaaattga cgatctatta ttgccaggaa acacgaattt accatggact   2640
tcataagcta atttgcgata ggcctgcacc cttaaggagg aaaaaaacat gtcagagttg   2700
agagccttca gtgccccagg gaaagcgtta ctagctggtg atatttagt tttagataca    2760 aaatatgaag catttgtagt cggattatcg gcaagaatgc atgctgtagc ccatccttac   2820
ggttcattgc aagggtctga taagtttgaa gtgcgtgtga aagtaaaca atttaaagat    2880 ggggagtggc tgtaccatat aagtcctaaa agtggcttca ttcctgtttc gataggcgga   2940
tctaagaacc cttcattga aaaagttatc gctaacgtat ttagctactt taaacctaac   3000
atggacgact actgcaatag aaacttgttc gttattgata ttttctctga tgatgcctac   3060
cattctcagg aggatagcgt taccgaacat cgtggcaaca aagattgag ttttcattcg    3120 cacagaattg aagaagttcc caaaacaggg ctgggctcct cggcaggttt agtcacagtt   3180
ttaactacag ctttggcctc cttttttgta tcggacctgg aaaataatgt agacaaatat   3240
agagaagtta ttcataattt agcacaagtt gctcattgtc aagctcaggg taaaattgga   3300
agcgggtttg atgtagcggc ggcagcatat ggatctatca gatatagaag attcccaccc   3360
gcattaatct ctaatttgcc agatattgga agtgctactt acggcagtaa actggcgcat   3420
ttggttgatg aagaagactg gaatattacg attaaaagta accatttacc ttcgggatta   3480
actttatgga tgggcgatat taagaatggt tcagaaacag taaaactggt ccagaaggta   3540
aaaaattggt atgattcgca tatgccagaa agcttgaaaa tatatacaga actcgatcat   3600
gcaaattcta gatttatgga tggactatct aaactagatc gcttacacga gactcatgac   3660
```

```
gattacagcg atcagatatt tgagtctctt gagaggaatg actgtacctg tcaaaagtat    3720
cctgaaatca cagaagttag agatgcagtt gccacaatta gacgttcctt tagaaaaata    3780
actaaagaat ctggtgccga tatcgaacct cccgtacaaa ctagcttatt ggatgattgc    3840
cagaccttaa aaggagttct tacttgctta atacctggtg ctggtggtta tgacgccatt    3900
gcagtgatta ctaagcaaga tgttgatctt agggctcaaa ccgctaatga caaaagattt    3960
tctaaggttc aatggctgga tgtaactcag gctgactggg gtgttaggaa agaaaaagat    4020
ccggaaactt atcttgataa ataacttaag gtagctgcat gcagaattcg cccttaagga    4080
ggaaaaaaaa atgaccgttt acacagcatc cgttaccgca cccgtcaaca tcgcaaccct    4140
taagtattgg gggaaaaggg acacgaagtt gaatctgccc accaattcgt ccatatcagt    4200
gactttatcg caagatgacc tcagaacgtt gacctgcgcg gctactgcac ctgagtttga    4260
acgcgacact ttgtggttaa atggagaacc acacagcatc gacaatgaaa gaactcaaaa    4320
ttgtctgcgc gacctacgcc aattaagaaa ggaaatggaa tcgaaggacg cctcattgcc    4380
cacattatct caatggaaac tccacattgt ctccgaaaat aactttccta cagcagctgg    4440
tttagcttcc tccgctgctg gctttgctgc attggtctct gcaattgcta agttatacca    4500
attaccacag tcaacttcag aaatatctag aatagcaaga aaggggtctg gttcagcttg    4560
tagatcgttg tttggcggat acgtggcctg ggaaatggga aaagctgaag atggtcatga    4620
ttccatggca gtacaaatcg cagacagctc tgactggcct cagatgaaag cttgtgtcct    4680
agttgtcagc gatattaaaa aggatgtgag ttccactcag ggtatgcaat gaccgtggc    4740 aacctccgaa ctatttaaag aaagaattga acatgtcgta ccaaagagat ttgaagtcat    4800
gcgtaaagcc attgttgaaa agatttcgc caccttttgca aaggaaacaa tgatggattc    4860
caactctttc catgccacat gtttggactc tttccctcca atattctaca tgaatgacac    4920
ttccaagcgt atcatcagtt ggtgccacac cattaatcag ttttacggag aaacaatcgt    4980
tgcatacacg tttgatgcag gtccaaatgc tgtgttgtac tacttagctg aaaatgagtc    5040
gaaactcttt gcatttatct ataaattgtt tggctctgtt cctggatggg acaagaaatt    5100
tactactgag cagcttgagg cttttcaacca tcaatttgaa tcatctaact ttactgcacg    5160
tgaattggat cttgagttgc aaaaggatgt tgccagagtg atttttaactc aagtcggttc    5220 aggcccacaa gaaacaaacg aatctttgat tgacgcaaag actggtctac caaaggaata    5280
agatcaattc gctgcatcgc ccttaggagg taaaaaaaaa tgactgccga caacaatagt    5340
atgccccatg gtgcagtatc tagttacgcc aaattagtgc aaaaccaaac acctgaagac    5400
attttggaag agtttcctga aattattcca ttacaacaaa gacctaatac ccgatctagt    5460
gagacgtcaa atgacgaaag cggagaaaca tgtttttctg gtcatgatga ggagcaaatt    5520
aagttaatga atgaaaattg tattgttttg gattgggacg ataatgctat tggtgccggt    5580
accaagaaag tttgtcattt aatggaaaat attgaaaagg gtttactaca tcgtgcattc    5640
tccgtcttta ttttcaatga acaaggtgaa ttacttttac aacaaagagc cactgaaaaa    5700
ataactttcc ctgatctttg gactaacaca tgctgctctc atccactatg tattgatgac    5760
gaattaggtt tgaagggtaa gctagacgat aagattaagg gcgctattac tgcggcggtg    5820
agaaaactag atcatgaatt aggtattcca gaagatgaaa ctaagacaag gggtaagttt    5880
cactttttaa acagaatcca ttacatggca ccaagcaatg aaccatgggg tgaacatgaa    5940
attgattaca tccattttta taagatcaac gctaaagaaa acttgactgt caacccaaac    6000
gtcaatgaag ttagagactt caaatggtt tcaccaaatg atttgaaaac tatgtttgct    6060
```

-continued

```
gacccaagtt acaagtttac gccttggttt aagattattt gcgagaatta cttattcaac    6120
tggtgggagc aattagatga cctttctgaa gtggaaaatg acaggcaaat tcatagaatg    6180
ctataacaac gcgtctacaa ataaaaaagg cacgtcagat gacgtgcctt ttttcttggg    6240
gccgaaaaat gccccgctta cgcagggcat ccatttatta ctcaaccgta accgattttg    6300
ccaggttacg cggctggtca acgtcggtgc ctttgatcag cgcgacatgg taagccagca    6360
gctgcagcgg aacggtgtag aagatcggtg caatcacctc ttccacatgc ggcatctcga    6420
tgatgtgcat gttatcgcta cttacaaaac ccgcatcctg atcggcgaag acatacaact    6480
gaccgccacg cgcgcgaact tcttcaatgt tggatttcag ttttccagc aattcgttgt     6540
tcggtgcaac aacaataacc ggcatatcgg catcaattag cgccagcgga ccgtgtttca    6600
gttcgccagc agcgtaggct tcagcgtgaa tgtaagagat ctctttcaac ttcaatgcgc    6660
cttccagcgc gattgggtac tgatcgccac ggcccaggaa cagcgcgtga tgtttgtcag    6720
agaaatcttc tgccagcgct tcaatgcgtt tgtcctgaga cagcatctgc tcaatacggc    6780
tcggcagcgc ctgcagacca tgcacgatgt catgttcaat ggaggcatcc agacctttca    6840
ggcgagacag cttcgccacc agcatcaaca gcacagttaa ctgagtggtg aatgctttag    6900
tggatgccac gccgatttct gtacccgcgt tggtcattag cgccagatcg gattcgcgca    6960
ccagagaaga acccggaacg ttacagattg ccagtgaacc aaggtaaccc agctctttcg    7020
acagacgcag gccagccagg gtatccgcgg tttcgccaga ctgtgacaag gtgatcatca    7080
ggctgttacg acgcacggca gatttgcgat agcggaattc agaggcgatt tcgacgtcgc    7140
acggaatacc tgctagcgat tcaaaccagt agcgggaaac cataccggag ttataagaag    7200
taccacaggc gaggatctga atatgctcaa ccttcgacag cagttcgtcg gcgttcggtc    7260
ccagctcgct taaatcaacc tgaccgtggc tgatgcgtcc ggtaagggtg ttttgatcg     7320
cgttcggctg ttcgtagatc tctttctgca tgtagtgacg gtaaatgcct ttatcgcccg    7380
cgtcatattg cagattggat tcgatatcct gacgttttac ttccgcgcca gttttatcga    7440
agatgtttac cgaacggcga gtga                                           7464
```

<210> SEQ ID NO 65
<211> LENGTH: 70
<212> TYPE: DNA
<213> ORGANISM: Artificial Sequence
<220> FEATURE:
<223> OTHER INFORMATION: Primer (APtacKKDyIv03_6038-36-5)

<400> SEQUENCE: 65

```
gataaagtct tcagtctgat ttaaataagc gttgatattc agtcaattac tgaagcctgc    60
tttttttatac                                                          70
```

<210> SEQ ID NO 66
<211> LENGTH: 71
<212> TYPE: DNA
<213> ORGANISM: Artificial Sequence
<220> FEATURE:
<223> OTHER INFORMATION: Primer (SPtacKKDyIv02_6038-36-3)

<400> SEQUENCE: 66

```
tcaccaaaaa taataacctt tcccggtgca gaagttaaga acggtaatga catggcagtc    60
tccttgtgtg a                                                         71
```

<210> SEQ ID NO 67

```
<211> LENGTH: 40
<212> TYPE: DNA
<213> ORGANISM: Artificial Sequence
<220> FEATURE:
<223> OTHER INFORMATION: Primer for amplifying IspSK gene

<400> SEQUENCE: 67
gaagtccagg aggacataca atgtgtgcga cctcttctca                        40

<210> SEQ ID NO 68
<211> LENGTH: 40
<212> TYPE: DNA
<213> ORGANISM: Artificial Sequence
<220> FEATURE:
<223> OTHER INFORMATION: Primer for amplifying IspSK gene

<400> SEQUENCE: 68
tgcctgcagg tcgactctag ttagacatac atcagctggt                        40

<210> SEQ ID NO 69
<211> LENGTH: 40
<212> TYPE: DNA
<213> ORGANISM: Artificial Sequence
<220> FEATURE:
<223> OTHER INFORMATION: Primer for amplifying IspSP gene

<400> SEQUENCE: 69
gaagtccagg aggacataca atgtgctctg tttctaccga                        40

<210> SEQ ID NO 70
<211> LENGTH: 40
<212> TYPE: DNA
<213> ORGANISM: Artificial Sequence
<220> FEATURE:
<223> OTHER INFORMATION: Primer for amplifying IspSP gene

<400> SEQUENCE: 70
tgcctgcagg tcgactctag ttaacgttcg aacggcagaa                        40

<210> SEQ ID NO 71
<211> LENGTH: 40
<212> TYPE: DNA
<213> ORGANISM: Artificial Sequence
<220> FEATURE:
<223> OTHER INFORMATION: Primer for amplifying IspSM gene

<400> SEQUENCE: 71
gaagtccagg aggacataca atgtccgccg tttcaagcca                        40

<210> SEQ ID NO 72
<211> LENGTH: 40
<212> TYPE: DNA
<213> ORGANISM: Artificial Sequence
<220> FEATURE:
<223> OTHER INFORMATION: Primer for amplifying IspSM gene

<400> SEQUENCE: 72
tgcctgcagg tcgactctag ttagttaatc gggaacgggt                        40

<210> SEQ ID NO 73
<211> LENGTH: 40
<212> TYPE: DNA
<213> ORGANISM: Artificial Sequence
<220> FEATURE:
<223> OTHER INFORMATION: Primer for amplifying nucleotide sequence of
      promoter region for elongation factor, Tu (P0480)
```

<400> SEQUENCE: 73
ggtacccggg gatcctctag agatcgttta gatccgaagg                                 40

<210> SEQ ID NO 74
<211> LENGTH: 40
<212> TYPE: DNA
<213> ORGANISM: Artificial Sequence
<220> FEATURE:
<223> OTHER INFORMATION: Primer for amplifying P0480 that is used in
      combination with ispSK

<400> SEQUENCE: 74
tgagaagagg tcgcacacat tgtatgtcct cctggacttc                                 40

<210> SEQ ID NO 75
<211> LENGTH: 40
<212> TYPE: DNA
<213> ORGANISM: Artificial Sequence
<220> FEATURE:
<223> OTHER INFORMATION: Primer for amplifying P0480 that is used in
      combination with ispSP

<400> SEQUENCE: 75
tcggtagaaa cagagcacat tgtatgtcct cctggacttc                                 40

<210> SEQ ID NO 76
<211> LENGTH: 40
<212> TYPE: DNA
<213> ORGANISM: Artificial Sequence
<220> FEATURE:
<223> OTHER INFORMATION: Primer for amplifying P0480 that is used in
      combination with ispSM

<400> SEQUENCE: 76
tggcttgaaa cggcggacat tgtatgtcct cctggacttc                                 40

<210> SEQ ID NO 77
<211> LENGTH: 362
<212> TYPE: DNA
<213> ORGANISM: Artificial Sequence
<220> FEATURE:
<223> OTHER INFORMATION: Nucleotide sequence of promoter region for
      elongation factor, Tu (P0480)

<400> SEQUENCE: 77
agatcgttta gatccgaagg aaaacgtcga aaagcaattt gcttttcgac gccccacccc          60
gcgcgtttta gcgtgtcagt agacgcgtag ggtaagtggg gtagcggctt gttagatatc         120
ttgaaatcgg ctttcaacag cattgatttc gatgtattta gctggccgtt accctgcgaa         180
tgtccacagg gtagctggta gtttgaaaat caacgccgtt gcccttagga ttcagtaact         240
ggcacatttt gtaatgcgct agatctgtgt gcccagtctt ccaggctgct tatcacagtg         300
aaagcaaaac caattcgtgg ctgcgaaagt cgtagccacc acgaagtcca ggaggacata         360
ca                                                                        362

<210> SEQ ID NO 78
<211> LENGTH: 5629
<212> TYPE: DNA
<213> ORGANISM: Artificial Sequence
<220> FEATURE:
<223> OTHER INFORMATION: Nucleotide sequence of shuttle vector for
      E.coli (pVK9)

<400> SEQUENCE: 78

```
gaggtctgcc tcgtgaagaa ggtgttgctg actcatacca ggcctgaatc gccccatcat    60
ccagccagaa agtgagggag ccacggttga tgagagcttt gttgtaggtg acgggatc    120
ttttctacgg ggtctgacgc tcagtggaac gaaaactcac gttaagggat tttggtcatg   180
agattatcaa aaaggatcat gcgagcaacc tccataagat cagctaggcg atctttggga   240
gcagtccttg tcgcgttacg aggtgagccg gtggggaacc gttagctgcc tatggtgtga   300
gccccctag agagcttcaa gagcaatcag cccgacctag aaaggaggcc aagagagaga   360
cctacggggg gaaccgtttt ctgcctacga gatgggcaca ttactgggaa gctttacggc   420
gtcctcgtgg aagttcaatg cccgcagact taagtgctct attcacggtc tgacgtgaca   480
cgctaaattc agacatagct tcattgattg tcggccacga gccagtctct ccctcaacag   540
tcataaacca acctgcaatg gtcaagcgat ttcctttagc tttcctagct tgtcgttgac   600
tggacttagc tagttttcct cgctgtgctc gggcgtactc actgtttggg tcttccagc   660
gttctgcggc cttttaccg ccacgtcttc ccatagtggc cagagctttt cgccctcggc    720
tgctctgcgt ctctgtctga cgagcaggga cgactggctg gcctttagcg acgtagccgc   780
gcacacgtcg cgccatcgtc tggcggtcac gcatcggcgg cagatcaggc tcacggccgt   840
ctgctccgac cgcctgagcg acggtgtagg cacgctcgta ggcgtcgatg atcttggtgt   900
cttttaggcg ctcaccagcc gcttttaact ggtatcccac agtcaaagcg tggcgaaaag   960
ccgtctcatc acgggcggca cgccctggag cagtccagag gacacggacg ccgtcgatca  1020
gctctccaga cgcttcagcg gcgctcggca ggcttgcttc aagcgtggca agtgcttttg  1080
cttccgcagt ggcttttctt gccgcttcga tacgtgcccg tccgctagaa aactcctgct  1140
catagcgttt tttaggtttt tctgtgcctg agatcatgcg agcaacctcc ataagatcag  1200
ctaggcgatc cacgcgattg tgctgggcat gccagcggta cgcggtggga tcgtcggaga  1260
cgtgcagtgg ccaccggctc agcctatgtg aaaaagcctg gtcagcgccg aaaacgcggg  1320
tcatttcctc ggtcgttgca gccagcaggc gcatattcgg gctgctcatg cctgctgcgg  1380
catacaccgg atcaatgagc cagatgagct ggcatttccc gctcagtgga ttcacgccga  1440
tccaagctgc cgcttttttcc aggcgtgccc agcgctccaa aatcgcgtag acctcggggt  1500
ttacgtgctc gattttcccg ccggcctggt ggctcggcac atcaatgtcc aggacaagca  1560
cggctgcgtg ctgcgcgtgc gtcagagcaa catactggca ccgggcaagc gattttgaac  1620
caactcggta taacttcggc tgtgtttctc ccgtgtccgg gtctttgatc caagcgctgg  1680
cgaagtcgcg ggtcttgctg ccctggaaat tttctctgcc caggtgagcg aggaattcgc  1740
ggcggtcttc gctcgtccag ccacgtgatc gcagcgcgag ctcgggatgg gtgtcgaaca  1800
gatcagcgga aaatttccag gccggtgtgt caatgtctcg tgaatccgct agagtcattt  1860
ttgagcgctt tctcccaggt ttggactggg ggttagccga cgccctgtga gttaccgctc  1920
acggggcgtt caacattttt caggtattcg tgcagcttat cgcttcttgc cgcctgtgcg  1980
cttttcgac gcgcgacgct gctgccgatt cggtgcaggt ggtggcggcg ctgacacgtc  2040
ctgggcggcc acggccacac gaaacgcggc atttacgatg tttgtcatgc ctgcgggcac  2100
cgcgccacga tcgcggataa ttctcgctgc cgcttccagc tctgtgacga ccatggccaa  2160
aatttcgctc gggggacgca cttccagcgc catttgcgac ctagccgcct ccagctcctc  2220
ggcgtggcgt ttgttggcgc gctcgcggct ggctgcggca cgacacgcat ctgagcaata  2280
ttttgcgcgc cgtcctcgcg ggtcaggccg gggaggaatc aggccaccgc agtaggcgca  2340
actgattcga tcctccacta ctgtgcgtcc tcctggcgct gccgagcacg cagctcgtca  2400
```

```
gccagctcct caagatccgc cacgagagtt tctaggtcgc tcgcggcact ggcccagtct    2460
cgtgatgctg gcgcgtccgt cgtatcgaga gctcggaaaa atccgatcac cgttttttaaa   2520 tcgacggcag catcgagcgc gtcggactcc agcgcgacat cagagagatc catagctgat    2580
gattcgggcc aattttggta cttcgtcgtg aaggtcatga caccattata acgaacgttc    2640
gttaaagttt ttggcggaaa atcacgcggc acgaaaattt tcacgaagcg ggactttgcg    2700
cagctcaggg gtgctaaaaa ttttgtatcg cacttgattt ttccgaaaga cagattatct    2760
gcaaacggtg tgtcgtattt ctggcttggt ttttaaaaaa tctggaatcg aaaatttgcg    2820
gggcgaccga gaagtttttt acaaaaggca aaaactttt cgggatcagc taggcgatcc     2880
acgcgattgt gctgggcatg ccagcggtac gcggtgggat cgtcggagac gtgcagtggc    2940
caccggctca gcctatgtga aaaagcctgg tcagcgccga aaacgcgggt catttcctcg    3000
gtcgttgcag ccagcaggcg catattcggg ctgctcatgc ctgctgcggc atacaccgga    3060
tcggaccagt tggtgatttt gaactttttgc tttgccacgg aacggtctgc gttgtcggga   3120
agatgcgtga tctgatcctt caactcagca aaagttcgat ttattcaaca aagccacgtt    3180
gtgtctcaaa atctctgatg ttacattgca caagataaaa atatatcatc atgaacaata    3240
aaactgtctg cttacataaa cagtaataca aggggtgtta tgagccatat tcaacgggaa    3300
acgtcttgct cgaagccgcg attaaattcc aacatggatg ctgatttata tgggtataaa    3360
tgggctcgcg ataatgtcgg gcaatcaggt gcgacaatct atcgattgta tgggaagccc    3420
gatgcgccag agttgtttct gaaacatggc aaaggtagcg ttgccaatga tgttacagat    3480
gagatggtca gactaaactg gctgacggaa tttatgcctc ttccgaccat caagcatttt    3540
atccgtactc ctgatgatgc atggttactc accactgcga tccccgggaa aacagcattc    3600
caggtattag aagaatatcc tgattcaggt gaaaatattg ttgatgcgct ggcagtgttc    3660
ctgcgccggt tgcattcgat tcctgtttgt aattgtcctt ttaacagcga tcgcgtattt    3720
cgtctcgctc aggcgcaatc acgaatgaat aacggtttgg ttgatgcgag tgattttgat    3780
gacgagcgta atggctggcc tgttgaacaa gtctggaaag aaatgcataa gcttttgcca    3840
ttctcaccgg attcagtcgt cactcatggt gatttctcac ttgataacct tatttttgac    3900
gaggggaaat taataggttg tattgatgtt ggacgagtcg gaatcgcaga ccgataccag    3960
gatcttgcca tcctatggaa ctgcctcggt gagttttctc cttcattaca gaaacggctt    4020
tttcaaaaat atggtattga taatcctgat atgaataaat tgcagtttca tttgatgctc    4080
gatgagtttt tctaatcaga attggttaat tggttgtaac actggcagag cattacgctg    4140
acttgacggg acggcggctt tgttgaataa atcgcattcg ccattcaggc tgcgcaactg    4200
ttgggaaggg cgatcggtgc gggcctcttc gctattacgc cagctggcga agggggatg     4260 tgctgcaagg cgattaagtt gggtaacgcc agggttttcc cagtcacgac gttgtaaaac    4320 gacgccagt gaattcgagc tcggtacccg gggatcctct agagtcgacc tgcaggcatg     4380
caagcttggc gtaatcatgg tcatagctgt ttcctgtgtg aaattgttat ccgctcacaa    4440
ttccacacaa catacgagcc ggaagcataa agtgtaaagc ctggggtgcc taatgagtga    4500
gctaactcac attaattgcg ttgcgctcac tgcccgcttt ccagtcggga aacctgtcgt    4560
gccagctgca ttaatgaatc ggccaacgcg cggggagagg cggtttgcgt attggcgaac    4620
ttttgctgag ttgaaggatc agatcacgca tcttcccgac aacgcagacc gttccgtggc    4680
aaagcaaaag ttcaaaatca gtaaccgtca gtgccgataa gttcaaagtt aaacctggtg    4740
```

```
ttgataccaa cattgaaacg ctgatcgaaa acgcgctgaa aaacgctgct gaatgtgcga      4800
gcttcttccg cttcctcgct cactgactcg ctgcgctcgg tcgttcggct gcggcgagcg      4860
gtatcagctc actcaaaggc ggtaatacgg ttatccacag aatcagggga taacgcagga      4920
aagaacatgt gagcaaaagg ccagcaaaag gccaggaacc gtaaaaaggc cgcgttgctg      4980 gcgttttttcc ataggctccg ccccctgac gagcatcaca aaaatcgacg ctcaagtcag      5040
aggtggcgaa acccgacagg actataaaga taccaggcgt ttccccctgg aagctccctc      5100
gtgcgctctc ctgttccgac cctgccgctt accggatacc tgtccgcctt tctcccttcg      5160
ggaagcgtgg cgctttctca atgctcacgc tgtaggtatc tcagttcggt gtaggtcgtt      5220
cgctccaagc tgggctgtgt gcacgaaccc cccgttcagc ccgaccgctg cgccttatcc      5280
ggtaactatc gtcttgagtc aacccggta agacacgact tatcgccact ggcagcagcc      5340
actggtaaca ggattagcag agcgaggtat gtaggcggtg ctacagagtt cttgaagtgg      5400
tggcctaact acggctacac tagaaggaca gtatttggta tctgcgctct gctgaagcca      5460
gttaccttcg gaaaaagagt tggtagctct tgatccggca aacaaaccac cgctggtagc      5520
ggtggttttt ttgtttgcaa gcagcagatt acgcgcagaa aaaaaggatc tcaagaagat      5580
cctttgatct tttctacggg gtctgacgct cagtggaacg atccgtcga                 5629
```

<210> SEQ ID NO 79
<211> LENGTH: 7690
<212> TYPE: DNA
<213> ORGANISM: Artificial Sequence
<220> FEATURE:
<223> OTHER INFORMATION: Nucleotide sequence of plasmid for expressing
  ispSK gene (pVK9-P0480-ispSK)

<400> SEQUENCE: 79

```
gaggtctgcc tcgtgaagaa ggtgttgctg actcatacca ggcctgaatc gccccatcat        60
ccagccagaa agtgagggag ccacggttga tgagagcttt gttgtaggtg gacggggatc       120
ttttctacgg ggtctgacgc tcagtggaac gaaaactcac gttaagggat tttggtcatg       180
agattatcaa aaaggatcat gcgagcaacc tccataagat cagctaggcg atctttggga       240
gcagtccttg tcgcgttacg aggtgagccg gtggggaacc gttagctgcc tatggtgtga       300
gcccccctag agagcttcaa gagcaatcag cccgacctag aaaggaggcc aagagagaga       360
cctacggggg gaaccgtttt ctgcctacga gatgggcaca ttactgggaa gctttacggc       420
gtcctcgtgg aagttcaatg cccgcagact taagtgctct attcacggtc tgacgtgaca       480
cgctaaattc agacatagct tcattgattg tcggccacga gccagtctct ccctcaacag       540
tcataaacca acctgcaatg gtcaagcgat ttcctttagc tttcctagct tgtcgttgac       600
tggacttagc tagtttttct cgctgtgctc ggcgtactc actgtttggg tctttccagc        660
gttctgcggc cttttaccg ccacgtcttc ccatagtggc cagagctttt cgccctcggc        720
tgctctgcgt ctctgtctga cgagcaggga cgactgctg gcctttagcg acgtagccgc        780
gcacacgtcg cgccatcgtc tggcggtcac gcatcggcgg cagatcaggc tcacggccgt       840
ctgctccgac cgcctgagcg acggtgtagg cacgctcgta ggcgtcgatg atcttggtgt       900 ctttaggcg ctcaccagcc gcttttaact ggtatcccca agtcaaagcg tggcgaaaag       960
ccgtctcatc acgggcggca cgccctggag cagtccagag gacacggacg ccgtcgatca      1020
gctctccaga cgcttcagcg gcgctcggca ggcttgcttc aagcgtggca agtgcttttg      1080
cttccgcagt ggcttttctt gccgcttcga tacgtgcccg tccgctagaa aactcctgct      1140
```

-continued

```
catagcgttt tttaggtttt tctgtgcctg agatcatgcg agcaacctcc ataagatcag   1200
ctaggcgatc cacgcgattg tgctgggcat gccagcggta cgcggtggga tcgtcggaga   1260
cgtgcagtgg ccaccggctc agcctatgtg aaaaagcctg gtcagcgccg aaaacgcggg   1320
tcatttcctc ggtcgttgca gccagcaggc gcatattcgg gctgctcatg cctgctgcgg   1380
catacaccgg atcaatgagc cagatgagct ggcatttccc gctcagtgga ttcacgccga   1440
tccaagctgg cgcttttcc aggcgtgccc agcgctccaa aatcgcgtag acctcggggt    1500
ttacgtgctc gattttcccg ccggcctggt ggctcggcac atcaatgtcc aggacaagca   1560
cggctgcgtg ctgcgcgtgc gtcagagcaa catactggca ccgggcaagc gattttgaac   1620
caactcggta taacttcggc tgtgtttctc ccgtgtccgg gtctttgatc caagcgctgg   1680
cgaagtcgcg ggtcttgctg ccctggaaat tttctctgcc caggtgagcg aggaattcgc   1740
ggcggtcttc gctcgtccag ccacgtgatc gcagcgcgag ctcgggatgg gtgtcgaaca   1800
gatcagcgga aaatttccag gccggtgtgt caatgtctcg tgaatccgct agagtcattt   1860
ttgagcgctt tctcccaggt ttggactggg ggttagccga cgcccgtgta gttaccgctc    1920
acggggcgtt caacattttt caggtattcg tgcagcttat cgcttcttgc cgcctgtgcg    1980 cttttttcgac gcgcgacgct gctgccgatt cggtgcaggt ggtggcggcg ctgacacgtc   2040
ctgggcggcc acggccacac gaaacgcggc atttacgatg tttgtcatgc ctgcgggcac   2100
cgcgccacga tcgcggataa ttctcgctgc cgcttccagc tctgtgacga ccatggccaa   2160
aatttcgctc gggggacgca cttccagcgc catttgcgac ctagccgcct ccagctcctc   2220
ggcgtggcgt ttgttggcgc gctcgcggct ggctgcggca cgacacgcat ctgagcaata   2280
ttttgcgcgc cgtcctcgcg ggtcaggccg gggaggaatc aggccaccgc agtaggcgca   2340
actgattcga tcctccacta ctgtgcgtcc tcctggcgct gccagcacg cagctcgtca    2400 gccagctcct caagatccgc cacgagagtt tctaggtcgc tcgcggcact ggcccagtct   2460
cgtgatgctg gcgcgtccgt cgtatcgaga gctcggaaaa atccgatcac cgttttaaa    2520 tcgacggcag catcgagcgc gtcggactcc agcgcgacat cagagagatc catagctgat   2580
gattcgggcc aattttggta cttcgtcgtg aaggtcatga caccattata acgaacgttc   2640
gttaaagttt ttggcggaaa atcacgcggc acgaaaattt tcacgaagcg ggactttgcg   2700
cagctcaggg gtgctaaaaa ttttgtatcg cacttgatt ttccgaaaga cagattatct    2760
gcaaacggtg tgtcgtattt ctggcttggt ttttaaaaaa tctggaatcg aaaatttgcg   2820
gggcgaccga gaagtttttt acaaaaggca aaaactttt cgggatcagc taggcgatcc    2880
acgcgattgt gctgggcatg ccagcggtac gcggtgggat cgtcggagac gtgcagtggc   2940
caccggctca gcctatgtga aaagcctgg tcagcgccga aaacgcggt catttcctcg     3000 gtcgttgcag ccagcaggcg catattcggg ctgctcatgc ctgctgcggc atacaccgga   3060
tcggaccagt tggtgatttt gaacttttgc tttgccacgg aacggtctgc gttgtcggga   3120
agatgcgtga tctgatcctt caactcagca aaagttcgat ttattcaaca aagccacgtt   3180
gtgtctcaaa atctctgatg ttacattgca caagataaaa atatatcatc atgaacaata   3240
aaactgtctg cttacataaa cagtaataca aggggtgtta tgagccatat tcaacgggaa   3300
acgtcttgct cgaagccgcg attaaattcc aacatggatg ctgatttata tgggtataaa   3360
tgggctcgcg ataatgtcgg gcaatcaggt gcgacaatct atcgattgta tgggaagccc   3420
gatgcgccaa agttgtttct gaaacatggc aaaggtagcg ttgccaatga tgttacagat   3480
gagatggtca gactaaactg gctgacggaa tttatgcctc ttccgaccat caagcatttt   3540
```

```
atccgtactc ctgatgatgc atggttactc accactgcga tccccgggaa aacagcattc   3600
caggtattag aagaatatcc tgattcaggt gaaaatattg ttgatgcgct ggcagtgttc   3660
ctgcgccggt tgcattcgat tcctgtttgt aattgtcctt ttaacagcga tcgcgtattt   3720
cgtctcgctc aggcgcaatc acgaatgaat aacggtttgg ttgatgcgag tgattttgat   3780
gacgagcgta atggctggcc tgttgaacaa gtctggaaag aaatgcataa gcttttgcca   3840
ttctcaccgg attcagtcgt cactcatggt gatttctcac ttgataacct tattttgac   3900 gaggggaaat taataggttg tattgatgtt ggacgagtcg gaatcgcaga ccgataccag   3960
gatcttgcca tcctatggaa ctgcctcggt gagttttctc cttcattaca gaaacggctt   4020
tttcaaaaat atggtattga taatcctgat atgaataaat tgcagtttca tttgatgctc   4080
gatgagtttt tctaatcaga attggttaat tggttgtaac actggcagag cattacgctg   4140
acttgacggg acggcggctt tgttgaataa atcgcattcg ccattcaggc tgcgcaactg   4200
ttgggaaggg cgatcggtgc gggcctcttc gctattacgc cagctggcga aaggggatg    4260 tgctgcaagg cgattaagtt gggtaacgcc agggttttcc cagtcacgac gttgtaaaac   4320
gacggccagt gaattcgagc tcggtacccg gggatcctct agagatcgtt tagatccgaa   4380
ggaaaacgtc gaaaagcaat ttgcttttcg acgccccacc ccgcgcgttt tagcgtgtca   4440
gtagacgcgt agggtaagtg gggtagcggc ttgttagata tcttgaaatc ggctttcaac   4500
agcattgatt tcgatgtatt tagctggccg ttaccctgcg aatgtccaca gggtagctgg   4560
tagtttgaaa atcaacgccg ttgcccttag gattcagtaa ctggcacatt ttgtaatgcg   4620
ctagatctgt gtgcccagtc ttccaggctg cttatcacag tgaaagcaaa accaattcgt   4680
ggctgcgaaa gtcgtagcca ccacgaagtc caggaggaca tacaatgtgt gcgacctctt   4740
ctcaatttac tcagattacc gagcataatt cccgtcgttc cgcaaactat cagccaaacc   4800
tgtggaattt cgaattcctg caatccctgg agaacgacct gaaagtggaa aagctggagg   4860
agaaagcgac caaactggag gaagaagttc gctgcatgat caaccgtgta gacacccagc   4920
cgctgtccct gctggagctg atcgacgatg tgcagcgcct gggtctgacc tacaaatttg   4980
aaaaagacat cattaaagcc ctggaaaaca tcgtactgct ggacgaaaac aaaaagaaca   5040
aatctgacct gcacgcaacc gctctgtctt tccgtctgct gcgtcagcac ggtttcgagg   5100
tttctcagga tgttttgag cgtttcaagg ataagaagg tggttcagc ggtgaactga     5160 aaggtgacgt ccaaggcctg ctgagcctgt atgaagcgtc ttacctgggt tcgagggtg    5220 agaacctgct ggaggaggcg cgtacctttt ccatcaccca cctgaagaac aacctgaaag   5280
aaggcattaa taccaaggtt gcagaacaag tgagccacgc cctggaactg ccatatcacc   5340
agcgtctgca ccgtctggag gcacgttggt tcctggataa atacgaaccg aaagaaccgc   5400
atcaccagct gctgctggag ctggcgaagc tggattttaa catggtacag accctgcacc   5460
agaaagagct gcaagatctg tcccgctggt ggaccgagat gggcctggct agcaaactgg   5520
attttgtacg cgaccgcctg atggaagttt atttctgggc actgggtatg cgccagacc    5580 cgcagtttgg tgaatgtcgc aaagctgtta ctaaaatgtt tggtctggtg acgatcatcg   5640
atgacgtgta tgacgtttat ggcactctgg acgaactgca actgttcacc gatgctgtag   5700
agcgctggga cgttaacgct attaacaccc tgccggacta tatgaaactg tgtttcctgg   5760
cactgtacaa caccgttaac gacacgtcct attctattct gaaagagaaa ggtcataaca   5820
acctgtccta tctgacgaaa agctggcgtg aactgtgcaa agcctttctg caagaggcga   5880
```

```
aatggtccaa caacaaaatt atcccggctt tctccaagta cctggaaaac gccagcgttt    5940
cctcctccgg tgtagcgctg ctggcgccgt cttactttc cgtatgccag cagcaggaag    6000
acatctccga ccacgcgctg cgttccctga ccgacttcca tggtctggtg cgttctagct    6060
gcgttatctt ccgcctgtgc aacgatctgg ccacctctgc ggcggagctg aacgtggcg    6120 agactaccaa ttctatcatt agctacatgc acgaaaacga tggtaccagc gaggaacagg    6180
cccgcgaaga actgcgtaaa ctgatcgacg ccgaatggaa aaagatgaat cgtgaacgcg    6240
ttagcgactc caccctgctg cctaaagcgt tcatggaaat cgcagttaac atggcacgtg    6300
tttcccactg cacctaccag tatggcgatg gtctgggtcg cccagactac gcgactgaaa    6360
accgcatcaa actgctgctg attgacccct tcccgattaa ccagctgatg tatgtctaac    6420
tagagtcgac ctgcaggcat gcaagcttgg cgtaatcatg gtcatagctg tttcctgtgt    6480
gaaattgtta tccgctcaca attccacaca acatacgagc cggaagcata agtgtaaag    6540 cctggggtgc ctaatgagtg agctaactca cattaattgc gttgcgctca ctgcccgctt    6600
tccagtcggg aaacctgtcg tgccagctgc attaatgaat cggccaacgc gcggggagag    6660
gcggtttgcg tattggcgaa cttttgctga gttgaaggat cagatcacgc atcttcccga    6720
caacgcagac cgttccgtgg caaagcaaaa gttcaaaatc agtaaccgtc agtgccgata    6780
agttcaaagt taaacctggt gttgatacca acattgaaac gctgatcgaa aacgcgctga    6840
aaaacgctgc tgaatgtgcg agcttcttcc gcttcctcgc tcactgactc gctgcgctcg    6900
gtcgttcggc tgcggcgagc ggtatcagct cactcaaagg cggtaatacg ttatccaca    6960 gaatcagggg ataacgcagg aaagaacatg tgagcaaaag gccagcaaaa ggccaggaac    7020
cgtaaaaagg ccgcgttgct ggcgtttttc cataggctcc gcccccctga cgagcatcac    7080
aaaaatcgac gctcaagtca gaggtggcga acccgacag gactataaag ataccaggcg    7140
tttccccctg gaagctccct cgtgcgctct cctgttccga ccctgccgct taccggatac    7200
ctgtccgcct ttctcccttc gggaagcgtg gcgctttctc aatgctcacg ctgtaggtat    7260
ctcagttcgg tgtaggtcgt tcgctccaag ctgggctgtg tgcacgaacc ccccgttcag    7320
cccgaccgct gcgccttatc cggtaactat cgtcttgagt ccaacccggt aagacacgac    7380
ttatcgccac tggcagcagc cactggtaac aggattagca gagcgaggta tgtaggcggt    7440
gctacagagt tcttgaagtg gtggcctaac tacggctaca ctagaaggac agtatttggt    7500
atctgcgctc tgctgaagcc agttaccttc ggaaaaagag ttggtagctc ttgatccggc    7560
aaacaaacca ccgctggtag cggtggtttt tttgtttgca agcagcagat tacgcgcaga    7620
aaaaaaggat ctcaagaaga tcctttgatc ttttctacgg ggtctgacgc tcagtggaac    7680
gatccgtcga                                                           7690
```

<210> SEQ ID NO 80
<211> LENGTH: 7675
<212> TYPE: DNA
<213> ORGANISM: Artificial Sequence
<220> FEATURE:
<223> OTHER INFORMATION: Nucleotide sequence of plasmid for expressing ispSP gene (pVK9-P0480-ispSP)

<400> SEQUENCE: 80

```
gaggtctgcc tcgtgaagaa ggtgttgctg actcatacca ggcctgaatc gccccatcat      60
ccagccagaa agtgagggag ccacggttga tgagagcttt gttgtaggtg gacggggatc     120
ttttctacgg ggtctgacgc tcagtggaac gaaaactcac gttaagggat tttggtcatg    180
```

```
agattatcaa aaaggatcat gcgagcaacc tccataagat cagctaggcg atctttggga    240
gcagtccttg tcgcgttacg aggtgagccg gtggggaacc gttagctgcc tatggtgtga    300
gcccccctag agagcttcaa gagcaatcag cccgacctag aaaggaggcc aagagagaga    360
cctacggggg gaaccgtttt ctgcctacga gatgggcaca ttactgggaa gctttacggc    420
gtcctcgtgg aagttcaatg cccgcagact taagtgctct attcacggtc tgacgtgaca    480
cgctaaattc agacatagct tcattgattg tcggccacga gccagtctct ccctcaacag    540
tcataaacca acctgcaatg gtcaagcgat ttcctttagc tttcctagct tgtcgttgac    600
tggacttagc tagttttctc cgctgtgctc gggcgtactc actgtttggg tctttccagc    660
gttctgcggc cttttaccg ccacgtcttc ccatagtggc cagagctttt cgccctcggc    720
tgctctgcgt ctctgtctga cgagcaggga cgactggctg cctttagcg acgtagccgc    780 gcacacgtcg cgccatcgtc tggcggtcac gcatcggcgg cagatcaggc tcacggccgt    840
ctgctccgac cgcctgagcg acggtgtagg cacgctcgta ggcgtcgatg atcttggtgt    900
cttttaggcg ctcaccagcc gcttttaact ggtatcccac agtcaaagcg tggcgaaaag    960
ccgtctcatc acgggcggca cgccctggag cagtccagag gacacggacg ccgtcgatca   1020
gctctccaga cgcttcagcg gcgctcggca ggcttgcttc aagcgtggca agtgcttttg   1080
cttccgcagt ggcttttctt gccgcttcga tacgtgcccg tccgctagaa aactcctgct   1140
catagcgttt tttaggtttt tctgtgcctg agatcatgcg agcaacctcc ataagatcag   1200
ctaggcgatc cacgcgattg tgctgggcat gccagcggta cgcggtggga tcgtcggaga   1260
cgtgcagtgg ccaccggctc agcctatgtg aaaaagcctg gtcagcgccg aaaacgcggg   1320
tcatttcctc ggtcgttgca gccagcaggc gcatattcgg gctgctcatg cctgctgcgg   1380
catacaccgg atcaatgagc cagatgagct ggcatttccc gctcagtgga ttcacgccga   1440
tccaagctgg cgcttttcc aggcgtgccc agcgctccaa aatcgcgtag acctcggggt   1500
ttacgtgctc gattttcccg ccggcctggt ggctcggcac atcaatgtcc aggacaagca   1560
cggctgcgtg ctgcgcgtgc gtcagagcaa catactggca ccgggcaagc gattttgaac   1620
caactcggta taacttcggc tgtgtttctc ccgtgtccgg gtctttgatc caagcgctgg   1680
cgaagtcgcg ggtcttgctg ccctggaaat tttctctgcc caggtgagcg aggaattcgc   1740
ggcggtcttc gctcgtccag ccacgtgatc gcagcgcgag ctcggatgg gtgtcgaaca   1800 gatcagcgga aaatttccag gccggtgtgt caatgtctcg tgaatccgct agagtcattt   1860
ttgagcgctt tctcccaggt ttggactggg ggttagccga cgccctgtga gttaccgctc   1920
acggggcgtt caacatttt caggtattcg tgcagcttat cgcttcttgc cgcctgtgcg   1980 cttttcgac gcgcgacgct gctgccgatt cggtgcaggt ggtggcggcg ctgacacgtc   2040
ctgggcggcc acgccacac gaaacgcggc atttacgatg tttgtcatgc ctgcgggcac   2100
cgcgccacga tcgcggataa ttctcgctgc cgcttccagc tctgtgacga ccatggccaa   2160
aatttcgctc gggggacgca cttccagcgc catttgcgac ctagccgcct ccagctcctc   2220
ggcgtggcgt ttgttggcgc gctcgcggct ggctgcggca cgacacgcat ctgagcaata   2280
ttttgcgcgc cgtcctcgcg ggtcaggccg gggaggaatc aggccaccgc agtaggcgca   2340
actgattcga tcctccacta ctgtgcgtcc tcctggcgct gccgagcacg cagctcgtca   2400
gccagctcct caagatccgc cacgagagtt tctaggtcgc tcgcggcact ggcccagtct   2460
cgtgatgctg gcgcgtccgt cgtatcgaga gctcggaaaa atccgatcac cgttttaaa   2520 tcgacggcag catcgagcgc gtcggactcc agcgcgacat cagagagatc catagctgat   2580
```

```
gattcgggcc aattttggta cttcgtcgtg aaggtcatga caccattata acgaacgttc   2640
gttaaagttt ttggcggaaa atcacgcggc acgaaaattt tcacgaagcg ggactttgcg   2700
cagctcaggg gtgctaaaaa ttttgtatcg cacttgattt ttccgaaaga cagattatct   2760
gcaaacggtg tgtcgtattt ctggcttggt ttttaaaaaa tctggaatcg aaaatttgcg   2820
gggcgaccga aagttttttt acaaaaggca aaaacttttt cgggatcagc taggcgatcc   2880
acgcgattgt gctgggcatg ccagcggtac gcggtgggat cgtcgagac gtgcagtggc   2940 caccggctca gcctatgtga aaaagcctgg tcagcgccga aaacgcgggt catttcctcg   3000
gtcgttgcag ccagcaggcg catattcggg ctgctcatgc ctgctgcggc atacaccgga   3060
tcggaccagt tggtgatttt gaacttttgc tttgccacgg aacggtctgc gttgtcggga   3120
agatgcgtga tctgatcctt caactcagca aaagttcgat ttattcaaca aagccacgtt   3180
gtgtctcaaa atctctgatg ttacattgca caagataaaa atatatcatc atgaacaata   3240
aaactgtctg cttacataaa cagtaataca aggggtgtta tgagccatat tcaacgggaa   3300
acgtcttgct cgaagccgcg attaaattcc aacatggatg ctgatttata tgggtataaa   3360
tgggctcgcg ataatgtcgg gcaatcaggt gcgacaatct atcgattgta tgggaagccc   3420
gatgcgccag agttgtttct gaaacatggc aaaggtagcg ttgccaatga tgttacagat   3480
gagatggtca gactaaactg gctgacggaa tttatgcctc ttccgaccat caagcatttt   3540
atccgtactc ctgatgatgc atggttactc accactgcga tccccgggaa aacagcattc   3600
caggtattag aagaatatcc tgattcaggt gaaaatattg ttgatgcgct ggcagtgttc   3660
ctgcgccggt tgcattcgat tcctgtttgt aattgtcctt ttaacagcga tcgcgtattt   3720
cgtctcgctc aggcgcaatc acgaatgaat aacggtttgg ttgatgcgag tgattttgat   3780
gacgagcgta atggctggcc tgttgaacaa gtctggaaag aaatgcataa gcttttgcca   3840
ttctcaccgg attcagtcgt cactcatggt gatttctcac ttgataacct tattttgac    3900 gaggggaaat taataggttg tattgatgtt ggacgagtcg gaatcgcaga ccgataccag   3960
gatcttgcca tcctatggaa ctgcctcggt gagttttctc cttcattaca gaaacggctt   4020
tttcaaaaat atggtattga taatcctgat atgaataaat tgcagtttca tttgatgctc   4080
gatgagtttt tctaatcaga attggttaat tggttgtaac actggcagag cattacgctg   4140
acttgacggg acggcggctt tgttaataa atcgcattcg ccattcaggc tgcgcaactg   4200
ttgggaaggg cgatcggtgc gggcctcttc gctattacgc cagctggcga aggggggatg   4260
tgctgcaagg cgattaagtt gggtaacgcc agggttttcc cagtcacgac gttgtaaaac   4320
gacggccagt gaattcgagc tcggtacccg gggatcctct agagatcgtt tagatccgaa   4380
ggaaaacgtc gaaaagcaat tgcttttcg acgccccacc ccgcgcgttt tagcgtgtca   4440
gtagacgcgt agggtaagtg gggtagcggc ttgttagata tcttgaaatc ggctttcaac   4500
agcattgatt tcgatgtatt tagctggccg ttaccctgcg aatgtccaca gggtagctgg   4560
tagtttgaaa atcaacgccg ttgcccttag gattcagtaa ctggcacatt ttgtaatgcg   4620
ctagatctgt gtgcccagtc ttccaggctg cttatcacag tgaaagcaaa accaattcgt   4680
ggctgcgaaa gtcgtagcca ccacgaagtc caggaggaca tacaatgtgc tctgtttcta   4740
ccgagaacgt ttccttcact gagacggaaa ccgaggcacg tcgtagcgcg aactacgagc   4800
cgaatagctg ggactacgat ttcctgctgt cttccgatac tgacgaatct attgaggtgt   4860
acaaagacaa agcaaagaaa ctggaggctg aagtgcgccg cgaaattaac aacgagaaag   4920
```

```
ctgaattcct gactctgctg gagctgatcg ataacgtaca gcgcctgggt ctgggttacc    4980
gcttcgaatc tgatatccgt cgcgcactgg atcgtttcgt aagcagcggc ggtttcgatg    5040
gcgtgaccaa aacgagcctg cacgctaccg cgctgtcctt ccgtctgctg cgtcagcacg    5100
gcttcgaagt ttctcaggaa gcattctccg gtttcaaaga tcaaaacggt aacttcctgg    5160
aaaacctgaa agaagacact aaggcgatcc tgagcctgta tgaggcaagc tttctggccc    5220
tggagggtga aacatcctg gatgaggcgc gcgtattcgc catctcccat ctgaaagagc    5280
tgtctgaaga gaaaatcggt aaggaactgg cagagcaggt taatcacgca ctggaactgc    5340
cgctgcatcg tcgtacccag cgtctggagg cggtttggtc catcgaagcg taccgcaaaa    5400
aggaggatgc taaccaggtt ctgctggaac tggccatcct ggactacaac atgatccagt    5460
ccgtttacca gcgtgatctg cgtgaaacct cccgttggtg gcgccgtgtg ggcctggcga    5520
ccaaactgca cttcgctaag gaccgcctga ttgagtcttt ttactgggca gtcggcgttg    5580
cgttcgaacc tcagtattct gactgccgta acagcgttgc gaaaatgttc agcttcgtta    5640
ctattatcga cgacatctac gacgtttacg gtactctgga cgagctggaa ctgtttaccg    5700
acgctgtcga acgttgggat gttaacgcca tcaacgatct gcctgactac atgaaactgt    5760
gcttcctggc actgtataac acgatcaacg aaattgcata cgacaacctg aaagacaaag    5820
gtgaaaacat cctgccgtac ctgactaaag cgtgggcgga tctgtgtaac gcttttctgc    5880
aagaagcgaa atggctgtat aacaaatcca ctccgacctt tgacgattat ttcggcaatg    5940
cctggaaatc cagctctggc ccgctgcaac tgatcttcgc ttattttgcg gttgtccaaa    6000
acatcaaaaa ggaggaaatt gaaaacctgc aaaaatacca cgatatcatt agccgtcctt    6060
ctcatatctt tcgcctgtgc aacgacctgg caagcgcgtc cgcagagatc gcacgtggcg    6120
aaaccgctaa ctctgtttcc tgctacatgc gcaccaaggg catttccgaa gagctggcaa    6180
ccgagagcgt aatgaatctg atcgacgaaa cctgtaagaa aatgaacaaa gaaaaactgg    6240
gtggctccct gttcgctaaa ccgttcgtag agactgctat taacctgcag cgtcagagcc    6300
actgcaccta ccacaatggt gacgcacata ctagcccgga tgaactgact cgtaaacgtg    6360
tactgtctgt tatcaccgaa ccgattctgc cgttcgaacg ttaactagag tcgacctgca    6420
ggcatgcaag cttggcgtaa tcatggtcat agctgtttcc tgtgtgaaat tgttatccgc    6480
tcacaattcc acacaacata cgagccggaa gcataaagtg taaagcctgg ggtgcctaat    6540
gagtgagcta actcacatta attgcgttgc gctcactgcc cgctttccag tcgggaaacc    6600
tgtcgtgcca gctgcattaa tgaatcggcc aacgcgcggg gagaggcggt ttgcgtattg    6660
gcgactttt gctgagttga aggatcagat cacgcatctt cccgacaacg cagaccgttc    6720
cgtggcaaag caaagttca aaatcagtaa ccgtcagtgc cgataagttc aaagttaaac    6780
ctggtgttga taccaacatt gaaacgctga tcgaaaacgc gctgaaaaac gctgctgaat    6840
gtgcgagctt cttccgcttc ctcgctcact gactcgctgc gctcggtcgt tcggctgcgg    6900
cgagcggtat cagctcactc aaaggcggta atacggttat ccacagaatc aggggataac    6960
gcaggaaaga acatgtgagc aaaaggccag caaaaggcca ggaaccgtaa aaaggccgcg    7020
ttgctggcgt ttttccatag gctccgcccc cctgacgagc atcacaaaaa tcgacgctca    7080
agtcagaggt ggcgaaaccc gacaggacta taaagatacc aggcgtttcc ccctggaagc    7140
tccctcgtgc gctctcctgt tccgaccctg ccgcttaccg gatacctgtc gcctttctc    7200
ccttcgggaa gcgtggcgct ttctcaatgc tcacgctgta ggtatctcag ttcggtgtag    7260
gtcgttcgct ccaagctggg ctgtgtgcac gaacccccg ttcagcccga ccgctgcgcc    7320
```

```
ttatccggta actatcgtct tgagtccaac ccggtaagac acgacttatc gccactggca    7380
gcagccactg gtaacaggat tagcagagcg aggtatgtag gcggtgctac agagttcttg    7440
aagtggtggc ctaactacgg ctacactaga aggacagtat ttggtatctg cgctctgctg    7500
aagccagtta ccttcggaaa aagagttggt agctcttgat ccggcaaaca aaccaccgct    7560
ggtagcggtg gttttttttgt ttgcaagcag cagattacgc gcagaaaaaa aggatctcaa    7620
gaagatcctt tgatctttc tacggggtct gacgctcagt ggaacgatcc gtcga          7675
```

<210> SEQ ID NO 81
<211> LENGTH: 7647
<212> TYPE: DNA
<213> ORGANISM: Artificial Sequence
<220> FEATURE:
<223> OTHER INFORMATION: Nucleotide sequence of plasmid for expressing
      ispSK gene (pVK9-P0480-ispSM)

<400> SEQUENCE: 81

```
gaggtctgcc tcgtgaagaa ggtgttgctg actcatacca ggcctgaatc gccccatcat      60
ccagccagaa agtgagggag ccacggttga tgagagcttt gttgtaggtg acgggggatc     120
ttttctacgg ggtctgacgc tcagtggaac gaaaactcac gttaagggat tttggtcatg    180
agattatcaa aaaggatcat gcgagcaacc tccataagat cagctaggcg atctttggga    240
gcagtccttg tcgcgttacg aggtgagccg gtggggaacc gttagctgcc tatggtgtga    300 gccccctag agagcttcaa gagcaatcag cccgacctag aaaggaggcc aagagagaga    360
cctacggggg gaaccgtttt ctgcctacga gatgggcaca ttactgggaa gctttacggc    420
gtcctcgtgg aagttcaatg cccgcagact taagtgctct attcacggtc tgacgtgaca    480
cgctaaattc agacatagct tcattgattg tcggccacga gccagtctct ccctcaacag    540
tcataaacca acctgcaatg gtcaagcgat ttcctttagc tttcctagct tgtcgttgac    600
tggacttagc tagttttttct cgctgtgctc gggcgtactc actgtttggg tcttccagc    660 gttctgcggc cttttttaccg ccacgtcttc ccatagtggc cagagctttt cgccctcggc    720
tgctctgcgt ctctgtctga cgagcaggga cgactggctg gcctttagcg acgtagccgc    780
gcacacgtcg cgccatcgtc tggcggtcac gcatcggcgg cagatcaggc tcacggccgt    840
ctgctccgac cgcctgagcg acggtgtagg cacgctcgta ggcgtcgatg atcttggtgt    900
cttttaggcg ctcaccagcc gcttttaact ggtatcccac agtcaaagcg tggcgaaaag    960
ccgtctcatc acgggcggca cgccctggag cagtccagag acacggacg ccgtcgatca    1020 gctctccaga cgcttcagcg cgcgctcggca ggcttgcttc aagcgtggca agtgctttttg    1080 cttccgcagt ggcttttctt gccgcttcga tacgtgcccg tccgctagaa aactcctgct    1140
catagcgttt tttaggtttt tctgtgcctg agatcatgcg agcaacctcc ataagatcag    1200
ctaggcgatc cacgcgattg tgctgggcat gccagcggta cgcggtggga tcgtcggaga    1260
cgtgcagtgg ccaccggctc agcctatgtg aaaaagcctg gtcagcgccg aaaacgcggg    1320
tcatttcctc ggtcgttgca gccagcaggc gcatattcgg gctgctcatg cctgctgcgg    1380
catacaccgg atcaatgagc cagatgagct ggcatttccc gctcagtgga ttcacgccga    1440
tccaagctgg cgcttttttcc aggcgtgccc agcgctccaa aatcgcgtag acctcgggt     1500 ttacgtgctc gattttcccg ccggcctggt ggctcggcac atcaatgtcc aggacaagca    1560 cggctgcgt ctgcgcgtgc gtcagagcaa catactggca ccgggcaagc gatttttgaac    1620 caactcggta taacttcggc tgtgtttctc ccgtgtccgg gtctttgatc caagcgctgg    1680
```

-continued

```
cgaagtcgcg ggtcttgctg ccctggaaat tttctctgcc caggtgagcg aggaattcgc   1740
ggcggtcttc gctcgtccag ccacgtgatc gcagcgcgag ctcgggatgg gtgtcgaaca   1800
gatcagcgga aaatttccag gccggtgtgt caatgtctcg tgaatccgct agagtcattt   1860
ttgagcgctt tctcccaggt ttggactggg ggttagccga cgccctgtga gttaccgctc   1920
acggggcgtt caacattttt caggtattcg tgcagcttat cgcttcttgc cgcctgtgcg   1980 cttttcgac gcgcgacgct gctgccgatt cggtgcaggt ggtggcggcg ctgacacgtc    2040
ctgggcggcc acggccacac gaaacgcggc atttacgatg tttgtcatgc ctgcgggcac   2100
cgcgccacga tcgcggataa ttctcgctgc cgcttccagc tctgtgacga ccatggccaa   2160
aatttcgctc gggggacgca cttccagcgc catttgcgac ctagccgcct ccagctcctc   2220
ggcgtggcgt tgttggcgc gctcgcggct ggctgcggca cgacacgcat ctgagcaata    2280
ttttgcgcgc cgtcctcgcg ggtcaggccg gggaggaatc aggccaccgc agtaggcgca   2340
actgattcga tcctccacta ctgtgcgtcc tcctggcgct gccgagcacg cagctcgtca   2400
gccagctcct caagatccgc cacgagagtt tctaggtcgc tcgcggcact ggcccagtct   2460
cgtgatgctg gcgcgtccgt cgtatcgaga gctcggaaaa atccgatcac cgttttaaa    2520 tcgacggcag catcgagcgc gtcggactcc agcgcgacat cagagagatc catagctgat   2580
gattcgggcc aattttggta cttcgtcgtg aaggtcatga caccattata acgaacgttc   2640
gttaaagttt ttggcggaaa atcacgcggc acgaaaattt tcacgaagcg ggactttgcg   2700
cagctcaggg gtgctaaaaa ttttgtatcg cacttgattt ttccgaaaga cagattatct   2760
gcaaacggtg tgtcgtattt ctggcttggt ttttaaaaaa tctggaatcg aaaatttgcg   2820
gggcgaccga gaagtttttt acaaaaggca aaaactttt cgggatcagc taggcgatcc    2880
acgcgattgt gctgggcatg ccagcggtac gcggtgggat cgtcggagac gtgcagtggc   2940
caccggctca gcctatgtga aaaagcctgg tcagcgccga aaacgcgggt catttcctcg   3000
gtcgttgcag ccagcaggcg catattcggg ctgctcatgc ctgctgcggc atacaccgga   3060
tcggaccagt tggtgatttt gaacttttgc tttgccacgg aacggtctgc gttgtcggga   3120
agatgcgtga tctgatcctt caactcagca aaagttcgat ttattcaaca aagccacgtt   3180
gtgtctcaaa atctctgatg ttacattgca caagataaaa atatatcatc atgaacaata   3240
aaactgtctg cttacataaa cagtaataca aggggtgtta tgagccatat tcaacgggaa   3300
acgtcttgct cgaagccgcg attaaattcc aacatggatg ctgatttata tgggtataaa   3360
tgggctcgcg ataatgtcgg gcaatcaggt gcgacaatct atcgattgta tgggaagccc   3420
gatgcgccag agttgtttct gaaacatggc aaaggtagcg ttgccaatga tgttacagat   3480
gagatggtca gactaaactg gctgacggaa tttatgcctc ttccgaccat caagcatttt   3540
atccgtactc ctgatgatgc atggttactc accactgcga tccccgggaa aacagcattc   3600
caggtattag aagaatatcc tgattcaggt gaaatattg ttgatgcgct ggcagtgttc    3660
ctgcgccggt tgcattcgat tcctgtttgt aattgtcctt ttaacagcga tcgcgtattt   3720
cgtctcgctc aggcgcaatc acgaatgaat aacggtttgg ttgatgcgag tgattttgat   3780
gacgagcgta atggctggcc tgttaacaa gtctggaaag aaatgcataa gcttttgcca    3840
ttctcaccgg attcagtcgt cactcatggt gatttctcac ttgataacct tattttgac    3900 gaggggaaat taataggttg tattgatgtt ggacgagtcg gaatcgcaga ccgataccag   3960
gatcttgcca tcctatggaa ctgcctcggt gagttttctc cttcattaca gaaacggctt   4020
```

```
tttcaaaaat atggtattga taatcctgat atgaataaat tgcagtttca tttgatgctc    4080
gatgagtttt tctaatcaga attggttaat tggttgtaac actggcagag cattacgctg    4140
acttgacggg acggcggctt tgttgaataa atcgcattcg ccattcaggc tgcgcaactg    4200
ttgggaaggg cgatcggtgc gggcctcttc gctattacgc cagctggcga aaggggatg     4260
tgctgcaagg cgattaagtt gggtaacgcc agggttttcc cagtcacgac gttgtaaaac    4320
gacggccagt gaattcgagc tcggtacccg gggatcctct agagatcgtt tagatccgaa    4380
ggaaaacgtc gaaaagcaat tgcttttcg acgccccacc ccgcgcgttt tagcgtgtca     4440
gtagacgcgt agggtaagtg gggtagcggc ttgttagata tcttgaaatc ggctttcaac    4500
agcattgatt tcgatgtatt tagctggccg ttaccctgcg aatgtccaca gggtagctgg    4560
tagtttgaaa atcaacgccg ttgcccttag gattcagtaa ctggcacatt ttgtaatgcg    4620
ctagatctgt gtgcccagtc ttccaggctg cttatcacag tgaaagcaaa accaattcgt    4680
ggctgcgaaa gtcgtagcca ccacgaagtc caggaggaca tacaatgtcc gccgtttcaa    4740
gccagttctc tcaaatcgcc gaagacaata gccgtcgctc agcaaattat catccgaatc    4800
tgtgggactt tgaatttctg cagtctctgg aaaacgatag taaaatggaa aaactggaag    4860
aaaaagccac caaactggaa gaagaagtgc gtaacatgat gaatgaagcg aaaacggaag    4920
ccctgagcct gctggaactg attgatgacg tccaacgcct gggtctgacc tacaaattcg    4980
aaaaagatat catcaaagca ctggaaaaaa ttgtcccgct ggacgaatca ggtctgcacg    5040
tgacgtctct gagttttcgt atcctgcgcc agcatggctt cgaagtttcg caagatgtct    5100
ttaaacgttt caaagacaaa gaaggcgtt tctgcgcgga actgaaagat gacgtgcagg     5160
gtctgctgtc cctgtatgaa gcctcatacc tgggttttga aggcgaatcc ctgctggatg    5220
aagcgcgcgc cttctcaatt acccacctga aaaacaatct gaacaaaggc atcaatacga    5280
aagtggcaca gcaagttagc catgctctgg aactgccgta tcaccgtcgc ctgcatcgtc    5340
tggaagcacg ctggctgctg ataaatacg aaccgaaaga accgcatcac catctgctgc     5400
acgaactggc gaaactggac tttaatctgg ttcagtcgct gtatcaaaaa gaactgcgtg    5460
aactgagcct gtggtggcgc gaaattggtc tgacctctaa actggatttt gtgcgtgacc    5520
gcctgatgga agtttacttc tgggcactgg gcatggctcc ggatccgcag tttagcgaat    5580
gccgtaaagt ggttaccaaa atgttcggtc tggtcacgat tatcgatgac gtctatgatg    5640
tgtacggcac cctggacgaa ctgcaactgt tcacggatgc ggtcgaacgc tgggacgtga    5700
acgccatcaa taccctgccg gattatatga actgtgtta tctggcgctg tacaacaccg     5760
ttaatgacac ggcctatagc atcctgaaag aaaaaggtca taacaacatc tcgtacctga    5820
ccaaaagctg gtgcgaactg tgtaaagcgt ttctgcagga agccaaatgg tctaacaaca    5880
aaatcatccc ggcattcaac aaatacctgg ataatgctag tgttagctct agtggcgtcg    5940
cactgctggc tccgtcctac tttctggtgt gtcaggaaca agatatttct gaccaggcgc    6000
tgcacagtct gaccaacttt catggtctgg ttcgttcctc atgcaccatc ttccgcctgt    6060
gtaatgatct ggcgacgtcg agcgccgaac tggaacgtgg cgaaaccacg aactcgatta    6120
ccagctatat gcacgaaaat gaaacgagtg aagaacaggc atgcaaagaa ctgcgtaacc    6180
tgatcgatgc tgaatggaag aaaatgaacg aagaacgcgt gtccaattca accctgccga    6240
aagcctttcg tgaaattgca atcaatatgg ctcgcatttc ccattgtacg tatcagtacg    6300
gcgatggtct gggccgcccg gactacacga ccgaaaccg tattaaactg ctgctgattg      6360
acccgttccc gattaactag agtcgacctg caggcatgca agcttggcgt aatcatggtc    6420
```

-continued

```
atagctgttt cctgtgtgaa attgttatcc gctcacaatt ccacacaaca tacgagccgg   6480
aagcataaag tgtaaagcct ggggtgccta atgagtgagc taactcacat taattgcgtt   6540
gcgctcactg cccgctttcc agtcgggaaa cctgtcgtgc cagctgcatt aatgaatcgg   6600
ccaacgcgcg gggagaggcg gtttgcgtat tgggcgaactt ttgctgagtt gaaggatcag  6660
atcacgcatc ttcccgacaa cgcagaccgt tccgtggcaa agcaaaagtt caaaatcagt   6720
aaccgtcagt gccgataagt tcaaagttaa acctggtgtt gataccaaca ttgaaacgct   6780
gatcgaaaac gcgctgaaaa acgctgctga atgtgcgagc ttcttccgct tcctcgctca   6840
ctgactcgct gcgctcggtc gttcggctgc ggcgagcggt atcagctcac tcaaaggcgg   6900
taatacggtt atccacagaa tcaggggata acgcaggaaa gaacatgtga gcaaaaggcc   6960
agcaaaaggc caggaaccgt aaaaaggccg cgttgctggc gtttttccat aggctccgcc   7020
cccctgacga gcatcacaaa aatcgacgct caagtcagag gtggcgaaac ccgacaggac   7080
tataaagata ccaggcgttt ccccctggaa gctccctcgt gcgctctcct gttccgaccc   7140
tgccgcttac cggatacctg tccgcctttc tcccttcggg aagcgtggcg ctttctcaat   7200
gctcacgctg taggtatctc agttcggtgt aggtcgttcg ctccaagctg gctgtgtgc   7260 acgaaccccc cgttcagccc gaccgctgcg ccttatccgg taactatcgt cttgagtcca   7320
acccggtaag acacgactta tcgccactgg cagcagccac tggtaacagg attagcagag   7380
cgaggtatgt aggcggtgct acagagttct tgaagtggtg gcctaactac ggctacacta   7440
gaaggacagt atttggtatc tgcgctctgc tgaagccagt taccttcgga aaaagagttg   7500
gtagctcttg atccggcaaa caaaccaccg ctggtagcgg tggtttttt gtttgcaagc   7560 agcagattac gcgcagaaaa aaaggatctc aagaagatcc tttgatcttt tctacggggt   7620
ctgacgctca gtggaacgat ccgtcga                                      7647
```

<210> SEQ ID NO 82
<211> LENGTH: 41
<212> TYPE: DNA
<213> ORGANISM: Artificial Sequence
<220> FEATURE:
<223> OTHER INFORMATION: Primer for amplifying IspSK gene

<400> SEQUENCE: 82
gggaatatta agcttggtac catgtgtgcg acctcttctc a                      41

<210> SEQ ID NO 83
<211> LENGTH: 41
<212> TYPE: DNA
<213> ORGANISM: Artificial Sequence
<220> FEATURE:
<223> OTHER INFORMATION: Primer for amplifying IspSK gene

<400> SEQUENCE: 83
agtggatccg agctcggtac cttagacata catcagctgg t                      41

<210> SEQ ID NO 84
<211> LENGTH: 41
<212> TYPE: DNA
<213> ORGANISM: Artificial Sequence
<220> FEATURE:
<223> OTHER INFORMATION: Primer for amplifying IspSP gene

<400> SEQUENCE: 84
gggaatatta agcttggtac catgtgctct gtttctaccg a                      41

<210> SEQ ID NO 85
<211> LENGTH: 41
<212> TYPE: DNA
<213> ORGANISM: Artificial Sequence
<220> FEATURE:
<223> OTHER INFORMATION: Primer for amplifying IspSP gene

<400> SEQUENCE: 85
agtggatccg agctcggtac cttaacgttc gaacggcaga a        41

<210> SEQ ID NO 86
<211> LENGTH: 41
<212> TYPE: DNA
<213> ORGANISM: Artificial Sequence
<220> FEATURE:
<223> OTHER INFORMATION: Primer for amplifying IspSM gene

<400> SEQUENCE: 86
gggaatatta agcttggtac catgtccgcc gtttcaagcc a        41

<210> SEQ ID NO 87
<211> LENGTH: 41
<212> TYPE: DNA
<213> ORGANISM: Artificial Sequence
<220> FEATURE:
<223> OTHER INFORMATION: Primer for amplifying IspSM gene

<400> SEQUENCE: 87
agtggatccg agctcggtac cttagttaat cgggaacggg t        41

<210> SEQ ID NO 88
<211> LENGTH: 24
<212> TYPE: DNA
<213> ORGANISM: Artificial Sequence
<220> FEATURE:
<223> OTHER INFORMATION: PCR primer 1 for pCold-TF

<400> SEQUENCE: 88
cctaccttcg ataccaccac tacc        24

<210> SEQ ID NO 89
<211> LENGTH: 30
<212> TYPE: DNA
<213> ORGANISM: Artificial Sequence
<220> FEATURE:
<223> OTHER INFORMATION: PCR primer 2 for pCold-TF

<400> SEQUENCE: 89
taggtaatct ctgcttaaaa gcacagaatc        30

<210> SEQ ID NO 90
<211> LENGTH: 44
<212> TYPE: DNA
<213> ORGANISM: Artificial Sequence
<220> FEATURE:
<223> OTHER INFORMATION: PCR primer 1 for IspSM gene

<400> SEQUENCE: 90
ggtagtggtg gtatcgaagg taggatgtcc gccgtttcaa gcca        44

<210> SEQ ID NO 91
<211> LENGTH: 53
<212> TYPE: DNA
<213> ORGANISM: Artificial Sequence
<220> FEATURE:
<223> OTHER INFORMATION: IspSM PCR primer 2

<400> SEQUENCE: 91
gattctgtgc ttttaagcag agattaccta ttagttaatc gggaacgggt caa        53

<210> SEQ ID NO 92
<211> LENGTH: 7365
<212> TYPE: DNA
<213> ORGANISM: Artificial Sequence
<220> FEATURE:
<223> OTHER INFORMATION: Nucleotide sequence of plasmid for expressing
      IspSM gene (pCold-TF-IspSM)

<400> SEQUENCE: 92

| aaggaatggt gtggccgatt aatcataaat atgaaaaata attgttgcat cacccgccaa | 60 |
|---|---|
| tgcgtggctt aatgcacatc aaattgtgag cggataacaa tttgatgtgc tagcgcatat | 120 |
| ccagtgtagt aaggcaagtc ccttcaagag ttatcgttga taccctcgt agtgcacatt | 180 |
| cctttaacgc ttcaaaatct gtaaagcacg ccatatcgcc gaaaggcaca cttaattatt | 240 |
| aagaggtaat acaccatgaa tcacaaagtg catcatcatc atcatcacat gcaagtttca | 300 |
| gttgaaacca ctcaaggcct tggccgccgt gtaacgatta ctatcgctgc tgacagcatc | 360 |
| gagaccgctg ttaaaagcga gctggtcaac gttgcgaaaa agtacgtat tgacggcttc | 420 |
| cgcaagggca agtgccaat gaatatcgtt gctcagcgtt atggcgcgtc tgtacgccag | 480 |
| gacgttctgg gtgacctgat gagccgtaac ttcattgacg ccatcattaa agaaaaaatc | 540 |
| aatccggctg cgcaccgac ttatgttccg ggcgaataca agctgggtga agacttcact | 600 |
| tactctgtag agtttgaagt ttatccggaa gttgaactgc aaggtctgga agcgatcgaa | 660 |
| gttgaaaaac cgatcgttga agtgaccgac gctgacgttg acggcatgct ggatactctg | 720 |
| cgtaaacagc aggcgacctg gaaagaaaaa gacggcgctg ttgaagcaga agaccgcgtg | 780 |
| accatcgact tcaccggttc tgtagacggc gaagagttcg aaggcggtaa agcgtctgat | 840 |
| ttcgtactgg cgatgggcca gggtcgtatg atccccgggct ttgaagacgg tatcaaaggc | 900 |
| cacaaagctg gcgaagagtt caccatcgac gtgaccttcc cggaagaata ccacgcagaa | 960 |
| aacctgaaag gtaaagcagc gaaattcgct atcaacctga gaaagttga agagcgtgaa | 1020 |
| ctgccggaac tgaccgcaga gttcatcaaa cgtttcggcg ttgaagatgg ttccgtagaa | 1080 |
| ggtctgcgcg ctgaagtgcg taaaaacatg gagcgcgagc tgaagagcgc catccgtaac | 1140 |
| cgcgttaagt ctcaggcgat cgaaggtctg gtaaaagcta acgacatcga cgtaccggct | 1200 |
| gcgctgatcg acagcgaaat cgacgttctg cgtcgccagg ctgcacagcg tttcggtggc | 1260 |
| aacgaaaaac aagctctgga actgccgcgc gaactgttcg aagaacaggc taaacgccgc | 1320 |
| gtagttgttg gcctgctgct gggcgaagtt atccgcacca acgagctgaa agctgacgaa | 1380 |
| gagcgcgtga aaggcctgat cgaagagatg gcttctgcgt acgaagatcc gaaagaagtt | 1440 |
| atcgagttct acagcaaaaa caagaactg atggacaaca tgcgcaatgt tgctctggaa | 1500 |
| gaacaggctg ttgaagctgt actggcgaaa gcgaagtga ctgaaaaaga aaccactttc | 1560 |
| aacgagctga tgaaccagca ggcgtccgcg ggtctggaag ttctgttcca ggggccctcc | 1620 |
| gcgggtctgg tgccacgcgg tagtggtggt atcgaaggta gatgtccgc cgtttcaagc | 1680 |
| cagttctctc aaatcgccga agacaatagc cgtcgctcag caattatca tccgaatctg | 1740 |
| tgggactttg aatttctgca gtctctggaa aacgatagta aatggaaaa actggaagaa | 1800 |
| aaagccacca aactggaaga agaagtgcgt aacatgatga atgaagcgaa aacggaagcc | 1860 |
| ctgagcctgc tggaactgat tgatgacgtc aacgcctgg gtctgaccta caaattcgaa | 1920 |

```
aaagatatca tcaaagcact ggaaaaaatt gtcccgctgg acgaatcagg tctgcacgtg    1980
acgtctctga gttttcgtat cctgcgccag catggcttcg aagtttcgca agatgtcttt    2040
aaacgtttca aagacaaaga aggcggtttc tgcgcggaac tgaaagatga cgtgcagggt    2100
ctgctgtccc tgtatgaagc ctcatacctg ggttttgaag cgaatccct gctggatgaa    2160 gcgcgcgcct tctcaattac ccacctgaaa aacaatctga acaaaggcat caatacgaaa    2220
gtggcacagc aagttagcca tgctctggaa ctgccgtatc accgtcgcct gcatcgtctg    2280
gaagcacgct ggctgctgga taaatacgaa ccgaaagaac cgcatcacca tctgctgcac    2340
gaactggcga actggacttt aatctggtt cagtcgctgt atcaaaaaga actgcgtgaa    2400
ctgagcctgt ggtggcgcga aattggtctg acctctaaac tggattttgt gcgtgaccgc    2460
ctgatggaag tttacttctg ggcactgggc atggctccgg atccgcagtt tagcgaatgc    2520
cgtaaagtgg ttaccaaaat gttcggtctg gtcacgatta tcgatgacgt ctatgatgtg    2580
tacggcaccc tggacgaact gcaactgttc acggatgcgg tcgaacgctg ggacgtgaac    2640
gccatcaata ccctgccgga ttatatgaaa ctgtgttatc tggcgctgta caacaccgtt    2700
aatgacacgg cctatagcat cctgaaagaa aaaggtcata acaacatctc gtacctgacc    2760
aaaagctggt gcgaactgtg taaagcgttt ctgcaggaag ccaaatggtc taacaacaaa    2820
atcatcccgg cattcaacaa ataccctggat aatgctagtg ttagctctag tggcgtcgca    2880
ctgctggctc cgtcctactt tctggtgtgt caggaacaag atatttctga ccaggcgctg    2940
cacagtctga ccaactttca tggtctggtt cgttcctcat gcaccatctt ccgcctgtgt    3000
aatgatctgg cgacgtcgag cgccgaactg gaacgtggcg aaaccacgaa ctcgattacc    3060
agctatatgc acgaaaatga aacgagtgaa gaacaggcat gcaaagaact gcgtaacctg    3120
atcgatgctg aatggaagaa aatgaacgaa gaacgcgtgt ccaattcaac cctgccgaaa    3180
gcctttcgtg aaattgcaat caatatggct cgcatttccc attgtacgta tcagtacggc    3240
gatggtctgg gccgcccgga ctacacgacc gaaaaccgta ttaaactgct gctgattgac    3300
ccgttcccga ttaactaata ggtaatctct gcttaaaagc acagaatcta agatccctgc    3360
catttggcgg ggattttttt atttgttttc aggaaataaa taatcgatcg cgtaataaaa    3420
tctattatta tttttgtgaa gaataaattt gggtgcaatg agaatgcgca ggcccttcg    3480 tctcgcgcgt ttcggtgatg acggtgaaaa cctctgacac atgcagctcc cggagacggt    3540
cacagcttgt ctgtaagcgg atgccgggag cagacaagcc cgtcagggcg cgtcagcggg    3600
tgttggcggg tgtcggggct ggcttaacta tgcggcatca gagcagattg tactgagagt    3660
gcaccataaa attgtaaacg ttaatatttt gttaaaattc gcgttaaatt tttgttaaat    3720
cagctcattt tttaaccaat aggccgaaat cggcaaaatc ccttataaat caaagaata    3780 gcccgagata gggttgagtg ttgttccagt ttggaacaag agtccactat taaagaacgt    3840
ggactccaac gtcaaaggc gaaaaaccgt ctatcagggc gatggcccac tacgtgaacc    3900
atcacccaaa tcaagttttt tggggtcgag gtgccgtaaa gcactaaatc ggaaccctaa    3960
agggagcccc cgatttagag cttgacgggg aaagccggcg aacgtggcga gaaggaagg    4020 gaagaaagcg aaaggagcgg cgctagggc gctggcaagt gtagcggtca cgctgcgcgt    4080
aaccaccaca cccgccgcgc ttaatgcgcc gctacagggc gcgtactatg gttgctttga    4140
cgtatgcggt gtgaaatacc gcacagatgc gtaaggagaa aataccgcat caggcgtcag    4200
gtggcacttt tcggggaaat gtgcgcggaa cccctatttg tttatttttc taaatacatt    4260
```

```
caaatatgta tccgctcatg agacaataac cctgataaat gcttcaataa tattgaaaaa    4320
ggaagagtat gagtattcaa catttccgtg tcgcccttat tcccttttt gcggcatttt     4380 gccttcctgt ttttgctcac ccagaaacgc tggtgaaagt aaaagatgct gaagatcagt    4440
tgggtgcacg agtgggttac atcgaactgg atctcaacag cggtaagatc cttgagagtt    4500
ttcgccccga agaacgtttt ccaatgatga gcacttttaa agttctgcta tgtggcgcgg    4560
tattatcccg tattgacgcc gggcaagagc aactcggtcg ccgcatacac tattctcaga    4620
atgacttggt tgagtactca ccagtcacag aaaagcatct tacggatggc atgacagtaa    4680
gagaattatg cagtgctgcc ataaccatga gtgataacac tgcggccaac ttacttctga    4740
caacgatcgg aggaccgaag gagctaaccg cttttttgca acatggggg atcatgtaa      4800 ctcgccttga tcgttgggaa ccggagctga atgaagccat accaaacgac gagcgtgaca    4860
ccacgatgcc tgtagcaatg gcaacaacgt tgcgcaaact attaactggc gaactactta    4920
ctctagcttc ccggcaacaa ttaatagact ggatggaggc ggataaagtt gcaggaccac    4980
ttctgcgctc ggcccttccg gctggctggt ttattgctga taaatctgga gccggtgagc    5040
gtgggtctcg cggtatcatt gcagcactgg ggccagatgg taagccctcc cgtatcgtag    5100
ttatctacac gacggggagt caggcaacta tggatgaacg aaatagacag atcgctgaga    5160
taggtgcctc actgattaag cattggtaac tgtcagacca agtttactca tatatacttt    5220
agattgattt aaaacttcat ttttaattta aaaggatcta ggtgaagatc cttttgata    5280 atctcatgac caaaatccct taacgtgagt tttcgttcca ctgagcgtca gaccccgtag    5340
aaaagatcaa aggatcttct tgagatcctt ttttctgcg cgtaatctgc tgcttgcaaa     5400
caaaaaaacc accgctacca gcggtggttt gtttgccgga tcaagagcta ccaactcttt    5460
ttccgaaggt aactggcttc agcagagcgc agataccaaa tactgttctt ctagtgtagc    5520
cgtagttagg ccaccacttc aagaactctg tagcaccgcc tacatacctc gctctgctaa    5580
tcctgttacc agtggctgct gccagtggcg ataagtcgtg tcttaccggg ttggactcaa    5640
gacgatagtt accggataag gcgcagcggt cgggctgaac ggggggttcg tgcacacagc    5700
ccagcttgga gcgaacgacc tacaccgaac tgagatacct acagcgtgag ctatgagaaa    5760
gcgccacgct tcccgaaggg agaaaggcgg acaggtatcc ggtaagcggc agggtcggaa    5820
caggagagcg cacgagggag cttccagggg gaaacgcctg gtatctttat agtcctgtcg    5880
ggtttcgcca cctctgactt gagcgtcgat ttttgtgatg ctcgtcaggg ggcggagcc     5940 tatgaaaaaa cgccagcaac gcggccttt tacggttcct ggccttttgc tggccttttg    6000
ctcacatagt catgccccgc gcccaccgga aggagctgac tgggttgaag gctctcaagg    6060
gcatcggtcg agatcccggt gcctaatgag tgagctaact acattaatt gcgttgcgct     6120 cactgcccgc tttccagtcg ggaaacctgt cgtgccagct gcattaatga atcggccaac    6180
gcgcggggag aggcggtttg cgtattgggc gccagggtgg tttttctttt caccagtgag    6240
acgggcaaca gctgattgcc cttcaccgcc tggccctgag agagttgcag caagcggtcc    6300
acgctggttt gccccagcag gcgaaaatcc tgtttgatgg tggttaacgg cgggatataa    6360
catgagctgt cttcggtatc gtcgtatccc actaccgaga tatccgcacc aacgcgcagc    6420
ccggactcgg taatggcgcg cattgcgccc agcgccatct gatcgttggc aaccagcatc    6480
gcagtgggaa cgatgccctc attcagcatt tgcatggttt gttgaaaacc ggacatggca    6540
ctccagtcgc cttcccgttc cgctatcggc tgaatttgat tgcgagtgag atatttatgc    6600
cagccagcca gacgcagacg cgccgagaca gaacttaatg ggcccgctaa cagcgcgatt    6660
```

```
tgctggtgac ccaatgcgac cagatgctcc acgcccagtc gcgtaccgtc ttcatgggag    6720
aaaataatac tgttgatggg tgtctggtca gagacatcaa gaaataacgc cggaacatta    6780
gtgcaggcag cttccacagc aatggcatcc tggtcatcca gcggatagtt aatgatcagc    6840
ccactgacgc gttgcgcgag aagattgtgc accgccgctt tacaggcttc gacgccgctt    6900
cgttctacca tcgacaccac cacgctggca cccagttgat cggcgcgaga tttaatcgcc    6960
gcgacaattt gcgacggcgc gtgcagggcc agactggagg tggcaacgcc aatcagcaac    7020
gactgtttgc ccgccagttg ttgtgccacg cggttgggaa tgtaattcag ctccgccatc    7080
gccgcttcca cttttcccg cgttttcgca gaaacgtggc tggcctggtt caccacgcgg    7140
gaaacggtct gataagagac accggcatac tctgcgacat cgtataacgt tactggtttc    7200
acattcacca ccctgaattg actctcttcc gggcgctatc atgccatacc gcgaaaggtt    7260
ttgcgccatt cgatggtgtc cgggatctcg acgctctccc ttatgcgact cctgcattag    7320
gaagcagccc agtagtaggt tgaggccgtt gagcaccgcc gccgc                    7365
```

<210> SEQ ID NO 93
<211> LENGTH: 48
<212> TYPE: DNA
<213> ORGANISM: Artificial Sequence
<220> FEATURE:
<223> OTHER INFORMATION: PCR primer 1 for amplifying IspSP gene

<400> SEQUENCE: 93

```
ggtagtggtg gtatcgaagg taggatgtgc tctgtttcta ccgagaac                 48
```

<210> SEQ ID NO 94
<211> LENGTH: 52
<212> TYPE: DNA
<213> ORGANISM: Artificial Sequence
<220> FEATURE:
<223> OTHER INFORMATION: PCR primer 2 for amplifying IspSP gene

<400> SEQUENCE: 94

```
gattctgtgc ttttaagcag agattaccta ttaacgttcg aacggcagaa tc            52
```

<210> SEQ ID NO 95
<211> LENGTH: 7389
<212> TYPE: DNA
<213> ORGANISM: Artificial Sequence
<220> FEATURE:
<223> OTHER INFORMATION: Nucleotide sequence of plasmid for expressing
      IspSP gene (pCold-TF-IspSP)

<400> SEQUENCE: 95

```
aaggaatggt gtggccgatt aatcataaat atgaaaaata attgttgcat cacccgccaa    60
tgcgtggctt aatgcacatc aaattgtgag cggataacaa tttgatgtgc tagcgcatat    120
ccagtgtagt aaggcaagtc ccttcaagag ttatcgttga taccctcgt agtgcacatt    180 cctttaacgc ttcaaaatct gtaaagcacg ccatatcgcc gaaaggcaca cttaattatt    240
aagaggtaat acaccatgaa tcacaaagtg catcatcatc atcatcacat gcaagtttca    300
gttgaaacca ctcaaggcct tggccgccgt gtaacgatta ctatcgctgc tgacagcatc    360
gagaccgctg ttaaaagcga gctggtcaac gttgcgaaaa agtacgtat tgacggcttc    420 cgcaagggca aagtgccaat gaatatcgtt gctcagcgtt atggcgcgtc tgtacgccag    480
gacgttctgg gtgacctgat gagccgtaac ttcattgacg ccatcattaa agaaaaaatc    540
aatccggctg gcgcaccgac ttatgttccg ggcgaataca agctgggtga agacttcact    600
```

```
tactctgtag agtttgaagt ttatccggaa gttgaactgc aaggtctgga agcgatcgaa    660
gttgaaaaac cgatcgttga agtgaccgac gctgacgttg acggcatgct ggatactctg    720
cgtaaacagc aggcgacctg gaaagaaaaa gacggcgctg ttgaagcaga agaccgcgtg    780
accatcgact tcaccggttc tgtagacggc gaagagttcg aaggcggtaa agcgtctgat    840
ttcgtactgg cgatgggcca gggtcgtatg atcccgggct ttgaagacgg tatcaaaggc    900
cacaaagctg gcgaagagtt caccatcgac gtgaccttcc cggaagaata ccacgcagaa    960
aacctgaaag gtaaagcagc gaaattcgct atcaacctga gaaagttga agagcgtgaa   1020
ctgccggaac tgaccgcaga gttcatcaaa cgtttcggcg ttgaagatgg ttccgtagaa   1080
ggtctgcgcg ctgaagtgcg taaaaacatg gagcgcgagc tgaagagcgc catccgtaac   1140
cgcgttaagt ctcaggcgat cgaaggtctg gtaaaagcta acgacatcga cgtaccggct   1200
gcgctgatcg acagcgaaat cgacgttctg cgtcgccagg ctgcacagcg tttcggtggc   1260
aacgaaaaac aagctctgga actgccgcgc gaactgttcg aagaacaggc taaacgccgc   1320
gtagttgttg gcctgctgct gggcgaagtt atccgcacca acgagctgaa agctgacgaa   1380
gagcgcgtga aaggcctgat cgaagagatg gcttctgcgt acgaagatcc gaaagaagtt   1440
atcgagttct acagcaaaaa caaagaactg atggacaaca tgcgcaatgt tgctctggaa   1500
gaacaggctg ttgaagctgt actggcgaaa gcgaaagtga ctgaaaaaga aaccactttc   1560
aacgagctga tgaaccagca ggcgtccgcg ggtctggaag ttctgttcca ggggccctcc   1620
gcgggtctgg tgccacgcgg tagtggtggt atcgaaggta ggatgtgctc tgtttctacc   1680
gagaacgttt ccttcactga cacggaaacc gaggcacgtc gtagcgcgaa ctacgagccg   1740
aatagctggg actacgattt cctgctgtct tccgatactg acgaatctat tgaggtgtac   1800
aaagacaaag caaagaaact ggaggctgaa gtgcgccgcg aaattaacaa cgagaaagct   1860
gaattcctga ctctgctgga gctgatcgat aacgtacagc gcctgggtct gggttaccgc   1920
ttcgaatctg atatccgtcg cgcactggat cgtttcgtaa gcagcggcgg tttcgatggc   1980
gtgaccaaaa cgagcctgca cgctaccgcg ctgtccttcc gtctgctgcg tcagcacggc   2040
ttcgaagttt ctcaggaagc attctccggt ttcaaagatc aaaacggtaa cttcctggaa   2100
aacctgaaag aagacactaa ggcgatcctg agcctgtatg aggcaagctt tctggccctg   2160
gagggtgaga acatcctgga tgaggcgcgc gtattcgcca tctcccatct gaaagagctg   2220
tctgaagaga aaatcggtaa ggaactggca gagcaggtta atcacgcact ggaactgccg   2280
ctgcatcgtc gtacccagcg tctggaggcg gtttggtcca tcgaagcgta ccgcaaaaag   2340
gaggatgcta accaggttct gctggaactg gccatcctgg actacaacat gatccagtcc   2400
gtttaccagc gtgatctgcg tgaaacctcc cgttggtggc gccgtgtggg cctggcgacc   2460
aaactgcact tcgctaagga ccgcctgatt gagtcttttt actgggcagt cggcgttgcg   2520
ttcgaacctc agtattctga ctgccgtaac agcgttgcga aaatgttcag cttcgttact   2580
attatcgacg acatctacga cgtttacggt actctggacg agctggaact gtttaccgac   2640
gctgtcgaac gttgggatgt taacgccatc aacgatctgc ctgactacat gaaactgtgc   2700
ttcctggcac tgtataacac gatcaacgaa attgcatacg acaacctgaa agacaaaggt   2760
gaaaacatcc tgccgtacct gactaaagcg tgggcggatc tgtgtaacgc ttttctgcaa   2820
gaagcgaaat ggctgtataa caaatccact ccgacctttg acgattattt cggcaatgcc   2880
tggaaatcca gctctggccc gctgcaactg atcttcgctt attttgcggt tgtccaaaac   2940
```

```
atcaaaaagg aggaaattga aaacctgcaa aaataccacg atatcattag ccgtccttct    3000
catatctttc gcctgtgcaa cgacctggca agcgcgtccg cagagatcgc acgtggcgaa    3060
accgctaact ctgtttcctg ctacatgcgc accaagggca tttccgaaga gctggcaacc    3120
gagagcgtaa tgaatctgat cgacgaaacc tgtaagaaaa tgaacaaaga aaaactgggt    3180
ggctccctgt tcgctaaacc gttcgtagag actgctatta acctggcacg tcagagccac    3240
tgcacctacc acaatggtga cgcacatact agcccggatg aactgactcg taaacgtgta    3300
ctgtctgtta tcaccgaacc gattctgccg ttcgaacgtt aataggtaat ctctgcttaa    3360
aagcacagaa tctaagatcc ctgccatttg gcggggattt ttttatttgt tttcaggaaa    3420
taaataatcg atcgcgtaat aaaatctatt attattttttg tgaagaataa atttgggtgc    3480
aatgagaatg cgcaggccct ttcgtctcgc gcgtttcggt gatgacggtg aaaacctctg    3540
acacatgcag ctcccggaga cggtcacagc ttgtctgtaa gcggatgccg ggagcagaca    3600
agcccgtcag ggcgcgtcag cgggtgttgg cgggtgtcgg gctggctta actatgcggc    3660 atcagagcag attgtactga gagtgcacca taaaattgta aacgttaata ttttgttaaa    3720
attcgcgtta aattttttgtt aaatcagctc atttttttaac caataggccg aaatcggcaa    3780
aatcccttat aaatcaaaag aatagcccga gatagggttg agtgttgttc cagttttgga    3840
caagagtcca ctattaaaga acgtggactc caacgtcaaa gggcgaaaaa ccgtctatca    3900
gggcgatggc ccactacgtg aaccatcacc caaatcaagt ttttttgggt cgaggtgccg    3960
taaagcacta atcggaacc ctaaagggag ccccgatt agagcttgac gggaaaagcc    4020
ggcgaacgtg gcgagaaagg aagggaagaa agcgaaagga gcgggcgcta gggcgctggc    4080
aagtgtagcg gtcacgctgc gcgtaaccac cacacccgcc gcgcttaatg cgccgctaca    4140
gggcgcgtac tatggttgct ttgacgtatg cggtgtgaaa taccgcacag atgcgtaagg    4200
agaaaatacc gcatcaggcg tcaggtggca ctttcgggg aaatgtgcgc ggaacccta    4260 tttgtttatt tttctaaata cattcaaata tgtatccgct catgagacaa taaccctgat    4320
aaatgcttca ataatattga aaaggaaga gtatgagtat tcaacatttc cgtgtcgccc    4380
ttattccctt ttttgcggca ttttgccttc ctgtttttgc tcacccagaa acgctggtga    4440
aagtaaaaga tgctgaagat cagttgggtg cacgagtggg ttacatcgaa ctggatctca    4500
acagcggtaa gatccttgag agttttcgcc ccgaagaacg ttttccaatg atgagcactt    4560
ttaaagttct gctatgtggc gcggtattat cccgtattga cgccgggcaa gagcaactcg    4620
gtcgccgcat acactattct cagaatgact tggttgagta ctcaccagtc acagaaaagc    4680
atcttacgga tggcatgaca gtaagagaat tatgcagtgc tgccataacc atgagtgata    4740
acactgcggc caacttactt ctgacaacga tcggaggacc gaaggagcta accgcttttt    4800
tgcacaacat gggggatcat gtaactcgcc ttgatcgttg gaaccggag ctgaatgaag    4860 ccataccaaa cgacgagcgt gacaccacga tgcctgtagc aatggcaaca acgttgcgca    4920
aactattaac tggcgaacta cttactctag cttcccggca acaattaata gactggatgg    4980
aggcggataa agttgcagga ccacttctgc gctcggccct tccggctggc tggtttattg    5040
ctgataaatc tggagccggt gagcgtgggt ctcgcggtat cattgcagca ctggggccag    5100
atggtaagcc ctcccgtatc gtagttatct acacgacggg gagtcaggca actatggatg    5160
aacgaaatag acagatcgct gagataggtg cctcactgat taagcattgg taactgtcag    5220
accaagttta ctcatatata ctttagattg atttaaaact tcattttttaa tttaaaagga    5280 tctaggtgaa gatccttttt gataatctca tgaccaaaat cccttaacgt gagttttcgt    5340
```

```
tccactgagc gtcagacccc gtagaaaaga tcaaaggatc ttcttgagat cctttttttc   5400
tgcgcgtaat ctgctgcttg caaacaaaaa aaccaccgct accagcggtg gtttgtttgc   5460
cggatcaaga gctaccaact cttttccga aggtaactgg cttcagcaga gcgcagatac    5520
caaatactgt tcttctagtg tagccgtagt taggccacca cttcaagaac tctgtagcac   5580
cgcctacata cctcgctctg ctaatcctgt taccagtggc tgctgccagt ggcgataagt   5640
cgtgtcttac cgggttggac tcaagacgat agttaccgga taaggcgcag cggtcgggct   5700 gaacggggg ttcgtgcaca cagcccagct tggagcgaac gacctacacc gaactgagat    5760
acctacagcg tgagctatga gaaagcgcca cgcttcccga agggagaaag gcggacaggt   5820
atccggtaag cggcagggtc ggaacaggag agcgcacgag ggagcttcca gggggaaacg   5880
cctggtatct ttatagtcct gtcgggtttc gccacctctg acttgagcgt cgattttgt    5940 gatgctcgtc agggggcgg agcctatgga aaaacgccag caacgcggcc ttttacggt     6000 tcctggcctt ttgctggcct tttgctcaca tagtcatgcc ccgcgcccac cggaaggagc   6060
tgactgggtt gaaggctctc aagggcatcg gtcgagatcc cggtgcctaa tgagtgagct   6120
aacttacatt aattgcgttg cgctcactgc ccgctttcca gtcgggaaac ctgtcgtgcc   6180
agctgcatta atgaatcggc caacgcgcgg ggagaggcgg tttgcgtatt gggcgccagg   6240 gtggttttc ttttcaccag tgagacgggc aacagctgat tgcccttcac cgcctggccc   6300
tgagagagtt gcagcaagcg gtccacgctg gtttgcccca gcaggcgaaa atcctgtttg   6360
atggtggtta acgcgggat ataacatgag ctgtcttcgg tatcgtcgta tcccactacc    6420
gagatatccg caccaacgcg cagcccggac tcggtaatgg cgcgcattgc gcccagcgcc   6480
atctgatcgt tggcaaccag catcgcagtg ggaacgatgc cctcattcag catttgcatg   6540
gtttgttgaa aaccggacat ggcactccag tcgccttccc gttccgctat cggctgaatt   6600
tgattgcgag tgagatattt atgccagcca gccagacgca gacgcgccga gacagaactt   6660
aatgggcccg ctaacagcgc gatttgctgg tgacccaatg cgaccagatg ctccacgccc   6720
agtcgcgtac cgtcttcatg ggagaaaata atactgttga tgggtgtctg gtcagagaca   6780
tcaagaaata acgccggaac attagtgcag gcagcttcca cagcaatggc atcctggtca   6840
tccagcggat agttaatgat cagcccactg acgcgttgcg cgagaagatt gtgcaccgcc   6900
gctttacagg cttcgacgcc gcttcgttct accatcgaca ccaccacgct ggcacccagt   6960
tgatcggcgc gagatttaat cgccgcgaca atttgcgacg gcgcgtgcag ggccagactg   7020
gaggtggcaa cgccaatcag caacgactgt ttgcccgcca gttgttgtgc cacgcggttg   7080
ggaatgtaat tcagctccgc catcgccgct tccactttt cccgcgtttt cgcagaaacg   7140
tggctggcct ggttcaccac gcgggaaacg gtctgataag agacaccggc atactctgcg   7200
acatcgtata acgttactgg tttcacattc accaccctga attgactctc ttccgggcgc   7260
tatcatgcca taccgcgaaa ggttttgcgc cattcgatgg tgtccgggat ctcgacgctc   7320
tcccttatgc gactcctgca ttaggaagca gcccagtagt aggttgaggc cgttgagcac   7380
cgccgccgc                                                          7389
```

<210> SEQ ID NO 96
<211> LENGTH: 50
<212> TYPE: DNA
<213> ORGANISM: Artificial Sequence
<220> FEATURE:
<223> OTHER INFORMATION: Primer 1 for amplifying IspSK gene

<400> SEQUENCE: 96

```
ggtagtggtg gtatcgaagg taggatgtgt gcgacctctt ctcaatttac        50
```

<210> SEQ ID NO 97
<211> LENGTH: 56
<212> TYPE: DNA
<213> ORGANISM: Artificial Sequence
<220> FEATURE:
<223> OTHER INFORMATION: Primer 2 for amplifying IspSK gene

<400> SEQUENCE: 97

```
gattctgtgc ttttaagcag agattaccta ttagacatac atcagctggt taatcg    56
```

<210> SEQ ID NO 98
<211> LENGTH: 7404
<212> TYPE: DNA
<213> ORGANISM: Artificial Sequence
<220> FEATURE:
<223> OTHER INFORMATION: Nucleotide sequence of plasmid for expressing
      IspSK gene (pCold-TF-IspSK)

<400> SEQUENCE: 98

```
aaggaatggt gtggccgatt aatcataaat atgaaaaata attgttgcat cacccgccaa    60
tgcgtggctt aatgcacatc aaattgtgag cggataacaa tttgatgtgc tagcgcatat   120
ccagtgtagt aaggcaagtc ccttcaagag ttatcgttga taccctcgt agtgcacatt    180
cctttaacgc ttcaaaatct gtaaagcacg ccatatcgcc gaaaggcaca cttaattatt   240
aagaggtaat acaccatgaa tcacaaagtg catcatcatc atcatcacat gcaagtttca   300
gttgaaacca ctcaaggcct tggccgccgt gtaacgatta ctatcgctgc tgacagcatc   360
gagaccgctg ttaaaagcga gctggtcaac gttgcgaaaa agtacgtat tgacggcttc    420
cgcaagggca aagtgccaat gaatatcgtt gctcagcgtt atggcgcgtc tgtacgccag   480
gacgttctgg gtgacctgat gagccgtaac ttcattgacg ccatcattaa agaaaaaatc   540
aatccggctg gcgcaccgac ttatgttccg ggcgaataca agctgggtga agacttcact   600
tactctgtag agtttgaagt ttatccggaa gttgaactgc aaggtctgga agcgatcgaa   660
gttgaaaaac cgatcgttga agtgaccgac gctgacgttg acggcatgct ggatactctg   720
cgtaaacagc aggcgacctg gaaagaaaaa gacggcgctg ttgaagcaga agaccgcgtg   780
accatcgact tcaccggttc tgtagacggc gaagagttcg aaggcggtaa agcgtctgat   840
ttcgtactgg cgatgggcca gggtcgtatg atcccgggct tgaagacgg tatcaaaggc   900
cacaaagctg gcgaagagtt caccatcgac gtgaccttcc cggaagaata ccacgcagaa   960
aacctgaaag gtaaagcagc gaaattcgct atcaacctga gaaagttga gagcgtgaa    1020
ctgccggaac tgaccgcaga gttcatcaaa cgtttcggcg ttgaagatgg ttccgtagaa   1080
ggtctgcgcg ctgaagtgcg taaaaacatg gagcgcgagc tgaagagcgc catccgtaac   1140
cgcgttaagt ctcaggcgat cgaaggtctg gtaaaagcta acgacatcga cgtaccggct   1200
gcgctgatcg acagcgaaat cgacgttctg cgtcgccagg ctgcacagcg tttcggtggc   1260
aacgaaaaac aagctctgga actgccgcgc gaactgttcg aagaacaggc taaacgccgc   1320
gtagttgttg gcctgctgct gggcgaagtt atccgcacca acgagctgaa agctgacgaa   1380
gagcgcgtga aaggcctgat cgaagagatg gcttctgcgt acgaagatcc gaaagaagtt   1440
atcgagttct acagcaaaaa caaagaactg atggacaaca tgcgcaatgt tgctctggaa   1500
gaacaggctg ttgaagctgt actggcgaaa gcgaaagtga ctgaaaaaga aaccactttc   1560
```

```
aacgagctga tgaaccagca ggcgtccgcg ggtctggaag ttctgttcca ggggccctcc      1620
gcgggtctgg tgccacgcgg tagtggtggt atcgaaggta ggatgtgtgc gacctcttct      1680
caatttactc agattaccga gcataattcc cgtcgttccg caaactatca gccaaacctg      1740
tggaatttcg aattcctgca atccctggag aacgacctga agtggaaaa gctggaggag       1800 aaagcgacca aactggagga agaagttcgc tgcatgatca accgtgtaga cacccagccg      1860
ctgtccctgc tggagctgat cgacgatgtg cagcgcctgg gtctgaccta caaatttgaa      1920
aaagacatca ttaaagccct ggaaaacatc gtactgctgg acgaaaacaa aaagaacaaa      1980
tctgacctgc acgcaaccgc tctgtctttc cgtctgctgc gtcagcacgg tttcgaggtt      2040
tctcaggatg ttttttgagcg tttcaaggat aaagaaggtg gtttcagcgg tgaactgaaa     2100
ggtgacgtcc aaggcctgct gagcctgtat gaagcgtctt acctgggttt cgagggtgag      2160
aacctgctgg aggaggcgcg tacctttttcc atcacccacc tgaagaacaa cctgaaagaa     2220
ggcattaata ccaaggttgc agaacaagtg agccacgccc tggaactgcc atatcaccag      2280
cgtctgcacc gtctggaggc acgttggttc ctggataaat acgaaccgaa agaaccgcat      2340
caccagctgc tgctggagct ggcgaagctg gatttttaaca tggtacagac cctgcaccag    2400
aaagagctgc aagatctgtc ccgctggtgg accgagatgg gcctggctag caaactggat     2460
tttgtacgcg accgcctgat ggaagtttat ttctgggcac tgggtatggc gccagacccg     2520
cagtttggtg aatgtcgcaa agctgttact aaaatgtttg gtctggtgac gatcatcgat     2580
gacgtgtatg acgtttatgg cactctggac gaactgcaac tgttcaccga tgctgtagag    2640
cgctgggacg ttaacgctat taacaccctg ccggactata tgaaactgtg ttttcctggca   2700 ctgtacaaca ccgttaacga cacgtcctat tctattctga agagaaagg tcataacaac      2760 ctgtcctatc tgacgaaaag ctggcgtgaa ctgtgcaaag cctttctgca agaggcgaaa     2820
tggtccaaca acaaaattat cccggctttc tccaagtacc tggaaaacgc cagcgttcc     2880 tcctccggtg tagcgctgct ggcgccgtct tactttccg tatgccagca gcaggaagac      2940
atctccgacc acgcgctgcg ttccctgacc gacttccatg gtctggtgcg ttctagctgc     3000
gttatcttcc gcctgtgcaa cgatctggcc acctctgcgg cggagctgga acgtggcgag     3060
actaccaatt ctatcattag ctacatgcac gaaaacgatg gtaccagcga ggaacaggcc     3120
cgcgaagaac tgcgtaaact gatcgacgcc gaatggaaaa agatgaatcg tgaacgcgtt     3180
agcgactcca ccctgctgcc taaagcgttc atggaaatcg cagttaacat ggcacgtgtt    3240
tcccactgca cctaccagta tggcgatggt ctgggtcgcc cagactacgc gactgaaaac    3300
cgcatcaaac tgctgctgat tgaccctttc ccgattaacc agctgatgta tgtctaatag    3360
gtaatctctg cttaaaagca cagaatctaa gatccctgcc atttggcggg gatttttta    3420 tttgttttca ggaaataaat aatcgatcgc gtaataaaat ctattattat ttttgtgaag    3480
aataaatttg ggtgcaatga gaatgcgcag gcccttttcgt ctcgcgcgtt tcggtgatga    3540
cggtgaaaac ctctgacaca tgcagctccc ggagacggtc acagcttgtc tgtaagcgga    3600
tgccgggagc agacaagccc gtcagggcgc gtcagcgggt gttggcgggt gtcgggctg     3660 gcttaactat gcggcatcag agcagattgt actgagagtg caccataaaa ttgtaaacgt    3720
taatattttg ttaaaattcg cgttaaattt tgttaaatc agctcatttt ttaaccaata     3780
ggccgaaatc ggcaaaatcc cttataaatc aaaagaatag cccgagatag ggttgagtgt    3840
tgttccagtt tggaacaaga gtccactatt aaagaacgtg gactccaacg tcaaggggcg    3900
aaaaaccgtc tatcagggcg atggcccact acgtgaacca tcacccaaat caagtttttt    3960
```

```
ggggtcgagg tgccgtaaag cactaaatcg gaaccctaaa gggagccccc gatttagagc    4020
ttgacgggga aagccggcga acgtggcgag aaaggaaggg aagaaagcga aaggagcggg    4080
cgctagggcg ctggcaagtg tagcggtcac gctgcgcgta accaccacac ccgccgcgct    4140
taatgcgccg ctacagggcg cgtactatgg ttgctttgac gtatgcggtg tgaaataccg    4200
cacagatgcg taaggagaaa ataccgcatc aggcgtcagg tggcacttttt cggggaaatg    4260 tgcgcggaac ccctatttgt ttatttttct aaatacattc aaatatgtat ccgctcatga    4320
gacaataacc ctgataaatg cttcaataat attgaaaaag gaagagtatg agtattcaac    4380
atttccgtgt cgcccttatt ccctttttttg cggcattttg ccttcctgtt tttgctcacc    4440
cagaaacgct ggtgaaagta aaagatgctg aagatcagtt gggtgcacga gtgggttaca    4500
tcgaactgga tctcaacagc ggtaagatcc ttgagagttt cgccccgaa gaacgttttc     4560 caatgatgag cacttttaaa gttctgctat gtggcgcggt attatcccgt attgacgccg    4620
ggcaagagca actcggtcgc cgcatacact attctcagaa tgacttggtt gagtactcac    4680
cagtcacaga aaagcatctt acggatggca tgacagtaag agaattatgc agtgctgcca    4740
taaccatgag tgataacact gcggccaact tacttctgac aacgatcgga ggaccgaagg    4800
agctaaccgc ttttttgcac aacatggggg atcatgtaac tcgccttgat cgttgggaac    4860
cggagctgaa tgaagccata ccaaacgacg agcgtgacac cacgatgcct gtagcaatgg    4920
caacaacgtt gcgcaaacta ttaactggcg aactacttac tctagcttcc cggcaacaat    4980
taatagactg gatggaggcg gataaagttg caggaccact tctgcgctcg gcccttccgg    5040
ctggctggtt tattgctgat aaatctggag ccggtgagcg tgggtctcgc ggtatcattg    5100
cagcactggg gccagatggt aagccctccc gtatcgtagt tatctacacg acggggagtc    5160
aggcaactat ggatgaacga atagacaga tcgctgagat aggtgcctca ctgattaagc    5220
attggtaact gtcagaccaa gtttactcat atatacttta gattgattta aaacttcatt    5280
tttaatttaa aaggatctag gtgaagatcc ttttttgataa tctcatgacc aaaatccctt    5340
aacgtgagtt ttcgttccac tgagcgtcag accccgtaga aaagatcaaa ggatcttctt    5400
gagatccttt ttttctgcgc gtaatctgct gcttgcaaac aaaaaaacca ccgctaccag    5460
cggtggtttg tttgccggat caagagctac caactctttt tccgaaggta actggcttca    5520
gcagagcgca gataccaaat actgttcttc tagtgtagcc gtagttaggc caccacttca    5580
agaactctgt agcaccgcct acatacctcg ctctgctaat cctgttacca gtggctgctg    5640
ccagtggcga taagtcgtgt cttaccgggt tggactcaag acgatagtta ccggataagg    5700
cgcagcggtc gggctgaacg gggggttcgt gcacacagcc cagcttggag cgaacgacct    5760
acaccgaact gagataccta cagcgtgagc tatgagaaag cgccacgctt cccgaaggga    5820
gaaaggcgga caggtatccg gtaagcggca gggtcggaac aggagagcgc acgagggagc    5880
ttccaggggg aaacgcctgg tatctttata gtcctgtcgg gtttcgccac ctctgacttg    5940
agcgtcgatt tttgtgatgc tcgtcagggg ggcggagcct atggaaaaac gccagcaacg    6000
cggccttttt acggttcctg gccttttgct ggccttttgc tcacatagtc atgcccgcg    6060 cccaccggaa ggagctgact gggttgaagg ctctcaaggg catcggtcga tcccggtg     6120 cctaatgagt gagctaactt acattaattg cgttgcgctc actgcccgct ttccagtcgg    6180
gaaacctgtc gtgccagctg cattaatgaa tcggccaacg cgcggggaga ggcggtttgc    6240
gtattgggcg ccagggtggt ttttctttc accagtgaga cgggcaacag ctgattgccc    6300
```

```
ttcaccgcct ggccctgaga gagttgcagc aagcggtcca cgctggtttg ccccagcagg    6360
cgaaaatcct gtttgatggt ggttaacggc gggatataac atgagctgtc ttcggtatcg    6420
tcgtatccca ctaccgagat atccgcacca acgcgcagcc cggactcggt aatggcgcgc    6480
attgcgccca gcgccatctg atcgttggca accagcatcg cagtgggaac gatgccctca    6540
ttcagcattt gcatggtttg ttgaaaaccg gacatggcac tccagtcgcc ttcccgttcc    6600
gctatcggct gaatttgatt gcgagtgaga tatttatgcc agccagccag acgcagacgc    6660
gccgagacag aacttaatgg gcccgctaac agcgcgattt gctggtgacc caatgcgacc    6720
agatgctcca cgcccagtcg cgtaccgtct tcatgggaga aaataatact gttgatgggt    6780
gtctggtcag agacatcaag aaataacgcc ggaacattag tgcaggcagc ttccacagca    6840
atggcatcct ggtcatccag cggatagtta atgatcagcc cactgacgcg ttgcgcgaga    6900
agattgtgca ccgccgcttt acaggcttcg acgccgcttc gttctaccat cgacaccacc    6960
acgctggcac ccagttgatc ggcgcgagat ttaatcgccg cgacaatttg cgacggcgcg    7020
tgcagggcca gactggaggt ggcaacgcca atcagcaacg actgtttgcc cgccagttgt    7080
tgtgccacgc ggttgggaat gtaattcagc tccgccatcg ccgcttccac ttttttcccgc   7140 gttttcgcag aaacgtggct ggcctggttc accacgcggg aaacggtctg ataagagaca    7200
ccggcatact ctgcgacatc gtataacgtt actggtttca cattcaccac cctgaattga    7260
ctctcttccg ggcgctatca tgccataccg cgaaaggttt tgcgccattc gatggtgtcc    7320
gggatctcga cgctctccct tatgcgactc ctgcattagg aagcagccca gtagtaggtt    7380
gaggccgttg agcaccgccg ccgc                                           7404
```